US009476099B2

(12) United States Patent
Spinella et al.

(10) Patent No.: US 9,476,099 B2
(45) Date of Patent: Oct. 25, 2016

(54) METHOD FOR DETERMINING SENSITIVITY TO DECITABINE TREATMENT

(71) Applicant: TRUSTEES OF DARTMOUTH COLLEGE, Hanover, NH (US)

(72) Inventors: Michael Spinella, Hanover, NH (US); Maroun J. Beyrouthy, Lebanon, NH (US)

(73) Assignee: Trustees of Dartmouth College, Hanover, NH (US)

( * ) Notice: Subject to any disclaimer, the term of this patent is extended or adjusted under 35 U.S.C. 154(b) by 0 days.

(21) Appl. No.: 14/416,142

(22) PCT Filed: Jul. 31, 2013

(86) PCT No.: PCT/US2013/052899
§ 371 (c)(1),
(2) Date: Jan. 21, 2015

(87) PCT Pub. No.: WO2014/025582
PCT Pub. Date: Feb. 13, 2014

(65) Prior Publication Data
US 2015/0197813 A1 Jul. 16, 2015

Related U.S. Application Data

(63) Continuation of application No. 13/571,482, filed on Aug. 10, 2012, now abandoned.

(51) Int. Cl.
*C12Q 1/68* (2006.01)
*A61K 33/24* (2006.01)
*G01N 33/53* (2006.01)
*A61K 31/7068* (2006.01)
*G01N 33/574* (2006.01)

(52) U.S. Cl.
CPC ......... *C12Q 1/6886* (2013.01); *A61K 31/7068* (2013.01); *A61K 33/24* (2013.01); *G01N 33/57484* (2013.01); *C12Q 2600/106* (2013.01); *C12Q 2600/154* (2013.01); *C12Q 2600/158* (2013.01); *C12Q 2600/16* (2013.01); *G01N 2333/4703* (2013.01); *G01N 2333/4706* (2013.01); *G01N 2333/70596* (2013.01)

(58) Field of Classification Search
None
See application file for complete search history.

(56) References Cited

U.S. PATENT DOCUMENTS

| | | | |
|---|---|---|---|
| 6,613,753 B2 | 9/2003 | Rubinfeld et al. | 514/49 |
| 2004/0224919 A1 | 11/2004 | Rubinfeld et al. | 514/50 |
| 2007/0105133 A1 | 5/2007 | Clarke et al. | 435/6.12 |
| 2007/0287676 A1 | 12/2007 | Guo et al. | 514/43 |
| 2009/0214420 A1 | 8/2009 | Brown | 424/1.49 |
| 2012/0156312 A1 | 6/2012 | Spinella et al. | 424/649 |

FOREIGN PATENT DOCUMENTS

WO WO 2012/031008 A2 3/2012
WO WO 2012/118856 A1 9/2012

OTHER PUBLICATIONS

Tsai et al Cancer Cell. Mar. 20, 2012. 21(3):430-446 and Supplemental pages 1-18.*
Agilent Technologies. DNA Oligo Microarray Gene Lists and Annotations, available via url: <chem.agilent.com/cag/bsp/gene_lists.asp> printed on Mar. 1, 2016.*
Abele et al. "The EORTC Early Clinical Trials Cooperative Group Experience with 5-Aza-2'-deoxycytidine (NSC 127716) in Patients with Colo-rectal, Head and Neck, Renal Carcinomas and Malignant Melanomas" European Journal of Cancer and Clinical Oncology 1987 23(12):1921-1924.
Adewumi et al. "Characterization of Human Embryonic Stem Cell Lines by the International Stem Cell Initiative" Nature Biotechnology 2007 vol. 25(7):803-816.
Al-Hajj et al. "Prospective Identification of Tumorigenic Breast Cancer Cells" Proceedings of the National Academy of Sciences 2003 100(7):3983-3988 with correction.
Berger et al. "Evaluation of Three mRNA Markers for the Detection of Lymph Node Metastases" Anticancer Research 2006 26:3855-3860.
Beyrouthy et al. "High DNA Methyltransferase 3B Expression Mediates 5-Aza-Deoxycytidine Hypersensitivity in Testicular Germ Cell Tumors" Cancer Research 2009 69(24):9360-9366.
Biswal et al. "Acute Hypersensitivity of Pluripotent Testicular Cancer-derived Embryonal Carcinoma to Low-dose 5-Aza Deoxycytidine is Associated with Global DNA Damage-associated p53 Activation, Anti-pluripotency and DNA Demethylation" PLOS ONE 2012 7(12):E53003.
Chaudhary, U.B. and Haldas, J.R. "Long-Term Complications of Chemotherapy for Germ Cell Tumours" Drugs 2003 63(15):1565-1577.
Clark, A.T. "The Stem Cell Identity of Testicular Cancer" Stem Cell Review 2007 3:49-59.
Clarke et al. "Cancer Stem Cells—Perspectives on Current Status and Future Directions: AACR Workshop on Cancer Stem Cells" Cancer Research 2006 66(19):9339-9344.
Clavel et al. "5-Aza-2'-deoxycytidine (NSC 127716) in Non-Seminomatous Testicular Cancer. Phase II from the EORTC Early Clinical Trials Cooperative Group and Genito-Urinary Group" Annals of Oncology 1992 3(5):399-400.
Curtin et al. "Retinoic Acid Activates p53 in Human Embryonal Carcinoma Through Retinoid Receptor-Dependent Stimulation of p53 Transactivation Function" Oncogene 2001 20:2559-2569.
Dichtel-Danjoy et al. "SoxF is Part of a Novel Negative-feedback Loop in the Wingless Pathway the Controls Proliferation in the *Drosophila* Wing Disc" Development 2009 136:761-769.

(Continued)

*Primary Examiner* — Carla Myers
(74) *Attorney, Agent, or Firm* — Licata & Tyrrell P.C.

(57) ABSTRACT

The present invention is a gene expression panel of chemotherapeutic drug-resistant cancer stem cells comprising RIN1, SOX15 and TLR4. In one embodiment the cancer stem cells are testicular cancer germ cells. The present invention provides for a kit and method for determining response to treatment with decitabine at low doses.

3 Claims, 17 Drawing Sheets

(56) References Cited

OTHER PUBLICATIONS

Figure 1:
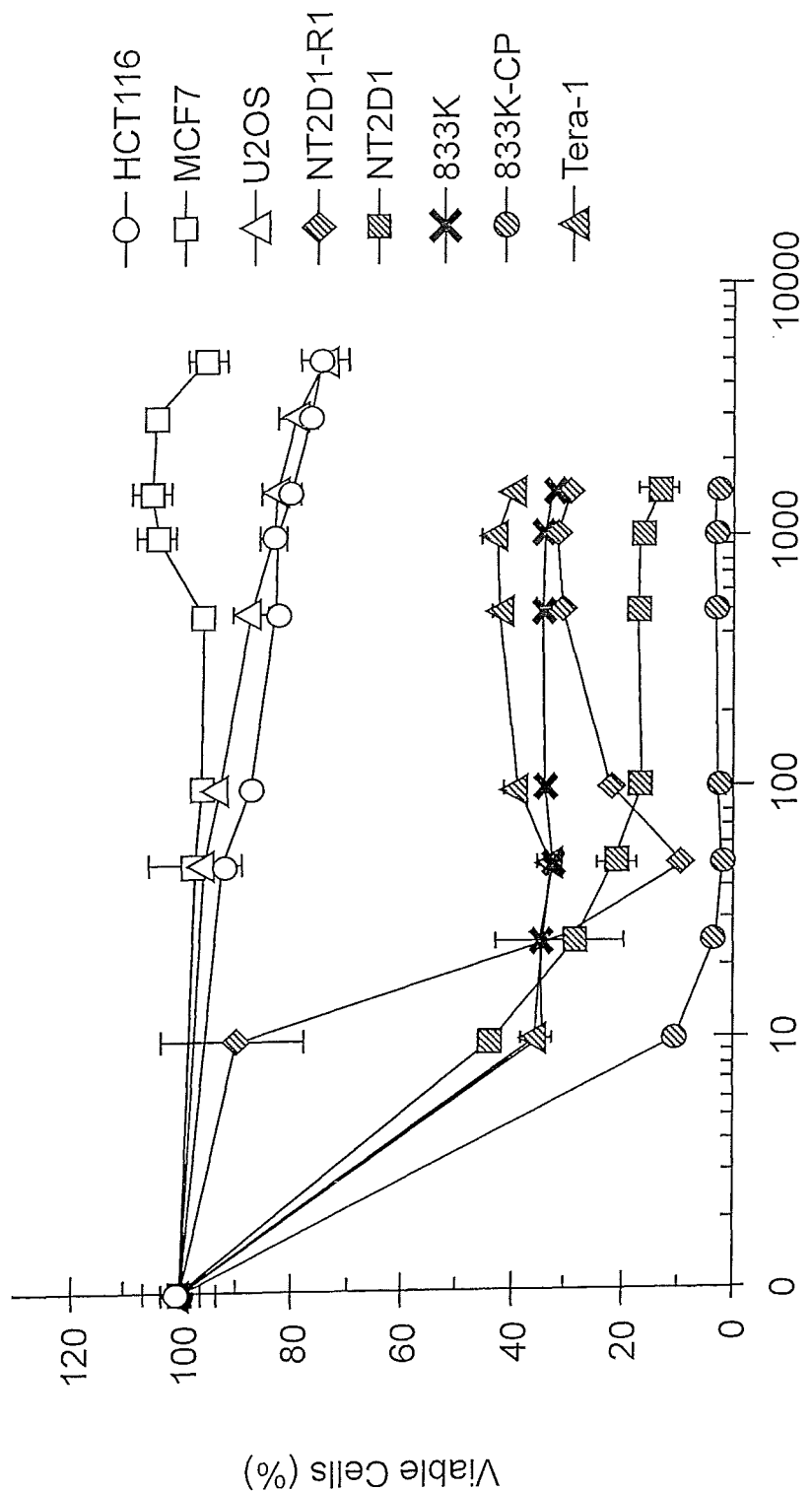

Einhorn, L.H. "Curing Metastatic Testicular Cancer" Proceedings of the National Academy of Sciences 2002 99(7):4592-4595.
El-Helw, L. and Coleman, R.E. "Salvage, Dose Intense and High-Dose Chemotherapy for the Treatment of Poor Prognosis or Recurrent Germ Cell Tumours" Cancer Treatment Reviews 2005 31:197-209.
Garcia-Manero, G. "Demethylating Agents in Myeloid Malignancies" Current Opinion in Oncology 2008 20:705-710.
Giuliano et al. "Testicular Germ Cell Tumors: A Paradigm for the Successful Treatment of Solid Tumor Stem Cells" Current Cancer Therapy Reviews 2006 2(3):255-270.
Hermann et al. "Distinct Populations of Cancer Stem Cells Determine Tumor Growth and Metastatic Activity in Human Pancreatic Cancer" Cell Stem Cell 2007 1:313-323.
Houldsworth et al. "Biology and Genetics of Adult Male Germ Cell Tumors" Journal of Clinical Oncology 2006 24(35):5512-5518.
Huang et al. "Toll-like Receptors on Tumor Cells Faciliate Evasion of Immune Surveillance" Cancer Research 2005 65:5009-5014.
Issa, J.J. "DNA Methylation as a Therapeutic Target in Cancer" Clin Cancer Res 2007 13(6):1634-1637.
Jones, P.A. and Baylin, S.B. "The Epigenomics of Cancer" Cell 2007 128:683-692.
Kantarjian et al. "Results of a Randomized Study of 3 Schedules of Low-dose Decitabine in Higher-Risk Myelodysplastic Syndrome and Chronic Myelomoncytic Leukemia" Blood 2007 109(1):52-57.
Kerley-Hamilton et al. "The Direct p53 Target Gene, FLJ11259/DRAM, is a Member of a Novel Family of Transmembrane Proteins" Biochimica et Biophysica Acta 2007 1769(4):209-219.
Kerley-Hamilton et al. "A p53-Dominant Transcriptional Response to Cisplatin in Testicular Germ Cell Tumor-Derived Human Embyronal Carcinoma" Oncogene 2005 24:6090-6100.
Kondagunta et al. "Etoposide and Cisplatin Chemotherapy for Metastatic Good-Risk Germ Cell Tumors" Journal of Clinical Oncology 2005 23(36):9290-9294.
Korkola et al. "Down-Regulation of Stem Cell Genes, Including Those in a 200-kb Gene Cluster at 12p13.31, is Associated with in vivo Differentiation of Human Male Germ Cell Tumors" Cancer Research 2006 66(2):820-827.
Li et al. "Distinct Regulatory Mechanisms and Functions for p53-Activated and p53-Repressed DNA Damage Response Genes in Embryonic Stem Cells" Molecular Cell 2012 46:30-42.
Lin et al. "p53 Induces Differentiation of Mouse Embryonic Stem Cells by Suppressing *Nanog* Expression" Nature Cell Biology 2005 7(2):165-171.
Linhart et al. "Dnmt3b Promotes Tumorigenesis in vivo by Gene-specific de novo Methylation and Transcriptional Silencing" Genes Dev. 2007 21:3110-3122.
Missiaglia et al. "Growth Delay of Human Pancreatic Cancer Cells by Methylase Inhibitor 5-aza-2'-deoxycytidine Treatment is Associated with Activation of the Interferon Signalling Pathway" Oncogene 2005 24:199-211.
Mueller et al. "Downregulation of *RUNX3* and *TES* by Hypermethylation in Glioblastoma" Oncogene 2007 26:583-593.
Müller et al. "Regulatory Networks Define Phenotypic Classes of Human Stem Cell Lines" Nature 2008 455(7211):401-405.

Qin et al. "Mechanisms of Resistance to 5-aza-2'-deoxycytidine in Human Cancer Cell Lines" Blood 2009 113(3):659-667.
Schlosser et al. "Dissection of Transcriptional Programmes in Response to Serum and c-Myc in Human B-Cell Line" Oncogene 2005 24:520-524.
Schuhmacher et al. "The Transcriptional Program of a Human B Cell Line in Response to Myc" Nucleic Acids Research 2001 29(2):397-406.
Senda et al. "Analysis of RIN1 Gene Expression in Colorectal Cancer" Oncology Reports 2007 17:1171-1175.
Shen et al. "Drug Sensitivity Prediction by CpG Island Methylation Profile in the NCI-60 Cancer Cell Line Panel" Cancer Research 2007 67(23):11335-11343.
Singh et al. "Identification of Human Brain Tumour Initiating Cells" Nature 2004 432:396-401.
Skotheim et al. "Differentiation of Human Embryonal Carcinomas in vitro and in vivo Reveals Expression Profiles Relevant to Normal Development" Cancer Research 2005 65(13):5588-5598.
Sperger et al. "Gene Expression Patterns in Human Embryonic Stem Cells and Human Pluripotent Germ Cell Tumors" Proceedings of the National Academy of Sciences 2003 100(23):13350-13355.
Streit et al. "Northern Blot Analysis for Detection and Quatification of RNA in Pancreatic Cancer Cells and Tissues" Nature Protocols 2009 4(1):3743.
Zhang et al. "Expression and Significance of TLR4 and HIF-1α in Pancreatic Ductal Adenocarcinoma" World J. Gastroenterol. 2010 16(23):2881-2888.
Office Communication dated Nov. 20, 2012 from U.S. Appl. No. 13/393,290, filed Feb. 29, 2012.
Office Communication dated Jan. 14, 2013 from U.S. Appl. No. 13/393,290, filed Feb. 29, 2012.
Office Communication dated Aug. 14, 2013 from U.S. Appl. No. 13/393,290, filed Feb. 29, 2012.
Office Communication dated Sep. 23, 2013 from U.S. Appl. No. 13/393,290, filed Feb. 29, 2012.
Office Communication dated Jul. 3, 2014 from U.S. Appl. No. 13/393,290, filed Feb. 29, 2012.
Office Communication dated Nov. 6, 2014 from U.S. Appl. No. 13/393,290, filed Feb. 29, 2012.
Office Communication dated Aug. 26, 2013 from U.S. Appl. No. 13/571,482, filed Aug. 10, 2012.
Office Communication dated Dec. 2, 2013 from U.S. Appl. No. 13/571,482, filed Aug. 10, 2012.
Office Communication dated Apr. 18, 2014 from U.S. Appl. No. 13/571,482, filed Aug. 10, 2012.
Office Communication dated Jul. 22, 2014 from U.S. Appl. No. 13/571,482, filed Aug. 10, 2012.
Office Communication dated Oct. 28, 2014 from U.S. Appl. No. 13/571,482, filed Aug. 10, 2012.
International Search Report from PCT/US10/47140, Oct. 18, 2010, PCT.
International Preliminary Report on Patentability from PCT/US10/47140, Mar. 15, 2012, PCT.
International Search Report from PCT/US13/52899, Dec. 19, 2013, OCT.
International Preliminary Report on Patentability from PCT/US2013/052899 dated Feb. 19, 2015.

* cited by examiner

METHOD FOR DETERMINING SENSITIVITY TO DECITABINE TREATMENT

This invention was made with government support under Grant No. CA104312 awarded by the National Institutes of Health. The U.S. government has certain rights in this invention.

INTRODUCTION

This application is a U.S. National Stage Application of PCT/US2013/052899 filed Jul. 31, 2013 and claims the benefit of priority to U.S. application Ser. No. 13/571,482 filed Aug. 10, 2012, the contents of each of which are incorporated herein by reference in their entireties.

BACKGROUND OF THE INVENTION

Recent evidence indicates that cells within a tumor are heterogeneous and represent different stages of development (Clarke et al. 2006. *Cancer Res.* 66:9339-9344). In certain types of cancer, a population of cells has been identified that are termed cancer stem cells, where a cancer stem cell is defined as a cell that has the capacity to self-renew and to cause the heterogeneous lineages of cancer cells that comprise a tumor. Experimentally, such cells are ones that have the ability to generate a continuously growing tumor (Clarke et al. 2006. *Cancer Res.* 66:9339-9344). Cancer stem cells can arise from normal stem cells but also from cells that acquire the capacity to self-renew potentially due to a series of mutagenic events within the cell. There is considerable interest in the role of cancer stem cells in certain types of cancer. Cancer types that have been associated with the presence of cancer stem cells include breast cancer (Al-Hajj et al. 2003. *PNAS* 100:3983-3988), pancreatic cancer (Hermann et al. 2007. *Cell Stem Cell* 1:313-323), brain cancer (Singh et al. 2004. *Nature* 432:396-401), and testicular cancer (Houldsworth et al. 2006. *J. Clin. Oncol.* 24:5512-5518; Clark A. T. 2007. *Stem Cell Rev.* 3:49-59.

Testicular germ cell tumors (TGCTs), the most common solid tumors of adolescent and young men, are thought to derive from transformation of primordial germ cells (PGCs) or early gonocytes (Houldsworth et al. 2006. *J. Clin. Oncol.* 24:5512-5518; Clark A. T. 2007. *Stem Cell Rev.* 3:49-59). TGCTs are classified as seminomas and nonseminomas (Houldsworth et al. 2006. *J. Clin. Oncol.* 24:5512-5518). Within nonseminomas are undifferentiated, pluripotent cells, known as embryonal carcinoma (EC) cells. EC cells are proposed to represent the stem cells of TGCTs and to be the malignant counterparts to embryonic stem (ES) cells (Houldsworth et al. 2006. *J. Clin. Oncol.* 24:5512-5518; Clark A. T. 2007. *Stem Cell Rev.* 3:49-59). EC cells can differentiate in vivo toward extra-embryonic tissues and embryonic tissues.

Patients with TGCTs, even those with advanced metastatic disease, are successfully treated with cisplatin-based chemotherapeutic regimens (Giuliano et al. 2006. *Curr. Cancer Ther. Rev.* 2:255-270; Einhorn, L. H. 2002. *Proc. Natl. Acad. Sci. USA* 99:4592-4595). However, 15-20% of patients are refractory to treatment and succumb to progressive disease (El-Helw, L. and R. E. Coleman. 2005. *Cancer Treat. Rev.* 31:197-209). Some germ cell tumor patients who initially respond to treatment can exhibit a late relapse and have a poor prognosis (Giuliano et al. 2006. *Curr. Cancer Ther. Rev.* 2:255-270; El-Helw, L. and R. E. Coleman. 2005. *Cancer Treat. Rev.* 31:197-209). Additionally, testicular cancer survivors have increased incidence of infertility, cardiovascular disease and secondary malignancies (Chaudhary et al. 2003. *Drugs* 63:1565-1577), all of which can affect ultimate survival and quality of life of testicular cancer patients. Mouse models of testicular cancer do exist, but they do no recapitulate key features of the human malignancy (Houldsworth et al. 2006. *J. Clin. Oncol.* 24:5512-5518).

Mechanisms of inherent or acquired cisplatin resistance in other tumors have not yet provided insights into the exquisite cisplatin-sensitivity of TGCTs (Giuliano et al. 2006. *Curr. Cancer Ther. Rev.* 2:255-270). That patients with advanced stage TGCTs can be cured implies that the stem cells of TGCTs are effectively targeted with cisplatin-based chemotherapy (Houldsworth et al. 2006. *J. Clin. Oncol.* 24:5512-5518; Giuliano et al. 2006. *Curr. Cancer Ther. Rev.* 2:255-270). There is a need to identify other chemotherapeutic agents for use in the patients that do not respond to cisplatin therapy, or that have become resistant to cisplatin therapy.

DNA methylation inhibitors, another class of chemotherapeutic agents, have been found to be more active in leukemia than in solid tumor cells (Qin et al. 2009. *Blood* 113:659-667). One such drug, 5-aza-deoxycytidine, also known as decitabine, has been shown to be useful for treating leukemia (e.g., Garcia-Manero, G. 2008. *Curr. Opin. Oncol.* 20:705-710). Decitabine is currently approved in the United States for the treatment of myelodysplastic syndromes which include leukemia. Although many papers describe the efficacy of decitabine in the treatment of leukemia, the published medical literature does not support the use of decitabine in the treatment of other types of cancer. For example, Abele et al. (1987. *Eur. J. Cancer Clin. Oncol.* 23:1921-1924) described the use of decitabine at a dose of 75 mg/m$^2$ (3 treatments in one day; repeated once a week for 5 weeks) for treatment of colorectal cancer, cancer of the head and neck, renal carcinoma, or malignant melanoma. The authors reported that decitabine showed no efficacy against any of the forms of cancer. In another study (Clavel et al. 1992. *Ann Oncol.* 3:399-400), decitabine was tested in a Phase II clinical trial in patients with non-seminiferous testicular cancer (i.e., germ cell testicular cancer). The authors used a decitabine dose of 75 mg/m$^2$ (3 infusions in one day, repeated once a week for 5 weeks; the standard leukemia regimen) and reported that the drug showed "no activity" in these patients.

U.S. Pat. No. 6,613,753 teaches administering the DNA methylation inhibitor decitabine, in combination with an anti-neoplastic agent, to treat cancer. A long list of cancers is disclosed, including testicular cancer. The patent teaches use of decitabine in combination with chemotherapeutic agents that include cisplatin and to treat cisplatin resistance. The patent teaches and claims a preferred dose range for decitabine of 1-20 mg/m$^2$/day. No data are provided showing successful treatment of germ cell testicular cancer with this regimen.

SUMMARY OF THE INVENTION

The present invention is a gene expression panel, kit and method for determining sensitivity to decitabine treatment. The gene expression panel is composed of Toll-Like Receptor 4 (TLR4), SOX15, and RIN1. The kit includes a detection mechanism for determining the expression of TLR4, RIN1, and SOX15 and is of particular use in the determining sensitivity to decitabine treatment in testicular germ cell cancer. The method of the invention involves the steps of determining the expression of TLR4, RIN1, and SOX15 in a sample from a cancer patient receiving decitabine treatment and comparing said expression with a control, wherein increased expression of TLR4, RIN1 and SOX15 in the patient sample as compared to the control is indicative of sensitivity to decitabine treatment.

DETAILED DESCRIPTION OF THE DRAWINGS

FIG. 1 depicts the results of experiments showing that EC cell lines are sensitive to low dose decitabine. Indicated doses of decitabine were added fresh each day for three days to exponentially growing cultures. Viable cell growth and survival were measured. Data are normalized to no drug treatment. EC cells are NT2/D1, NT2D1/R1, 833K, 833KCP, and Tera-1. Data are the average of 3 experiments in biological duplicate except for MCF-7 cells, which were assayed twice. Error bars are standard deviation (S.D.).

Figure 2:
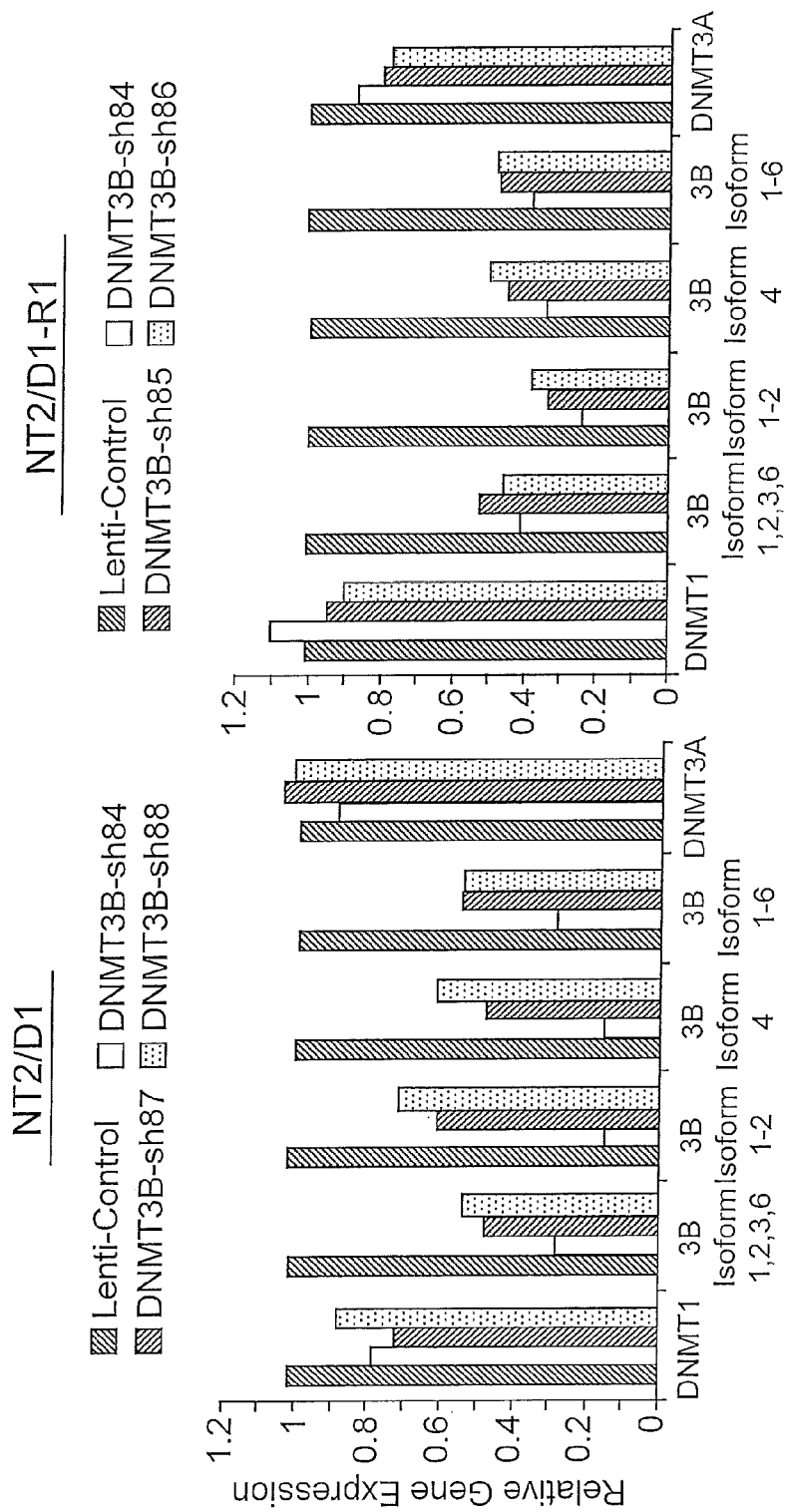

FIG. 2 depicts DNMT3B knock down results in resistance to decitabine in EC cells. Results of real-time PCR assays of DNMT3B isoforms in control NT2/D1 and in NT2/D1-R1 cells and cells treated with DNMT3B shRNA lentiviruses are shown. Knock down results in resistance to decitabine in EC cells.

Figure 3:
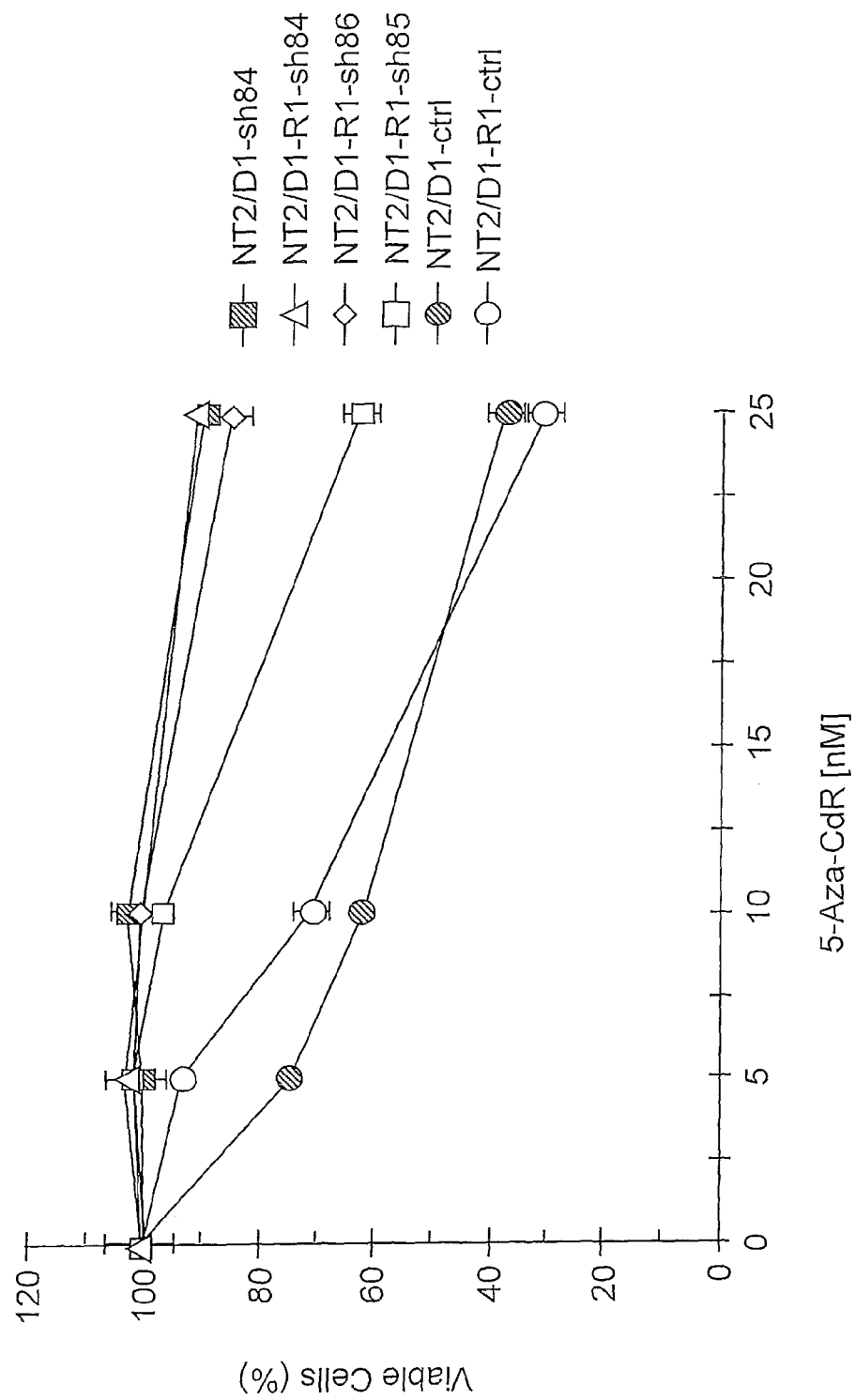

FIG. 3 depicts DNMT3B knock down results in resistance to decitabine in EC cells. Dose-response is observed after 3 day of decitabine treatment in lentiviral control NT2/D1 as well as NT2/D1-R1 cells (ctrl) and cells treated with DNMT3B sh84, 85 and 86. Data are the average of biological triplicates and are representative of at least two experiments. Error bars are S.D.

Figure 4:
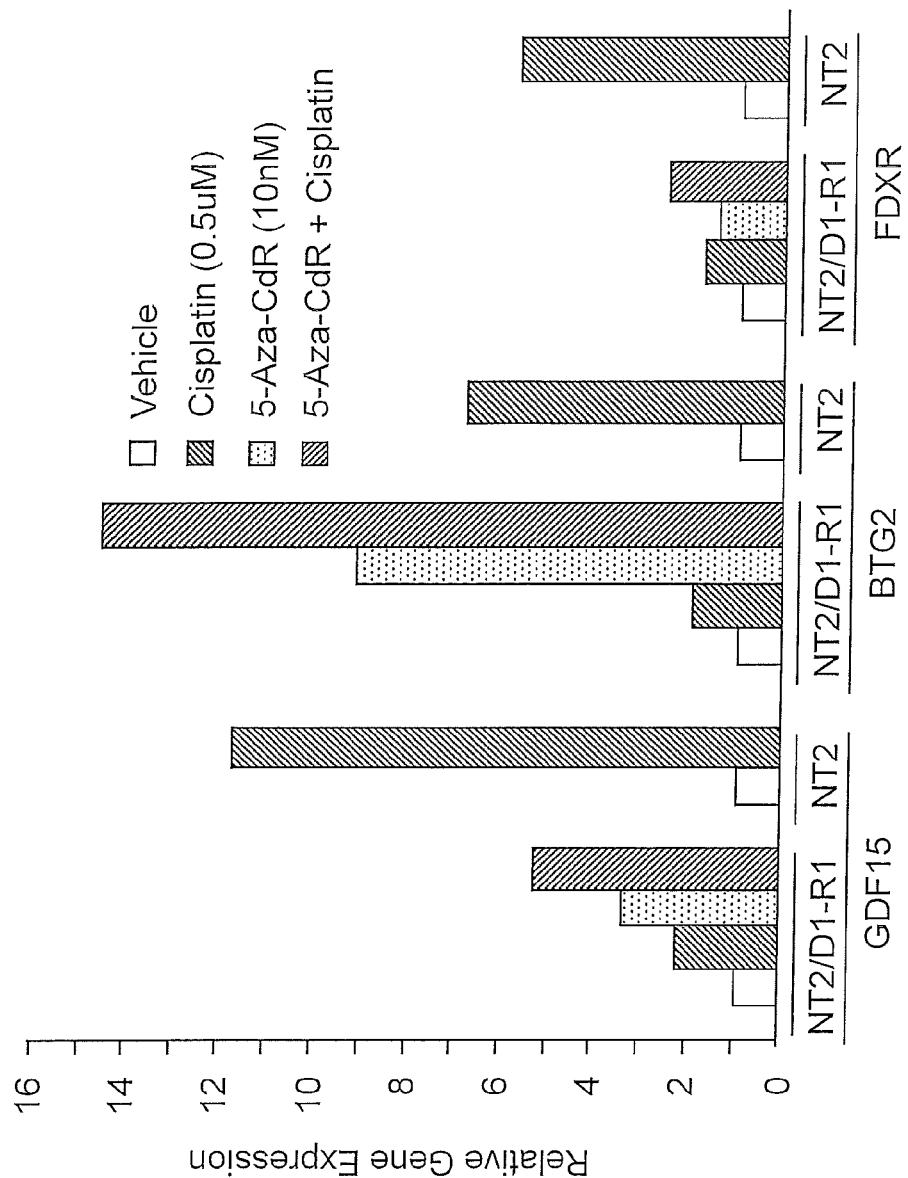

FIG. 4 depicts the effects of pretreatment with low dose decitabine to restore cisplatin sensitivity to cisplatin-resistant EC cells. NT2/D1-R1 cells were pretreated with vehicle or decitabine (10 nM) for 3 days before replating and 24 hour recovery followed by indicated cisplatin treatments for 6 hours. NT2/D1 cells were only treated with cisplatin. Cells were assayed 24 hours later for expression of indicated p53 target genes by real-time PCR assays.

Figure 5:
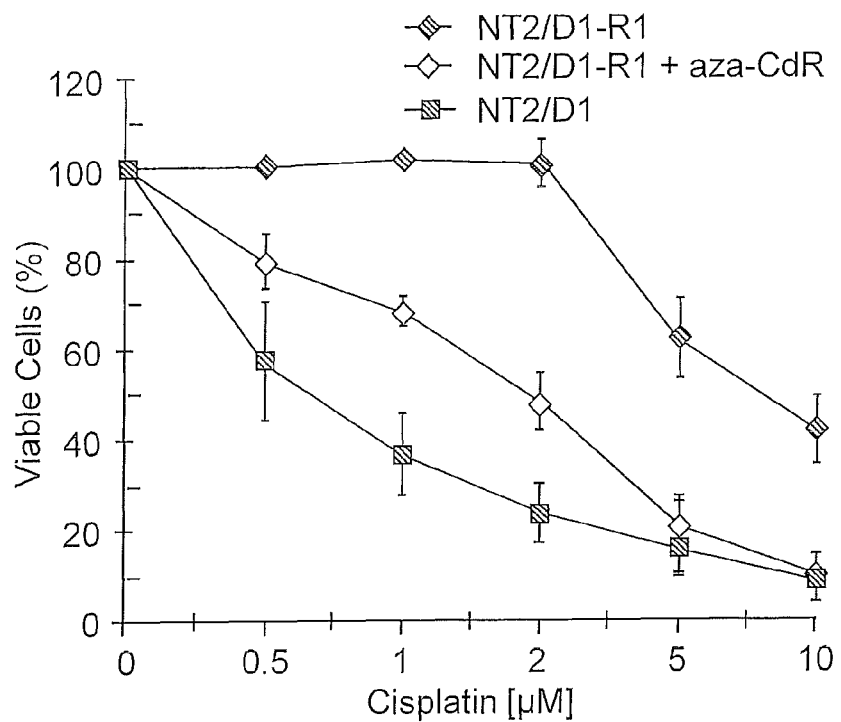

FIG. 5 depicts the effects of pretreatment with low dose decitabine to restore cisplatin sensitivity to cisplatin-resistant EC cells. Cells were pretreated with vehicle or decitabine for 3 days before replating and 24 hours recovery followed by indicated cisplatin treatments for 6 hours. Cell viability was assayed 3 days later. For NT2D1-R1 cells, 10 nM decitabineR was employed. For 833K-CP cells, 2.5 nM decitabine was employed. Data are the average of biological triplicates and representative of at least two experiments. Error bars are standard error of the mean (SEM).

Figure 6:
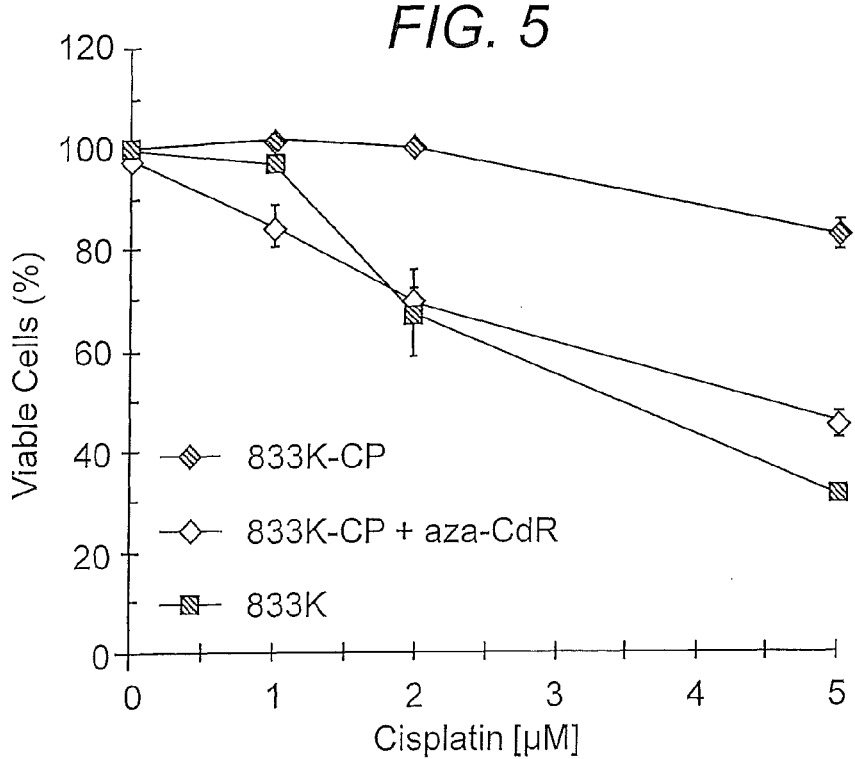

FIG. 6 also depicts the effects of pretreatment with low dose decitabine to restore cisplatin sensitivity to cisplatin-resistant EC cells. Cells were pretreated with vehicle or decitabine for 3 days before replating and 24 hours recovery followed by indicated cisplatin treatments for 6 hours. Cell viability was assayed 3 days later. For NT2D1-R1 cells, 10 nM decitabineR was employed. For 833K-CP cells, 2.5 nM decitabine was employed. Data are the average of biological triplicates and representative of at least two experiments. Error bars are SEM.

Figure 7:
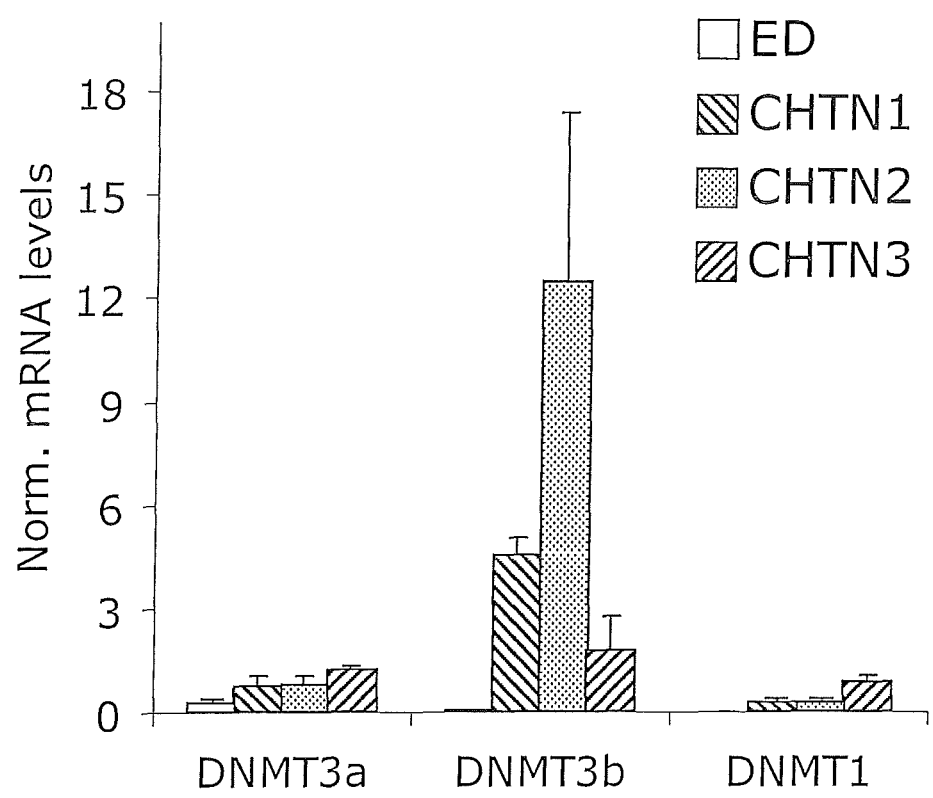

FIG. 7 depicts DNMT3B expression in clinical tumor samples. The graphs show levels of mRNA expression quantified with RT-PCR analysis of DNMTs. The samples tested included a mature teratoma (ED) and 3 different testicular germ cell tumors (denoted CHTN1 through CHTN-3, wherein CHTN is the Connective Human Tissue Network). Bars represent standard deviation from the mean of two determinations.

Figure 8:
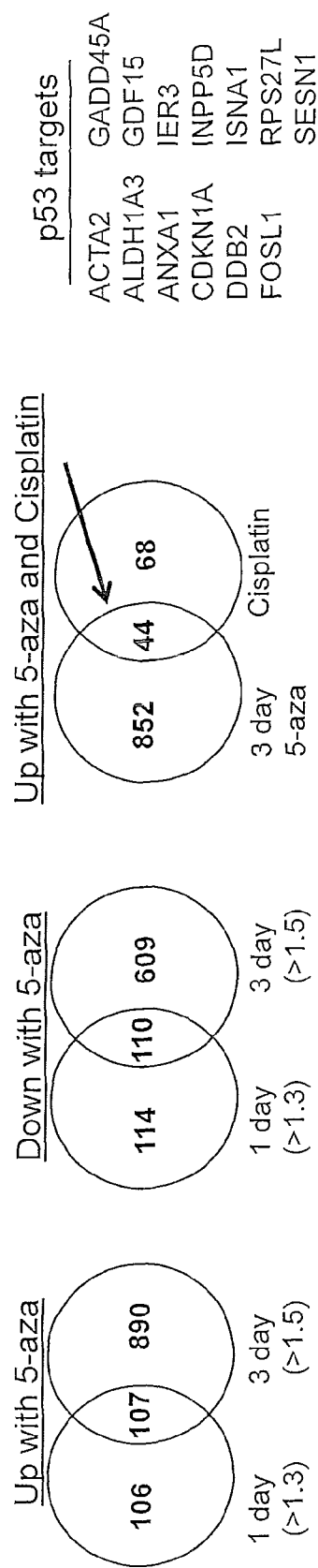

FIG. 8 depicts the effects of low dose decitabine to induce distinct genome-wide activation of 53 target genes and to repress expression of puripotency genes in EC cells. Shown are Venn diagrams of the gene expression microarray data. The diagrams show that there is a large overlap in the genes up-regulated (left) and down-regulated (middle) in NT2/D1 cells with 1 day of low dose (10 nM) decitabine treatment (fold change>1.3) as compared to 3 days of treatment with decitabine (fold change>1.5). A Venn diagram (right) of microarray data is also presented showing a large degree of overlap in genes upregulated 1.5-fold or greater by both 3 days of treatment with decitabine and cisplatin. Expression levels for the genes depicted in each Venn diagram were altered with p value, p<0.05. Of the overlap genes, 13 are known p53 target genes in NT2/D1 cells.

Figure 9:
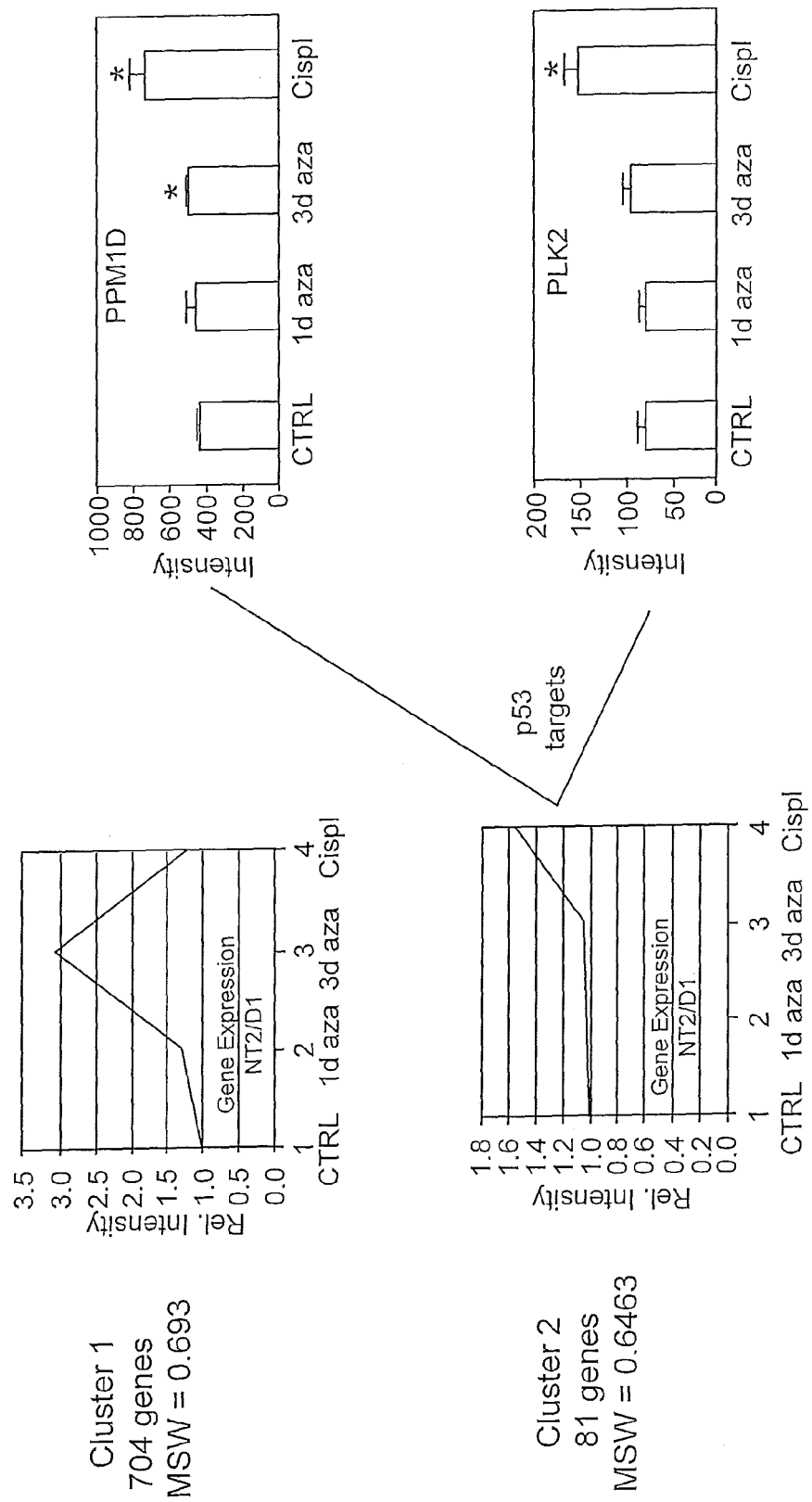
Figure 9:
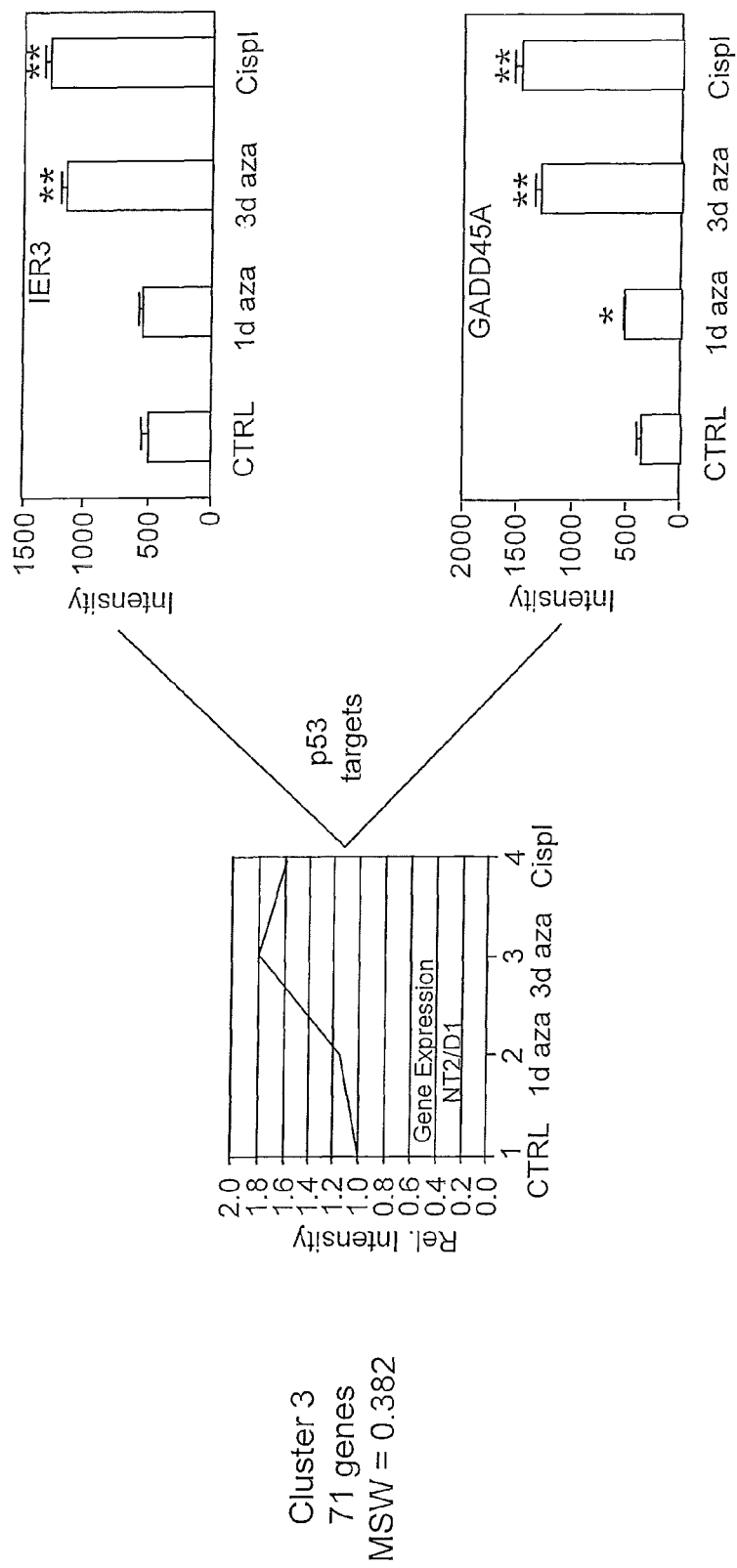
Figure 9:
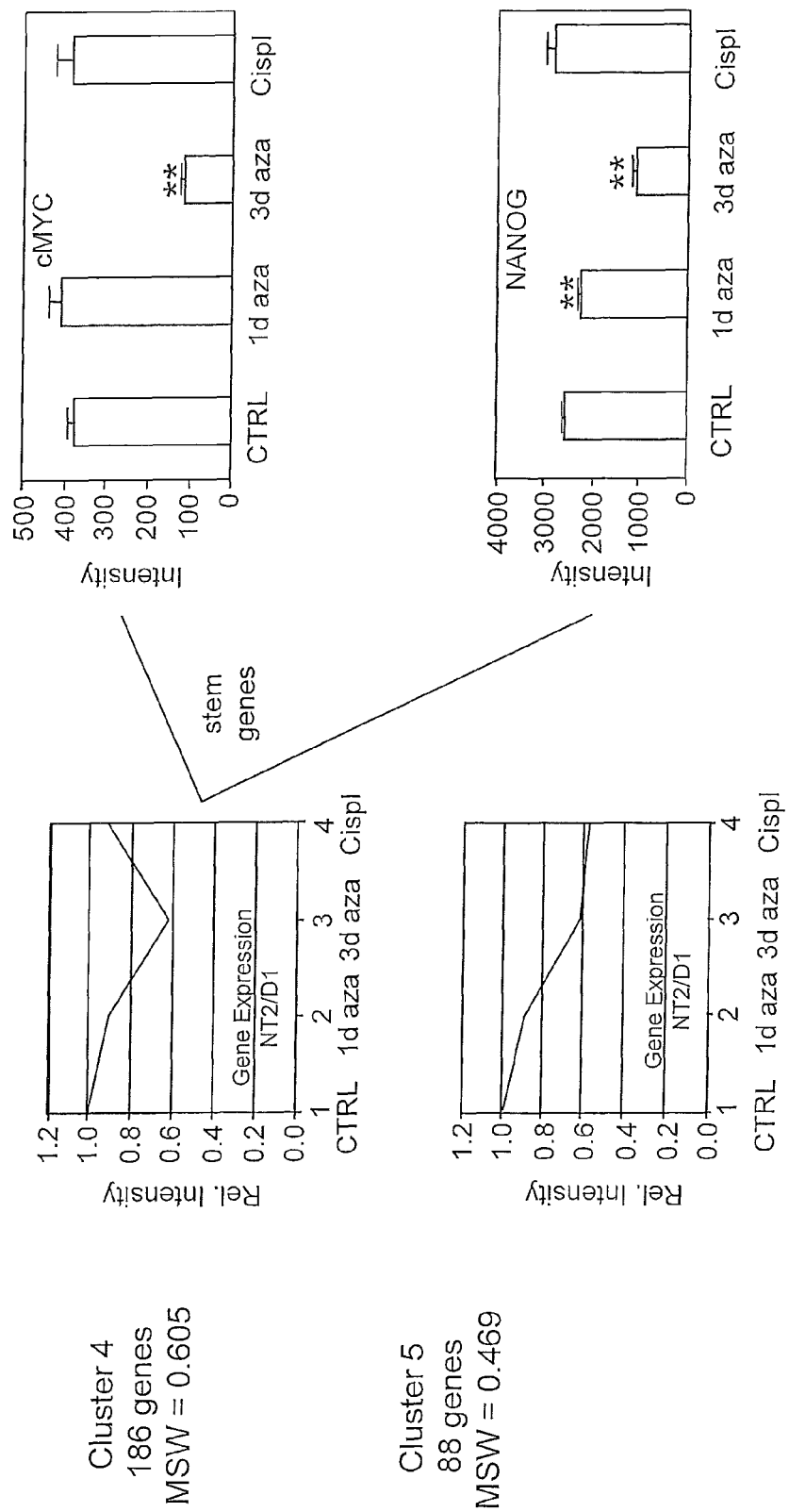
Figure 10A:
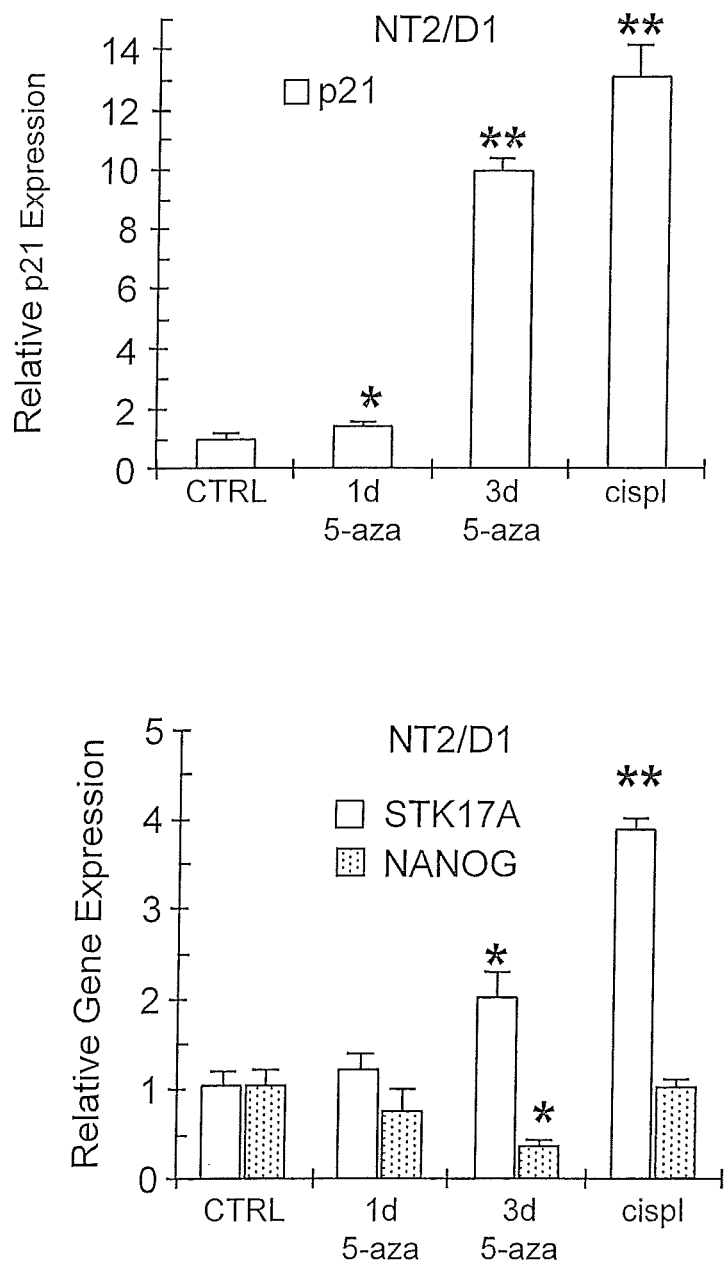
Figure 10B:
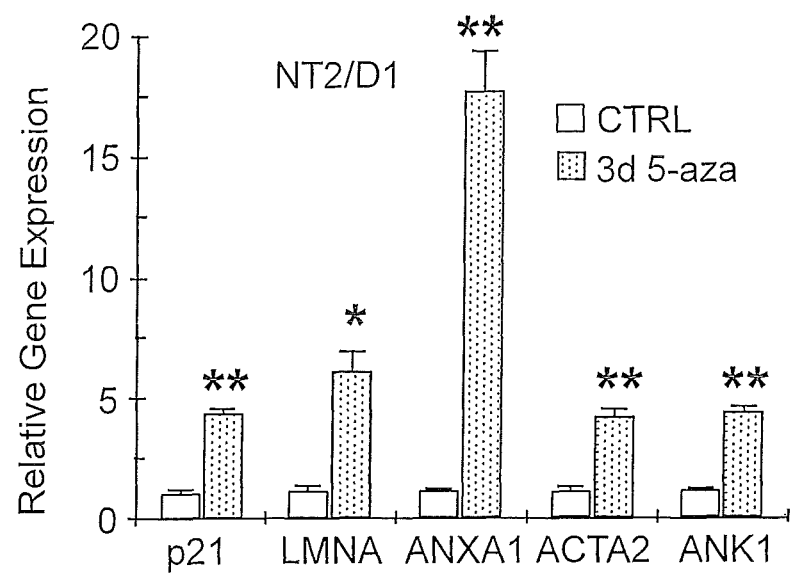
Figure 10C:
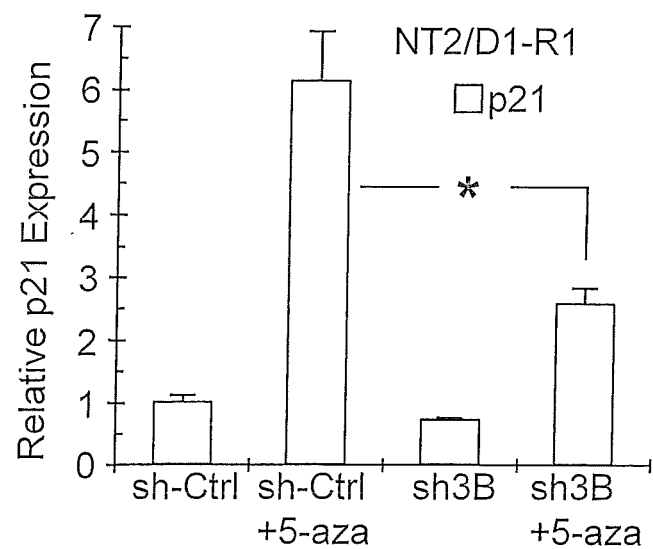
Figure 10C:
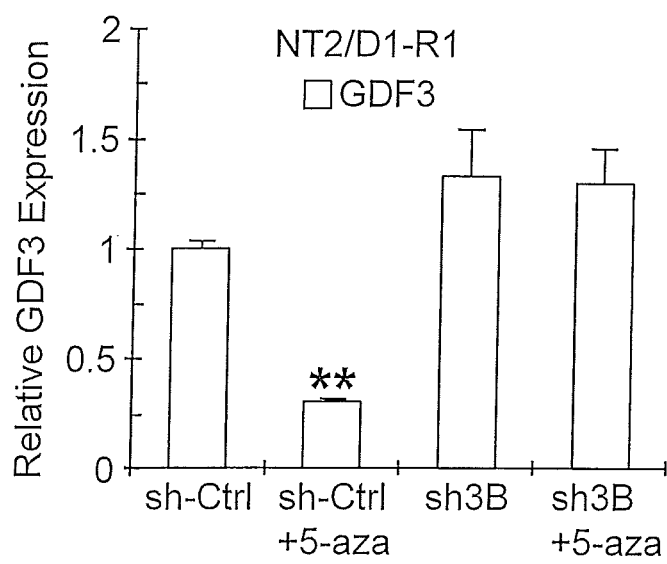

FIG. 9 depicts the results of the partitioning around mediods (PAM) analysis of regulated genes whose expression was regulated by treatment with low dose decitabine and cisplatin in NT2/D1 cells. Shown are the genes whose expression levels changed by 1.5 fold or greater. The number of genes in each of the five clusters and the mean silhouette width (MSW) value for each cluster is indicated. Expression intensity values for representative genes in Cluster 2, Cluster 3, and Cluster 4 are provided on the left. Error bars are S.E.M. *=p<0.05; **=p<0.005 compared to untreated controls.

FIG. 10 depicts results of experiments using RT-PCR to confirm the decitabine-dependent gene regulation results obtained in NT2/D1, NT2/D1-R1, and DNMT3B knockdown (sh-3B) cells. As shown, STK17A, p21, LMNA, ANXA1, ACTA2 and ANK1 are p53 target genes while GDF3 and NANOG are pluripotency genes.

Figure 11:
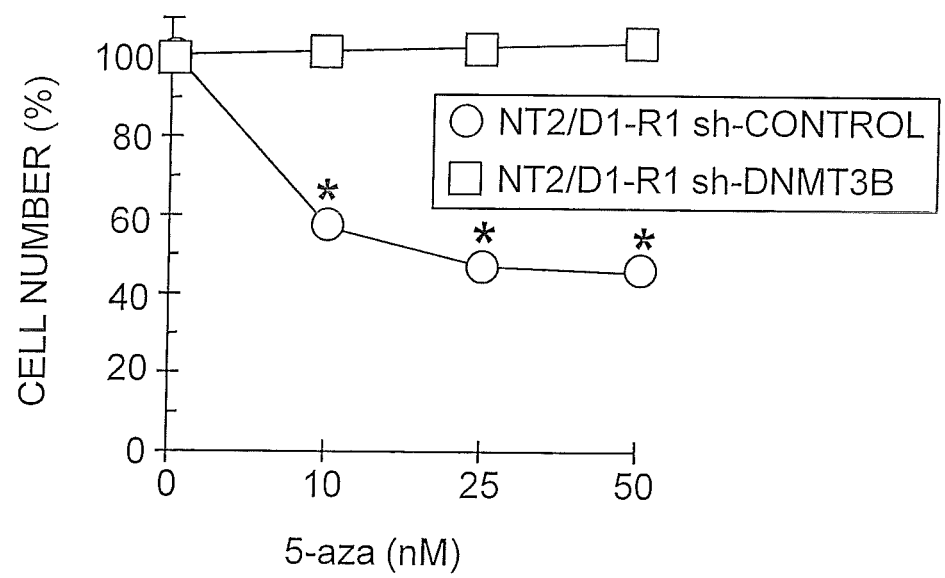

FIG. 11 depicts results of experiments showing that knockdown of DNMT3B in EC cells resulted in resistance to low-dose decitabine (10 nM) treatment. Indicated doses of decitabine were added fresh each day for 3 days to exponentially growing cultures of NT2/D1-R1 lentiviral control cells and NT2/D1-R1 cells stably expressing a lentiviral shDNMT3B construct. Viable cell growth and survival were measured. Data was normalized to no drug treatment. Error bars (within symbols) are standard deviation. * p=<0.05 compared to untreated controls.

Figure 12:
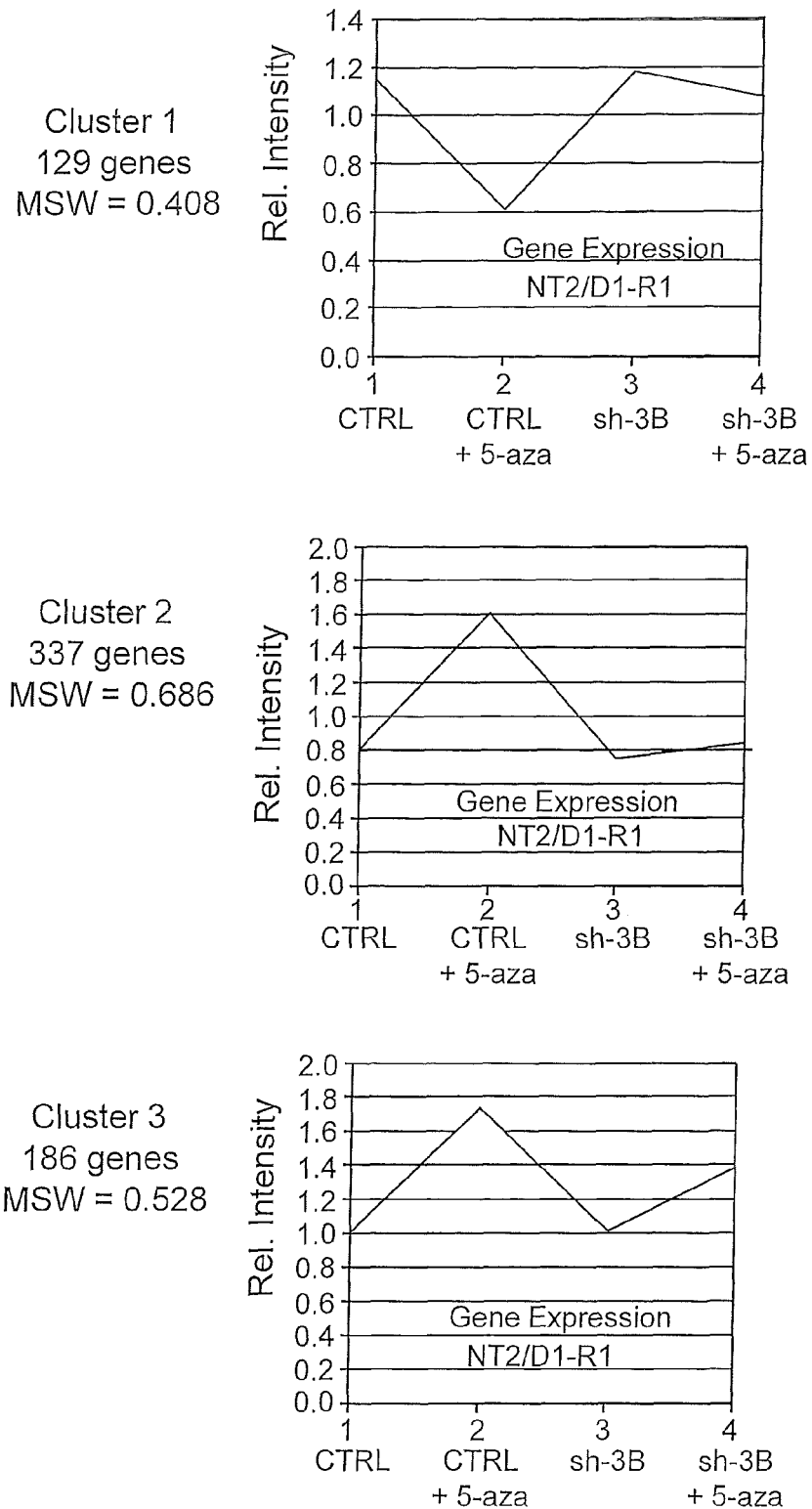
Figure 12:
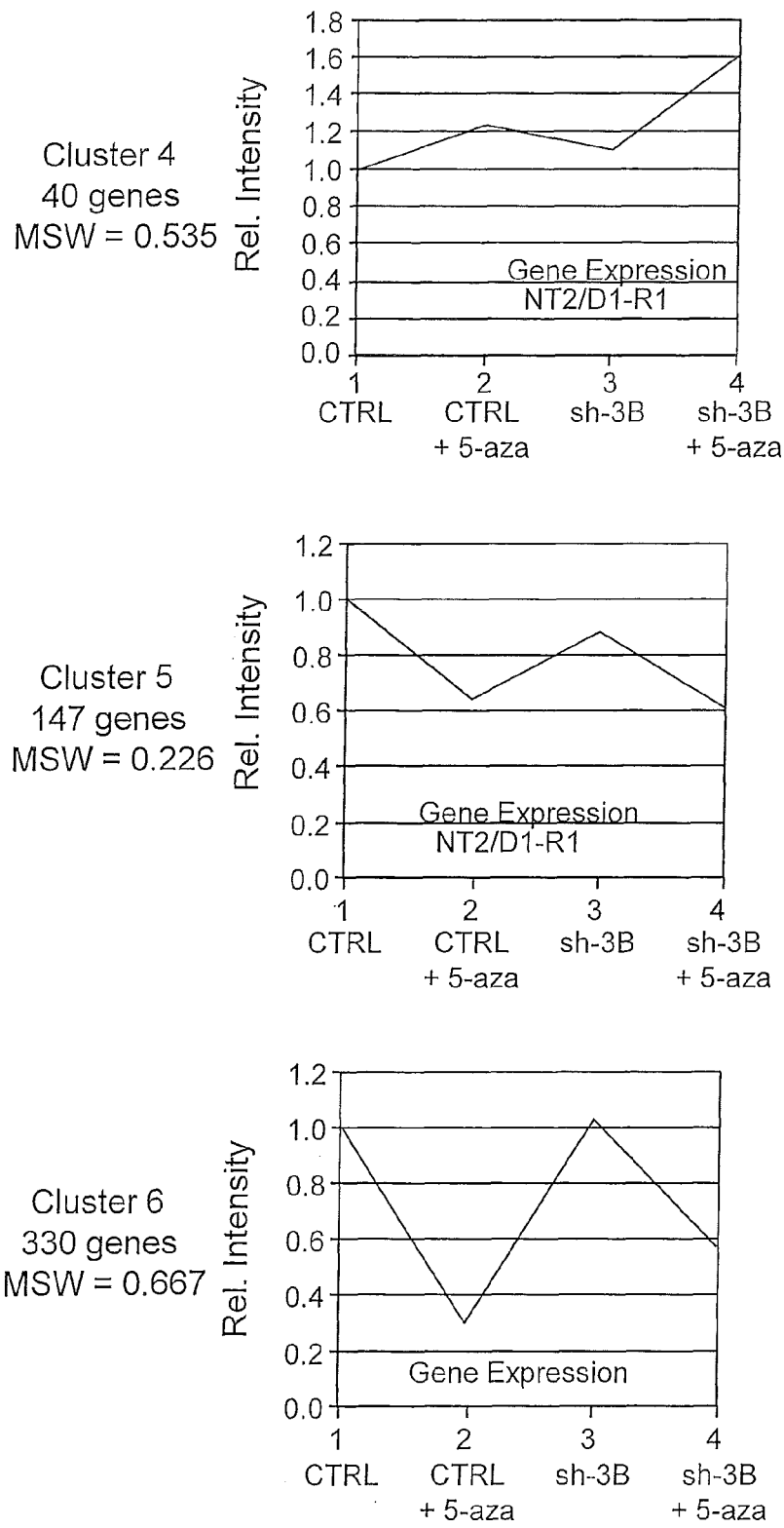

FIG. 12 depicts results of PAM analysis of decitabine-regulated genes in control versus DNMT3B knockdown (sh-3B) cells.

Figure 13:
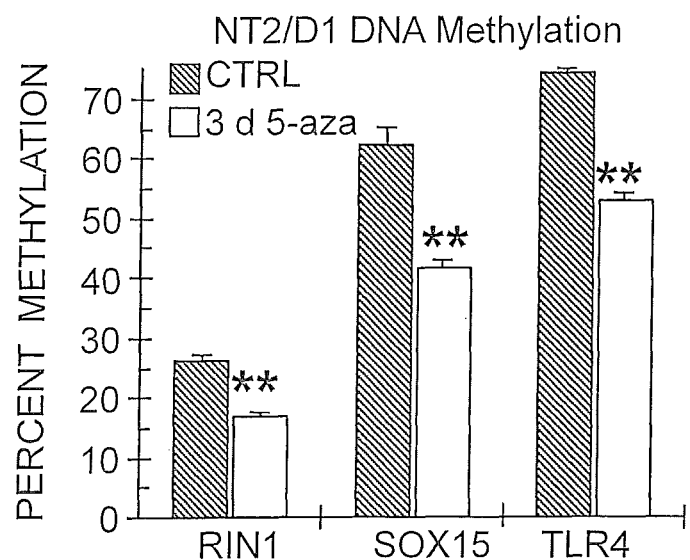

FIG. 13 depicts results of experiments performed to confirm the effect of decitabine in EC cells on promoter DNA methylation. Shown is the decrease observed in DNA methylation of the RIN1, SOX15 and TLR4 promoter with 3 days of low dose (10 nM) decitabine treatment of NT2/D1 cells as determined by bisulfite pyrosequencing. The graph depicts an average of triplicate sample determinations. Error bars are standard deviation. **=p<0.005. SOX15 values represent the average methylation value across two CpG sites. RIN1 and TRL4 values represent the average methylation across three CpG sites.

Figure 14:
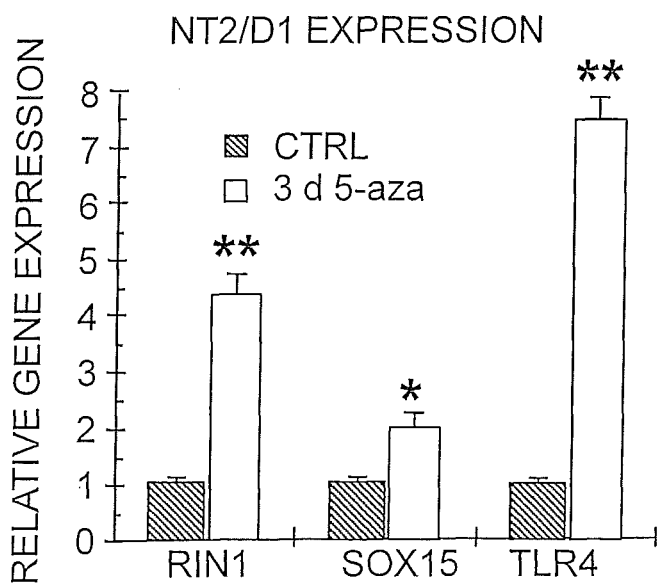

FIG. 14 depicts results of experiments performed to confirm the effect of decitabine in EC cells on promoter DNA methylation. Shown is the increase in gene expression of RIN1, SOX15 and TLR4 with 3 days of low dose (10 nM) decitabine treatment of NT2/D1 cells as determined by real-time PCR. The graph depicts an average of triplicate sample determinations. Error bars are standard deviation. *=p<0.05; **=p<0.005.

DETAILED DESCRIPTION OF THE INVENTION

Recent evidence suggests that pluripotent embryonal carcinoma (EC) cells share many characteristics with rare cancer stem cells of common somatic cancers of the brain, breast and pancreas. These rare cancer stem cells are the cells that need to be targeted for cure. It has now been found that one type of cancer stem cells, TGCT cells, are extremely responsive to the DNA methylation inhibitor decitabine (5-aza-deoxycytidine or 5-aza-CdR). Doses of decitabine that are at least an order of magnitude lower than doses used clinically to treat leukemia (e.g., doses in the low nanomolar range) have been found to be effective in inhibiting growth of TGCT cells. The hypersensitivity of TGCT cells was also found to be associated with high levels of expression of the pluripotency-associated DNA methyltransferase 3B (DNMT3B). Thus increased expression of DNMT3B is a biomarker of sensitivity to low dose decitabine in the cancer stem cells of testicular cancer (i.e. EC cells). Moreover, the same sensitivity is expected for cancer stem cells of other tumor types. In yet further experiments, it has been found that several other genes that are induced with decitabine treatment for TGCT include Ras and Rab interactor 1 (RIN1; Accession # NM-004292.2), Sex Determining Region Y-box 15 (SOX15; Accession # NM-006942.1) and toll-like receptor 4 (TLR-4; Accession # NM-138554.4). Thus, these three genes have been these genes are now identified as novel tumor suppressor genes in TGCT cells as biomarkers for decitabine-sensitive cancer cells.

In the context of the present invention, a "low dose" of decitabine is defined as a dose that is at least an order of magnitude lower than the doses that have been used for treatment of leukemia (10 to 20 mg/m$^2$/day; current labeling for the product in the *Physician's Desk Reference* and as discussed in Kantarjian et al. 2007. *Blood* 109:52-57). In the context of the present invention, an "effective amount" and a "therapeutically effective" dose of a chemotherapeutic drug, such as cisplatin, are defined as being doses that are used routinely by physicians in the treatment of cancer (i.e., for testicular cancer 20 mg/m$^2$/day×5 days is used; Kondagunta, G. V. et al. 2005. *J. Clin. Oncol.* 23:9290-9294). Other therapeutically effective doses of other chemotherapeutic drugs that are typically used in cancer can be found in sources such as the *Physician's Desk Reference*, a reference that lists commonly used doses of drugs approved for use by the U.S. Food and Drug Administration as part of the drug labeling included in the reference. Further, one of skill in the art would be familiar with choosing such dosing regimens based upon their own experience with patients. Cisplatin use in the present invention represents conventional cytotoxic therapy that produces its anti-cancer effects by generating DNA damage or other genotoxic stress within cancer cells. However, one of skill in the art would understand that the findings described in the present invention with cisplatin would likely apply to other cytotoxic drugs. For example, testicular cancer patients are treated with a cocktail of drugs that include cisplatin, etoposide, vinblastine and bleomycin. Patients that become resistant to cisplatin usually also become simultaneously resistant to these other cytotoxic drugs as well. Thus, cisplatin-resistant cancer stem cells explored in the experiments described with the present invention would also be resistant to the other commonly used cytotoxic drugs. Therefore, the ability of low dose decitibine to reverse cisplatin resistance extends to reversing resistance to other cytotoxic drugs and even the entire class of cytotoxic drugs, which includes but is not limited to cisplatin, etoposide, vinblastine and bleomycin.

Experiments were first performed to determine whether various EC cell lines were sensitive to DNA methylation inhibition using decitabine. Cell growth and viability of five EC cell lines (NT2/D1, NT2D1/R1, 833K, 833KCP, and Tera-1) were determined, including two cell lines that are cisplatin-resistant (NT2/D1-R1 and 833KCP). Three control somatic tumor cell lines were also tested (HCT116, MCF7 and U2OS). Doses of decitabine from 10 to 5000 nM were added fresh each day for three days to exponentially growing cells in culture. Viable cell growth and survival were measured using Cell-Titre Glo (Promega) assays. As shown in FIG. 1, growth of all EC cell lines was inhibited with decitabine treatment. The NT2/D1 and 833K cell lines were the most highly sensitive to decitabine treatment, with $IC_{50}$ values calculated to be in the range of 5 to 25 nM (FIG. 1). These doses are substantially lower that the doses routinely reported for growth inhibition of solid somatic tumors exposed to decitabine which are typically in the range of 500 nM to 10 μM (Qin et al. 2009. *Blood* 113:659-667; Shen et al. 2007. *Cancer Res.* 67:11335-11343). These higher values are similar to the values shown in FIG. 1 for somatic tumor cell lines (MCF7, U2OS and HCT116). U87 glioblastomoa cells were also unaffected by decitabine treatment at doses as high as 1 μM. The cell lines most sensitive to decitabine treatment were the cisplatin-resistant cell line, 833K-CP (also known as 833K64-CP10), and the cisplatin-resistant lines NT2/D1 and NT2/D1-R1.

Recent microarray studies have indicated that ES cells and EC cells, as well as clinical EC cells and non-seminomas, express high levels of mRNA for DNMT3B as compared to expression levels seen in normal and somatic tumors (Sperger et al. 2003. *Proc. Natl. Acad. Sci USA* 100:13350-13355; Muller et al. 2008. *Nature* 455:401-405; Skotheim et al. 2005. *Cancer Res.* 65:5588-5598). However, this differential expression has not been confirmed or shown at the protein level. Therefore, experiments were performed to determine the level of DNMT3B protein expression in the various EC cell lines as compared to the somatic tumor cell lines previously tested. Western blot analysis was used to determine expression levels of DNMT3B in the EC cell lines (NT2/D1, NT2/D1-R1, 833K, 833KCP, Tera-1, and 2102EP) as well as in the somatic cell lines HCT116, U2OS and MCF7, and the lung cancer cell lines HOP62, H197, U1752, A549 and H157. The DNMT3B antibodies ab2851 and H-230 were used in the analyses. A striking difference in DNMT3B protein expression was found in the EC cell lines NT2/D1, NT2/D1-R1, 833K, 833K-CP, Tera-1 and 2102EP as compared to the somatic tumor cell lines HCT116, U2OS, MCF7 and the six lung cancer cell lines tested. Importantly, the high expression of DNMT3B in EC cells could be repressed with a shRNA specific for DNMT3B and could be detected with two distinct DNMT3B antibodies. Densitometry measurements revealed at least a 30-fold increase in DNMT3B expression in the EC cells as compared to somatic tumor cells. Thus, the hypersensitivity of TGCTs to low dose decitabine was shown to be associated with high expression of DNMT3B in EC cells. These data indicated that expression of high levels of DNMT3B in tumor cells is a biomarker for cells that are especially sensitive to decitabine growth inhibition In order to confirm the connection between decitabine growth inhibition sensitivity and high levels of DNMT3B expression in EC cells, experiments were performed where DNMT3B expression was knocked down. Five distinct lentiviral shRNAs for DNMT3B (sh84, sh85, sh86, sh87, and sh88) were used to knock down DNMT3B expression. Six potential alternatively spliced isoforms of DNMT3B exist; the most biologically relevant isoforms are variants 1, 2, 3 and 6 (Jones, P. A. and S. B. Baylin. 2007. *Cell* 128:683-692). Quantitative RT-PCR assays employing isoform-specific primers revealed that the shRNAs (relative to controls) reduced expression of the DNMT3B isoforms. Western blot analysis of NT2/D1 and NT2/D1-R1 cells was also performed with cells treated with DNMT3B shRNA (sh84, sh85, sh86, sh88, sh84, sh87, sh88) and employing DNMT3B antibody, H-230. The results confirmed the reduced expression of DNMT3B when the shRNA were employed. None of the DNMT3B-specific shRNAs affected levels of DNMT1 or DNMT3A (FIG. 2). DNMT3B targeting shRNAs also reduced DNMT3B protein in both NT2/D1 and NT2/D1-R1 cells. Since NT2/D1 cells stably expressing sh84 and NT2/D1-R1 cells stably expressing sh84, sh85 and sh86 had the most efficient knock down of DNMT3B expression (FIG. 2), these cells were tested for decitabine sensitivity. It was found that cells expressing DNMT3B-targeting shRNAs exhibited dramatic reduction of decitabine sensitivity as compared to control cells (FIG. 3). However, knockdown of DNMT3B by itself had no apparent effect on the growth of NT2/D1 or NT2/D1-R1 cells. These results strongly support a functional link between sensitivity of EC cells to decitabine and high DNMT3B expression in these same cells. These data also indicated that expression of high levels of DNMT3B in tumor cells is a biomarker for cells that are especially sensitive to decitabine growth inhibition. With the link between decitabine sensitivity and DNMT3B expression established, experiments were then performed to examine the effects of decitabine in restoring cisplatin sensitivity to cisplatin-resistant tumor cells using decitabine. It had been previously reported that cisplatin causes a global p53-dominant transcriptional response in EC cells (Kerley-Hamilton et al. 2005. *Oncogene* 24:6090-6100). Through microarray and other studies it was found that the p53 response is repressed in NT2/D1-R1 cells despite having abundant wild-type p53 expression (Curtin et al. 2001. *Oncogene* 20:2559-2569; Kerley-Hamilton et al. *Biochim. Biophys. Acta* 2007. 1769:209-219; Kerley-Hamilton et al. 2005. *Oncogene* 24:6090-6100). With these new experiments, it was shown that pre-treatment of NT2/D1-R1 cells with low dose (10 nM) decitabine for 3 days at least partially restored cisplatin (treatment for 6 hours) induction of the p53 target genes GDF15, BTG2 and FDXR in NT2/D1-R1 cells (FIG. 4). This dose of decitabine had been shown to inhibit proliferation of NT2/D1-R1 cells by only 10% versus control (FIG. 1). Viable cells were counted and replated after decitabine treatment and allowed to recover for 24 hours before cisplatin treatment. Results showed that pretreatment with low dose decitabine restored cisplatin-induced growth suppression and toxicity to two separate cisplatin-resistant cell lines, NT2/D1-R1 and 833K-CP (FIGS. 5 and 6). 833K-CP cells were pretreated with 2.5 nM 5-aza-CdR, a dose that results in a 10% growth inhibition (FIG. 1). These data demonstrated that decitabine treatment of cisplatin-resistant tumor cells restores cisplatin sensitivity as measured by a cytotoxic response in cisplatin-resistant EC cells. Therefore, contacting cisplatin-resistant EC cells with low doses of decitabine before cisplatin is a method of inhibiting tumor cell growth in the drug-resistant cells.

It has also been found that three day low-dose decitabine treatment (10 nM) results in apoptotic responses in NT2/D1 and NT2/D1-R1 cells as determined by poly(ADP-ribose) polymerase (PARP) cleavage and induction of cells with sub G1 DNA content (with prominent G2 arrest) while cisplatin treatment (0.5 μM) induces these responses only in cisplatin-sensitive NT2/D1 cells. Notably, NT2/D1-R1 cells are co-resistant to a variety of conventional DNA damaging chemotherapeutics, suggesting that the decitabine response in NT2/D1 and NT2/D1-R1 cells is mechanistically distinct from the classical DNA damage response. Low dose decitabine also resulted in a significant reduction in global DNA methylation in NT2/D1 cells as assessed by repetitive long interspersed nuclear element-1 (LINE-1) element bisulfite pyrosequencing. All of these data confirm the unique sensitivity of TGCTs to decitabine and the link of the drug to decreases in global DNA methylation.

With data demonstrating that DNMT3B was a tumor marker in established in vitro tumor cell lines, the overexpression of DNMT3B in tumor cell lines was then confirmed in clinical samples (FIG. 7). Using quantitative RT-PCR methods, mRNA levels of DNMT3A, DNMT3B and DNMT1 were quantified in a mature teratoma sample (ED) and three different testicular germ cell tumors (denoted CHTN1 through CHTN-3, wherein CHTN is the Connective Human Tissue Network). As can be seen in FIG. 7, DNMT3B expression was increased in the testicular germ cell tumor clinical samples, indicating that this protein is a marker for tumors in vivo as well as in vitro.

Therefore, these experiments have shown that TGCT cells are hypersensitive to the DNA methylation inhibitor decitabine. Further, it has been shown that this response was integrally associated with very high levels of DNMT3B protein, validating this protein as an important target of decitabine-mediated hypersensitivity in cisplatin-sensitive as well as cisplatin-resistant TGCT cells. These data indicate that TGCT cells may be distinctly sensitive to DNA methylation inhibitors due to high levels of DNMT3B that are likely a result of the primary germ cell origins of EC cells and their similarities to ES cells, which also are known to express high levels of DNMT3B (Sperger et al. 2003. *Proc. Natl. Acad. Sci. USA* 100:13350-13355; Muller et al. 2008. *Nature* 455:401-405). This finding is consistent with the fact that genomic studies have highlighted DNMT3B as a marker of pluripotency (Sperger et al. 2003. *Proc. Natl. Acad. Sci. USA* 100:13350-13355; Muller et al. 2008. *Nature* 455:401-405).

Further experiments were also performed to examine the effects of low dose decitabine treatment on gene expression profiles in EC cells. A series of microarray-based gene expression analyses were conducted that compared gene expression changes in NT2/D1 cells treated with 10 nM decitabine for 1 or 3 days to NT2/D1 cells treated with 0.5 μM cisplatin for 6 hours followed by a 24 hour recovery. The cisplatin treatment protocol has been previously described (Kerley-Hamilton et al. 2005. *Oncogene* 24:6090-6100). In the context of the present invention the 10 nM decitabine treatment for either 1 or 3 days is defined as a "low dose" decitabine treatment protocol. While effects on cell viability and proliferation were minimal after 1 day of cisplatin treatment, robust anti-proliferation and cell death effects were observed by day two of treatment. Three days of decitabine treatment was chosen for further experiments because demethylation is expected to require several cell doublings for incorporation of the decitabine analog into DNA (NT2/D1 cells double every 24 hours). Treatment with 10 nM decitabine for only one day was included to assess the time-course of decitabine effects.

Array data indicated there was a robust reprogramming of gene expression after three days treatment with decitabine, with a bias toward up-regulation of gene expression. The same effect was not observed in cells treated with cisplatin; gene expression levels were not dramatically altered in cisplatin-treated cells. Compared to the number of genes altered with the three day decitabine treatment protocol, gene expression levels rarely increased by more than 1.5-fold or more when only one day treatment of decitabine was employed as well. Hierarchical cluster analysis was performed on the 898 genes whose expression levels changed by more that 1.5-fold between the 4 treatment groups (control, cisplatin, 1-day decitabine, 3-day decitabine). The genes clustered into distinct patterns. A subset of genes was shown to be regulated in a similar manner by decitabine and cisplatin treatment. However, there were large and prominent clusters of genes that were up-regulated or down-regulated with only decitabine treatment, and to a much lesser extent with only cisplatin treatment. This pattern indicated that decitabine and cisplatin shared common mechanisms of action, but that decitabine was acting through additional mechanisms not shared with cisplatin. Interestingly, while the number of genes with robust 1.5-fold changes after 1 day treatment with decitabine was small (35 genes), many of the genes whose expression levels had changed after 3 days of decitabine treatment were also similarly regulated after only 1 day of decitabine exposure, albeit resulting in a lower response level. Approximately 50% of the genes whose expression levels were either up-regulated or down-regulated by the one day decitabine treatment to a level of 1.3-fold or more were also up-regulated or down-regulated by more than 1.5-fold after 3 days of decitabine exposure (FIG. 8).

Next, partitioning around medoids (PAM) analysis was performed on the 1130 genes whose expression levels changed by 1.5-fold or greater as compared to control treatment. Five different gene clusters were identified as listed in (Tables 1-4) and shown in FIG. 9. The largest cluster (Cluster 1; Table 1) was comprised of 704 genes that were primarily up-regulated only with 3 days of decitabine treatment. This large group of genes was therefore identified as containing genes that potentially mediate the unique hypersensitivity of decitabine in EC cells. Cluster 2 (Table 2), which contained 81 unique genes, included genes whose expression levels were increased only by cisplatin treatment; this cluster included many p53 targets including PLK2 and PPM1D, indicating that decitabine induced expression of only a subset of the p53 target genes that are induced by the DNA damaging agent cisplatin. By contrast the 71 genes of Cluster 3 (Table 3), whose expression was upregulated by both decitabine treatment and cisplatin treatment, were prominently enriched in p53 target genes including IER3, p21 and GADD45A. Of the 44 genes whose expression level was up-regulated 1.5-fold or more by both cisplatin and 3 days of decitabine exposure, had been previously identified as cisplatin-inducible p53-target genes (Kerley-Hamilton et al. 2005. *Oncogene* 24:6090-6100). Cluster 4 (Table 4), which included 186 genes, was enriched in pluripotency genes including Myc, NANOG and GDF3, indicating that decitabine treatment acutely down-regulated master regulators of pluripotency in NT2/D1 cells. The set of 88 genes represented by Cluster 5 (Table 5) included genes whose expression levels were down-regulated by both decitabine treatment and cisplatin treatment. Changes in gene expression levels of representative genes for each cluster were confirmed in independent samples by real-time PCR (FIG. 10).

TABLE 1

| Gene Title | Gene ID |
| --- | --- |
| CDC42 effector protein (Rho GTPase binding) 5 | CDC42EP5 |
| Silver homolog (mouse) | SILV |
| Complement component 5 | C5 |
| LEM domain containing 2 | LEMD2 |

TABLE 1-continued

| Gene Title | Gene ID |
| --- | --- |
| Nuclear factor of kappa light polypeptide gene enhancer in B-cells 1 | NFKB1 |
| ADP-ribosylation-like factor 6 interacting protein 5 | ARL6IP5 |
| Methylthioribose-1-phosphate isomerase homolog (*S. cerevisiae*) | MRI1 |
| Vacuolar protein sorting 37 homolog D (*S. cerevisiae*) | VPS37D |
| Synaptotagmin XIII | SYT13 |
| Von Willebrand factor A domain containing 5A | VWA5A |
| Haloacid dehalogenase-like hydrolase domain containing 3 | HDHD3 |
| Ras homolog gene family, member Q | RHOQ |
| Alanyl-tRNA synthetase | AARS |
| F-box and leucine-rich repeat protein 20 | FBXL20 |
| Histidine triad nucleotide binding protein 2 | HINT2 |
| Coiled-coil domain containing 136 | CCDC136 |
| Dicarbonyl/L-xylulose reductase | DCXR |
| Spermatogenesis associated 20 | SPATA20 |
| Protein phosphatase 3 (formerly 2B), catalytic subunit, gamma isoform | PPP3CC |
| PREDICTED: misc_RNA (LOC728537), miscRNA. | — |
| Calcium/calmodulin-dependent protein kinase II inhibitor 1 | CAMK2N1 |
| SMAD family member 6 | SMAD6 |
| Mannosidase, beta A, lysosomal | MANBA |
| N-myc downstream regulated 1 | NDRG1 |
| S100 calcium binding protein A10 | S100A10 |
| hypothetical LOC400043 | — |
| Single-strand-selective monofunctional uracil-DNA glycosylase 1 | SMUG1 |
| Otoferlin | OTOF |
| Polymerase (RNA) III (DNA directed) polypeptide G (32 kD)-like | POLR3GL |
| RAS-like, family 12 | RASL12 |
| PREDICTED: similar to solute carrier family 29 (nucleoside transporters), member 4 (LOC | |
| Peroxisome proliferator-activated receptor gamma | PPARG |
| Guanine nucleotide binding protein (G protein), gamma 7 | GNG7 |
| Cytochrome b-561 domain containing 1 | CYB561D1 |
| Kelch-like 12 (*Drosophila*) | KLHL12 |
| Peroxisomal proliferator-activated receptor A interacting complex 285 | PRIC285 |
| AHNAK nucleoprotein | AHNAK |
| Host cell factor C1 regulator 1 (XPO1 dependent) | HCFC1R1 |
| Pleckstrin homology domain containing, family A (phosphoinositide binding specific) mem | PLEKHA2 |
| Transcribed locus, strongly similar to XP_001151823.1 PREDICTED: hypothetical protein heterogeneous nuclear ribonucleoprotein D-like (HNRPDL), transcript variant 3, transcribe | |
| RCC1 domain containing 1 | RCCD1 |
| Protein C receptor, endothelial (EPCR) | PROCR |
| Chromosome 5 open reading frame 32 | C5orf32 |
| Signal transducer and activator of transcription 2, 113 kDa | STAT2 |
| Heat shock protein family B (small), member 11 | HSPB11 |
| Nucleotide-binding oligomerization domain containing 1 | NOD1 |
| Family with sequence similarity 167, member A | FAM167A |
| Tubulin, gamma 1 | TUBG1 |
| RNA pseudouridylate synthase domain containing 3 | RPUSD3 |
| Brevican | BCAN |
| Bestrophin 1 | BEST1 |
| Inhibin, beta E | INHBE |
| Chromosome 13 open reading frame 15 | C13orf15 |
| Regulator of G-protein signaling 10 | RGS10 |
| 6-phosphofructo-2-kinase/fructose-2,6-biphosphatase 4 | PFKFB4 |
| Cullin-associated and neddylation-dissociated 2 (putative) | CAND2 |
| Nucleoporin 62 kDa C-terminal like | NUP62CL |
| Leukotriene A4 hydrolase | LTA4H |
| Laminin, alpha 5 | LAMA5 |
| Cellular retinoic acid binding protein 1 | CRABP1 |
| Muscleblind-like 3 (*Drosophila*) | MBNL3 |

TABLE 1-continued

| Gene Title | Gene ID |
|---|---|
| Chloride channel Ka | CLCNKA |
| Xylosyltransferase II | XYLT2 |
| Ubiquitin-conjugating enzyme E2L 6 | UBE2L6 |
| WD repeat domain 54 | WDR54 |
| Acyl-Coenzyme A dehydrogenase family, member 11 | ACAD11 |
| G protein-coupled receptor 56 | GPR56 |
| PREDICTED: hypothetical protein LOC652097 (LOC652097), mRNA. | — |
| Tumor necrosis factor, alpha-induced protein 8-like 1 | TNFAIP8L1 |
| Transmembrane protein 91 | TMEM91 |
| Solute carrier family 22, member 18 | SLC22A18 |
| Tubulin, gamma 2 | TUBG2 |
| Peripherin | PRPH |
| Sirtuin (silent mating type information regulation 2 homolog) 4 (S. cerevisiae) | SIRT4 |
| E74-like factor 3 (ets domain transcription factor, epithelial-specific) | ELF3 |
| Zinc finger protein 467 | ZNF467 |
| EH domain binding protein 1-like 1 | EHBP1L1 |
| Scavenger receptor class A, member 5 (putative) | SCARA5 |
| Protein tyrosine phosphatase domain containing 1 | PTPDC1 |
| GATS protein-like 3 | GATSL3 |
| Ladinin 1 | LAD1 |
| PREDICTED: dual specificity phosphatase 22 (DUSP22), mRNA. | — |
| Interferon, alpha-inducible protein 6 | IFI6 |
| Ataxin 3 | ATXN3 |
| PREDICTED: misc_RNA (LOC100130291), miscRNA. | — |
| Protein kinase C, delta | PRKCD |
| Lymphocyte-activation gene 3 | LAG3 |
| AXL receptor tyrosine kinase | AXL |
| Tripartite motif-containing 68 | TRIM68 |
| Acyl-Coenzyme A oxidase 2, branched chain | ACOX2 |
| Leucine rich repeat containing 26 | LRRC26 |
| Nudix (nucleoside diphosphate linked moiety X)-type motif 14 | NUDT14 |
| S100 calcium binding protein A10 | S100A10 |
| Phytanoyl-CoA 2-hydroxylase | PHYH |
| KIAA1949 | KIAA1949 |
| Tetraspanin 7 | TSPAN7 |
| Interferon regulatory factor 1 | IRF1 |
| Galactosidase, beta 1 | GLB1 |
| Peripheral myelin protein 22 | PMP22 |
| Interferon, alpha-inducible protein 27-like 2 | IFI27L2 |
| Heat shock 70 kDa protein 12A | HSPA12A |
| zinc finger protein 702 (pseudogene) (ZNF702P), non-coding RNA. | — |
| Chromosome 11 open reading frame 75 | C11orf75 |
| TIMP metallopeptidase inhibitor 1 | TIMP1 |
| ISG15 ubiquitin-like modifier | ISG15 |
| Troponin C type 2 (fast) | TNNC2 |
| KN motif and ankyrin repeat domains 4 | KANK4 |
| Forkhead box I2 | FOXI2 |
| Transmembrane protein 54 | TMEM54 |
| Nuclear receptor subfamily 1, group H, member 3 | NR1H3 |
| Zinc finger, DHHC-type containing 19 | ZDHHC19 |
| olfactory receptor, family 2, subfamily A, member 9 pseudogene | — |
| Sorbin and SH3 domain containing 3 | SORBS3 |
| RAB11 family interacting protein 1 (class I) | RAB11FIP1 |
| RAS-like, family 10, member A | RASL10A |
| Interferon stimulated exonuclease gene 20 kDa | ISG20 |
| BCL2-associated athanogene 3 | BAG3 |
| KDEL (Lys-Asp-Glu-Leu) endoplasmic reticulum protein retention receptor 3 | KDELR3 |
| BAI1-associated protein 2-like 1 | BAIAP2L1 |
| NEDD4 binding protein 2-like 1 | N4BP2L1 |
| Troponin C type 1 (slow) | TNNC1 |
| Adenosine A2b receptor | ADORA2B |
| Acyl-CoA synthetase family member 2 | ACSF2 |
| Solute carrier family 29 (nucleoside transporters), member 4 | SLC29A4 |
| Coenzyme Q10 homolog A (S. cerevisiae) | COQ10A |
| Protein phosphatase 1, regulatory (inhibitor) subunit 15A | PPP1R15A |
| Sterile alpha motif domain containing 14 | SAMD14 |
| Rab interacting lysosomal protein-like 1 | RILPL1 |
| Keratin associated protein 21-1 | KRTAP21-1 |
| Iroquois homeobox 3 | IRX3 |
| Mannose-6-phosphate receptor binding protein 1 | M6PRBP1 |
| Family with sequence similarity 107, member A | FAM107A |
| tachykinin 3 | — |
| Jun oncogene | JUN |
| MAX interactor 1 | MXI1 |
| Stathmin-like 4 | STMN4 |
| Ras-related GTP binding D | RRAGD |
| Tumor necrosis factor receptor superfamily, member 1B | TNFRSF1B |
| Integrin beta 1 binding protein 3 | ITGB1BP3 |
| Cytochrome P450, family 26, subfamily B, polypeptide 1 | CYP26B1 |
| MAP kinase interacting serine/threonine kinase 2 | MKNK2 |
| Myosin, heavy chain 11, smooth muscle | MYH11 |
| Pleckstrin homology domain containing, family H (with MyTH4 domain) member 3 | PLEKHH3 |
| Rac/Cdc42 guanine nucleotide exchange factor (GEF) 6 | ARHGEF6 |
| Solute carrier family 24 (sodium/potassium/calcium exchanger), member 6 | SLC24A6 |
| Polycystic kidney disease 1-like 2 | PKD1L2 |
| Von Willebrand factor | VWF |
| Lectin, galactoside-binding, soluble, 1 | LGALS1 |
| MIF4G domain containing | MIF4GD |
| B-cell CLL/lymphoma 6, member B (zinc finger protein) | BCL6B |
| Numb homolog (Drosophila) | NUMB |
| Fanconi anemia, complementation group E | FANCE |
| ATPase, Ca++ transporting, plasma membrane 4 | ATP2B4 |
| Synaptosomal-associated protein, 91 kDa homolog (mouse) | SNAP91 |
| Thioredoxin interacting protein | TXNIP |
| Optineurin | OPTN |
| S100 calcium binding protein A13 | S100A13 |
| Calcium channel, voltage-dependent, gamma subunit 6 | CACNG6 |
| Biliverdin reductase B (flavin reductase (NADPH)) | BLVRB |
| Mixed lineage kinase domain-like | MLKL |
| Phospholipase A2, group IIA (platelets, synovial fluid) | PLA2G2A |
| SEC22 vesicle trafficking protein homolog A (S. cerevisiae) | SEC22A |
| Splicing factor, arginine/serine-rich 14 | SFRS14 |
| Deoxyribonuclease II, lysosomal | DNASE2 |
| Dickkopf homolog 3 (Xenopus laevis) | DKK3 |
| Integrin beta 1 binding protein 3 | ITGB1BP3 |
| PREDICTED: acetylserotonin O-methyltransferase-like (ASMTL), mRNA. | — |
| C-mer proto-oncogene tyrosine kinase | MERTK |
| Hairy and enhancer of split 4 (Drosophila) | HES4 |
| Calponin 1, basic, smooth muscle | CNN1 |
| Tumor protein D52-like 1 | TPD52L1 |
| Angiogenin, ribonuclease, RNase A family, 5 | ANG |
| LIM homeobox 2 | LHX2 |
| Septin 4 | 4-Sep |
| Rho family GTPase 2 | RND2 |
| ATPase, Na+/K+ transporting, alpha 2 (+) polypeptide | ATP1A2 |
| Chromosome 7 open reading frame 44 | C7orf44 |
| CAP-GLY domain containing linker protein 3 | CLIP3 |
| Protein S (alpha) | PROS1 |
| V-ral simian leukemia viral oncogene homolog B (ras related; GTP binding protein) | RALB |
| LFNG O-fucosylpeptide 3-beta-N-acetylglucosaminyltransferase | LFNG |
| Translocator protein (18 kDa) | TSPO |
| Peptidase domain containing associated with muscle regeneration 1 | PAMR1 |
| Thrombospondin 4 | THBS4 |
| GATA binding protein 5 | GATA5 |
| Mitogen-activated protein kinase kinase kinase 8 | MAP3K8 |
| RAD52 motif 1 | RDM1 |
| Nuclear factor (erythroid-derived 2), 45 kDa | NFE2 |
| Serine peptidase inhibitor, Kunitz type, 2 | SPINT2 |
| endogenous retroviral sequence K, 6 | — |

TABLE 1-continued

| Gene Title | Gene ID |
|---|---|
| Collagen, type XIII, alpha 1 | COL13A1 |
| PDZ and LIM domain 3 | PDLIM3 |
| Histidine rich calcium binding protein | HRC |
| S100 calcium binding protein A13 | S100A13 |
| Chromosome 12 open reading frame 76 | C12orf76 |
| Harakiri, BCL2 interacting protein (contains only BH3 domain) | HRK |
| Arginine decarboxylase | ADC |
| Chromosome 7 open reading frame 41 | C7orf41 |
| Regulating synaptic membrane exocytosis 3 | RIMS3 |
| AarF domain containing kinase 2 | ADCK2 |
| Scavenger receptor class B, member 2 | SCARB2 |
| Echinoderm microtubule associated protein like 3 | EML3 |
| Interleukin 11 receptor, alpha | IL11RA |
| Rap guanine nucleotide exchange factor (GEF)-like 1 | RAPGEFL1 |
| Calcium channel, voltage-dependent, beta 3 subunit | CACNB3 |
| Multiple PDZ domain protein | MPDZ |
| RASD family, member 2 | RASD2 |
| PREDICTED: KIAA0363 protein (KIAA0363), mRNA. | — |
| Filamin A interacting protein 1 | FILIP1 |
| Transmembrane channel-like 6 | TMC6 |
| PTEN induced putative kinase 1 | PINK1 |
| StAR-related lipid transfer (START) domain containing 8 | STARD8 |
| Carcinoembryonic antigen-related cell adhesion molecule 1 (biliary glycoprotein) | CEACAM1 |
| Regulator of G-protein signaling 20 | RGS20 |
| Sushi-repeat-containing protein, X-linked | SRPX |
| Trafficking protein particle complex 6A | TRAPPC6A |
| Chromosome 5 open reading frame 41 | C5orf41 |
| hypothetical LOC728855 (LOC728855), non-coding RNA. | — |
| Prostaglandin reductase 1 | PTGR1 |
| G protein-coupled receptor 56 | GPR56 |
| Chloride channel Ka | CLCNKA |
| Hypothetical protein LOC147646 | LOC147646 |
| Ral guanine nucleotide dissociation stimulator | RALGDS |
| Enolase 3 (beta, muscle) | ENO3 |
| Ribosomal protein S29 | RPS29 |
| Contactin associated protein 1 | CNTNAP1 |
| Spermidine/spermine N1-acetyltransferase 1 | SAT1 |
| ATPase, H+ transporting, lysosomal 31 kDa, V1 subunit E2 | ATP6V1E2 |
| Chromosome 22 open reading frame 9 | C22orf9 |
| Potassium inwardly-rectifying channel, subfamily J, member 4 | KCNJ4 |
| RAB13, member RAS oncogene family | RAB13 |
| Polycystic kidney disease 1-like 2 | PKD1L2 |
| Myosin, light chain 6B, alkali, smooth muscle and non-muscle | MYL6B |
| DnaJ (Hsp40) homolog, subfamily B, member 2 | DNAJB2 |
| Peroxiredoxin 5 | PRDX5 |
| Chloride intracellular channel 6 | CLIC6 |
| Mitogen-activated protein kinase kinase kinase 6 | MAP3K6 |
| TSC22 domain family, member 3 | TSC22D3 |
| Peptide YY | PYY |
| DNA-damage-inducible transcript 3 | DDIT3 |
| TOX high mobility group box family member 2 | TOX2 |
| Ankyrin repeat domain 24 | ANKRD24 |
| Ankyrin repeat and BTB (POZ) domain containing 1 | ABTB1 |
| Polymerase I and transcript release factor | PTRF |
| E74-like factor 4 (ets domain transcription factor) | ELF4 |
| Cyclin B1 interacting protein 1 | CCNB1IP1 |
| Related RAS viral (r-ras) oncogene homolog | RRAS |
| Zinc finger protein 792 | ZNF792 |
| Tudor domain containing 7 | TDRD7 |
| Syntaxin 3 | STX3 |
| Interferon induced transmembrane protein 1 (9-27) | IFITM1 |
| NEDD4 binding protein 2-like 1 | N4BP2L1 |
| Tctex1 domain containing 1 | TCTEX1D1 |
| EGF-containing fibulin-like extracellular matrix protein 2 | EFEMP2 |
| S100 calcium binding protein A4 | S100A4 |
| Angiopoietin-like 4 | ANGPTL4 |
| S100 calcium binding protein A4 | S100A4 |
| Interferon induced transmembrane protein 2 (1-8D) | IFITM2 |
| PREDICTED: chromosome 12 open reading frame 47 (C12orf47), misc RNA. | — |
| Apelin receptor | APLNR |
| Protor-2 | FLJ14213 |
| RAS guanyl releasing protein 2 (calcium and DAG-regulated) | — |
| Cytochrome P450, family 4, subfamily F, polypeptide 22 | CYP4F22 |
| Activating transcription factor 5 | ATF5 |
| Tetratricopeptide repeat domain 23 | TTC23 |
| Carbonic anhydrase XII | CA12 |
| Tight junction protein 3 (zona occludens 3) | TJP3 |
| Transcription elongation factor A (SII), 2 | TCEA2 |
| Collagen, type XI, alpha 1 | COL11A1 |
| Integrin, alpha 5 (fibronectin receptor, alpha polypeptide) | ITGA5 |
| Small G protein signaling modulator 1 | SGSM1 |
| Src homology 2 domain containing E | SHE |
| Naked cuticle homolog 2 (Drosophila) | NKD2 |
| Chromosome 1 open reading frame 54 | C1orf54 |
| inositol polyphosphate-5-phosphatase J | — |
| KDEL (Lys-Asp-Glu-Leu) endoplasmic reticulum protein retention receptor 3 | KDELR3 |
| Calpain 11 | CAPN11 |
| RAB7, member RAS oncogene family-like 1 | RAB7L1 |
| PREDICTED: misc_RNA (LOC100132535), miscRNA. | — |
| Interleukin 10 receptor, beta | IL10RB |
| Solute carrier family 27 (fatty acid transporter), member 1 | SLC27A1 |
| Kinesin-associated protein 3 | KIFAP3 |
| Adrenomedullin 2 | ADM2 |
| ATPase, Ca++ transporting, plasma membrane 4 | ATP2B4 |
| Gem (nuclear organelle) associated protein 8 | GEMIN8 |
| Solute carrier family 7, (neutral amino acid transporter, y+ system) member 10 | SLC7A10 |
| Carbonic anhydrase IV | CA4 |
| Actin filament associated protein 1-like 2 | AFAP1L2 |
| Slingshot homolog 3 (Drosophila) | SSH3 |
| Anterior pharynx defective 1 homolog B (C. elegans) | APH1B |
| Delta-like 3 (Drosophila) | DLL3 |
| Phosphatidylinositol glycan anchor biosynthesis, class X | PIGX |
| RAB3A interacting protein (rabin3)-like 1 | RAB3IL1 |
| Fc fragment of IgE, low affinity II, receptor for (CD23) | FCER2 |
| Iroquois homeobox 6 | IRX6 |
| OCIA domain containing 2 | OCIAD2 |
| Rho GTPase activating protein 9 | ARHGAP9 |
| Acetylserotonin O-methyltransferase-like | ASMTL |
| Zinc finger protein 823 | ZNF823 |
| SECIS binding protein 2 | SECISBP2 |
| Biglycan | BGN |
| Lysyl oxidase-like 4 | LOXL4 |
| Cyclin G1 | CCNG1 |
| Myotubularin related protein 11 | MTMR11 |
| ribonuclease, RNase A family, 4 | — |
| BTG family, member 3 | BTG3 |
| Down syndrome critical region gene 6 | DSCR6 |
| LIM domain only 2 (rhombotin-like 1) | LMO2 |
| HD domain containing 3 | HDDC3 |
| Coactosin-like 1 (Dictyostelium) | COTL1 |
| Active BCR-related gene | ABR |
| Asialoglycoprotein receptor 1 | ASGR1 |
| Uroplakin 1A | UPK1A |
| Stathmin-like 2 | STMN2 |
| MFNG O-fucosylpeptide 3-beta-N-acetylglucosaminyltransferase | MFNG |
| Spermatogenesis associated 17 | SPATA17 |
| Fibulin 2 | FBLN2 |
| Pregnancy up-regulated non-ubiquitously expressed CaM kinase | PNCK |
| Transgelin 3 | TAGLN3 |
| Nuclear factor of kappa light polypeptide gene enhancer in B-cells inhibitor, zeta | NFKBIZ |
| Family with sequence similarity 43, member B | FAM43B |

TABLE 1-continued

| Gene Title | Gene ID |
|---|---|
| Glutathione S-transferase omega 2 | GSTO2 |
| Cyclin O | CCNO |
| Hydroxysteroid (17-beta) dehydrogenase 14 | HSD17B14 |
| PREDICTED: similar to ZMYM6 protein (LOC100130633), mRNA. | — |
| DEAD (Asp-Glu-Ala-Asp) box polypeptide 50 | DDX50 |
| Pleckstrin homology domain containing, family B (evectins) member 1 | PLEKHB1 |
| Small trans-membrane and glycosylated protein | SMAGP |
| Src homology 2 domain containing transforming protein D | SHD |
| Nudix (nucleoside diphosphate linked moiety X)-type motif 18 | NUDT18 |
| Zinc finger protein 823 | ZNF823 |
| Collagen, type I, alpha 1 | COL1A1 |
| PREDICTED: similar to hCG1811002 (LOC100134361), mRNA. | — |
| Occludin/ELL domain containing 1 | OCEL1 |
| Sulfotransferase family, cytosolic, 2B, member 1 | SULT2B1 |
| Interleukin 32 | IL32 |
| Chondroitin sulfate proteoglycan 4 | CSPG4 |
| Phosphomannomutase 1 | PMM1 |
| Ring finger protein 39 | RNF39 |
| HLA complex P5 | HCP5 |
| Leucine-rich, glioma inactivated 1 | LGI1 |
| Claudin 23 | CLDN23 |
| Dual specificity phosphatase 3 | DUSP3 |
| Phosphoenolpyruvate carboxykinase 2 (mitochondrial) | PCK2 |
| MLX interacting protein-like | MLXIPL |
| Tetraspanin 7 | TSPAN7 |
| PREDICTED: similar to ribosomal protein L13a, transcript variant 4 (LOC283340), mRNA- | |
| Vasohibin 1 | VASH1 |
| SPOC domain containing 1 | SPOCD1 |
| Collagen, type XIII, alpha 1 | COL13A1 |
| Kruppel-like factor 6 | KLF6 |
| Chromosome 1 open reading frame 26 | C1orf26 |
| 5-hydroxytryptamine (serotonin) receptor 3A | HTR3A |
| Renin binding protein | RENBP |
| Chromosome 19 open reading frame 66 | C19orf66 |
| Opiate receptor-like 1 | OPRL1 |
| Secretogranin II (chromogranin C) | SCG2 |
| Delta-like 1 homolog (Drosophila) | DLK1 |
| SH2 domain containing 3C | SH2D3C |
| Kinesin family member 15 | KIF15 |
| Contactin associated protein-like 2 | CNTNAP2 |
| Aryl hydrocarbon receptor interacting protein-like 1 | AIPL1 |
| Interleukin 20 receptor beta | IL20RB |
| PREDICTED: hypothetical protein LOC100132774, transcript variant 2 (LOC100132774) | |
| Chromosome 5 open reading frame 41 | C5orf41 |
| Chemokine (C—X—C motif) ligand 14 | CXCL14 |
| Early growth response 1 | EGR1 |
| Family with sequence similarity 65, member A | FAM65A |
| Neuronal PAS domain protein 1 | NPAS1 |
| Enolase 2 (gamma, neuronal) | ENO2 |
| MOB1, Mps One Binder kinase activator-like 2C (yeast) | MOBKL2C |
| SCO-spondin homolog (Bos taurus) | SSPO |
| Radial spoke 3 homolog (Chlamydomonas) | RSPH3 |
| 5'-nucleotidase domain containing 3 | — |
| FERM domain containing 8 | FRMD8 |
| Synaptogyrin 1 | SYNGR1 |
| PREDICTED: radical fringe homolog (Drosophila) (RFNG), mRNA. | — |
| Dickkopf homolog 3 (Xenopus laevis) | DKK3 |
| Kruppel-like factor 9 | KLF9 |
| Tudor domain containing 5 | TDRD5 |
| Solute carrier family 25, member 42 | SLC25A42 |
| Coiled-coil domain containing 151 | CCDC151 |
| Niemann-Pick disease, type C2 | NPC2 |
| Chromosome 19 open reading frame 62 | C19orf62 |
| RAB7A, member RAS oncogene family | RAB7A |
| Leucine rich repeat containing 28 | LRRC28 |
| Pleckstrin homology domain containing, family G (with RhoGef domain) member 4 | PLEKHG4 |

TABLE 1-continued

| Gene Title | Gene ID |
|---|---|
| Myb-related transcription factor, partner of profilin | MYPOP |
| FXYD domain containing ion transport regulator 5 | FXYD5 |
| Heat shock 22 kDa protein 8 | HSPB8 |
| CD70 molecule | CD70 |
| ribosomal protein L23a pseudogene 53 (RPL23AP53), non-coding RNA. | — |
| Family with sequence similarity 120B | FAM120B |
| Immunoglobulin superfamily, DCC subclass, member 3 | IGDCC3 |
| PREDICTED: hypothetical protein LOC727820 (LOC727820), mRNA. | — |
| PREDICTED: chromosome 14 open reading frame 78 (C14orf78), mRNA. | — |
| RAB32, member RAS oncogene family | RAB32 |
| Protein phosphatase 1, regulatory (inhibitor) subunit 14A | PPP1R14A |
| Dual specificity phosphatase 5 | DUSP5 |
| Family with sequence similarity 131, member A | FAM131A |
| Phospholipase A2, group XVI | PLA2G16 |
| Ras-related C3 botulinum toxin substrate 2 (rho family, small GTP binding protein Rac2) | RAC2 |
| Roadblock domain containing 3 | ROBLD3 |
| Lactamase, beta | LACTB |
| PREDICTED: similar to hCG1983233 (LOC100134304), mRNA. | — |
| Solute carrier family 16, member 3 (monocarboxylic acid transporter 4) | SLC16A3 |
| Prostaglandin reductase 1 | PTGR1 |
| Plasminogen activator, urokinase | PLAU |
| Zinc finger and BTB domain containing 46 | ZBTB46 |
| SRY (sex determining region Y)-box 18 | SOX18 |
| PREDICTED: similar to creatine kinase, mitochondrial 1B precursor (LOC649970), mRNA | — |
| Activating transcription factor 3 | ATF3 |
| Differentially expressed in FDCP 8 homolog (mouse) | DEF8 |
| Zinc finger, CCHC domain containing 12 | ZCCHC12 |
| SET domain, bifurcated 2 | SETDB2 |
| Microtubule-associated protein 1 light chain 3 alpha | MAP1LC3A |
| Kallikrein-related peptidase 6 | KLK6 |
| Basic helix-loop-helix family, member e40 | BHLHE40 |
| Tyrosine kinase with immunoglobulin-like and EGF-like domains 1 | TIE1 |
| PREDICTED: misc_RNA (LOC392437), miscRNA. | — |
| B-cell CLL/lymphoma 6 | BCL6 |
| Eukaryotic elongation factor-2 kinase | EEF2K |
| Monoamine oxidase A | MAOA |
| Gem (nuclear organelle) associated protein 8 | GEMIN8 |
| PREDICTED: similar to hCG2040918 (LOC100131138), mRNA. | — |
| Chromosome 6 open reading frame 57 | C6orf57 |
| Family with sequence similarity 71, member F1 | FAM71F1 |
| Mitogen-activated protein kinase kinase kinase kinase 2 | MAP4K2 |
| Coagulation factor XII (Hageman factor) | F12 |
| RAB24, member RAS oncogene family | RAB24 |
| Solute carrier family 13 (sodium-dependent citrate transporter), member 5 | SLC13A5 |
| Secernin 1 | SCRN1 |
| NDRG family member 4 | NDRG4 |
| Clone 24583 mRNA sequence | — |
| Glucosamine-6-phosphate deaminase 1 | GNPDA1 |
| Fibronectin type III domain containing 5 | FNDC5 |
| Carboxymethylenebutenolidase homolog (Pseudomonas) | CMBL |
| Sulfatase modifying factor 2 | SUMF2 |
| Spermatogenesis associated 7 | SPATA7 |
| Prolyl 4-hydroxylase, alpha polypeptide II | P4HA2 |
| Hexosaminidase B (beta polypeptide) | HEXB |
| Stathmin-like 2 | STMN2 |
| DNA fragmentation factor, 45 kDa, alpha polypeptide | DFFA |
| Cysteine conjugate-beta lyase, cytoplasmic | CCBL1 |
| PREDICTED: arachidonate 5-lipoxygenase (ALOX5), mRNA. | — |
| Runt-related transcription factor 3 | RUNX3 |

TABLE 1-continued

| Gene Title | Gene ID |
|---|---|
| Beta-2-microglobulin | B2M |
| Glutathione S-transferase omega 1 | GSTO1 |
| Kelch-like 5 (Drosophila) | KLHL5 |
| Amyloid beta (A4) precursor protein-binding, family B, member 3 | APBB3 |
| Retinoic acid receptor responder (tazarotene induced) 3 | RARRES3 |
| Dual specificity phosphatase 10 | DUSP10 |
| La ribonucleoprotein domain family, member 6 | LARP6 |
| MHC class I polypeptide-related sequence A | MICA |
| Palladin, cytoskeletal associated protein | PALLD |
| Tetratricopeptide repeat domain 3 | TTC3 |
| Chromosome 4 open reading frame 31 | C4orf31 |
| Hect domain and RLD 5 | HERC5 |
| Prostaglandin-endoperoxide synthase 1 (prostaglandin G/H synthase and cyclooxygenase | PTGS1 |
| Adenosine deaminase | ADA |
| Enoyl Coenzyme A hydratase domain containing 2 | ECHDC2 |
| Chromodomain helicase DNA binding protein 3 | CHD3 |
| DEAH (Asp-Glu-Ala-His) box polypeptide 32 | DHX32 |
| Chromosome 5 open reading frame 4 | C5orf4 |
| Inositol 1,4,5-triphosphate receptor, type 3 | ITPR3 |
| SID1 transmembrane family, member 2 | SIDT2 |
| Chemokine (C-C motif) receptor 7 | CCR7 |
| Integrin, alpha X (complement component 3 receptor 4 subunit) | ITGAX |
| Sequestosome 1 | SQSTM1 |
| PREDICTED: lemur tyrosine kinase 3 (LMTK3), mRNA. | — |
| Mitogen-activated protein kinase kinase kinase kinase 1 | MAP4K1 |
| Transcribed locus | — |
| Microtubule-associated protein 1 light chain 3 gamma | MAP1LC3C |
| PQ loop repeat containing 3 | PQLC3 |
| Family with sequence similarity 162, member B | FAM162B |
| Leucine rich repeat containing 42 | LRRC42 |
| Peptidylprolyl isomerase C (cyclophilin C) | PPIC |
| Transcribed locus, strongly similar to XP_001164657.1 PREDICTED: dual-specificity tyro- | |
| Papilin, proteoglycan-like sulfated glycoprotein | PAPLN |
| Forkhead box D2 | FOXD2 |
| NHL repeat containing 3 | NHLRC3 |
| Solute carrier family 35 (CMP-sialic acid transporter), member A1 | SLC35A1 |
| Myelin protein zero-like 2 | MPZL2 |
| Cytoplasmic polyadenylation element binding protein 1 | CPEB1 |
| PREDICTED: hypothetical protein LOC202781 (LOC202781), mRNA. | — |
| Chromosome 16 open reading frame 73 | C16orf73 |
| DEAD (Asp-Glu-Ala-Asp) box polypeptide 25 | DDX25 |
| Calcium modulating ligand | CAMLG |
| Lysophospholipase-like 1 | LYPLAL1 |
| Syndecan binding protein (syntenin) | SDCBP |
| Fucosidase, alpha-L-1, tissue | FUCA1 |
| Transcription elongation factor A (SII)-like 2 | TCEAL2 |
| Cellular retinoic acid binding protein 2 | CRABP2 |
| ADAM metallopeptidase domain 19 (meltrin beta) | ADAM19 |
| Chromosome 6 open reading frame 125 | C6orf125 |
| Indoleamine 2,3-dioxygenase 1 | IDO1 |
| Tetraspanin 31 | TSPAN31 |
| hypothetical LOC92659 (LOC92659), non-coding RNA. | — |
| Craniofacial development protein 1 | CFDP1 |
| Selenophosphate synthetase 2 | SEPHS2 |
| Mitochondrial translational initiation factor 3 | MTIF3 |
| Interleukin 28 receptor, alpha (interferon, lambda receptor) | IL28RA |
| COMM domain containing 3 | COMMD3 |
| Family with sequence similarity 161, member A | FAM161A |
| Potassium inwardly-rectifying channel, subfamily J, member 8 | KCNJ8 |
| Argininosuccinate synthetase 1 | ASS1 |
| Pituitary tumor-transforming 1 | PTTG1 |
| Chromatin modifying protein 2A | CHMP2A |
| NOL1/NOP2/Sun domain family, member 7 | NSUN7 |
| OMA1 homolog, zinc metallopeptidase (S. cerevisiae) | OMA1 |
| ATP-binding cassette, sub-family G (WHITE), member 1 | ABCG1 |
| De-etiolated homolog 1 (Arabidopsis) | DET1 |
| Hypothetical LOC29092 | HSPC157 |
| Immunoglobulin superfamily, member 3 | IGSF3 |
| Similar to hCG38149 | LOC728715 |
| Nedd4 family interacting protein 2 | NDFIP2 |
| FXYD domain containing ion transport regulator 6 | FXYD6 |
| RAB23, member RAS oncogene family | RAB23 |
| Zinc finger protein 337 | ZNF337 |
| Synaptotagmin VII | SYT7 |
| Amyotrophic lateral sclerosis 2 (juvenile) | ALS2 |
| Ephrin-A1 | EFNA1 |
| Kelch-like 36 (Drosophila) | KLHL36 |
| Zinc finger protein 330 | ZNF330 |
| Leucine proline-enriched proteoglycan (leprecan) 1 | LEPRE1 |
| Transcription factor AP-2 gamma (activating enhancer binding protein 2 gamma) | TFAP2C |
| Zinc finger, AN1-type domain 2B | ZFAND2B |
| Bardet-Biedl syndrome 2 | BBS2 |
| Tripartite motif-containing 4 | TRIM4 |
| Cyclin-dependent kinase inhibitor 3 | CDKN3 |
| Interferon, alpha-inducible protein 27-like 2 | IFI27L2 |
| Adaptor-related protein complex 3, mu 2 subunit | AP3M2 |
| Proteasome (prosome, macropain) activator subunit 1 (PA28 alpha) | PSME1 |
| Chromosome 6 open reading frame 129 | C6orf129 |
| aminolevulinate dehydratase | — |
| chromosome 14 open reading frame 167 (C14orf167), transcript variant 2, non-coding RN- | |
| Dynein, axonemal, light intermediate chain 1 | DNALI1 |
| Proline rich 13 | PRR13 |
| Progestin and adipoQ receptor family member III | PAQR3 |
| Synuclein, alpha (non A4 component of amyloid precursor) | SNCA |
| Chromosome 21 open reading frame 58 | C21orf58 |
| Chromosome 17 open reading frame 49 | C17orf49 |
| Phospholipase C, gamma 2 (phosphatidylinositol-specific) | PLCG2 |
| EFR3 homolog B (S. cerevisiae) | EFR3B |
| Carbonyl reductase 4 | CBR4 |
| PREDICTED: hypothetical protein LOC644128 (LOC644128), mRNA. | — |
| Transmembrane protein 144 | TMEM144 |
| Splicing factor, arginine/serine-rich 18 | SFRS18 |
| Folliculin interacting protein 1 | FNIP1 |
| Cysteine-rich with EGF-like domains 1 | CRELD1 |
| Cadherin 10, type 2 (T2-cadherin) | CDH10 |
| Zinc finger protein 197 | ZNF197 |
| Latent transforming growth factor beta binding protein 4 | LTBP4 |
| Mannosyl (beta-1,4-)-glycoprotein beta-1,4-N-acetylglucosaminyltransferase | MGAT3 |
| Ciliary neurotrophic factor receptor | CNTFR |
| Complement component 1, q subcomponent-like 4 | C1QL4 |
| PREDICTED: similar to 60S ribosomal protein L7a (LOC644029), mRNA. | — |
| Transcription factor B1, mitochondrial | TFB1M |
| SRY (sex determining region Y)-box 21 | SOX21 |
| Monocyte to macrophage differentiation-associated | MMD |
| Prodynorphin | PDYN |
| Interleukin 27 receptor, alpha | IL27RA |
| Mannosidase, alpha, class 2B, member 2 | MAN2B2 |
| WD repeat domain 33 | WDR33 |
| Lix1 homolog (mouse)-like | LIX1L |
| Cathepsin L1 | CTSL1 |
| Chromosome 9 open reading frame 140 | C9orf140 |
| Adipose differentiation-related protein | ADFP |
| TM2 domain containing 1 | TM2D1 |
| Oxysterol binding protein-like 6 | OSBPL6 |
| Endoplasmic reticulum metallopeptidase 1 | ERMP1 |
| Cathepsin L1 | CTSL1 |
| Transmembrane protein 31 | TMEM31 |
| PNMA-like 1 | PNMAL1 |

TABLE 1-continued

| Gene Title | Gene ID |
|---|---|
| Ring finger protein 14 | RNF14 |
| Mitochondrial fission regulator 1 | MTFR1 |
| CD52 molecule | CD52 |
| Transcribed locus | — |
| Delta-like 1 (*Drosophila*) | DLL1 |
| Coiled-coil domain containing 28B | CCDC28B |
| Protein phosphatase 1, regulatory (inhibitor) subunit 11 | PPP1R11 |
| Prolylcarboxypeptidase (angiotensinase C) | PRCP |
| Tryptophan rich basic protein | WRB |
| Chromosome 9 open reading frame 64 | C9orf64 |
| Chromosome 9 open reading frame 135 | C9orf135 |
| BCL2/adenovirus E1B 19 kDa interacting protein 3 | BNIP3 |
| ATP synthase, H+ transporting, mitochondrial F1 complex, epsilon subunit | ATP5E |
| HSPB (heat shock 27 kDa) associated protein 1 | HSPBAP1 |
| Anti-Mullerian hormone receptor, type II | AMHR2 |
| Selenoprotein M | SELM |
| SWI/SNF related, matrix associated, actin dependent regulator of chromatin, subfamily a | SMARCAL1 |
| PREDICTED: similar to hCG1983233 (LOC100133489), mRNA. | — |
| NIMA (never in mitosis gene a)-related kinase 2 | NEK2 |
| Microsomal glutathione S-transferase 2 | MGST2 |
| Oligodendrocyte lineage transcription factor 2 | OLIG2 |
| Tumor suppressor candidate 4 | TUSC4 |
| MAP kinase interacting serine/threonine kinase 1 | MKNK1 |
| PREDICTED: family with sequence similarity 89, member A (FAM89A), mRNA. | — |
| Chromosome 10 open reading frame 10 | C10orf10 |
| Zinc finger protein 319 | ZNF319 |
| AXL receptor tyrosine kinase | AXL |
| PREDICTED: similar to NACHT, leucine rich repeat and PYD (pyrin domain) containing 1 | |
| Alpha 1,4-galactosyltransferase | A4GALT |
| Calmodulin binding transcription activator 1 | CAMTA1 |
| Protein kinase-like protein SgK493 | SGK493 |
| Arrestin domain containing 2 | ARRDC2 |
| Negative regulator of ubiquitin-like proteins 1 | NUB1 |
| Sphingosine-1-phosphate receptor 5 | S1PR5 |
| Cyclin D-type binding-protein 1 | CCNDBP1 |
| Yippee-like 5 (*Drosophila*) | YPEL5 |
| Zinc finger, MYM-type 6 | ZMYM6 |
| Troponin I type 3 (cardiac) | TNNI3 |
| Protein kinase C, beta | PRKCB |
| PNMA-like 1 | PNMAL1 |
| Nudix (nucleoside diphosphate linked moiety X)-type motif 7 | NUDT7 |
| Sorting nexin 2 | SNX2 |
| Rho/rac guanine nucleotide exchange factor (GEF) 2 | ARHGEF2 |
| KIAA1305 | KIAA1305 |
| Potassium voltage-gated channel, shaker-related subfamily, member 5 | KCNA5 |
| Motile sperm domain containing 2 | MOSPD2 |
| COMM domain containing 6 | COMMD6 |
| Receptor accessory protein 6 | REEP6 |
| Chromosome 4 open reading frame 34 | C4orf34 |
| WD repeat, sterile alpha motif and U-box domain containing 1 | WDSUB1 |
| TP53 target 3 | TP53TG3 |
| Chromosome 9 open reading frame 95 | C9orf95 |
| Collagen triple helix repeat containing 1 | CTHRC1 |
| Lysophospholipase-like 1 | LYPLAL1 |
| Centrin, EF-hand protein, 3 (CDC31 homolog, yeast) | CETN3 |
| PREDICTED: leucine rich repeat containing 58 (LRRC58), mRNA. | — |
| Lactate dehydrogenase D | LDHD |
| FLJ42957 protein (FLJ42957), mRNA. | — |
| Rieske (Fe—S) domain containing | RFESD |
| Transmembrane protein 136 | TMEM136 |
| Solute carrier family 7 (cationic amino acid transporter, y+ system), member 5 | SLC7A5 |
| PREDICTED: acyl-Coenzyme A binding domain containing 7 (ACBD7), mRNA. | — |
| Leucine rich repeat containing 26 | LRRC26 |
| Cyclin B1 interacting protein 1 | CCNB1IP1 |
| EF-hand domain family, member D1 | EFHD1 |
| NOL1/NOP2/Sun domain family, member 4 | NSUN4 |
| Zinc finger and BTB domain containing 34 | ZBTB34 |
| Heterogeneous nuclear ribonucleoprotein A2/B1 | HNRNPA2B1 |
| G protein-coupled receptor 177 | GPR177 |
| TERF1 (TRF1)-interacting nuclear factor 2 | TINF2 |
| Dynein, cytoplasmic 2, light intermediate chain 1 | DYNC2LI1 |
| Galactose-1-phosphate uridylyltransferase | GALT |
| PREDICTED: misc_RNA (RPL12P6), miscRNA. | — |
| Dolichyl-phosphate (UDP-N-acetylglucosamine) N-acetylglucosaminephosphotransferase | DPAGT1 |
| Ankyrin repeat and death domain containing 1A | ANKDD1A |
| Zinc finger protein 330 | ZNF330 |
| Tuberous sclerosis 1 | TSC1 |
| Autism susceptibility candidate 2 | AUTS2 |
| Glutathione S-transferase alpha 4 | GSTA4 |
| Dysbindin (dystrobrevin binding protein 1) domain containing 2 | DBNDD2 |
| HERV-H LTR-associating 3 | HHLA3 |
| PREDICTED: hypothetical LOC401397 (LOC401397), mRNA. | — |
| Ephrin-B3 | EFNB3 |
| Fatty acid binding protein 3, muscle and heart (mammary-derived growth inhibitor) | FABP3 |
| Immunoglobulin superfamily, member 11 | IGSF11 |
| Tripeptidyl peptidase I | TPP1 |
| Bardet-Biedl syndrome 2 | BBS2 |
| Chromosome 9 open reading frame 23 | C9orf23 |
| hypothetical locus LOC678655 (LOC678655), non-coding RNA. | — |
| Neurotrophin 3 | NTF3 |
| FXYD domain containing ion transport regulator 5 | FXYD5 |
| Ring finger protein 149 | RNF149 |
| C-type lectin domain family 3, member B | CLEC3B |
| Kruppel-like factor 2 (lung) | KLF2 |
| Tachykinin 3 | TAC3 |
| Synaptotagmin XI | SYT11 |
| Pituitary tumor-transforming 1 | PTTG1 |
| Zinc finger protein 34 | ZNF34 |
| SECIS binding protein 2-like | SECISBP2L |
| RAB3A interacting protein (rabin3) | RAB3IP |
| Mucolipin 2 | MCOLN2 |
| Solute carrier family 25 (mitochondrial carrier; phosphate carrier), member 23 | SLC25A23 |
| Cyclin-dependent kinase inhibitor 1B (p27, Kip1) | CDKN1B |
| Reprimo, TP53 dependent G2 arrest mediator candidate | RPRM |
| Unc-5 homolog A (*C. elegans*) | UNC5A |
| Apolipoprotein C-I | APOC1 |
| Fibronectin leucine rich transmembrane protein 3 | FLRT3 |
| Family with sequence similarity 181, member B | FAM181B |
| Transmembrane protein 44 | TMEM44 |
| Erythropoietin receptor | EPOR |
| Ankyrin repeat and MYND domain containing 2 | ANKMY2 |
| chromosome 12 open reading frame 28 | — |
| IQ motif containing K | IQCK |
| Cadherin 1, type 1, E-cadherin (epithelial) | CDH1 |
| Thioesterase superfamily member 2 | THEM2 |
| Paraneoplastic antigen MA2 | PNMA2 |
| ADP-ribosylation factor-like 9 | ARL9 |
| DnaJ (Hsp40) homolog, subfamily C, member 27 | DNAJC27 |
| Solute carrier family 8 (sodium/calcium exchanger), member 2 | SLC8A2 |
| Claudin 10 | CLDN10 |
| Kelch domain containing 8B | KLHDC8B |
| Amyloid beta (A4) precursor protein-binding, family A, member 3 | APBA3 |
| Transcribed locus | — |
| Claudin 10 | CLDN10 |
| Kelch-like 24 (*Drosophila*) | KLHL24 |
| Neuronal pentraxin II | NPTX2 |
| Grancalcin, EF-hand calcium binding protein | GCA |
| PREDICTED: similar to M-phase phosphoprotein, mpp8 (LOC642333), mRNA. | — |
| Nuclear factor, interleukin 3 regulated | NFIL3 |

TABLE 2

| Gene Title | Gene ID |
| --- | --- |
| Anoctamin 1, calcium activated chloride channel | ANO1 |
| Sulfatase 2 | SULF2 |
| RNA, U1G2 small nuclear (RNU1G2), small | — |
| Bardet-Biedl syndrome 9 | BBS9 |
| Growth arrest and DNA-damage-inducible, alpha | GADD45A |
| Von Willebrand factor C and EGF domains | VWCE |
| Olfactomedin 1 | OLFM1 |
| Astrotactin 2 | ASTN2 |
| Polo-like kinase 2 (Drosophila) | PLK2 |
| Methionine sulfoxide reductase A | MSRA |
| Tumor necrosis factor receptor superfamily, member 10b | TNFRSF10B |
| Annexin A1 | ANXA1 |
| Endosulfine alpha | ENSA |
| ADP-ribosylation factor GTPase activating | ARFGAP3 |
| RNA, U4 small nuclear 2 (RNU4-2), small | — |
| CD44 molecule (Indian blood group) | CD44 |
| Plasminogen activator, tissue | PLAT |
| Nescient helix loop helix 2 | NHLH2 |
| Solute carrier family 30 (zinc transporter) | SLC30A1 |
| Adenylate kinase 3-like 1 | AK3L1 |
| PREDICTED: similar to hCG1644233 | — |
| Slowmo homolog 1 (Drosophila) | SLMO1 |
| Metallothionein 2A | MT2A |
| RNA, U1 small nuclear 5 (RNU1-5), small | — |
| Thymidylate synthetase | TYMS |
| Cysteine rich transmembrane BMP regulator 1 | CRIM1 |
| Grainyhead-like 3 (Drosophila) | GRHL3 |
| FOS-like antigen 1 | FOSL1 |
| Signal-induced proliferation-associated 1 like 2 | SIPA1L2 |
| Cyclin-dependent kinase inhibitor 1A (p21, Cip1) | CDKN1A |
| Zinc finger and SCAN domain containing 10 | ZSCAN10 |
| small nucleolar RNA, C/D box 3A | SNORD3A |
| Glutathione peroxidase 1 | GPX1 |
| RNA, 7SK small nuclear | — |
| Tropomyosin 3 | TPM3 |
| PREDICTED: misc_RNA (LOC100131093) | — |
| 2-oxoglutarate and iron-dependent oxygenase domain containing 1 | OGFOD1 |
| PREDICTED: misc_RNA (LOC441481) | — |
| SIL1 homolog, endoplasmic reticulum chaperone | SIL1 |
| B cell RAG associated protein | GALNAC4S-6ST |
| Chaperone, ABC1 activity of bc1 complex | CABC1 |
| PR domain containing 1, with ZNF domain | PRDM1 |
| Versican | VCAN |
| Inositol polyphosphate-5-phosphatase, 145 kDa | INPP5D |
| Phosphohistidine phosphatase 1 | PHPT1 |
| Kelch-like 7 (Drosophila) | KLHL7 |
| Protein kinase (cAMP-dependent, catalytic) inhibitor gamma | PKIG |
| small nucleolar RNA, C/D box 3C | SNORD3C |
| Oxysterol binding protein 2 | OSBP2 |
| Tripartite motif-containing 22 | TRIM22 |
| Ral guanine nucleotide dissociation stimulator-Like 1 | RGL1 |
| Solute carrier family 7 (cationic amino acid transporter) | SLC7A14 |
| Ribosomal protein S27-like | RPS27L |
| Hippocalcin-like 1 | HPCAL1 |
| Tumor necrosis factor receptor superfamily, member 10b | TNFRSF10B |
| Lecithin-cholesterol acyltransferase | LCAT |
| adaptor-related protein complex 1, sigma 1 | AP1S1 |
| Neuroligin 4, X-linked | NLGN4X |
| Cut-like homeobox 1 | CUX1 |
| Sestrin 1 | SESN1 |
| SIL1 homolog, endoplasmic reticulum chaperone | SIL1 |
| Sorting and assembly machinery component 50 homolog | SAMM50 |
| Spermatogenesis associated 18 homolog | SPATA18 |
| Fanconi anemia, complementation group C | FANCC |
| A kinase (PRKA) anchor protein 7 | AKAP7 |
| Transgelin | TAGLN |
| Damage-regulated autophagy modulator | DRAM |
| Integrin, beta 5 | ITGB5 |

TABLE 2-continued

| Gene Title | Gene ID |
| --- | --- |
| Regulator of calcineurin 1 | RCAN1 |
| Thioredoxin reductase 2 | TXNRD2 |
| Phosphodiesterase 4B, cAMP-specific | PDE4B |
| Ankyrin 1, erythrocytic | ANK1 |
| Adenylate kinase 3-like 1 | AK3L1 |
| Damage-specific DNA binding protein 2, 48 kDa | DDB2 |
| Actin, alpha 2, smooth muscle, aorta | ACTA2 |
| Interleukin 23, alpha subunit p19 | IL23A |
| Protein phosphatase 1D magnesium-dependent | PPM1D |
| Acyl-Coenzyme A dehydrogenase, very long chain | ACADVL |
| GLI pathogenesis-related 1 like 1 | GLIPR1L1 |
| Astrotactin 2 | ASTN2 |
| Solute carrier family 38, member 1 | SLC38A1 |

TABLE 3

| Gene Title | Gene ID |
| --- | --- |
| PREDICTED: meteorin, glial cell differentiation | — |
| Oxysterol binding protein-like 2 | OSBPL2 |
| SERTA domain containing 1 | SERTAD1 |
| Inhibitor of DNA binding 3, dominant negative | ID3 |
| Methylthioribose-1-phosphate isomerase homolog | MRI1 |
| PREDICTED: similar to Ras-related protein R | — |
| CAMP responsive element binding protein 5 | CREB5 |
| Integrin, alpha 3 (antigen CD49C, alpha 3 subunit of VLA-3 receptor) | ITGA3 |
| NudE nuclear distribution gene E homolog (A. nidulans)-like 1 | NDEL1 |
| Epithelial membrane protein 3 | EMP3 |
| Tribbles homolog 3 (Drosophila) | TRIB3 |
| CDNA clone IMAGE: 5261213 | — |
| Growth arrest and DNA-damage-inducible, alpha | GADD45A |
| Aldehyde dehydrogenase 1 family, member A3 | ALDH1A3 |
| SERTA domain containing 4 | SERTAD4 |
| Tuftelin 1 | TUFT1 |
| PREDICTED: misc_RNA (LOC100128326) | |
| FYVE, RhoGEF and PH domain containing 5 | FGD5 |
| F-box protein 22 | FBXO22 |
| non-protein coding RNA 152 | — |
| Breast carcinoma amplified sequence 4 | BCAS4 |
| Adrenomedullin | ADM |
| Cathepsin H | CTSH |
| 1-aminocyclopropane-1-carboxylate synthase | ACCS |
| Synaptotagmin-like 1 | SYTL1 |
| Complement factor D (adipsin) | CFD |
| Dual specificity phosphatase 13 | DUSP13 |
| Solute carrier family 3 (activators of dibasic and neutral amino acid transport), member 2 | SLC3A2 |
| TRAF3 interacting protein 2 | TRAF3IP2 |
| Growth arrest and DNA-damage-inducible, beta | GADD45B |
| Ras homolog gene family, member C | RHOC |
| Regulator of calcineurin 1 | RCAN1 |
| Rhomboid 5 homolog 1 (Drosophila) | RHBDF1 |
| S100 calcium binding protein A11 | S100A11 |
| Growth differentiation factor 15 | GDF15 |
| Stanniocalcin 2 | STC2 |
| Transforming, acidic coiled-coil containing protein 1 | TACC1 |
| G protein-coupled estrogen receptor 1 | GPER |
| WAP four-disulfide core domain 2 | WFDC2 |
| CAMP responsive element binding protein 5 | CREB5 |
| Filamin C, gamma (actin binding protein 280) | FLNC |
| Ras homolog gene family, member U | RHOU |
| Ubiquitin associated and SH3 domain containing B | UBASH3B |
| Sodium channel, nonvoltage-gated 1 alpha | SCNN1A |
| PDZ and LIM domain 1 | PDLIM1 |
| C1q and tumor necrosis factor related protein 6 | C1QTNF6 |
| Solute carrier family 44, member 2 | SLC44A2 |
| Fibulin 2 | FBLN2 |
| PREDICTED: hypothetical LOC387763 | — |
| LY6/PLAUR domain containing 1 | LYPD1 |
| Chromosome 1 open reading frame 183 | C1orf183 |
| Sterol carrier protein 2 | SCP2 |

TABLE 3-continued

| Gene Title | Gene ID |
|---|---|
| MRNA; cDNA DKFZp762M127 (from clone D DKFZp762M127) | — |
| Epstein-Barr virus induced 3 | EBI3 |
| Inositol polyphosphate-1-phosphatase | INPP1 |
| Coiled-coil domain containing 84 | CCDC84 |
| Transporter 1, ATP-binding cassette, sub-family B | TAP1 |
| Family with sequence similarity 46, member A | FAM46A |
| Transmembrane emp24 protein transport domain containing 3 | TMED3 |
| ATPase, Ca++ transporting, plasma membrane 4 | ATP2B4 |
| Serpin peptidase inhibitor, clade B (ovalbumin), member 6 | SERPINB6 |
| Immediate early response 3 | IER3 |
| CCAAT/enhancer binding protein (C/EBP), beta | CEBPB |
| CKLF-like MARVEL transmembrane domain containing 4 | CMTM4 |
| Inositol-3-phosphate synthase 1 | ISYNA1 |
| Islet cell autoantigen 1, 69 kDa | ICA1 |
| General transcription factor IIE, polypeptide 2 | GTF2E2 |
| G protein-coupled estrogen receptor 1 | GPER |
| PREDICTED: misc_RNA (LOC645638), miscRNA | |
| Eukaryotic translation elongation factor 1 alpha 2 | EEF1A2 |
| WD repeat domain 86 | WDR86 |

TABLE 4

| Gene Title | Gene ID |
|---|---|
| Mannosyl (alpha-1,3-)glycoprotein beta-1,4-N-acetylglucosaminyltransferase, isozyme C | MGAT4C |
| CD320 molecule | CD320 |
| Ephrin-B1 | EFNB1 |
| Ubiquitin specific peptidase 9, X-linked | USP9X |
| PREDICTED: misc_RNA | — |
| Methyltransferase like 7 | METTL7A |
| Family with sequence similarity 33, member A | FAM33A |
| GA binding protein transcription factor, beta subunit 1 | GABPB1 |
| PREDICTED: similar to | — |
| TIA1 cytotoxic granule-associated RNA binding protein | TIA1 |
| SET and MYND domain containing 3 | SMYD3 |
| KIAA0146 | KIAA0146 |
| PREDICTED: misc_RNA | — |
| RNA binding motif protein 15B | RBM15B |
| DEAD (Asp-Glu-Ala-Asp) box polypeptide 46 | DDX46 |
| PREDICTED: similar to | — |
| Diaphanous homolog 2 | DIAPH2 |
| Dual specificity phosphatase 6 | DUSP6 |
| C-myc-P64 mRNA, initiating from promoter P0 | |
| SKI-like oncogene | SKIL |
| Phosphatidic acid phosphatase type 2B | PPAP2B |
| Transcribed locus | — |
| Metallothionein 1X | MT1X |
| Methyl-CpG binding domain protein 3 | MBD3 |
| PREDICTED: inositol | |
| Membrane protein, palmitoylated 6 (MAGUK p55 subfamily member 6) | MPP6 |
| Microtubule-associated protein 7 | MAP7 |
| Synaptotagmin binding, cytoplasmic RNA interacting protein | SYNCRIP |
| Metallothionein 1H | MT1H |
| Pleckstrin homology-like domain, family A, member 1 | PHLDA1 |
| Abhydrolase domain containing 5 | ABHD5 |
| Left-right determination factor 1 | LEFTY1 |
| Basonuclin 2 | BNC2 |
| Chromosome 10 open reading frame 2 | C10orf2 |
| COX4 neighbor | COX4NB |
| Related RAS viral (r-ras) oncogene homolog 2 | RRAS2 |
| Acireductone dioxygenase 1 | ADI1 |
| Chromosome 11 open reading frame 51 | C11orf51 |
| G patch domain containing 2 | GPATCH2 |

TABLE 4-continued

| Gene Title | Gene ID |
|---|---|
| Deleted in bladder cancer 1 | DBC1 |
| C-myc-P64 mRNA, initiating from promoter P0 | |
| Fas (TNFRSF6) associated factor 1 | FAF1 |
| SET domain containing 1A | SETD1A |
| Growth differentiation factor 3 | GDF3 |
| Ubiquitin specific peptidase 16 | USP16 |
| Hairy/enhancer-of-split realted from YRPW motif 2 | HEY2 |
| BEN domain containing 3 | BEND3 |
| Chromatin accessibility complex 1 | CHRAC1 |
| Metallothionein 1F | MT1F |
| Transmembrane protein 132D | TMEM132D |
| Fermitin family homolog 1 | FERMT1 |
| Phosphatidic acid phospatase type 2B | PPAP2B |
| Solute carrier family 22 (extraneuronal monoamine transporter), member 3 | SLC22A3 |
| Adaptor-related protein complex 1, sigma 2 subunit | AP1S2 |
| Asparagine-linked glycosylation 5, dolichyl-phosphate beta-glucosyltransferase homolog | ALG5 |
| LanC lantibiotic synthetase component C-like 2 | LANCL2 |
| GTF2I repeat domain containing 2 | GTF2IRD2 |
| Zinc finger CCCH-type containing 4 | ZC3H4 |
| Suppressor of cytokine signaling 2 | SOCS2 |
| Thrombospondin 2 | THBS2 |
| DNA (cytosine-5-)-methyltransferase 3 beta | DNMT3B |
| G protein-coupled receptor 64 | GPR64 |
| chaperonin containing T | — |
| Kallmann syndrome 1 sequence | KAL1 |
| Ras-like without CAAX 2 | RIT2 |
| Similar to hCG2042915 | LOC100129673 |
| metallothionein E | MTE |
| TIMP metallopeptidase inhibitor 4 | TIMP4 |
| PREDICTED: similar to | — |
| Ribosomal protein S6 kinase, 90 kDa, polypeptide 2 | RPS6KA2 |
| G protein-coupled receptor 1 | GPR1 |
| Cytochrome c, somatic | CYCS |
| SIVA1, apoptosis-inducing factor | SIVA1 |
| Ribosomal RNA processing 12 homolog | RRP12 |
| Odz, odd Oz/ten-m homolog 3 | ODZ3 |
| Transcription elongation regulator 1-like | TCERG1L |
| Serine/threonine kinase 11 interacting protein | STK11IP |
| ArfGAP with GTPase domain, ankyrin repeat and PH domain 1 | AGAP1 |
| High-mobility group nucleosomal binding protein 2 | HMGN2 |
| Phorbol-12-myristate-13-acetate-induced protein 1 | PMAIP1 |
| Metallothionein 1A | MT1A |
| Cytochrome P450, family 26, subfamily a, polypeptide 1 | CYP26A1 |
| Methylenetetrahydrofolate dehydroenase (NADP+ dependent) 1-like | MTHFD1L |
| High-mobility group nucleosomal binding domain 2 | HMGN2 |
| Metallothionein 1M | MT1M |
| Zinc finger protein 597 | ZNF597 |
| Acetyl-Coenzyme A acetyltransferase 2 | ACAT2 |
| Transcription factor 4 | TCF4 |
| Transmembrane protein 222 | TMEM222 |
| Zinc finger protein 827 | ZNF827 |
| Stromal antigen 1 | STAG1 |
| Phenylalanyl-tRNA synthetase 2, mitochondrial | FARS2 |
| Adaptor-related protein complex 1, sigma 2 subunit | AP1S2 |
| NADH dehydrogenase (ubiquinone) 1 alpha subcomplex, 9, 39 kDa | NDUFA9 |
| Pyridine nucleotide-disulphide oxidoreductase domain 1 | PYROXD1 |
| Selenophosphate synthetase 1 | SEPHS1 |
| Vesicle amine transport protein 1 homolog-like | VAT1L |
| Polymerase (DNA-directed), delta interacting protein 2 | POLDIP2 |
| PREDICTED: misc_RNA | — |
| Insulin-degrading enzyme | IDE |
| Chromosome 3 open reading frame 59 | C3orf59 |
| Cdk5 and Abl enzyme substrate 1 | CABLES1 |
| Adenylate kinase 2 | AK2 |

TABLE 4-continued

| Gene Title | Gene ID |
| --- | --- |
| Methyltransferase 11 domain containing 1 | METT11D1 |
| N-acetylglucosamine-1-phosphodiester alpha-N-acetylglucosaminidase | NAGPA |
| NEL-like 2 (chicken) | NELL2 |
| Glycoprotein M6B | GPM6B |
| Connective tissue growth factor | CTGF |
| X-ray repair complementing defective repair in Chinese hamster cells 5 | XRCC5 |
| TRM5 tRNA methyltransferase 5 homolog | TRMT5 |
| Glypican 4 | GPC4 |
| Phosphoribosylformylglycinamidine synthase | PFAS |
| Tudor domain containing 3 | TDRD3 |
| Recombination signal binding protein for immunoglobulin kappa J region | RBPJ |
| Phosphatidylinositol glyan anchor biosynthesis, class W | PIGW |
| Eukaryotic translation initiation factor 6 | EIF6 |
| ADP-ribosylhydrolase like 1 | ADPRHL1 |
| Echinoderm microtubule associated protein like 1 | EML1 |
| Ubiquitin-conjugating enzyme E2C | UBE2C |
| Tight junction protein 2 | TJP2 |
| KIAA0114 | KIAA0114 |
| Scaffold attachment factor B2 | SAFB2 |
| Paroxysmal nonkinesigenic dyskinesia | PNKD |
| Methylenetetrahydrofolate dehydrogenase (NADP+ dependent) 1 | MTHFD1 |
| PREDICTED: similar to CDNA FLJ31750 fis, clone NT2RI2007406 | — |
| Polymerase (DNA directed), alpha 1, catalytic subunit | POLA1 |
| Chromosome 12 open reading frame 26 | C12orf26 |
| Nanog homeobox | NANOG |
| Recombination signal binding protein for immunoglobulin kappa J region | RBPJ |
| Tenascin C | TNC |
| Nebulette | NEBL |
| Forkhead box O4 | FOXO4 |
| Coiled-coil-helix-coiled-coil-helix domain containing 3 | CHCHD3 |
| ADP-ribosylation factor guanine nucleotide-exchange factor 1 | ARFGEF1 |
| PREDICTED: misc_RNA | — |
| Androgen-induced 1 | AIG1 |
| Integrin alpha FG-GAP repeat containing 2 | ITFG2 |
| DEAD (Asp-Glu-Ala-Asp) box polypeptide 23 | DDX23 |
| G protein-coupled receptor 64 | GPR64 |
| chromosome 6 open reading frame | — |
| DnaJ (Hsp40) homolog, subfamily B, member 6 | DNAJB6 |
| ATPase inhibitory factor 1 | ATPIF1 |
| Histone cluster 1, H1c | HIST1H1C |
| Potassium voltage-gated channel, Shal-related subfamily, member 2 | KCND2 |
| Gamma-aminobutyric acid (GABA) A receptor, subunit beta 3 | GABRB3 |
| Zinc finger and SCAN domain containing 2 | ZSCAN2 |
| Ornithine decarboxylase, structural 1 | ODC1 |
| Kinesin family member 11 | KIF11 |
| MLF1 interacting protein | MLF1IP |
| Protein phosphatase 2, regulatory subunit B, beta polyglutamine binding protein | PPP2R2B |
| Oxysterol binding protein-like 10 | OSBPL10 |
| Mediator complex subunit 27 | MED27 |
| Penta-EF-hand domain containing 1 | PEF1 |
| BH3 interacting domain | BID |
| Lysosomal protein transmembrane 4 beta | LAPTM4B |
| Cytochrome P450, family 26, subfamily a, polypeptide 1 | CYP26A1 |
| NEDD8 activating enzyme E1 subunit 1 | NAE1 |
| Sterol-C4-methyl oxidase-like | SC4MOL |
| Tenascin C | TNC |
| Connective tissue growth factor | CTGF |
| CDK5 regulatory subunit associated protein 1-like 1 | CDKAL1 |
| Pleckstrin homology-like domain, family A, member 1 | PHLDA1 |
| 24-dehydrocholesterol reductase | DHCR24 |
| Polymerase (RNA) II (DNA directed) polypeptide L | POLR2L |

TABLE 4-continued

| Gene Title | Gene ID |
| --- | --- |
| Chromosome 3 open reading frame 26 | C3orf26 |
| Suppressor of cytokine signaling 2 | SOCS2 |
| Chromosome 1 open reading frame 53 | C1orf53 |
| Neuritin 1-like | NRN1L |
| CSE1 chromosome segregation 1-like | CSE1L |
| RAS-like, family 11, member B | RASL11B |
| PREDICTED: hypothetical | — |
| Stromal antigen 1 | STAG1 |
| Zinc finger, DHHC-type containing 16 | ZDHHC16 |
| Transmembrane protein 208 | TMEM208 |
| Acetyl-Coenzyme A carboxylase alpha | ACACA |
| ADAM metallopeptidase with thrombospondin type 1 motif, 8 | ADAMTS8 |
| Transmembrane protein 39b | TMEM39B |
| Exosome component 5 | EXOSC5 |
| Glypican 6 | GPC6 |
| Solute carrier family 13 (sodium-dependent dicarboxylate transporter), member 3 | SLC13A3 |
| Polymerase (RNA) III (DNA directed) polypeptide B | POLR3B |
| Transmembrane 4 L six family member 18 | TM4SF18 |
| USP6 N-terminal like | USP6NL |
| Glycoprotein M6B | GPM6B |

TABLE 5

| Gene Title | Gene ID |
| --- | --- |
| PREDICTED: hypothetical LOC72 | — |
| High-mobility group box 2 | HMGB2 |
| PREDICTED: misc_RNA (LOC72 | — |
| G patch domain containing 4 | GPATCH4 |
| F-box protein 30 | FBXO30 |
| ATPase, class VI, type 11C | ATP11C |
| Proteasome (prosome, macropain) 26S subunit, non-ATPase, 12 | PSMD12 |
| 3-hydroxy-3-methylglutaryl-Coenzyme A reductase | HMGCR |
| Mex-3 homolog C (*C. elegans*) | MEX3C |
| Inhibitor of growth family, member 1 | ING1 |
| Der1-like domain family, member 1 | DERL1 |
| Proteolipid protein 1 | PLP1 |
| Ribosomal protein L37a | RPL37A |
| Chromosome 13 open reading frame 34 | C13orf34 |
| Shisa homolog 3 (*Xenopus laevis*) | SHISA3 |
| PREDICTED: misc_RNA (LOC20 | — |
| Septin 3 | SEPT3 |
| Cytochrome P450, family 20, subfamily A, polypeptide 1 | CYP20A1 |
| Ribosomal protein L7 pseudogene 20 | RPL7P20 |
| Chromosome 12 open reading frame 11 | C12orf11 |
| Karyopherin alpha 2 (RAG cohort 1, importin alpha 1) | KPNA2 |
| TAR DNA binding protein | TARDBP |
| SRY (sex determining region Y)-box 11 | SOX11 |
| Budding uninhibited by benzimidazoles 1 homolog beta | BUB1B |
| Isopentenyl-diphosphate delta isomerase 1 | IDI1 |
| Discs, large (*Drosophila*) homolog-associated protein 5 | DLGAP5 |
| 3-hydroxy-3-methylglutaryl-Coenzyme A synthase 1 | HMGCS1 |
| DEAD (Asp-Glu-Ala-Asp) box polypeptide 10 | DDX10 |
| Shisa homolog 2 (*Xenopus laevis*) | SHISA2 |
| Leucine zipper transcription factor-like 1 | LZTFL1 |
| EMG1 nucleolar protein homolog (*S. cerevisiae*) | EMG1 |
| RNA binding motif protein 12 | RBM12 |
| Cathepsin C | CTSC |
| Histone cluster 1, H2bd | HIST1H2BD |
| Suppressor of Ty 4 homolog 1 | SUPT4H1 |
| Budding uninhibited by benzimidazoles 1 homolog | BUB1 |
| HESX homeobox 1 | HESX1 |
| DEAD (Asp-Glu-Ala-Asp) box polypeptide 28 | DDX28 |
| Discoidin, CUB and LCCL domain containing 2 | DCBLD2 |
| PREDICTED: misc_RNA (LOC72 | |

TABLE 5-continued

| Gene Title | Gene ID |
|---|---|
| Transcribed locus | — |
| Transcribed locus | — |
| Poliovirus receptor-related 1 (herpesvirus entry mediator C) | PVRL1 |
| Zinc finger protein 22 (KOX 15) | ZNF22 |
| Dihydrolipoamide S-acetyltransferase | DLAT |
| Neuroligin 4, Y-linked | NLGN4Y |
| Polo-like kinase 1 (*Drosophila*) | PLK1 |
| PREDICTED: misc_RNA (LOC10 | — |
| High-mobility group box 1 | HMGB1 |
| LEM domain containing 3 | LEMD3 |
| Kinesin family member 23 | KIF23 |
| Enhancer of yellow 2 homolog | ENY2 |
| PREDICTED: misc_RNA (LOC44 | — |
| Beta-1,3-glucuronyltransferase 1 | B3GAT1 |
| HORMA domain containing 1 | HORMAD1 |
| Multiple EGF-like-domains 10 | MEGF10 |
| UDP-glucose pyrophosphorylase 2 | UGP2 |
| Leucine carboxyl methyltransferase 2 | LCMT2 |
| Kelch repeat and BTB (POZ) domain containing 7 | KBTBD7 |
| Formin-like 2 | FMNL2 |
| Zinc finger protein 609 | ZNF609 |
| Squalene epoxidase | SQLE |
| Topoisomerase (DNA) II alpha 170 kDa | TOP2A |
| PDS5, regulator of cohesion maintenance, homolog B | PDS5B |
| Splicing factor, arginine/serine-rich 3 | SFRS3 |
| 7 Leucine-rich repeats and immunoglobulin-like domains 1 | LRIG1 |
| Signal recognition particle 9-like 1 | SRP9L1 |
| Neuronal pentraxin I | NPTX1 |
| DEP domain containing 1B | DEPDC1B |
| Lin-9 homolog (*C. elegans*) | LIN9 |
| Platelet-derived growth factor receptor, alpha | PDGFRA |
| ATP-binding cassette, sub-family E (OABP), member 1 | ABCE1 |
| Gap junction protein, alpha 1, 43k | GJA1 |
| Phospholipase C, eta 1 | PLCH1 |
| Translocase of inner mitochondrial member 23 homolog | TIMM23 |
| Janus kinase and microtubule interacting protein 2 | JAKMIP2 |
| Cell division cycle associated 3 | CDCA3 |
| COMM domain containing 10 | COMMD10 |
| Mediator complex subunit 7 | MED7 |
| Cell division cycle associated 2 | CDCA2 |
| Ribosomal protein L29 | RPL29 |
| TOX high mobility group box family member 3 | TOX3 |
| RAP1 interacting factor homolog | RIF1 |
| Hydrolethalus syndrome 1 | HYLS1 |
| Leucine zipper, putative tumor suppressor 1 | LZTS1 |
| Kelch repeat and BTB (POZ) domain containing 7 | KBTBD7 |
| Poly(A) binding protein interacting | |
| Farnesyl-diphosphate farnesyltransferase 1 | FDFT1 |

Gene set enrichment analysis (GSEA) was performed. Gene sets whose expression levels were up-regulated with cisplatin treatment were highly enriched for genes whose function has been linked to apoptosis, DNA damage, and p53 target genes (Table 6). The gene set with the highest normalized enrichment score (NES) was from a previous microarray based observation that cisplatin mediates a p53-dominant transcriptional response in NT2/D1 cells (Kerley-Hamilton et al. 2005. *Oncogene* 24:6090-6100). Genes whose expression was up-regulated following decitabine exposure were also enriched for gene sets corresponding to apoptosis, DNA damage and p53 target genes. However, there were gene sets significantly depleted only after decitabine treatment that are highly expressed in ES cells and representative of core stem cell and pluripotency pathways. Target genes of the induced pluripotency core stem cell factor Myc (Schlosser et al. 2005. *Oncogene* 24:520-524; Schuhmacher et al. 2001. *Nucleic Acids Res.* 29:397-406) were also highly repressed in NT2/D1 cells with decitabine treatment (Table 6). DAVID (Database for Annotation, Visualization and Integrated Discovery) analysis was performed and also indicated that decitabine represses ES genes and genes with binding sites for pluripotent transcription factors SRY and OCT (Table 7). Additionally, several gene sets comprised of genes previously shown to be induced or repressed by high-dose decitabine in somatic cancer cells (Missiaglia et al. 2005. *Oncogene* 24:199-211; Mueller et al. 2007. *Oncogene* 26:583-593) were enriched or depleted after low-dose decitabine treatment of NT2/D1 cells (Table 6). These genes are distinct from the p53 target and pluripotent gene sets mentioned above. These data confirmed that cisplatin and decitabine share mechanisms of toxicity that are represented by DNA damage inducible p53 target genes, but also demonstrated that additional mechanisms related to anti-pluripotency and demethylation are likely operating in decitabine treated cells.

TABLE 6

| Gene Set Name | Size | NES | p-val | FDR q-val |
|---|---|---|---|---|
| Gene Sets Enriched in NT2 Cells with Cisplatin Treatment (0.5 µM for 3 days) | | | | |
| KERLEY_RESPONSE_TO_CISPLATIN_UP | 39 | −3.0393 | 0 | 0 |
| AMIT_EGF_RESPONSE_480_HELA | 161 | −2.5999 | 0 | 0 |
| KANNAN_TP53_TARGETS_UP | 48 | −2.5961 | 0 | 0 |
| GENTILE_UV_LOW-DOSE-UP | 18 | −2.5543 | 0 | 0 |
| SCHAVOLT_TARGETS_OF_TP53_AND_TP63 | 16 | −2.4114 | 0 | 0 |
| DACOSTA_UV_RESPONSE_VIA_ERCC3_UP | 307 | −2.3411 | 0 | 0 |
| GENTILE_UV_LOW-DOSE-UP | 18 | −2.3213 | 0 | 0 |
| INGA_TP53_TARGETS | 16 | −2.3095 | 0 | 0 |
| WEIGEL_OXIDATIVE_STRESS_RESPONSE | 30 | −2.3010 | 0 | 0 |
| CONCANNON_APOPTOSIS_BY_EPOXOMICIN_UP | 233 | −2.2899 | 0 | 0 |
| AMUNDSON_DNA_DAMAGE_RESPONSE_TP53 | 16 | −2.2828 | 0 | 0 |
| AMIT_EGF_RESPONSE_120_MCF10A | 42 | −2.2779 | 0 | 0 |
| Gene Sets Enriched in NT2 Cells with 3-Day Decitabine Treatment (10 nM) | | | | |
| KERLEY_RESPONSE_TO_CISPLATIN_UP | 39 | −2.4408 | 0 | 0 |
| CONCANNON_APOPTOSIS_BY_EPOXOMICIN_UP | 233 | −2.2139 | 0 | 0 |
| MISSIAGLIA_REGULATED_BY_METHYLATION_UP | 99 | −2.1687 | 0 | 0 |
| MUELLER_METHYLATED_IN_GLIOBLASTOMA | 42 | −2.0961 | 0 | 0 |
| KYNG_DNA_DAMAGE_BY_UV | 25 | −2.0319 | 0 | $9.89 \times 10^{-4}$ |

TABLE 6-continued

| Gene Set Name | Size | NES | p-val | FDR q-val |
|---|---|---|---|---|
| RUGO_UV_RESPONSE | 25 | −1.9676 | 0 | $1.17 \times 10^{-3}$ |
| KIM_RESPONSE_TO_TSA_AND_DECITABINE_UP | 129 | −1.9665 | 0 | $1.16 \times 10^{-3}$ |
| HAMAI_APOPTOSIS_VIA_TRAIL_DN | 125 | −1.9615 | 0 | $1.24 \times 10^{-3}$ |
| HELLER_SILENCED_BY_METHYLATION_UP | 248 | −1.9604 | 0 | $1.35 \times 10^{-3}$ |
| INGA_TP53_TARGETS | 16 | −1.9327 | 0 | $1.52 \times 10^{-3}$ |
| Gene Sets Depleted in NT2 Cells with 3-Day Decitabine Treatment (10 nM) | | | | |
| BENPORATH_ES_1 | 372 | 2.6981 | 0 | 0 |
| SCHUHMACHER_MYC_TARGETS_UP | 69 | 2.5662 | 0 | 0 |
| WONG_EMBRYONIC_STEM_CELL_CORE | 331 | 2.4279 | 0 | 0 |
| SCHLOSSER_MYC_TARGETS_REPRESSED_BY_SERUM | 158 | 2.4043 | 0 | 0 |
| BENPORATH_ES_2 | 37 | 2.3953 | 0 | 0 |
| SCHLOSSER_MYC_TARGETS_AND_SERUM_RESPONSE_DN | 47 | 2.2821 | 0 | 0 |
| VSE2F_02 | 173 | 2.2708 | 0 | 0 |
| MUELLER_PLURINET | 294 | 2.2694 | 0 | 0 |
| BHATTACHARYA_EMBRYONIC_STEM_CELL | 75 | 2.2132 | 0 | 0 |
| PAL_PRMT5_TARGETS_UP | 182 | 2.2049 | 0 | 0 |
| MISSIAGLIA_REGULATED_BY_METHYLATION_DN | 97 | 2.1720 | 0 | $3.67 \times 10^{-4}$ |
| CONRAD_STEM_CELL | 37 | 2.1627 | 0 | $3.38 \times 10^{-4}$ |

TABLE 7

DAVID Gene Sets Depleted in NT2 Cells with 3-Day Decitabine Treatment (10 nM) and Showing a Greater than 0.5-Fold Change

| Gene Set Name | p-val | Benjamin |
|---|---|---|
| CGAP_SAGE_QUARTILE Stem cell 3rd | $2.30 \times 10^{-38}$ | $7.90 \times 10^{-36}$ |
| UCSC_TFBS E2F | $9.00 \times 10^{-16}$ | $7.80 \times 10^{-14}$ |
| UCSC_TFBS SRY | $1.90 \times 10^{-14}$ | $1.10 \times 10^{-12}$ |
| UCSC_TFBS OCT | $5.20 \times 10^{-10}$ | $2.30 \times 10^{-9}$ |

In earlier experiments it had been shown that knockdown of DNMT3B conferred substantial resistance to decitabine activity in EC cells (Beyrouthy et al. 2009. *Cancer Res.* 69:9360-9366). Since decitabine resistance to DNMT3B knockdown is dramatic in cisplatin-resistant NT2/D1-R1 cells, these cells were used to study the dependence of DNMT3B on decitabine treatment of EC cells. Knockdown of DNMT3B in NT2/D1-R1 cells resulted in extensive resistance to low-dose 3 day decitabine treatment compared to sh-control cells (FIG. 11). As in NT2/D1 cells, exposure of NT2/D1-R1 cells to decitabine induced apoptosis as determined by PARP cleavage and sub G1 DNA content with G2 arrest. Three day decitabine treatment also induced DNA damage as assessed by induction of phosphorylated H2AX. As expected, cisplatin does not induce PARP cleavage in cisplatin-resistant NT2/D1-R1 cells but can induce phospho-H2AX; these data indicates that cisplatin resistance is downstream of effective DNA damage induction. Importantly, decitabine-mediated H2AX activation also occurs in the presence of the caspase 3 inhibitor (Z-VAD-FMK) at concentrations that inhibit PARP cleavage. This result indicated that DNA damage mediated by low-dose decitabine treatment of NT2/D1-R1 cells is not due to secondary effects downstream of apoptosis.

Thus, data have shown that knockdown of DNMT3B in NT2/D1-R1 cells resulted in a substantial decrease in PARP cleavage compared to wild-type and sh-control NT2/D1-R1 cells. However, activation of H2AX and stabilization of p53 was shown to be similar in sh-control and sh-DNMT3B cells. Taken together, these data indicate that low-dose decitabine treatment is sufficient to cause DNA damage in EC cells. However, resistance observed in with knockdown of DNMT3B activity is likely due to a defect downstream of the induction of DNA damage. These data also indicate that induction of DNA damage, by itself, is not sufficient to account for the decitabine hypersensitivity observed in EC cells.

Genome-wide expression analysis was then performed with NT2/D1-R1 control and DNMT3B knockdown cells treated for 3 days with low-dose decitabine (10 nM). There was a large degree of overlap in decitabine-responsive genes in NT2/D1-R1 cells as compared to NT2/D1 cells (approximately 20%) and those genes upregulated by decitabine in NT2/D1-R1 cells were again associated with DNA damage and p53 activity, while those genes repressed by low-dose decitabine treatment were associated with differentiation state and pluripotency. The expression level of only a few genes was altered by DNMT3B knockdown alone in NT2/D1-R1 cells, and there was no correlation between the identity of those genes and the identity of the genes altered by decitabine treatment of NT2/D1-R1 cells. These data indicate that DNMT3B knockdown alone is not sufficient to allow re-expression of DNA methylated genes in NT2/D1-R1 cells. However, knockdown of DNMT3B substantially suppressed decitabine-mediated gene expression changes.

PAM analysis was performed on 1169 genes changed 1.5-fold or greater in various test groups (sh-control, sh-control combined with decitabine treatment, sh-DNMT3B, and sh-DNMT3B combined with decitabine treatment). Of the 6 clusters identified, Cluster 1 and Cluster 2 were particularly informative (FIG. 12). Cluster 1 represented 129 genes that were down-regulated by low dose decitabine treatment in control cells, but were not down-regulated by decitabine treatment in DNMT3B knockdown cells. Cluster 1 genes were enriched for pluripotency genes including NANOG, SOX2, PHC1, GDF3, DPPA2 and DPPA3. Cluster 2 represented 337 genes that were induced by treatment with decitabine only in control cells and not in sh-DNMT3B cells. Cluster 2 genes included the p53 target genes p21, GADD45A, BTG2, IER3 and GDF15. Lists of the genes are provided in Tables 8, Table 9 (Cluster 1), Table 10 (Cluster 2), Table 11 (Cluster 3), Table 12 (Cluster 4), Table 13 (Cluster 5), and Table 14 (Cluster 6). As before, gene expression changes for representative genes of Cluster 1 and Cluster 2 were confirmed in independent samples by real-time PCR.

TABLE 8

| GeneID | Gene Identifier | sh-Ctrl Mean (SEM) | sh-Ctrl + aza Mean (SEM) | sh-3B Mean (SEM) | sh-3B + aza Mean (SEM) |
|---|---|---|---|---|---|
| — | XR_016703 | 939.464 (32.0203) | 6659.76 (819.499) | 1017.38 (64.5843) | 4025.84 (598.188) |
| KRT8 | NM_002273 | 661.101 (18.5897) | 3394.59 (271.522) | 788.416 (16.6978) | 2758.76 (325.371) |
| ID3 | NM_002167 | 682.025 (11.3565) | 3392.56 (297.763) | 754.511 (29.5991) | 1623.89 (159.684) |
| CCND1 | NM_053056 | 934.758 (35.0516) | 4666.94 (620.002) | 1060.49 (24.3442) | 1996.23 (93.3019) |
| CDX1 | NM_001804 | 145.323 (14.2906) | 802.577 (208.148) | 149.078 (2.26373) | 237.199 (23.5743) |
| LEFTY2 | NM_003240 | 540.254 (54.9687) | 1161.57 (291.493) | 677.015 (14.2434) | 2484.87 (512.038) |
| CAV1 | NM_001753 | 166.108 (11.8847) | 740.14 (43.7631) | 173.564 (12.3631) | 402.328 (31.2986) |
| ANXA1 | NM_000700 | 180.28 (10.3292) | 1242.05 (310.943) | 140.16 (4.59723) | 394.045 (48.9357) |
| LOC647954 | XR_018676 | 371.299 (18.3423) | 1348.27 (156.199) | 401.401 (15.6799) | 1052.7 (168.915) |
| COL7A1 | NM_000094 | 306.625 (14.1418) | 1054.31 (106.867) | 412.11 (28.0476) | 746.239 (78.0898) |
| ODC1 | NM_002539 | 949.064 (3.84442) | 3243.03 (193.979) | 1142.48 (41.2679) | 2404.47 (288.66) |
| FLJ40504 | NM_173624 | 535.702 (11.4827) | 3003.39 (485.047) | 438.419 (16.0324) | 1376.6 (308.108) |
| EBI3 | NM_005755 | 179.212 (12.9894) | 650.267 (92.92) | 209.744 (23.3696) | 333.316 (13.5633) |
| PITX1 | NM_002653 | 161.011 (3.56531) | 947.042 (189.024) | 152.888 (8.62899) | 267.398 (42.2946) |
| — | XR_015970 | 302.005 (5.87674) | 1080.49 (115.338) | 341.293 (20.2855) | 527.915 (83.8663) |
| — | NR_003287 | 153.583 (1.23147) | 634.816 (111.13) | 155.049 (5.26575) | 182.319 (18.0503) |
| MCM4 | NM_005914 | 978.909 (120.279) | 2945.56 (290.835) | 1097.4 (117.626) | 2040.37 (325.256) |
| — | XR_017543 | 250.343 (23.5882) | 832.234 (120.08) | 272.62 (19.8914) | 410.447 (55.1761) |
| — | XR_017241 | 2187.66 (83.937) | 10363 (717.374) | 2111.5 (139.693) | 5144.11 (529.275) |
| GPR177 | NM_024911 | 157.532 (9.74476) | 515.533 (29.9235) | 166.529 (11.8381) | 239.092 (9.48369) |
| ZHX2 | NM_014943 | 144.714 (4.29429) | 479.456 (38.3953) | 149.362 (7.22661) | 196.281 (6.77062) |
| POLR1C | NM_203290 | 341.069 (20.1454) | 971.221 (104.641) | 377.811 (19.4337) | 557.268 (22.7948) |
| — | NM_002467 | 334.529 (14.2403) | 896.83 (52.3754) | 334.97 (12.1935) | 595.692 (64.2644) |
| EOMES | NM_005442 | 153.274 (8.73729) | 387.137 (21.4182) | 157.572 (9.69949) | 289.321 (45.9104) |
| HCLS1 | NM_005335 | 248.063 (13.701) | 319.822 (11.1025) | 515.056 (48.5545) | 494.474 (54.8749) |
| NBPF10 | NM_0010397 | 229.675 (8.0993) | 557.142 (28.2895) | 312.898 (29.1166) | 345.645 (46.9187) |
| GALNAC4S-6 | NM_015892 | 296.839 (12.3037) | 704.001 (31.9218) | 320.266 (6.30833) | 540.521 (58.2709) |
| ELF4 | NM_001421 | 260.412 (9.26481) | 721.011 (86.4657) | 285.393 (15.8578) | 365.338 (38.5447) |
| GAD1 | NM_013445 | 154.007 (4.7974) | 372.485 (62.7312) | 177.533 (6.93431) | 246.924 (6.27639) |
| RRM2 | NM_001034 | 373.185 (27.0771) | 697.476 (19.0976) | 431.963 (32.2537) | 799.058 (39.8682) |
| NBPF10 | NM_0010376 | 289.417 (36.9639) | 816.642 (63.2714) | 301.807 (21.4236) | 370.658 (13.1989) |
| DUSP5 | NM_004419 | 712.495 (0.51966) | 1627.42 (260.623) | 856.255 (6.1799) | 1159.02 (53.6468) |
| SUSD2 | NM_019601 | 1081.9 (95.3626) | 2570.13 (22.0519) | 1255.18 (50.443) | 1694.29 (223.774) |
| GPER | NM_0010399 | 122.941 (9.17814) | 305.922 (41.44) | 141.541 (4.93251) | 176.693 (7.49579) |
| NEFH | NM_021076 | 248.784 (15.2429) | 538.551 (37.9559) | 290.514 (10.1514) | 407.674 (37.4803) |
| GPATCH4 | NM_182679 | 531.576 (33.9461) | 1117.44 (47.0279) | 577.614 (16.7322) | 927.016 (49.3836) |
| NODAL | NM_018055 | 653.314 (10.6736) | 954.925 (176.59) | 702.464 (10.8625) | 1549.19 (143.276) |
| SQSTM1 | NM_003900 | 791.132 (101.88) | 2145.19 (235.967) | 847.788 (104.285) | 885.073 (185.305) |

TABLE 8-continued

| GeneID | Gene Identifier | sh-Ctrl Mean (SEM) | sh-Ctrl + aza Mean (SEM) | sh-3B Mean (SEM) | sh-3B + aza Mean (SEM) |
|---|---|---|---|---|---|
| JTV1 | NM_006303 | 836.156 (71.5929) | 1876.43 (59.4167) | 853.612 (32.7423) | 1336.75 (29.3406) |
| UTP14A | NM_006649 | 345.362 (10.0821) | 555.285 (36.5224) | 382.108 (6.55904) | 736.541 (87.1779) |
| — | XM_0011261 | 418.329 (54.6846) | 718.505 (24.269) | 478.004 (59.9252) | 824.879 (21.1692) |
| OAT | NM_000274 | 1520.24 (42.888) | 2902.41 (56.881) | 1675.81 (33.3735) | 2711.86 (215.074) |
| GEMIN4 | NM_015721 | 592.842 (21.4654) | 1411.28 (37.9521) | 643.716 (40.1201) | 784.75 (65.6464) |
| FAM53C | NM_016605 | 1108.02 (79.9802) | 2860.96 (332.282) | 1188.65 (86.2095) | 1227.05 (189.955) |
| PAK1IP1 | NM_017906 | 341.267 (18.2518) | 644.744 (59.1779) | 352.91 (25.8003) | 603.531 (33.9517) |
| GNL3 | NM_206826 | 880.322 (38.5451) | 1332.63 (25.6545) | 979.836 (108.692) | 1810.36 (184.169) |
| CXorf40A | NM_178124 | 147.805 (5.86439) | 324.823 (12.0078) | 162.105 (7.52664) | 203.34 (22.9434) |
| HSPH1 | NM_006644 | 262.078 (17.4206) | 565.151 (83.6464) | 262.748 (31.4946) | 389.459 (10.6619) |
| PPA2 | NM_006903 | 470.27 (70.3122) | 1058.5 (93.0895) | 516.8 (48.7963) | 606.161 (77.1646) |
| PLEKHF1 | NM_024310 | 311.194 (13.5548) | 716.406 (93.1492) | 353.391 (39.4928) | 367.904 (62.8141) |
| BCL11A | NM_022893 | 212.398 (13.6368) | 399.892 (9.12454) | 234.484 (8.95916) | 345.798 (25.8828) |
| TPRG1L | NM_182752 | 653.523 (40.4382) | 1513.68 (134.603) | 725.678 (19.7143) | 762.223 (36.0413) |
| RBM22 | NM_018047 | 475.348 (3.60796) | 921.101 (34.8647) | 555.988 (40.3502) | 700.828 (47.0413) |
| TNFRSF13B | NM_012452 | 118.102 (7.36616) | 179.31 (14.58) | 146.216 (5.14452) | 214.796 (4.68197) |
| RPL6 | NM_0010246 | 828.415 (33.9203) | 1189.55 (24.364) | 990.863 (50.6617) | 1608.44 (49.5642) |
| ADAMTSL2 | NM_014694 | 147.028 (4.40779) | 295.667 (5.87759) | 172.075 (12.3473) | 202.775 (13.9074) |
| C10orf2 | NM_021830 | 261.752 (8.60625) | 515.45 (43.8305) | 276.434 (12.6089) | 399.327 (22.0997) |
| SOCS2 | NM_003877 | 138.489 (6.45729) | 288.614 (23.0176) | 157.624 (3.19822) | 182.936 (4.1317) |
| GTF3C6 | NM_138408 | 277.945 (4.6041) | 503.701 (27.3301) | 299.099 (10.3001) | 454.993 (27.0327) |
| SOX15 | NM_006942 | 1373.75 (56.5037) | 2791.76 (61.2893) | 1684.29 (52.9834) | 1693.21 (399.993) |
| NUAK2 | NM_030952 | 156.241 (11.2858) | 309.88 (20.8698) | 166.516 (22.0381) | 225.181 (14.1962) |
| EMILIN2 | NM_032048 | 159.568 (3.23593) | 650.943 (142.32) | 154.482 (13.4556) | 230.192 (13.7139) |
| POLR1C | NM_203290 | 272.945 (13.768) | 533.492 (11.7102) | 277.13 (18.412) | 414.276 (25.3629) |
| WBSCR22 | NM_017528 | 612.76 (7.45233) | 1107.76 (86.9651) | 679.182 (39.3081) | 958.822 (113.016) |
| — | AW972815 | 305.716 (32.3265) | 1125.31 (128.08) | 270.83 (35.6167) | 584.452 (21.5251) |
| CXCL14 | NM_004887 | 166.112 (3.69156) | 366.998 (39.8941) | 179.058 (1.08967) | 194.723 (25.1375) |
| SLC20A1 | NM_005415 | 804.587 (65.1932) | 1468.1 (170.491) | 876.093 (28.2942) | 1225.68 (80.0895) |
| TTC4 | NM_004623 | 695.449 (71.9346) | 1457.62 (39.2762) | 753.328 (12.4946) | 851.239 (16.0648) |
| SIDT2 | NM_0010404 | 255.864 (3.60393) | 528.693 (11.3994) | 268.732 (7.25251) | 326.437 (4.29884) |
| SFXN4 | NM_213649 | 356.995 (4.72995) | 724.081 (57.2482) | 360.185 (9.56009) | 481.671 (51.4121) |
| MORF4L2 | NM_012286 | 1335.05 (110.174) | 1621.68 (88.9133) | 1666.49 (146.366) | 2564.56 (265.315) |
| CNN3 | NM_001839 | 548.965 (30.3403) | 1086.56 (91.6913) | 576.193 (21.7375) | 732.909 (30.5439) |
| LOC644422 | XR_019449 | 167.407 (9.28475) | 332.598 (20.6637) | 170.785 (1.49143) | 223.185 (7.26404) |
| ZDHHC6 | NM_022494 | 262.947 (14.8535) | 528.208 (57.5724) | 266.335 (7.03541) | 344.248 (13.9726) |
| CIRH1A | NM_032830 | 1023.87 (85.9679) | 1971.98 (91.0787) | 1033.33 (75.1533) | 1424.13 (31.2687) |
| AFMID | NM_0010109 | 145.341 (5.12306) | 303.389 (21.4296) | 151.685 (7.96125) | 172.091 (2.17213) |

TABLE 8-continued

| GeneID | Gene Identifier | sh-Ctrl Mean (SEM) | sh-Ctrl + aza Mean (SEM) | sh-3B Mean (SEM) | sh-3B + aza Mean (SEM) |
|---|---|---|---|---|---|
| HARS | NM_002109 | 1015 (36.4177) | 1887.22 (57.3733) | 1187.78 (85.2293) | 1283.03 (66.4611) |
| BIRC5 | NM_001168 | 398.443 (10.8381) | 873.507 (104.001) | 405.076 (20.478) | 423.791 (35.3993) |
| NAT5 | NM_181528 | 756.765 (25.7111) | 1401.34 (79.0161) | 765.601 (36.8799) | 1059.57 (7.61669) |
| — | NM_138781 | 249.008 (6.34243) | 484.429 (55.5007) | 270.866 (28.6628) | 305.526 (16.6262) |
| TNPO1 | NM_153188 | 212.391 (6.01729) | 439.283 (22.2189) | 224.417 (19.1861) | 240.816 (24.2538) |
| NFE2 | NM_006163 | 225.653 (15.0063) | 459.796 (59.7563) | 250.773 (9.48331) | 245.362 (14.8296) |
| NUAK2 | NM_030952 | 186.464 (18.5313) | 403.382 (44.827) | 190.446 (7.39217) | 195.684 (7.37747) |
| CTNNB1 | NM_0010982 | 187.98 (3.38026) | 342.941 (23.1544) | 194.408 (11.2697) | 258.366 (9.09644) |
| ANAPC13 | NM_015391 | 295.109 (29.3245) | 549.873 (32.5087) | 313.683 (27.6985) | 377.446 (5.74812) |
| METTL1 | NM_005371 | 220.988 (4.91808) | 412.423 (23.8754) | 249.784 (20.3642) | 266.779 (25.1809) |
| NP | NM_000270 | 262.891 (5.72715) | 475.426 (3.27757) | 286.578 (12.8262) | 340.821 (15.7205) |
| SRRT | NM_015908 | 2201.02 (104.969) | 4196.33 (145.971) | 2279.3 (178.694) | 2745.27 (246.757) |
| CA2 | NM_000067 | 368.429 (4.70918) | 678.212 (39.8074) | 373.76 (35.1039) | 486.868 (36.7221) |
| IL2RB | NM_000878 | 150.634 (0.16265) | 274.617 (7.75635) | 178.322 (7.54854) | 175.269 (5.41609) |
| ELF3 | NM_004433 | 162.2 (7.32619) | 306.008 (27.1411) | 165.295 (4.53983) | 204.8 (14.4594) |
| TRIM8 | NM_030912 | 461.997 (7.67774) | 922.659 (139.477) | 463.951 (21.6319) | 529.909 (5.59394) |
| CEACAM1 | NM_0010249 | 122.959 (5.93047) | 229.793 (15.0077) | 123.307 (14.0139) | 156.04 (15.2801) |
| PEG3 | NM_006210 | 223.903 (12.7531) | 442.766 (54.9472) | 224.489 (25.7424) | 256.384 (28.8589) |
| MTA2 | NM_004739 | 249.753 (6.1765) | 453.486 (35.58) | 250.97 (8.30477) | 325.004 (28.9476) |
| MYOF | NM_013451 | 156.568 (9.63279) | 302.746 (35.6581) | 165.275 (3.38893) | 177.015 (18.439) |
| CLCF1 | NM_013246 | 181.292 (4.15083) | 340.544 (44.7606) | 203.918 (13.379) | 200.181 (3.58036) |
| — | XM_0011281 | 1162.3 (44.1331) | 2231.09 (53.8074) | 1219.43 (157.654) | 1290.15 (77.6505) |
| GPR177 | NM_0010022 | 134.228 (3.92637) | 251.287 (18.672) | 136.645 (6.20366) | 158.032 (4.74092) |
| CXXC1 | NM_014593 | 965.225 (22.1296) | 1743.77 (141.76) | 1052 (17.6142) | 1121.15 (186.357) |
| CDKN1A | NM_000389 | 493.918 (15.6479) | 1938.97 (379.64) | 437.819 (31.7276) | 619.606 (46.5167) |
| ITPRIP | NM_033397 | 188.304 (11.2535) | 346.452 (25.1913) | 189.771 (4.30101) | 226.046 (14.0456) |
| SPANXD | NM_145665 | 113.792 (7.6613) | 210.19 (15.3632) | 128.415 (0.66569) | 121.39 (2.23503) |
| C16orf93 | NM_0010149 | 204.515 (5.46118) | 392.581 (30.2306) | 209.369 (3.21891) | 214.657 (8.35352) |
| C10orf58 | NM_032333 | 537.303 (23.4746) | 983.117 (128.424) | 570.823 (30.058) | 578.039 (35.0298) |
| GLIPR2 | NM_022343 | 207.876 (4.16287) | 792.16 (183.857) | 195.197 (11.8057) | 227.407 (22.8456) |
| MT1E | NM_175617 | 928.167 (39.6924) | 2437.55 (206.719) | 927.544 (34.8521) | 1985.42 (386.522) |
| H2AFY | NM_004893 | 682.744 (26.9686) | 2387.37 (493.052) | 674.831 (24.4591) | 843.815 (140.043) |
| SERPINE1 | NM_000602 | 167.727 (12.6984) | 539.652 (99.2447) | 166.827 (7.88377) | 246.121 (29.2138) |
| ANXA2 | NM_0010028 | 1298.86 (58.7071) | 3575.79 (455.27) | 1259.54 (20.7383) | 2283.3 (148.684) |
| RUNX3 | NM_004350 | 153.581 (7.4064) | 484.199 (82.9169) | 152.936 (13.7174) | 191.132 (8.95379) |
| HSPA1A | NM_005346 | 234.638 (42.9146) | 699.362 (22.8454) | 208.507 (22.484) | 348.731 (37.9253) |
| PLAU | NM_002658 | 320.671 (28.5863) | 1093.87 (150.733) | 269.181 (12.3156) | 325.966 (21.9001) |
| BTG2 | NM_006763 | 172.841 (16.6006) | 474.998 (41.83) | 160.671 (7.67618) | 242.194 (13.4971) |

TABLE 8-continued

| GeneID | Gene Identifier | sh-Ctrl Mean (SEM) | sh-Ctrl + aza Mean (SEM) | sh-3B Mean (SEM) | sh-3B + aza Mean (SEM) |
|---|---|---|---|---|---|
| KAT2A | NM_021078 | 625.475 (20.0121) | 1965.54 (268.778) | 505.085 (10.1805) | 704.033 (35.9594) |
| AHNAK | NM_001620 | 190.662 (16.4318) | 522.882 (100.468) | 180.675 (6.40295) | 254.833 (5.66672) |
| RSL1D1 | NM_015659 | 715.756 (75.416) | 1413.6 (47.0591) | 705.134 (29.0379) | 1458.69 (261.773) |
| IER3 | NM_003897 | 302.376 (8.62609) | 835.676 (79.9819) | 269.632 (20.3405) | 406.859 (59.6233) |
| KIAA0101 | NM_014736 | 172.228 (8.20582) | 468.29 (56.8067) | 160.779 (2.04659) | 230.187 (2.32793) |
| GPR56 | NM_201524 | 144.329 (7.01209) | 378.312 (19.8737) | 140.24 (7.24862) | 189.936 (17.0325) |
| LOC728715 | XM_0011282 | 626.687 (52.5016) | 1760.28 (90.4255) | 476.478 (48.4257) | 877.255 (76.9973) |
| SNAPC4 | NM_003086 | 454.449 (31.6562) | 1200.9 (50.2207) | 415.307 (22.6723) | 599.752 (69.9779) |
| TAGLN | NM_003186 | 398.603 (14.6043) | 1178.17 (253.329) | 297.321 (9.41711) | 489.068 (76.1558) |
| TNFRSF12A | NM_016639 | 209.318 (10.8962) | 519.778 (56.9505) | 191.098 (34.625) | 296.715 (5.50255) |
| NOP2 | NM_0010337 | 3340.39 (333.129) | 7589.18 (26.068) | 3340.37 (309.421) | 5354.42 (574.264) |
| CRABP2 | NM_001878 | 826.935 (54.41) | 2128.79 (105.947) | 813.074 (61.6381) | 1011.8 (180.932) |
| NTS | NM_006183 | 267.839 (15.8879) | 641.496 (62.6771) | 201.227 (3.05111) | 457.501 (50.5077) |
| HSPA8 | NM_153201 | 2644.33 (210.596) | 5257.42 (374.527) | 2532.05 (124.889) | 4636.48 (551.319) |
| MBNL3 | NM_133486 | 164.896 (4.23176) | 338.893 (25.219) | 161.054 (9.84153) | 272.09 (11.2128) |
| CATSPER2 | NM_172097 | 741.184 (56.9211) | 1806.2 (54.6731) | 693.372 (59.2636) | 970.22 (123.164) |
| HES2 | NM_019089 | 127.358 (13.3602) | 310.888 (15.6912) | 119.298 (10.5827) | 164.558 (9.02509) |
| GPR56 | NM_201525 | 162.082 (6.83548) | 392.608 (13.5547) | 156.4 (8.12154) | 205.229 (15.4069) |
| MYOF | NM_133337 | 238.917 (11.3756) | 612.957 (108.601) | 208.148 (1.61906) | 293.772 (13.0187) |
| HSPA8 | NM_006597 | 1953.26 (60.2522) | 3448.31 (196.684) | 1800.48 (37.9515) | 3799.27 (553.956) |
| NACC2 | NM_144653 | 221.69 (3.50086) | 566.307 (95.9771) | 202.252 (8.50651) | 245.995 (15.6435) |
| COL17A1 | NM_000494 | 204.861 (1.35337) | 521.166 (75.4752) | 184.748 (4.42723) | 230.283 (7.46781) |
| PEA15 | NM_003768 | 875.533 (95.6589) | 2263.16 (191.044) | 766.964 (56.9338) | 969.289 (222.911) |
| BAG3 | NM_004281 | 587.364 (53.0495) | 1275 (173.03) | 580.91 (70.5227) | 816.89 (27.7513) |
| CYR61 | NM_001554 | 263.968 (6.06602) | 634.193 (103.454) | 230.228 (6.14819) | 338.671 (21.1317) |
| GPR177 | NM_0010022 | 174.985 (5.7821) | 391.197 (25.5557) | 170.7 (17.8281) | 231.861 (9.12383) |
| SOCS2 | NM_003877 | 226.27 (25.4224) | 566.518 (49.4704) | 205.256 (4.94502) | 244.438 (10.4378) |
| GAD1 | NM_000817 | 140.525 (7.55922) | 287.008 (27.4159) | 136.205 (2.20126) | 204.457 (23.9336) |
| ADM | NM_001124 | 369.14 (10.2008) | 937.101 (52.1638) | 287.4 (14.4794) | 446.451 (3.59531) |
| NOP56 | NM_006392 | 1200.09 (41.6981) | 1764.44 (113.178) | 1172.75 (85.0749) | 2368.5 (265.134) |
| MRTO4 | NM_016183 | 452.735 (39.0319) | 893.853 (27.6321) | 443.441 (17.3963) | 654.553 (50.1488) |
| GNL3L | NM_019067 | 200.166 (10.1927) | 392.011 (52.0537) | 196.751 (14.2903) | 289.661 (26.0496) |
| CLDN10 | NM_006984 | 184.393 (9.70804) | 407.272 (48.9977) | 178.988 (6.96997) | 222.057 (3.42647) |
| NTF3 | NM_002527 | 136.527 (15.9153) | 286.374 (9.48815) | 126.29 (6.29161) | 184.819 (15.25) |
| DDX51 | NM_175066 | 752.732 (47.28) | 1671.08 (80.9607) | 629.693 (24.2562) | 1008.46 (145.3) |
| CUEDC1 | NM_017949 | 221.599 (21.0588) | 525.909 (65.8156) | 225.4 (17.6534) | 215.515 (25.8892) |
| RNMTL1 | NM_018146 | 326.899 (17.7095) | 708.14 (53.5108) | 289.041 (21.249) | 432.796 (78.7114) |
| MEPCE | NM_019606 | 340.169 (20.5585) | 786.84 (8.02392) | 324.938 (16.7257) | 354.1 (28.8374) |

TABLE 8-continued

| GeneID | Gene Identifier | sh-Ctrl Mean (SEM) | sh-Ctrl + aza Mean (SEM) | sh-3B Mean (SEM) | sh-3B + aza Mean (SEM) |
|---|---|---|---|---|---|
| DIMT1L | NM_014473 | 447.7 (28.3817) | 893.36 (53.1028) | 412.448 (19.9685) | 616.311 (79.315) |
| FAM123B | NM_152424 | 568.632 (7.94649) | 1182.82 (107.613) | 484.659 (44.9115) | 759.762 (111.224) |
| FOXO3 | NM_201559 | 286.942 (42.5274) | 639.391 (71.1807) | 298.316 (32.5898) | 274.369 (25.3302) |
| EIF2C2 | NM_012154 | 371.688 (20.046) | 794.459 (117.523) | 402.59 (16.4194) | 367.506 (33.8604) |
| — | NR_002773 | 298.387 (4.95143) | 596.315 (23.2182) | 268.584 (6.81065) | 394.199 (25.2647) |
| — | NM_0010397 | 355.633 (12.7974) | 736.286 (22.3784) | 355.26 (4.95528) | 405.052 (14.6378) |
| M6PRBP1 | NM_005817 | 945.418 (33.9145) | 2017.94 (187.863) | 1045.35 (89.2033) | 907.761 (75.7122) |
| CRIPT | NM_014171 | 287.643 (18.5602) | 613.112 (54.8496) | 264.696 (2.32539) | 325.647 (16.2233) |
| SPRYD5 | NM_032681 | 248.332 (15.039) | 519.493 (28.359) | 222.903 (10.6241) | 293.721 (23.4994) |
| SERTAD1 | NM_013376 | 260.131 (19.4785) | 534.101 (42.1077) | 254.011 (12.2351) | 291.604 (14.2626) |
| PPAN | NM_002566 | 280.23 (6.01936) | 615.062 (42.8451) | 259.749 (27.5665) | 287.832 (34.1589) |
| C9orf6 | NM_017832 | 177.691 (3.28834) | 333.034 (30.7863) | 174.724 (9.70791) | 227.753 (19.8826) |
| SLC2A1 | NM_006516 | 949.698 (54.8461) | 2016.96 (109.096) | 921.247 (47.8672) | 988.913 (136.296) |
| RPL7L1 | NM_198486 | 455.228 (5.06878) | 859.375 (48.6621) | 430.627 (30.3606) | 585.977 (45.8201) |
| — | NM_0010398 | 1579.84 (96.7949) | 3303.16 (90.5947) | 1346.44 (55.1799) | 1883.23 (107.739) |
| DNAJC28 | NM_017833 | 1509.41 (58.1483) | 3070.58 (174.052) | 1487.37 (123.639) | 1634.56 (131.968) |
| — | XM_940430 | 199.568 (6.46512) | 367.118 (4.80456) | 194.107 (1.53703) | 257.408 (11.7859) |
| GADD45A | NM_001924 | 304.175 (13.036) | 667.657 (105.878) | 276.499 (17.3044) | 305.399 (18.7753) |
| ZNFX1 | NM_021035 | 206.56 (3.86392) | 382.615 (25.7797) | 186.849 (14.4906) | 279.087 (27.5315) |
| PRAC | NM_032391 | 127.398 (3.76106) | 247.285 (19.5064) | 120.379 (3.84496) | 153.825 (7.33042) |
| HES1 | NM_005524 | 156.374 (4.26401) | 305.823 (8.29187) | 142.408 (6.53796) | 192.41 (4.96322) |
| ZMAT3 | NM_152240 | 338.981 (10.9394) | 634.904 (18.5799) | 314.055 (32.84) | 438.743 (32.4497) |
| CTGF | NM_001901 | 298.005 (17.0982) | 692.66 (121.785) | 231.314 (16.1882) | 312.636 (14.6907) |
| C1orf163 | NM_023077 | 208.328 (10.7788) | 385.081 (3.59788) | 196.089 (6.05884) | 270.284 (17.0935) |
| NLRP8 | NM_176811 | 422.891 (34.3201) | 858.775 (17.136) | 359.759 (31.189) | 518.355 (67.6571) |
| CDC20 | NM_001255 | 2743.97 (357.582) | 5845.72 (331.876) | 2441.57 (119.988) | 2939.41 (366.384) |
| — | NM_138687 | 314.496 (3.42833) | 642.121 (8.19151) | 295.714 (15.9921) | 342.655 (24.5844) |
| STEAP3 | NM_018234 | 197.243 (4.73056) | 382.05 (17.5356) | 185.77 (3.22643) | 234.396 (13.982) |
| LOC653506 | XM_927769 | 228.657 (11.626) | 487.585 (55.6996) | 209.71 (16.455) | 231.807 (23.0604) |
| ZFHX3 | NM_006885 | 123.524 (1.4759) | 236.556 (4.23205) | 118.583 (5.62249) | 145.596 (4.35087) |
| TRMT1 | NM_017722 | 1060.79 (8.33118) | 2051.53 (70.9897) | 985.732 (43.6438) | 1265.14 (59.7598) |
| HGS | NM_004712 | 1747.24 (88.7885) | 3576.41 (304.586) | 1654.92 (210.61) | 1850.7 (367.805) |
| — | BC036485 | 227.628 (14.1951) | 420.695 (26.8851) | 218.765 (16.0514) | 281.36 (14.2717) |
| C8orf37 | NM_177965 | 735.308 (9.91111) | 1391.88 (39.9705) | 734.819 (41.6552) | 832.056 (77.6894) |
| AVPI1 | NM_021732 | 336.102 (9.98454) | 689.506 (34.2192) | 311.905 (15.4246) | 349.363 (19.0459) |
| — | XR_016534 | 290.461 (16.6146) | 330.599 (17.0151) | 287.485 (21.3677) | 547.47 (39.3583) |
| RPL29 | NM_000992 | 850.812 (81.9707) | 1659.11 (147.873) | 820.642 (43.3244) | 929.253 (132.096) |
| NOL6 | NM_139235 | 468.883 (37.0856) | 862.977 (46.4984) | 411.721 (20.6346) | 607.721 (13.1661) |

TABLE 8-continued

| GeneID | Gene Identifier | sh-Ctrl Mean (SEM) | sh-Ctrl + aza Mean (SEM) | sh-3B Mean (SEM) | sh-3B + aza Mean (SEM) |
|---|---|---|---|---|---|
| ZNF652 | NM_014897 | 418.688 (17.344) | 768.42 (16.9844) | 397.724 (35.747) | 498.982 (80.4546) |
| RPL7L1 | NM_198486 | 1864.71 (120.432) | 3816.24 (382.962) | 1667.07 (100.864) | 1942.88 (212.587) |
| EZR | NM_003379 | 3280.29 (132.906) | 5960.79 (24.9611) | 3235.52 (294.957) | 3818.8 (260.272) |
| — | XM_371152 | 1215.5 (107.29) | 2348.63 (151.891) | 1078.64 (25.9841) | 1385.95 (152.327) |
| CTRL | NM_001907 | 147.332 (5.68074) | 275.875 (19.0284) | 133.702 (7.89697) | 172.788 (4.92068) |
| BMP4 | NM_130851 | 293.855 (7.57782) | 542.004 (40.8563) | 279.358 (19.4855) | 337.919 (7.87835) |
| SERTAD2 | NM_014755 | 227.367 (16.3374) | 411.818 (13.3041) | 226.444 (3.35136) | 255.317 (3.35004) |
| CSRNP1 | NM_033027 | 351.334 (16.9144) | 645.833 (36.7947) | 336.609 (28.0636) | 396.26 (37.6352) |
| — | NM_0010249 | 1737.65 (82.4975) | 3190.12 (311.418) | 1686.47 (94.5416) | 1918.92 (121.397) |
| — | XM_0011340 | 1612.44 (91.112) | 2929.49 (184.95) | 1494.1 (54.164) | 1861.22 (79.4874) |
| ARL16 | NM_0010400 | 371.745 (30.4437) | 689.727 (33.2685) | 319.648 (9.60756) | 444.702 (10.357) |
| IRF7 | NM_004029 | 195.28 (3.86031) | 354.559 (39.1758) | 187.722 (15.7166) | 217.082 (2.35701) |
| RABEPK | NM_005833 | 334.636 (11.7709) | 625.384 (31.2666) | 319.055 (28.0613) | 355.166 (31.8706) |
| MCART1 | NM_033412 | 898.749 (8.95738) | 1775.11 (67.5381) | 716.77 (45.8266) | 1041.04 (94.233) |
| DPH2 | NM_001384 | 664.955 (34.7752) | 1256.37 (86.9113) | 583.814 (24.894) | 750.324 (26.665) |
| ZNF14 | NM_021030 | 445.834 (32.0919) | 812.88 (88.9535) | 369.932 (34.0457) | 560.423 (35.3247) |
| BOP1 | NM_015201 | 2245.06 (122.236) | 4160.73 (40.8753) | 2031.1 (230.805) | 2512.24 (285.168) |
| ZNF430 | NM_025189 | 861.884 (67.9676) | 1697.41 (118.514) | 759.675 (63.0013) | 880.586 (68.7214) |
| — | NM_0010397 | 445.59 (42.8137) | 804.647 (49.7142) | 415.4 (28.6667) | 496.728 (28.7299) |
| MRPS12 | NM_033363 | 1392.54 (72.6212) | 2515.86 (136.323) | 1339.67 (40.8544) | 1488.43 (270.269) |
| AP3M2 | NM_006803 | 257.292 (3.30065) | 464.113 (50.0096) | 236.736 (5.83496) | 285.819 (31.8464) |
| C9orf80 | NM_021218 | 863.772 (45.3441) | 1694 (80.1222) | 730.994 (39.6039) | 902.518 (80.8519) |
| TAF15 | NM_139215 | 538.558 (20.7815) | 997.07 (106.894) | 497.509 (81.7999) | 562.412 (7.73367) |
| CD68 | NM_001251 | 183.881 (5.03466) | 341.656 (45.4141) | 173.104 (7.09524) | 186.139 (7.35918) |
| KRT80 | NM_182507 | 138.377 (7.58335) | 260.921 (30.6729) | 125.369 (7.6081) | 140.903 (8.39136) |
| — | NM_032794 | 1950.57 (171.291) | 3564.15 (429.374) | 1876.13 (41.9164) | 1952.67 (181.853) |
| KCNH6 | NM_030779 | 1368.31 (108.955) | 2568.3 (80.9088) | 1147.53 (94.1997) | 1496.54 (38.337) |
| RALGDS | NM_006266 | 521.958 (6.82149) | 1008.16 (157.097) | 572.425 (31.7986) | 403.295 (62.0558) |
| PTPRA | NM_022575 | 462.011 (31.0868) | 840.06 (67.2975) | 511.354 (64.4164) | 385.451 (43.9261) |
| CREB1 | NM_004379 | 1305.84 (69.3896) | 2568.48 (226.448) | 1000.59 (47.8454) | 1348.69 (149.317) |
| C5orf28 | NM_022483 | 458.444 (34.0554) | 825.244 (31.4418) | 384.359 (21.1475) | 462.812 (46.3122) |
| — | XM_934471 | 1437.48 (26.475) | 746.847 (27.6679) | 1788.18 (110.515) | 1738.13 (208.474) |
| SLC45A4 | NM_0010804 | 402.498 (15.6864) | 209.975 (10.9315) | 520.706 (57.322) | 442.386 (53.7131) |
| SEPHS1 | NM_012247 | 860.521 (16.7016) | 476.97 (44.8614) | 883.844 (80.149) | 1031.62 (105.754) |
| ACTB | NM_001101 | 10815.9 (479.667) | 5946.66 (679.567) | 11751.7 (860.651) | 11823.5 (936.38) |
| CCND3 | NM_001760 | 489.452 (55.1949) | 1241.36 (237.061) | 460.269 (59.8004) | 430.081 (47.6308) |
| SLC25A19 | NM_021734 | 253.47 (12.8474) | 618.118 (49.647) | 240.254 (41.5505) | 232.673 (17.586) |
| AK3L1 | NM_203464 | 544.878 (24.5012) | 275.404 (19.9062) | 576.921 (24.8178) | 605.066 (40.2727) |

TABLE 8-continued

| GeneID | Gene Identifier | sh-Ctrl Mean (SEM) | sh-Ctrl + aza Mean (SEM) | sh-3B Mean (SEM) | sh-3B + aza Mean (SEM) |
|---|---|---|---|---|---|
| IMPDH1 | NM_000883 | 582.502 (22.3637) | 1363.42 (30.4738) | 507.834 (19.3847) | 569.233 (81.5356) |
| CHEK2 | NM_007194 | 492.743 (31.0931) | 251.733 (18.0197) | 500.733 (31.4659) | 520.257 (37.5423) |
| HYOU1 | NM_006389 | 1153.03 (119.932) | 549.896 (40.0178) | 1382.78 (103.235) | 1158.3 (60.0782) |
| AK3L1 | NM_013410 | 980.139 (57.2917) | 481.15 (47.6765) | 1079.81 (13.9105) | 999.995 (39.8083) |
| — | BX094358 | 599.666 (50.5802) | 281.461 (31.8157) | 667.278 (22.6683) | 659.039 (94.8232) |
| C1orf86 | NM_182533 | 251.229 (13.9134) | 533.087 (74.4334) | 229.234 (14.2575) | 245.736 (23.8781) |
| MAP7D1 | NM_018067 | 1371.85 (132.209) | 3157.76 (452.17) | 1216.65 (44.7534) | 1149.31 (170.452) |
| HYOU1 | NM_006389 | 865.586 (47.386) | 383.335 (9.47112) | 1007.39 (84.7778) | 913.446 (122.877) |
| TXLNA | NM_175852 | 936.501 (27.4623) | 1910.37 (256.891) | 894.549 (60.798) | 906.107 (108.863) |
| NFKB1 | NM_003998 | 300.673 (19.0839) | 607.521 (74.0433) | 277.718 (20.6123) | 297.721 (7.0014) |
| SHCBP1 | NM_024745 | 1938.42 (116.555) | 3692.61 (481.774) | 1701.67 (63.1931) | 1898.21 (218.637) |
| — | NR_003664 | 2841.43 (220.294) | 5238.28 (632.258) | 2662.25 (82.7309) | 2731.19 (362.044) |
| CDAN1 | NM_138477 | 1765.94 (113.223) | 3294.29 (312.647) | 1548.04 (69.084) | 1744.74 (134.1) |
| ORAOV1 | NM_153451 | 446.991 (19.466) | 854.484 (76.8143) | 419.157 (29.5577) | 394.58 (36.3161) |
| GPR162 | NM_019858 | 457.866 (29.1966) | 925.24 (51.7312) | 386.866 (11.7842) | 405.798 (71.5966) |
| AIRE | NM_000383 | 1516.29 (138.047) | 2957.94 (314.545) | 1232.05 (56.2433) | 1482.29 (120.501) |
| FKTN | NM_006731 | 1575.55 (192.955) | 2943.61 (148.645) | 1418.27 (92.8426) | 1480.52 (97.1884) |
| MCM8 | NM_032485 | 690.311 (44.0713) | 1333.15 (30.3208) | 563.305 (17.7516) | 662.605 (132.367) |
| LEFTY1 | NM_020997 | 645.704 (52.3116) | 413.557 (106.359) | 523.897 (56.6491) | 1546.63 (101.508) |
| DPPA3 | NM_199286 | 1051.22 (71.5755) | 402.207 (56.1174) | 1235.55 (101.523) | 1088 (132.733) |
| VWCE | NM_152718 | 195.714 (15.7178) | 370.499 (37.4416) | 155.918 (3.4529) | 184.946 (20.9542) |
| GDF3 | NM_020634 | 4362.55 (121.48) | 1597.41 (470.762) | 5437.74 (299.863) | 4548.55 (479.286) |
| MKNK2 | NM_017572 | 672.762 (30.7392) | 1218.07 (89.1006) | 598.786 (16.2613) | 583.679 (75.9408) |
| GDF15 | NM_004864 | 1098.83 (68.7075) | 1811.42 (200.266) | 958.222 (30.7986) | 579.394 (57.8051) |
| — | CX782759 | 2608.16 (266.799) | 599.626 (158.493) | 3675.25 (85.782) | 3118.41 (620.976) |
| ATP5H | NM_006356 | 3327.25 (283.791) | 1827.42 (90.2969) | 3561.9 (195.789) | 3302.52 (260.963) |
| SMPDL3B | NM_014474 | 266.875 (11.0095) | 147.882 (11.4625) | 320.805 (9.60331) | 219.611 (20.6863) |
| C1orf172 | NM_152365 | 280.722 (19.8091) | 155.416 (5.65074) | 290.419 (8.1623) | 263.604 (8.16459) |
| — | AF038185 | 395.983 (22.5518) | 219.816 (26.63) | 408.449 (23.5231) | 363.06 (23.0498) |
| AK3L1 | AK026966 | 1454.48 (116.009) | 740.197 (109.271) | 1612.36 (109.83) | 1409.29 (120.185) |
| VAMP1 | NM_014231 | 311.535 (19.0572) | 166.626 (10.1525) | 354.1 (9.19031) | 267.249 (16.4762) |
| GRM4 | NM_000841 | 500.783 (63.1581) | 236.702 (14.4499) | 674.108 (60.561) | 443.133 (80.5622) |
| FAM162B | NM_0010854 | 1434.09 (53.7361) | 761.084 (74.6928) | 1477.23 (46.6045) | 1355.19 (160.803) |
| IDH1 | NM_005896 | 973.775 (33.3478) | 463.433 (50.2485) | 1159.73 (86.8218) | 951.536 (134.919) |
| EPB41L2 | NM_001431 | 522.607 (22.3674) | 280.879 (13.5011) | 573.757 (11.2326) | 445.729 (8.23489) |
| GSTM2 | NM_000848 | 917.059 (25.6169) | 482.815 (55.0295) | 1068.59 (20.8038) | 740.445 (78.7635) |
| SLC23A2 | NM_203327 | 382.564 (18.1789) | 208.577 (15.8692) | 418.617 (21.182) | 305.409 (9.88966) |
| ZNF423 | NM_015069 | 355.538 (18.1007) | 167.651 (24.6029) | 405.319 (57.3958) | 338.339 (18.1931) |

TABLE 8-continued

| GeneID | Gene Identifier | sh-Ctrl Mean (SEM) | sh-Ctrl + aza Mean (SEM) | sh-3B Mean (SEM) | sh-3B + aza Mean (SEM) |
|---|---|---|---|---|---|
| THY1 | NM_006288 | 959.842 (15.155) | 467.59 (15.0043) | 1205.9 (56.4945) | 765.138 (30.0876) |
| DOCK6 | NM_020812 | 360.112 (19.079) | 199.254 (13.1123) | 379.465 (7.3152) | 276.857 (3.41046) |
| CBR3 | NM_001236 | 456.652 (8.38604) | 250.31 (16.1596) | 490.108 (20.2193) | 349.416 (31.5291) |
| FBLN1 | NM_001996 | 1909.15 (128.973) | 1019.54 (50.9345) | 1991.82 (80.5948) | 1551.47 (47.9018) |
| PNPLA6 | NM_006702 | 1204.5 (31.8298) | 590.61 (18.0774) | 1401.97 (54.9305) | 1004.26 (104.767) |
| — | XR_016056 | 586.838 (41.7793) | 307.339 (13.3137) | 593.751 (13.5009) | 497.712 (56.8167) |
| C20orf54 | NM_033409 | 297.112 (25.887) | 156.324 (9.53897) | 324.832 (30.489) | 231.372 (12.9975) |
| SORL1 | NM_003105 | 411.03 (25.902) | 222.532 (8.19) | 425.793 (23.1566) | 318.031 (8.07206) |
| MAP4K1 | NM_0010426 | 484.084 (9.74782) | 241.779 (37.7268) | 520.902 (44.6507) | 408.428 (14.746) |
| SH3GLB2 | NM_020145 | 2057.84 (56.5449) | 1094.76 (1.33113) | 2126.11 (82.9385) | 1605.53 (260.724) |
| SNRPN | NM_005678 | 2902.39 (154.014) | 1305.09 (140.059) | 3764.63 (187.11) | 2391.3 (558.172) |
| 6-Sep | NM_145799 | 276.34 (26.5361) | 135.649 (6.77121) | 294.952 (13.0073) | 235.319 (31.6151) |
| HIBADH | NM_152740 | 473.385 (10.9038) | 245.397 (16.5621) | 497.758 (15.2392) | 369.769 (27.2622) |
| HERC1 | NM_003922 | 502.354 (16.5002) | 269.7 (12.5924) | 542.017 (54.1589) | 365.473 (33.1637) |
| TRAPPC1 | NM_021210 | 2029.62 (36.3887) | 1113.09 (52.292) | 2032.69 (122.439) | 1500.51 (176.114) |
| MCCC1 | NM_020166 | 413.76 (20.5058) | 194.415 (10.0677) | 444.602 (5.8717) | 367.6 (41.5087) |
| AHCYL2 | NM_015328 | 296.899 (12.2076) | 161.711 (9.99277) | 306.323 (15.7635) | 214.792 (15.7122) |
| ITFG1 | NM_030790 | 472.582 (12.4272) | 231.062 (8.68692) | 513.52 (45.9188) | 383.136 (37.0472) |
| HEY2 | NM_012259 | 416.813 (25.3075) | 215.415 (7.82745) | 436.816 (7.76252) | 316.724 (13.6493) |
| DTD1 | NM_080820 | 551.161 (28.9145) | 274.751 (24.3164) | 569.699 (41.3657) | 439.551 (49.123) |
| FTO | NM_0010804 | 305.076 (8.49488) | 160.517 (10.5921) | 312.131 (20.2283) | 222.592 (31.1266) |
| GSTM1 | NM_000561 | 1315.72 (14.9948) | 615.754 (67.3337) | 1565.7 (134.081) | 1010.92 (95.5507) |
| HSD17B4 | NM_000414 | 1141.84 (13.2194) | 511.747 (30.3546) | 1288.26 (22.8959) | 983.536 (42.4656) |
| PLA2G16 | NM_007069 | 2304.75 (47.2614) | 974.632 (90.7276) | 3080.32 (96.8355) | 1835.68 (35.1715) |
| FBLN1 | NM_006486 | 1077.69 (28.0366) | 546.384 (33.0727) | 1268.27 (47.1129) | 717.356 (37.6239) |
| RND2 | NM_005440 | 1039.64 (9.45939) | 466.296 (43.1385) | 1093.2 (44.2267) | 919.058 (15.0542) |
| WARS | NM_173701 | 1189.5 (122.847) | 597.105 (49.3961) | 1317.72 (80.792) | 828.744 (12.233) |
| LSS | NM_002340 | 741.648 (39.7032) | 341.007 (15.8902) | 799.484 (76.5348) | 604.66 (28.6343) |
| SBK1 | NM_0010244 | 1548.35 (49.3897) | 714.199 (110.253) | 1732.46 (46.8177) | 1207.33 (180.919) |
| TMSB15B | NM_194324 | 460.378 (3.24036) | 249.778 (10.5133) | 490.87 (21.1481) | 296.089 (49.1712) |
| GLDC | NM_000170 | 1190.43 (88.6836) | 535.209 (37.971) | 1295.96 (67.6341) | 989.281 (28.8605) |
| DOCK1 | NM_001380 | 281.337 (34.5241) | 139.045 (5.49965) | 312.416 (20.9048) | 194.387 (20.0976) |
| NCOR2 | NM_0010772 | 731.212 (28.1899) | 337.98 (11.1386) | 771.861 (101.413) | 582.161 (18.8144) |
| SNRPN | NM_022806 | 2185.72 (95.3538) | 1024.33 (130.382) | 2370.81 (186.923) | 1659.18 (93.631) |
| ACACA | NM_198839 | 891.416 (101.87) | 486.802 (7.53213) | 894.175 (17.4646) | 575.516 (51.6513) |
| SNRPN | NM_022805 | 5011.83 (406.31) | 2746.18 (209.823) | 5492.35 (274.173) | 3030.07 (342.617) |
| — | DA728582 | 2134.36 (182.6) | 447.086 (116.046) | 2888.37 (188.245) | 2191.3 (179.196) |
| CALY | NM_015722 | 305.828 (21.0008) | 160.91 (21.4627) | 310.581 (31.491) | 200.788 (7.10093) |

TABLE 8-continued

| GeneID | Gene Identifier | sh-Ctrl Mean (SEM) | sh-Ctrl + aza Mean (SEM) | sh-3B Mean (SEM) | sh-3B + aza Mean (SEM) |
|---|---|---|---|---|---|
| KIAA0319L | NM_024874 | 466.54 (19.4002) | 224.266 (7.67042) | 473.013 (44.4962) | 347.668 (15.7843) |
| PBX3 | NM_006195 | 846.397 (30.9436) | 424.492 (37.9115) | 1066.11 (22.2716) | 501.214 (100.2) |
| FADS1 | NM_013402 | 423.234 (55.2345) | 213.868 (9.03868) | 436.388 (3.25931) | 283.591 (16.2501) |
| TMSB15A | NM_021992 | 357.437 (10.559) | 182.078 (17.7951) | 357.981 (10.3168) | 241.329 (2.6976) |
| AFAP1 | NM_198595 | 309.663 (12.4753) | 152.429 (9.8279) | 323.949 (29.0219) | 208.88 (10.5426) |
| FGGY | NM_018291 | 499.753 (24.3555) | 300.23 (39.5424) | 504.751 (14.8296) | 273.097 (16.8093) |
| CXCL12 | NM_199168 | 393.11 (11.6775) | 163.651 (12.4756) | 422.155 (28.0689) | 337.365 (53.5767) |
| SMYD3 | NM_022743 | 238.518 (7.89589) | 119.093 (2.66181) | 250.148 (7.35679) | 152.691 (20.4917) |
| IL27RA | NM_004843 | 491.006 (9.55591) | 249.252 (32.6904) | 533.924 (46.1167) | 298.759 (22.9807) |
| — | XM_0011331 | 390.265 (19.9877) | 187.11 (15.797) | 391.683 (17.0729) | 270.277 (11.3837) |
| MPRIP | NM_201274 | 592.703 (88.7014) | 293.22 (18.3072) | 620.619 (38.8987) | 380.751 (12.2073) |
| CAPZB | NM_004930 | 1424.75 (39.8911) | 599.586 (30.8728) | 1642.38 (95.2792) | 1083.44 (66.4319) |
| TM7SF2 | NM_003273 | 482.585 (28.8732) | 242.179 (7.16121) | 510.652 (19.7183) | 298.69 (38.6311) |
| GPM6B | NM_0010019 | 448.005 (18.8665) | 198.692 (15.8946) | 489.185 (22.5623) | 314.868 (7.33566) |
| SHMT2 | NM_005412 | 2937.92 (150.993) | 1530.93 (61.7206) | 3064.2 (62.0559) | 1686.65 (41.3403) |
| VCX | NM_013452 | 972.585 (62.5585) | 1222.83 (41.2226) | 684.234 (23.4204) | 393.99 (24.18) |
| CTDSPL | NM_005808 | 1818.65 (75.5941) | 663.303 (63.8829) | 2335.99 (45.6331) | 1529.19 (227.917) |
| MAL2 | NM_052886 | 453.358 (15.1232) | 198.618 (1.73661) | 477.035 (31.477) | 319.113 (34.8008) |
| GARNL4 | NM_015085 | 979.079 (54.6139) | 448.445 (20.8836) | 1004.22 (4.97451) | 654.41 (109.911) |
| MTHFD1L | NM_015440 | 859.566 (36.619) | 380.875 (46.8424) | 876.468 (25.3663) | 602.572 (29.6257) |
| ARHGEF10 | NM_014629 | 674.115 (43.3644) | 334.09 (13.8124) | 681.987 (6.88138) | 403.502 (20.5486) |
| C4orf34 | NM_174921 | 623.996 (40.169) | 285.198 (35.9182) | 664.88 (36.5176) | 398.736 (16.9996) |
| NUCB1 | NM_006184 | 7302.75 (193.437) | 3303.41 (105.413) | 7670.65 (449.742) | 4745.35 (783.765) |
| RGS4 | NM_005613 | 419.649 (16.2411) | 188.233 (4.57385) | 532.561 (32.5138) | 236.452 (7.82582) |
| DNAJB6 | NM_058246 | 1977.05 (31.9079) | 794.684 (9.62906) | 2051.02 (132.469) | 1506.85 (133.866) |
| ETV5 | NM_004454 | 1481.06 (178.07) | 650.096 (38.6953) | 1754.87 (156.134) | 881.925 (75.8402) |
| CHFR | NM_018223 | 306.354 (4.0942) | 142.421 (16.4551) | 329.179 (25.0972) | 179.656 (15.902) |
| HIST4H4 | NM_003541 | 502.954 (9.34189) | 218.72 (27.8347) | 526.407 (47.279) | 314.561 (42.669) |
| PACSIN1 | NM_020804 | 470.887 (21.1425) | 216.839 (28.3438) | 503.862 (46.5648) | 268.257 (32.7074) |
| — | XM_933796 | 661.671 (47.8413) | 270.602 (22.9775) | 741.059 (25.5479) | 430.873 (33.5584) |
| VCX2 | NM_016378 | 393.737 (3.76802) | 415.874 (14.5082) | 227.42 (8.92297) | 178.538 (8.62836) |
| CACNA2D2 | NM_006030 | 683.549 (10.8914) | 304.761 (29.9738) | 735.338 (54.988) | 398.095 (49.5916) |
| VCX3A | NM_016379 | 1055.52 (93.2712) | 1237.23 (22.6334) | 721.711 (44.1029) | 405.641 (33.7628) |
| ZSWIM4 | NM_023072 | 904.022 (32.1931) | 393.591 (26.0735) | 917.201 (69.3205) | 558.806 (40.233) |
| IDH1 | NM_005896 | 1833.6 (94.5406) | 668.525 (67.4381) | 1977.85 (169.857) | 1445.11 (58.2904) |
| MID1IP1 | NM_021242 | 1818.8 (92.7157) | 649.056 (125.917) | 1847.26 (144.529) | 1496.95 (182.438) |
| NCOR2 | NM_006312 | 1425.61 (89.021) | 493.089 (42.0838) | 1501.66 (89.0161) | 1205.94 (176.048) |
| PSAT1 | NM_021154 | 4269.73 (79.7447) | 1824.54 (172.122) | 4610.25 (101.787) | 2370.22 (397.638) |

TABLE 8-continued

| GeneID | Gene Identifier | sh-Ctrl Mean (SEM) | sh-Ctrl + aza Mean (SEM) | sh-3B Mean (SEM) | sh-3B + aza Mean (SEM) |
|---|---|---|---|---|---|
| SEMA4D | NM_006378 | 721.688 (20.8639) | 315.221 (18.1267) | 728.04 (35.1323) | 404.578 (16.2735) |
| TSPAN9 | NM_006675 | 2876.8 (55.8154) | 1313.95 (46.5726) | 3005.63 (81.0173) | 1493.67 (107.657) |
| TRAPPC9 | NM_031466 | 252.06 (18.5675) | 104.733 (1.11502) | 268.071 (18.2805) | 145.068 (13.4371) |
| VSNL1 | NM_003385 | 664.082 (30.7605) | 249.848 (44.0204) | 672.155 (32.0412) | 462.603 (55.167) |
| ABR | NM_001092 | 835.171 (41.5548) | 424.634 (7.23567) | 909.061 (87.1419) | 376.941 (61.9078) |
| VCX3B | NM_0010018 | 1231 (92.6352) | 1368.4 (66.1838) | 783.172 (35.0323) | 466.812 (15.3983) |
| F11R | NM_016946 | 431.3 (37.1858) | 182.523 (16.126) | 515.062 (45.3597) | 218.843 (28.9807) |
| PGM1 | NM_002633 | 4966.24 (354.985) | 1814.18 (289.766) | 5511.66 (285.757) | 3256.12 (189.964) |
| CHST13 | NM_152889 | 351.396 (18.6189) | 151.937 (15.635) | 351.594 (15.6055) | 184.993 (15.7897) |
| PQLC3 | NM_152391 | 521.577 (46.8384) | 198.571 (18.4892) | 573.261 (45.012) | 307.634 (20.8777) |
| — | AK056312 | 776.93 (31.7794) | 293.846 (3.36085) | 817.029 (45.8977) | 471.555 (50.7452) |
| PRSS8 | NM_002773 | 2112.48 (19.0924) | 991.013 (119.071) | 2428.58 (326.523) | 925.924 (229.115) |
| DYSF | NM_003494 | 569.946 (83.8977) | 188.291 (9.81529) | 761.688 (27.3465) | 345.371 (27.8583) |
| LRRC33 | NM_198565 | 412.509 (36.7577) | 145.858 (11.6371) | 448.424 (28.5266) | 257.521 (25.0088) |
| RPS6KA2 | NM_0010069 | 338.568 (12.0887) | 141.693 (2.89924) | 348.855 (20.4834) | 170.158 (5.01859) |
| SPSB2 | NM_032641 | 1291.41 (48.0775) | 474.363 (65.5182) | 1376 (136.578) | 738.293 (36.0834) |
| NFE2L3 | NM_004289 | 650.342 (72.4327) | 222.942 (7.91982) | 726.501 (10.0143) | 395.959 (11.552) |
| PEMT | NM_148172 | 1692.24 (34.588) | 595.006 (63.291) | 1715.07 (152.962) | 1036.99 (81.2632) |
| KIF1A | NM_004321 | 373.941 (22.8262) | 160.071 (17.7087) | 453.778 (56.491) | 150.02 (6.34837) |
| CA4 | NM_000717 | 3220.84 (197.035) | 1449.98 (136.284) | 3332.85 (331.796) | 1313.05 (94.4717) |
| TBCD | NM_005993 | 845.006 (89.9793) | 256.961 (24.1779) | 961.182 (94.9638) | 565.581 (82.4481) |
| C1orf115 | NM_024709 | 704.163 (14.4396) | 213.203 (10.4171) | 1051.37 (58.7942) | 380.885 (11.7809) |
| EVL | NM_016337 | 1570.81 (85.9921) | 537.424 (46.5407) | 1572.92 (140.662) | 840.767 (188.037) |
| LHFPL4 | NM_198560 | 738.283 (48.0298) | 215.926 (38.1602) | 768.626 (40.3841) | 515.175 (33.7063) |
| CRMP1 | NM_0010148 | 1094.31 (125.424) | 328.665 (28.6044) | 1159.4 (71.7301) | 628.721 (31.2996) |
| PEX14 | NM_004565 | 476.142 (32.8602) | 250.351 (19.0713) | 468.067 (8.37499) | 423.992 (18.5305) |
| DBC1 | NM_014618 | 365.545 (11.779) | 197.271 (29.3048) | 354.471 (13.5721) | 313.757 (8.33473) |
| SOX2 | NM_003106 | 539.035 (31.9509) | 271.23 (6.7198) | 522.243 (9.67616) | 507.636 (24.1006) |
| SND1 | NM_014390 | 1421.51 (99.7413) | 423.122 (15.4943) | 1455.05 (87.8882) | 806.495 (34.4959) |
| FDFT1 | NM_004462 | 805.077 (38.3506) | 417.59 (36.362) | 773.07 (21.5557) | 705.216 (22.1451) |
| ACSS2 | NM_0010765 | 974.282 (94.4309) | 354.703 (4.33329) | 1004.05 (51.7232) | 406.693 (8.40722) |
| — | XM_926633 | 7288.28 (764.348) | 1782.67 (546.468) | 7638.16 (331.94) | 6671.37 (327.897) |
| TUBB4 | NM_006087 | 498.565 (12.79) | 253.587 (34.9392) | 453.793 (30.3934) | 455.752 (34.2732) |
| HESX1 | NM_003865 | 419.65 (8.89191) | 204.885 (35.5091) | 408.992 (40.7057) | 379.045 (8.16583) |
| SCARB1 | NM_005505 | 849.919 (61.2638) | 433.694 (41.7993) | 840.292 (100.125) | 698.95 (30.5618) |
| APEH | NM_001640 | 1447.5 (62.106) | 720.135 (100.951) | 1437.32 (75.6359) | 1236.16 (58.4171) |
| FLNB | NM_001457 | 1242.38 (10.5224) | 679.266 (13.78) | 1145.24 (27.4122) | 960.275 (79.0905) |
| MAPKAP1 | NM_0010066 | 346.497 (2.56612) | 182.648 (10.1236) | 328.011 (5.01964) | 274.663 (15.2847) |

TABLE 8-continued

| GeneID | Gene Identifier | sh-Ctrl Mean (SEM) | sh-Ctrl + aza Mean (SEM) | sh-3B Mean (SEM) | sh-3B + aza Mean (SEM) |
|---|---|---|---|---|---|
| RNF130 | NM_018434 | 322.054 (18.8413) | 174.702 (16.9091) | 279.985 (16.8807) | 258.36 (6.42364) |
| GAS7 | NM_201433 | 414.79 (10.2688) | 225.598 (9.12015) | 391.312 (28.1223) | 308.927 (29.3185) |
| COMMD1 | NM_152516 | 445.256 (24.8057) | 235.362 (10.6053) | 444.414 (32.5124) | 327.95 (12.1442) |
| NGFRAP1 | NM_206917 | 2057.76 (139.245) | 1121.05 (153.463) | 1932.59 (135.042) | 1522.67 (108.945) |
| TIMP4 | NM_003256 | 793.016 (23.4655) | 389.521 (76.1499) | 782.817 (48.6274) | 657.953 (74.3942) |
| PTOV1 | NM_017432 | 1484.27 (70.0489) | 720.62 (78.3044) | 1479.15 (77.279) | 1244.12 (54.3859) |
| SEMA4B | NM_198925 | 573.74 (35.2603) | 288.428 (10.6589) | 568.203 (22.5904) | 455.134 (8.25516) |
| HINT2 | NM_032593 | 971.979 (56.3941) | 537.794 (42.6859) | 892.845 (37.6007) | 706.883 (68.7372) |
| TPST2 | NM_0010085 | 780.797 (42.1163) | 370.953 (14.9212) | 762.031 (84.005) | 683.535 (26.8071) |
| ADCK1 | NM_020421 | 397.044 (13.7174) | 203.584 (17.465) | 388.575 (3.21619) | 305.179 (9.36751) |
| RCN2 | NM_002902 | 1080.68 (82.9488) | 501.026 (23.0075) | 1080.29 (80.2777) | 957.657 (52.662) |
| SLC16A10 | NM_018593 | 305.552 (20.1356) | 159.709 (9.22618) | 305.354 (18.2496) | 222.7 (2.53837) |
| TCF7L1 | NM_031283 | 261.941 (23.4654) | 144.548 (10.1793) | 250.69 (6.14974) | 182.485 (18.6403) |
| XBP1 | NM_0010795 | 1036.57 (20.4988) | 505.041 (22.979) | 989.597 (72.6231) | 860.839 (38.105) |
| SLC3A2 | NM_0010132 | 1280.66 (11.5483) | 898.448 (18.4527) | 1200.52 (70.2036) | 701.201 (29.0765) |
| PTPLA | NM_014241 | 413.38 (10.7072) | 227.16 (18.0071) | 372.396 (21.1513) | 295.309 (10.1059) |
| DPYSL3 | NM_001387 | 1159.88 (73.238) | 602.964 (93.5883) | 1099.25 (70.367) | 841.778 (36.9212) |
| PPAP2A | NM_176895 | 751.024 (39.8609) | 348.062 (56.1313) | 719.451 (22.3359) | 646.273 (97.3807) |
| P4HB | NM_000918 | 2749.97 (125.612) | 1383.99 (98.3164) | 2662.89 (76.4163) | 2039.07 (61.2652) |
| — | NM_014745 | 469.578 (20.0315) | 379.916 (35.5681) | 379.986 (17.8335) | 246.953 (19.3285) |
| COMMD7 | NM_0010993 | 1747.17 (20.2441) | 915.427 (112.826) | 1644.39 (72.0024) | 1236.98 (59.2224) |
| WDR8 | NM_017818 | 1143.84 (44.3254) | 619.054 (46.655) | 978.712 (52.6508) | 819.149 (114.682) |
| RAB3IP | NM_175624 | 1245.12 (40.0288) | 601.056 (14.5566) | 1151.03 (89.5594) | 976.727 (53.9196) |
| C16orf35 | NM_0010394 | 880.909 (41.862) | 630.186 (19.2875) | 775.347 (60.6431) | 464.104 (42.3892) |
| LDB2 | NM_001290 | 377.137 (14.9497) | 202.228 (10.9641) | 338.037 (12.343) | 259.706 (5.20177) |
| FAM127A | NM_0010781 | 1576.17 (102.165) | 867.222 (32.4288) | 1478.47 (19.1772) | 1016.07 (103.634) |
| NKX3-2 | NM_001189 | 649.944 (46.5789) | 409.938 (20.4919) | 623.505 (32.4385) | 358.543 (48.7135) |
| NANOG | NM_024865 | 1615.23 (73.5148) | 706.99 (177.337) | 1600.86 (42.3966) | 1405.64 (30.283) |
| CLASP1 | NM_015282 | 605.453 (17.2563) | 301.334 (15.6635) | 557.603 (36.0498) | 448.757 (30.5339) |
| FOXN3 | NM_005197 | 606.17 (31.7259) | 274.017 (22.3254) | 567.027 (59.9708) | 518.292 (55.7388) |
| ZBTB46 | NM_025224 | 383.687 (11.0446) | 207.588 (10.5496) | 364.686 (14.8976) | 246.643 (5.7164) |
| JPH3 | NM_020655 | 321.934 (11.9548) | 167.797 (15.7516) | 309.721 (5.40978) | 214.843 (12.5716) |
| PITPNC1 | NM_181671 | 371.834 (14.0322) | 180.093 (18.498) | 337.818 (14.6743) | 287.618 (14.2824) |
| SCNN1A | NM_001038 | 3598.66 (76.1284) | 1925.98 (215.174) | 3323.62 (133.631) | 2384.6 (263.757) |
| TMC6 | NM_007267 | 654.062 (60.0035) | 346.392 (27.6314) | 616.246 (12.4071) | 426.897 (37.9538) |
| SURF6 | NM_006753 | 2636.78 (89.0803) | 1293.98 (200.638) | 2387.46 (158.851) | 1956.16 (70.6573) |
| MYO5C | NM_018728 | 302.027 (12.0445) | 151.991 (17.479) | 296.129 (16.1456) | 203.184 (13.6938) |
| — | XM_373896 | 589.859 (37.4234) | 276.846 (25.577) | 552.891 (35.2481) | 451.855 (42.3931) |

TABLE 8-continued

| GeneID | Gene Identifier | sh-Ctrl Mean (SEM) | sh-Ctrl + aza Mean (SEM) | sh-3B Mean (SEM) | sh-3B + aza Mean (SEM) |
|---|---|---|---|---|---|
| DLL3 | NM_016941 | 232.523 (1.70849) | 120.925 (3.41341) | 222.592 (13.4053) | 150.963 (21.5025) |
| MSRB2 | NM_012228 | 1396.86 (11.5706) | 934.409 (62.4701) | 1374.86 (67.4429) | 698.39 (139.978) |
| ODZ3 | NM_0010804 | 349.868 (28.4296) | 189.247 (8.95038) | 322.48 (25.3981) | 220.124 (11.2373) |
| RASIP1 | NM_017805 | 347.407 (13.2475) | 185.874 (9.8359) | 292.298 (22.588) | 236.587 (17.3224) |
| AGAP1 | NM_014914 | 353.271 (17.2229) | 188.156 (27.7669) | 323.277 (8.8413) | 225.72 (28.09) |
| HIST3H2A | NM_033445 | 526.843 (25.494) | 314.077 (31.9778) | 519.85 (17.296) | 282.379 (22.841) |
| EEF2K | NM_013302 | 349.163 (18.1287) | 243.652 (8.53643) | 263.939 (8.40019) | 192.65 (7.16798) |
| MAPK3 | NM_0010400 | 609.309 (14.5577) | 277.581 (18.9085) | 597.89 (47.3865) | 447.115 (16.1769) |
| LONP1 | NM_004793 | 1638.8 (97.9858) | 779.763 (86.7276) | 1479.27 (86.2817) | 1192.71 (39.4132) |
| PNKP | NM_007254 | 831.729 (4.26174) | 424.886 (41.6178) | 710.512 (30.9148) | 570.846 (48.4605) |
| RALY | NM_007367 | 1856.26 (93.0778) | 833.663 (106.343) | 1781.92 (131.376) | 1409.6 (24.2866) |
| REEP6 | NM_138393 | 1345.98 (33.4733) | 405.813 (72.8188) | 1394.43 (70.0609) | 581.805 (72.3121) |
| KIF1B | NM_015074 | 542.448 (35.7791) | 252.94 (26.1216) | 505.715 (43.3953) | 393.388 (33.1503) |
| GRAMD1A | NM_020895 | 1206.24 (32.8083) | 767.701 (21.5655) | 1157.7 (115.744) | 607.142 (135.356) |
| A4GALT | NM_017436 | 383.719 (16.5381) | 174.249 (15.0753) | 373.184 (38.6043) | 279.705 (25.1945) |
| HK1 | NM_033500 | 6683.15 (406.227) | 3617.1 (255.823) | 5689.74 (359.21) | 4205.36 (402.565) |
| CEBPB | NM_005194 | 1879.94 (86.26) | 1388.19 (46.9408) | 1643.04 (21.9076) | 886.982 (114.836) |
| PIM2 | NM_006875 | 2540.84 (163.345) | 985.879 (212.313) | 2428.25 (108.593) | 2475.84 (156.747) |
| SPRY1 | NM_005841 | 454.596 (42.444) | 248.973 (15.4323) | 380.597 (16.0983) | 278.849 (10.4434) |
| TRPC4AP | NM_015638 | 1461.04 (72.0728) | 633.52 (60.6265) | 1441.31 (107.435) | 1093.15 (51.0764) |
| ACACA | NM_198836 | 935.344 (15.9518) | 443.13 (13.4098) | 878.234 (40.77) | 630.777 (8.71227) |
| GLG1 | NM_012201 | 1660.15 (159.948) | 958.607 (55.8951) | 1493.7 (57.4739) | 913.909 (29.2559) |
| CLIP2 | NM_032421 | 349.177 (16.0507) | 175.136 (10.6462) | 329.234 (28.2097) | 216.273 (16.6972) |
| TCEA2 | NM_198723 | 869.705 (26.668) | 483.559 (9.92594) | 833.261 (14.1672) | 471.659 (80.0798) |
| IL21R | NM_181078 | 290.562 (13.0511) | 154.278 (5.38367) | 289.191 (33.4523) | 161.219 (2.0208) |
| TRPC4AP | NM_015638 | 2008.15 (47.6633) | 1094.19 (81.9314) | 1838.56 (78.9053) | 1137.74 (153.778) |
| SAT1 | NM_002970 | 3796.06 (159.986) | 1895.82 (140.237) | 3399.79 (122.818) | 2411.02 (232.065) |
| MED30 | NM_080651 | 1172.98 (70.6725) | 647.26 (96.0779) | 950.461 (23.4734) | 707.11 (62.9363) |
| GTF3C1 | NM_001520 | 882.777 (97.5792) | 387.976 (32.94) | 862.306 (82.9498) | 626.338 (60.4489) |
| SEMA6B | NM_032108 | 479.639 (40.66) | 218.592 (15.2408) | 457.202 (28.9847) | 327.203 (17.6714) |
| FAF1 | NM_007051 | 400.472 (12.5302) | 209.978 (21.3254) | 307.356 (12.2273) | 266.415 (1.03448) |
| APP | NM_201414 | 662.179 (30.5696) | 326.901 (71.7359) | 645.585 (34.2512) | 393.758 (12.7688) |
| HIST1H2BK | NM_080593 | 2290.03 (111.556) | 1316.1 (296.973) | 2215.91 (63.9799) | 1161.66 (126) |
| GAL | NM_015973 | 2521.57 (179.511) | 1375.17 (65.9664) | 1690.04 (124.262) | 1768.85 (107.733) |
| CD24 | NM_013230 | 4669.38 (145.11) | 1797.88 (594.695) | 4587.26 (301.249) | 4095.34 (392.362) |
| DGKQ | NM_001347 | 427.434 (2.85236) | 247.199 (15.7631) | 348.73 (13.3383) | 236.075 (19.6061) |
| CTNNBIP1 | NM_020248 | 297.729 (27.1809) | 144.946 (24.5867) | 276.99 (17.958) | 181.632 (10.5748) |
| C7orf47 | NM_145030 | 1069.24 (85.5786) | 466.635 (60.3389) | 1006.14 (57.034) | 749.147 (31.4512) |

TABLE 8-continued

| GeneID | Gene Identifier | sh-Ctrl Mean (SEM) | sh-Ctrl + aza Mean (SEM) | sh-3B Mean (SEM) | sh-3B + aza Mean (SEM) |
|---|---|---|---|---|---|
| ROD1 | NM_005156 | 1456.57 (85.5964) | 637.491 (40.522) | 1278.61 (69.3119) | 1065.57 (70.7049) |
| EXTL3 | NM_001440 | 1442.44 (184.937) | 695.163 (39.3411) | 1356.85 (65.92) | 869.111 (22.251) |
| SH2B3 | NM_005475 | 817.718 (13.3932) | 424.579 (12.6314) | 740.494 (71.6359) | 459.878 (11.3685) |
| PPP1R1B | NM_181505 | 999.572 (130.677) | 238.675 (38.5063) | 1059.88 (109.931) | 588.401 (105.412) |
| ANKRD9 | NM_152326 | 1319.07 (61.8728) | 614.423 (76.6807) | 1077.77 (57.5543) | 896.077 (137.822) |
| UNC84B | NM_015374 | 704.769 (25.8509) | 465.92 (69.4915) | 677.926 (45.9495) | 307.131 (34.7257) |
| SLC8A2 | NM_015063 | 337.319 (14.0669) | 166.295 (10.1846) | 256.518 (10.7032) | 221.546 (4.28774) |
| MKRN1 | NM_013446 | 6174.36 (486.027) | 2856.3 (354.036) | 5976.13 (360.922) | 3678.37 (219.342) |
| SRPX | NM_006307 | 420.027 (18.1621) | 222.901 (10.8741) | 382.977 (5.83385) | 221.585 (16.9638) |
| PCDH19 | NM_020766 | 299.075 (15.0696) | 151.727 (3.82729) | 227.237 (6.1737) | 187.553 (3.00266) |
| PCK2 | NM_0010180 | 228.587 (15.6057) | 116.02 (5.55181) | 206.601 (9.1667) | 126.174 (14.2876) |
| LDOC1 | NM_012317 | 1235.49 (48.2718) | 502.418 (38.849) | 1190.66 (76.6487) | 881.126 (34.0954) |
| NDUFS4 | NM_002495 | 653.938 (64.368) | 337.053 (40.4863) | 531.755 (8.05447) | 375.498 (34.4321) |
| LRBA | NM_006726 | 405.497 (30.3601) | 170.16 (7.69475) | 389.291 (8.91048) | 267.501 (9.13418) |
| CXCL16 | NM_022059 | 536.706 (18.7343) | 279.669 (4.34752) | 489.943 (67.1664) | 276.818 (21.6392) |
| FIGNL2 | NM_0010136 | 506.925 (10.6483) | 231.29 (17.8144) | 499.804 (23.4317) | 289.159 (7.68893) |
| HCFC1R1 | NM_0010020 | 1057.79 (52.2383) | 427.673 (56.696) | 908.615 (68.1348) | 798.561 (14.8011) |
| HIST1H2BK | NM_080593 | 676.541 (36.4741) | 332.966 (79.004) | 656.729 (18.5942) | 355.319 (34.8016) |
| NPAS1 | NM_002517 | 423.674 (21.0084) | 201.893 (22.1977) | 409.654 (29.8238) | 227.998 (10.4811) |
| C2orf34 | NM_024766 | 472.099 (18.0673) | 205.5 (17.361) | 450.292 (19.8179) | 286.591 (24.4891) |
| CD248 | NM_020404 | 335.325 (1.25921) | 178.853 (4.47745) | 294.978 (20.1426) | 166.587 (7.92504) |
| — | XM_943677 | 487.988 (17.7474) | 245.788 (11.6205) | 398.176 (15.7767) | 268.065 (10.2895) |
| LPCAT3 | NM_005768 | 911.397 (133.473) | 477.318 (50.7826) | 808.499 (31.2356) | 456.787 (41.8321) |
| RASL11B | NM_023940 | 968.373 (38.6263) | 432.564 (58.424) | 884.106 (21.9077) | 570.022 (95.4167) |
| ADCY1 | NM_021116 | 237.105 (20.0106) | 106.028 (5.53238) | 214.278 (7.11194) | 138.949 (7.30003) |
| EPHA1 | NM_005232 | 1284.12 (54.1861) | 497.427 (49.6354) | 1259.25 (83.8773) | 886.512 (67.98) |
| CYP2F1 | NM_000774 | 244.536 (25.8151) | 126.222 (4.16574) | 184.242 (19.1508) | 134.435 (4.28207) |
| PHC1 | NM_004426 | 2720.66 (66.7563) | 951.052 (89.0349) | 2712.74 (274.358) | 2226.1 (237.773) |
| CYP2S1 | NM_030622 | 1503.21 (66.9035) | 604.679 (17.6869) | 1351.24 (20.6452) | 1003.81 (55.4191) |
| CDH3 | NM_001793 | 1635.27 (150.8) | 651.295 (28.2827) | 1632.05 (123.77) | 1031.14 (58.7941) |
| EVI5L | NM_145245 | 496.469 (47.3006) | 247.813 (13.0532) | 431.965 (42.1126) | 248.688 (13.9658) |
| PDZD4 | NM_032512 | 424.67 (28.3627) | 182.348 (27.1679) | 320.052 (19.7062) | 283.495 (29.8776) |
| DDIT4 | NM_019058 | 1100.05 (62.2814) | 522.11 (37.6206) | 1015.54 (63.9391) | 558.55 (85.7859) |
| DYM | NM_017653 | 539.993 (8.79566) | 217.362 (15.2286) | 496.35 (32.6305) | 332.811 (20.3998) |
| NPTX2 | NM_002523 | 614.863 (32.602) | 367.499 (24.9334) | 464.639 (20.7964) | 279.223 (15.4993) |
| — | XM_932919 | 584.479 (35.0191) | 283.159 (21.4718) | 562.355 (44.871) | 278.004 (20.9993) |
| FCGBP | NM_003890 | 553.143 (23.234) | 247.577 (24.7701) | 546.42 (25.0261) | 279.685 (35.6146) |
| FAM125A | NM_138401 | 1154.73 (69.9518) | 564.523 (3.2198) | 1032.86 (87.5872) | 558.795 (101.827) |

TABLE 8-continued

| GeneID | Gene Identifier | sh-Ctrl Mean (SEM) | sh-Ctrl + aza Mean (SEM) | sh-3B Mean (SEM) | sh-3B + aza Mean (SEM) |
|---|---|---|---|---|---|
| CDC42EP5 | NM_145057 | 457.549 (10.1465) | 219.473 (15.1009) | 385.453 (28.222) | 232.63 (6.3718) |
| SLC22A23 | NM_021945 | 605.956 (43.6872) | 233.534 (29.5754) | 592.846 (13.2156) | 371.628 (4.08754) |
| TMEM145 | NM_173633 | 376.905 (19.3419) | 166.627 (11.9091) | 325.124 (21.4161) | 204.077 (5.97445) |
| UBE2E2 | NM_152653 | 875.56 (40.617) | 347.293 (36.745) | 813.061 (49.8966) | 521.892 (99.0979) |
| FGFRL1 | NM_021923 | 466.589 (25.3847) | 186.89 (4.87305) | 433.114 (31.9797) | 270.468 (8.59658) |
| GPM6B | NM_0010019 | 493.194 (43.4542) | 175.154 (31.3145) | 455.575 (25.9671) | 349.621 (29.8793) |
| RIMS3 | NM_014747 | 416.263 (26.1405) | 176.896 (21.528) | 401.96 (24.9602) | 213.386 (13.8168) |
| FGFR4 | NM_213647 | 437.331 (7.47605) | 157.294 (12.2527) | 395.035 (22.4033) | 300.931 (24.3113) |
| UMODL1 | NM_0010044 | 405.326 (22.3455) | 158.805 (20.8219) | 385.193 (36.5557) | 229.342 (7.69579) |
| MID1 | NM_033290 | 1406.33 (131.655) | 589.8 (71.9698) | 1235.94 (40.8209) | 760.305 (45.3113) |
| EGR1 | NM_001964 | 606.573 (21.6796) | 286.805 (38.4043) | 445.117 (23.7943) | 319.423 (22.2709) |
| BEX5 | NM_0010129 | 257.066 (15.9523) | 126.217 (8.02378) | 185.885 (19.2905) | 130.928 (4.02745) |
| TCL1B | NM_004918 | 351.686 (8.15563) | 153.793 (11.9617) | 343.978 (35.7196) | 165.929 (2.75399) |
| UNC5A | NM_133369 | 296.701 (4.65938) | 131.528 (16.0576) | 247.208 (3.90262) | 149.969 (3.55447) |
| HAGH | NM_005326 | 1187.83 (42.0833) | 489.251 (33.1324) | 1118.29 (22.6526) | 607.684 (112.285) |
| DNASE2 | NM_001375 | 546.328 (37.1456) | 284.64 (1.95312) | 473.172 (57.4402) | 227.812 (12.4744) |
| HIST2H2AA3 | NM_003516 | 634.02 (10.6615) | 280.617 (33.5137) | 589.255 (49.3938) | 292.12 (35.0052) |
| IRX4 | NM_016358 | 397.006 (16.8428) | 184.241 (9.02279) | 359.691 (44.4115) | 174.674 (2.54167) |
| TRIML2 | NM_173553 | 2583.14 (28.7012) | 898.532 (67.0449) | 2292.9 (49.0589) | 1673.82 (70.3956) |
| GPT2 | NM_133443 | 1484.26 (93.1233) | 644.895 (14.611) | 1361.99 (49.3194) | 676.267 (46.2252) |
| MAN1C1 | NM_020379 | 688.359 (16.6671) | 233.5 (46.406) | 671.266 (23.289) | 423.548 (9.38702) |
| SFRP2 | NM_003013 | 454.568 (37.07) | 173.209 (19.0325) | 449.592 (31.7953) | 229.369 (4.9009) |
| YBX2 | NM_015982 | 928.557 (33.8199) | 319.006 (29.2438) | 812.49 (67.2154) | 553.427 (81.2316) |
| NIPSNAP1 | NM_003634 | 855.499 (30.5733) | 328.797 (28.2029) | 635.574 (91.9316) | 470.354 (30.8616) |
| CBS | NM_000071 | 2154.85 (62.9171) | 851.462 (131.522) | 1879.27 (199.044) | 999.879 (241.463) |
| HIST2H2AC | NM_003517 | 676.99 (45.4449) | 273.165 (17.2612) | 582.912 (31.5485) | 308.41 (8.7712) |
| ADM2 | NM_024866 | 719.385 (20.3717) | 288.111 (18.3742) | 699.445 (74.0318) | 307.729 (36.7445) |
| HIST1H1C | NM_005319 | 605.306 (24.3204) | 230.637 (6.76681) | 536.866 (24.5208) | 283.591 (20.9271) |
| CECR1 | NM_177405 | 1496.95 (91.5205) | 454.023 (67.0525) | 1424.21 (79.6452) | 891.612 (21.632) |
| JARID2 | NM_004973 | 2175.8 (144.345) | 696.682 (147.814) | 1893.43 (80.6704) | 1212.35 (128.741) |
| FGFR4 | NM_213647 | 969.273 (103.608) | 281.175 (27.2535) | 858.006 (39.8455) | 643.373 (40.3293) |
| — | NM_0010137 | 905.921 (27.7753) | 324.85 (51.1542) | 749.662 (54.1817) | 428.676 (28.2396) |
| LRP5 | NM_002335 | 760.865 (40.6369) | 279.386 (14.854) | 704.556 (47.2422) | 325.443 (23.8015) |
| ACSS2 | NM_018677 | 1099.11 (83.3748) | 390.438 (10.5592) | 1072.01 (15.349) | 471.877 (41.8142) |
| IMPA2 | NM_014214 | 1286.12 (74.9133) | 397.771 (39.951) | 1131.69 (72.0422) | 705.875 (16.5425) |
| VAMP1 | NM_199245 | 1883.31 (116.075) | 617.976 (53.6642) | 1763.22 (66.269) | 849.7 (113.135) |
| ZCCHC12 | NM_173798 | 531.832 (14.3458) | 271.907 (10.9888) | 259.258 (9.25913) | 222.216 (16.484) |
| DNMT3B | NM_006892 | 1600.19 (103.428) | 746.872 (140.305) | 721.837 (44.9489) | 723.025 (94.1534) |

TABLE 8-continued

| GeneID | Gene Identifier | sh-Ctrl Mean (SEM) | sh-Ctrl + aza Mean (SEM) | sh-3B Mean (SEM) | sh-3B + aza Mean (SEM) |
|---|---|---|---|---|---|
| CMIP | NM_030629 | 1665.7 (121.785) | 412.706 (22.0847) | 1625.51 (96.3091) | 799.291 (199.722) |
| DNMT3B | NM_006892 | 4340.09 (122.204) | 1542.45 (186.451) | 2020.67 (123.448) | 1913.45 (62.6291) |
| C6orf221 | NM_0010173 | 1445.62 (91.2115) | 217.329 (41.6339) | 2074.21 (202.312) | 715.213 (22.6285) |
| ASNS | NM_133436 | 3298.54 (162.046) | 1236.21 (29.8228) | 3086.85 (235.047) | 815.556 (105.419) |
| GMDS | NM_001500 | 1150.67 (48.0716) | 299.245 (4.24516) | 1032.58 (83.9626) | 370.984 (54.3355) |
| PCK2 | NM_004563 | 878.537 (37.6739) | 169.884 (21.9788) | 816.952 (115.516) | 165.849 (4.77928) |
| DLL3 | NM_016941 | 1143.8 (52.5737) | 191.388 (13.4253) | 1049.06 (56.9121) | 252.327 (12.292) |
| DPPA5 | NM_0010252 | 1154.92 (14.5382) | 173.161 (24.5051) | 963.464 (60.6142) | 291.841 (9.99091) |
| KCNK12 | NM_022055 | 1322.42 (70.8269) | 186.264 (3.92932) | 793.294 (96.2082) | 232.052 (24.5617) |

TABLE 9

| Gene Title | Gene ID |
|---|---|
| Discs, large homolog 3 (*Drosophila*) | DLG3 |
| CTD (carboxy-terminal domain, RNA polymerase II, polypeptide A) small phosphatase-like | CTDSPL |
| Tetratricopeptide repeat domain 31 | TTC31 |
| Integrin, beta 5 | ITGB5 |
| PREDICTED: hypothetical protein LOC642945, transcript variant 2 | LOC642945 |
| INO80 complex subunit E | INO80E |
| Rho family GTPase 2 | RND2 |
| MAD2 mitotic arrest deficient-like 2 (yeast) | MAD2L2 |
| Reticulocalbin 2, EF-hand calcium binding domain | RCN2 |
| Transaldolase 1 | TALDO1 |
| Cytidine deaminase | CDA |
| Prostaglandin E synthase 3 (cytosolic) | PTGES3 |
| Hydroxysteroid (17-beta) dehydrogenase 4 | HSD17B4 |
| chromosome 12 open reading frame 32 | — |
| Pim-2 oncogene | PIM2 |
| Ubiquitin specific peptidase 44 | USP44 |
| Arginine-glutamic acid dipeptide (RE) repeats | RERE |
| Lysosomal protein transmembrane 4 beta | LAPTM4B |
| Proteasome (prosome, macropain) activator subunit 1 (PA28 alpha) | PSME1 |
| Adenylate kinase 3-like 1 | AK3L1 |
| PREDICTED: hypothetical LOC642817 (LOC642817), mRNA. | — |
| CD24 molecule | CD24 |
| Protein disulfide isomerase family A, member 6 | PDIA6 |
| ATP synthase, H+ transporting, mitochondrial F0 complex, subunit d | ATP5H |
| Polyhomeotic homolog 1 (*Drosophila*) | PHC1 |
| Intraflagellar transport 52 homolog (Chlamydomonas) | IFT52 |
| Abhydrolase domain containing 12B | ABHD12B |
| Ash2 (absent, small, or homeotic)-like (*Drosophila*) | ASH2L |
| Serine incorporator 2 | SERINC2 |
| Tubulin, beta 4 | TUBB4 |
| Sp8 transcription factor | SP8 |
| DA728582 NT2RM2 cDNA clone NT2RM2002174 5, mRNA sequence | |
| Tyrosylprotein sulfotransferase 2 | TPST2 |
| PREDICTED: similar to Tubulin alpha-2 chain (Alpha-tubulin 2) | |
| X-box binding protein 1 | XBP1 |
| Leucine rich repeat containing 47 | LRRC47 |
| Microsomal glutathione S-transferase 2 | MGST2 |
| Feline sarcoma oncogene | FES |
| INO80 complex subunit D | INO80D |
| Farnesyl-diphosphate farnesyltransferase 1 | FDFT1 |
| Leucine-rich repeats and immunoglobulin-like domains 1 | LRIG1 |
| Prostate tumor overexpressed 1 | PTOV1 |
| Chemokine (C—X—C motif) ligand 12 (stromal cell-derived factor 1) | CXCL12 |
| Succinate-CoA ligase, ADP-forming, beta subunit | SUCLA2 |
| CTP synthase II | CTPS2 |
| WD repeat domain 70 | WDR70 |
| Tubby like protein 4 | TULP4 |
| peptidylprolyl isomerase A processed pseudogene | — |
| Solute carrier family 45, member 4 | SLC45A4 |
| UDP-GlcNAc: betaGal beta-1,3-N-acetylglucosaminyltransferase 1 | B3GNT1 |
| ADP-ribosylation-like factor 6 interacting protein 6 | ARL6IP6 |
| Apolipoprotein B mRNA editing enzyme, catalytic polypeptide-like 3G | APOBEC3G |
| GLI family zinc finger 2 | GLI2 |
| Chromosome 5 open reading frame 13 | C5orf13 |
| mature T-cell proliferation 1 | — |
| SMT3 suppressor of mif two 3 homolog 3 (*S. cerevisiae*) | SUMO3 |
| Nanog homeobox | NANOG |
| Ring finger protein 130 | RNF130 |
| ATP citrate lyase | ACLY |
| SRY (sex determining region Y)-box 2 | SOX2 |
| N-acylaminoacyl-peptide hydrolase | APEH |
| Forkhead box N3 | FOXN3 |
| Lipopolysaccharide-induced TNF factor | LITAF |
| 7-dehydrocholesterol reductase | DHCR7 |
| CHK2 checkpoint homolog (*S. pombe*) | CHEK2 |
| Selenophosphate synthetase 1 | SEPHS1 |
| Methylcrotonoyl-Coenzyme A carboxylase 1 (alpha) | MCCC1 |
| Mediator complex subunit 25 | MED25 |
| Family with sequence similarity 162, member B | FAM162B |
| High-mobility group box 3 | HMGB3 |
| Low density lipoprotein receptor-related protein 4 | LRP4 |
| Spectrin, beta, non-erythrocytic 1 | SPTBN1 |
| Developmental pluripotency associated 2 | DPPA2 |
| Developmental pluripotency associated 3 | DPPA3 |
| Scavenger receptor class B, member 1 | SCARB1 |
| RAB3A interacting protein (rabin3) | RAB3IP |
| Growth differentiation factor 3 | GDF3 |
| Nuclear receptor co-repressor 2 | NCOR2 |
| Protein kinase (cAMP-dependent, catalytic) inhibitor beta | PKIB |

TABLE 9-continued

| Gene Title | Gene ID |
|---|---|
| Septin 6 | 6-Sep |
| Core-binding factor, runt domain, alpha subunit 2; translocated to, 2 | CBFA2T2 |
| Voltage-dependent anion channel 1 | VDAC1 |
| Chromosome 17 open reading frame 63 | C17orf63 |
| Single stranded DNA binding protein 3 | SSBP3 |
| Receptor (G protein-coupled) activity modifying protein 2 | RAMP2 |
| Chromosome 1 open reading frame 172 | C1orf172 |
| DCN1, defective in cullin neddylation 1, domain containing 5 (S. cere | DCUN1D5 |
| Glycine dehydrogenase (decarboxylating) | GLDC |
| HESC3_16_C05.g1_A036 Human embryonic stem cells cDNA clone | — |
| Adenylate kinase 3-like 1 | AK3L1 |
| Proteasome (prosome, macropain) 26S subunit, non-ATPase, 1 | PSMD1 |
| Latrophilin 1 | LPHN1 |
| PREDICTED: hypothetical protein LOC643272 (LOC643272), mRNA | — |
| Hydroxysteroid (17-beta) dehydrogenase 12 | HSD17B12 |
| Phosphatidic acid phosphatase type 2A | PPAP2A |
| Apolipoprotein B mRNA editing enzyme, catalytic polypeptide-like 3G | APOBEC3G |
| Hypoxia up-regulated 1 | HYOU1 |
| Zinc finger protein 423 | ZNF423 |
| Clone 23700 mRNA sequence | — |
| HESX homeobox 1 | HESX1 |
| Secretory carrier membrane protein 5 | SCAMP5 |
| Chromosome 10 open reading frame 76 | C10orf76 |
| PREDICTED: similar to cyclophilin-LC (COAS2) (LOC653505), mRNA | — |
| Isocitrate dehydrogenase 1 (NADP+), soluble | IDH1 |
| Adenylate kinase 3-like 1 | AK3L1 |
| Cingulin-like 1 | CGNL1 |
| Prickle homolog 1 (Drosophila) | PRICKLE1 |
| PREDICTED: membrane-associated ring finger (C3HC4) 3 | — |
| Peroxisomal biogenesis factor 14 | PEX14 |
| Sperm associated antigen 7 | SPAG7 |
| MIDI interacting protein 1 (gastrulation specific G12 homolog (zebrafish) | MID1IP1 |
| Erythrocyte membrane protein band 4.1-like 2 | EPB41L2 |
| TIMP metallopeptidase inhibitor 4 | TIMP4 |
| Akirin 2 | AKIRIN2 |
| PREDICTED: similar to WW domain binding protein 1 (LOC729843) | — |
| Deleted in bladder cancer 1 | DBC1 |
| Selenophosphate synthetase 1 | SEPHS1 |
| Host cell factor C1 regulator 1 (XPO1 dependent) | HCFC1R1 |
| Chromosome 9 open reading frame 140 | C9orf140 |
| Isocitrate dehydrogenase 1 (NADP+), soluble | IDH1 |
| Protein phosphatase 1, regulatory (inhibitor) subunit 16B | PPP1R16B |
| Mitogen-activated protein kinase kinase kinase kinase 1 | MAP4K1 |
| CD276 molecule | CD276 |
| Lysosomal protein transmembrane 4 beta | LAPTM4B |
| Actin, beta | ACTB |
| Malectin | MLEC |
| Hypoxia up-regulated 1 | HYOU1 |
| Scribbled homolog (Drosophila) | SCRIB |
| Transcribed locus | — |

TABLE 10

| Gene Title | Gene ID |
|---|---|
| Chromosome 1 open reading frame 86 | C1orf86 |
| Arylformamidase | AFMID |
| Interleukin 17 receptor B | IL17RB |
| Chromosome 6 open reading frame 153 | C6orf153 |
| DPH2 homolog (S. cerevisiae) | DPH2 |
| Mitochondrial carrier triple repeat 1 | MCART1 |

TABLE 10-continued

| Gene Title | Gene ID |
|---|---|
| Ras homolog gene family, member C | RHOC |
| Chromosome 16 open reading frame 48 | C16orf48 |
| Paternally expressed 3 | PEG3 |
| Limb bud and heart development homolog (mouse) | LBH |
| Phosphoprotein enriched in astrocytes 15 | PEA15 |
| G protein-coupled receptor 177 | GPR177 |
| Connective tissue growth factor | CTGF |
| Cell division cycle 37 homolog (S. cerevisiae) | CDC37 |
| Exportin 5 | XPO5 |
| Leukocyte immunoglobulin-like receptor, subfamily B (with TM and ITIM domains), member 3 | LILRB3 |
| G protein-coupled receptor 177 | GPR177 |
| Cadherin 2, type 1, N-cadherin (neuronal) | CDH2 |
| Ezrin | EZR |
| Sulfotransferase family, cytosolic, 1A, phenol-preferring, member 1 | SULT1A1 |
| Lectin, galactoside-binding, soluble, 7 | LGALS7 |
| Coiled-coil domain containing 85C | CCDC85C |
| Proteasome (prosome, macropain) 26S subunit, ATPase, 1 | PSMC1 |
| GLE1 RNA export mediator homolog (yeast) | GLE1 |
| Cystinosis, nephropathic | CTNS |
| Elastin microfibril interfacer 2 | EMILIN2 |
| Chromosome 8 open reading frame 37 | C8orf37 |
| Potassium voltage-gated channel, subfamily H (eag-related), member 6 | KCNH6 |
| WD repeat containing, antisense to TP53 | WRAP53 |
| Pleckstrin homology domain containing, family F (with FYVE domain) member 1 | PLEKHF1 |
| G protein-coupled receptor 162 | GPR162 |
| Solute carrier family 7 (cationic amino acid transporter, y+ system), member 5 | SLC7A5 |
| Suppressor of cytokine signaling 2 | SOCS2 |
| Adaptor-related protein complex 3, mu 2 subunit | AP3M2 |
| Chymotrypsin-like | CTRL |
| TAF15 RNA polymerase II, TATA box binding protein (TBP)-associated factor, 68 kDa | TAF15 |
| Transportin 1 | TNPO1 |
| Inositol 1,4,5-triphosphate receptor interacting protein | ITPRIP |
| Coiled-coil domain containing 102A | CCDC102A |
| SPANX family, member D | SPANXD |
| Serpin peptidase inhibitor, Clade E (nexin, plasminogen activator inhibitor type 1), member 1 | SERPINE1 |
| Neuron derived neurotrophic factor | NENF |
| SERTA domain containing 1 | SERTAD1 |
| Fanconi anemia, complementation group G | FANCG |
| PREDICTED: similar to Sorbitol dehydrogenase (L-iditol 2-dehydrogenase) (LOC653381), mRNA. | — |
| Trafficking protein particle complex 2-like | TRAPPC2L |
| solute carrier family 44, member 4 | — |
| Forkhead box O3 | FOXO3 |
| CXXC finger 1 (PHD domain) | CXXC1 |
| G protein-coupled receptor 177 | GPR177 |
| PRKR interacting protein 1 (IL11 inducible) | PRKRIP1 |
| NFKB repressing factor | NKRF |
| Chromosome 12 open reading frame 45 | C12orf45 |
| Testis expressed 10 | TEX10 |
| Gem (nuclear organelle) associated protein 4 | GEMIN4 |
| PREDICTED: chromosome 17 open reading frame 68 (C17orf68), mRNA. | — |
| K(lysine) acetyltransferase 2A | KAT2A |
| Similar to hCG38149 | LOC728715 |
| CKLF-like MARVEL transmembrane domain containing 3 | CMTM3 |
| Retinitis pigmentosa 9 (autosomal dominant) | RP9 |
| Dual adaptor of phosphotyrosine and 3-phosphoinositides | DAPP1 |
| ATP-binding cassette, sub-family F (GCN20), member 1 | ABCF1 |
| Budding uninhibited by benzimidazoles 3 homolog (yeast) | BUB3 |
| G protein-coupled estrogen receptor 1 | GPER |
| UTP23, small subunit (SSU) processome component, homolog (yeast) | UTP23 |
| F-box protein 6 | FBXO6 |
| Hairy and enhancer of split 1, (Drosophila) | HES1 |

TABLE 10-continued

| Gene Title | Gene ID |
|---|---|
| calcium binding protein P22 pseudogene (LOC729603) on chromosome 6. | — |
| Kruppel-like factor 6 | KLF6 |
| Mucolipin 3 | MCOLN3 |
| TraB domain containing | TRABD |
| Eukaryotic translation initiation factor 2C, 2 | EIF2C2 |
| hypothetical protein LOC641737 (FLJ44124), mRNA. | — |
| phosphatidylinositol-5-phosphate 4-kinase, type II, beta | — |
| Fukutin | FKTN |
| keratin associated protein 21-1 | — |
| hypothetical protein LOC642947 (LOC642947), mRNA. | — |
| SERTA domain containing 2 | SERTAD2 |
| Splicing factor 3a, subunit 3, 60 kDa | SF3A3 |
| Cardiotrophin-like cytokine factor 1 | CLCF1 |
| breast cancer metastasis suppressor 1 | — |
| KIAA0101 | KIAA0101 |
| Serine palmitoyltransferase, long chain base subunit 1 | SPTLC1 |
| TRM1 tRNA methyltransferase 1 homolog (S. cerevisiae) | TRMT1 |
| Etoposide induced 2.4 mRNA | EI24 |
| PR domain containing 4 | PRDM4 |
| Hairy and enhancer of split 2 (Drosophila) | HES2 |
| CDC-like kinase 3 | CLK3 |
| Myoferlin | MYOF |
| CGRP receptor component | CRCP |
| Zinc finger homeobox 3 | ZFHX3 |
| Colony stimulating factor 1 receptor | CSF1R |
| Ral guanine nucleotide dissociation stimulator | RALGDS |
| Zinc finger protein 689 | ZNF689 |
| Cathepsin B | CTSB |
| Hepatocyte growth factor-regulated tyrosine kinase substrate | HGS |
| PREDICTED: similar to activating signal cointegrator 1 complex subunit 3-like 1 (LOC650909), mRNA. | — |
| Zinc finger, AN1-type domain 2A | ZFAND2A |
| Bone marrow stromal cell antigen 2 | BST2 |
| GA binding protein transcription factor, beta subunit 2 | GABPB2 |
| Runt-related transcription factor 3 | RUNX3 |
| Rho guanine nucleotide exchange factor (GEF) 19 | ARHGEF19 |
| Mediator complex subunit 19 | MED19 |
| Annexin A1 | ANXA1 |
| STEAP family member 3 | STEAP3 |
| CDNA clone IMAGE: 5261213 | — |
| Caudal type homeobox 1 | CDX1 |
| Interleukin 2 receptor, beta | IL2RB |
| Inositol 1,4,5-triphosphate receptor, type 3 | ITPR3 |
| Gap junction protein, gamma 1, 45 kDa | GJC1 |
| Ubiquitin specific peptidase 3 | USP3 |
| Transmembrane protein 150 | TMEM150 |
| Nuclear factor of kappa light polypeptide gene enhancer in B-cells 1 | NFKB1 |
| Ribosomal protein L7-like 1 | RPL7L1 |
| Family with sequence similarity 65, member B | FAM65B |
| E74-like factor 3 (ets domain transcription factor, epithelial-specific ) | ELF3 |
| Integrator complex subunit 10 | INTS10 |
| ADP-ribosylation factor-like 16 | ARL16 |
| Zinc finger protein 652 | ZNF652 |
| Calcium and integrin binding 1 (calmyrin) | CIB1 |
| Taxilin alpha | TXLNA |
| Keratin 80 | KRT80 |
| PREDICTED: proteasome (prosome, macropain) 26S subunit, non-ATPase, 12 (PSMD12), mRNA. | — |
| Phosphodiesterase 4C, cAMP-specific (phosphodiesterase E1 dunce homolog, Drosophila) | PDE4C |
| Minichromosome maintenance complex component 8 | MCM8 |
| CDNA clone IMAGE: 5312122 | — |
| Variable charge, X-linked 2 | VCX2 |
| Keratin associated protein 6-3 | KRTAP6-3 |
| Alkaline phosphatase, placental (Regan isozyme) | ALPP |
| Galactosidase, alpha | GLA |
| Zinc finger protein 682 | ZNF682 |
| Interferon stimulated exonuclease gene 20 kDa | ISG20 |
| Plasminogen activator, urokinase | PLAU |
| SHC SH2-domain binding protein 1 | SHCBP1 |
| Cyclin D1 | CCND1 |
| Poly (ADP-ribose) polymerase family, member 3 | PARP3 |
| Variable charge, X-linked 2 | VCX2 |
| PREDICTED: phosphoglycerate mutase family member 5 (PGAM5), mRNA. | — |
| Apoptosis enhancing nuclease | AEN |
| DnaJ (Hsp40) homolog, subfamily C, member 28 | DNAJC28 |
| Cell division cycle 20 homolog (S. cerevisiae) | CDC20 |
| PREDICTED: hypothetical LOC126435 (LOC126435), mRNA | — |
| similar to envelope protein (LOC113386), mRNA. | — |
| Solute carrier family 25 (mitochondrial thiamine pyrophosphate carrier), member 19 | SLC25A19 |
| Hairy and enhancer of split 4 (Drosophila) | HES4 |
| Syndecan 1 | SDC1 |
| Mitochondrial ribosomal protein S12 | MRPS12 |
| Epithelial membrane protein 3 | EMP3 |
| Chromosome 11 open reading frame 17 | C11orf17 |
| BTG family, member 2 | BTG2 |
| Cation channel, sperm associated 2 | CATSPER2 |
| Similar to meteorin, glial cell differentiation regulator-like | LOC653506 |
| Signal recognition particle receptor, B subunit | SRPRB |
| Cysteine-rich, angiogenic inducer, 61 | CYR61 |
| Ring finger protein 1 | RING1 |
| DMC1 dosage suppressor of mck1 homolog, meiosis-specific homologous recombination (yeast) | DMC1 |
| Chemokine (C-C motif) receptor 7 | CCR7 |
| Frizzled homolog 2 (Drosophila) | FZD2 |
| Arginine vasopressin-induced 1 | AVPI1 |
| MAP7 domain containing 1 | MAP7D1 |
| Oral cancer overexpressed 1 | ORAOV1 |
| Prostate cancer susceptibility candidate | PRAC |
| Myoferlin | MYOF |
| MAP kinase interacting serine/threonine kinase 2 | MKNK2 |
| Chromosome X open reading frame 40A | CXorf40A |
| Cyclin-dependent kinase 10 | CDK10 |
| G protein-coupled receptor 56 | GPR56 |
| Integrator complex subunit 12 | INTS12 |
| DNL-type zinc finger | DNLZ |
| Pyrophosphatase (inorganic) 2 | PPA2 |
| SID1 transmembrane family, member 2 | SIDT2 |
| Growth arrest and DNA-damage-inducible, alpha | GADD45A |
| AHNAK nucleoprotein | AHNAK |
| Tumor protein p63 regulated 1-like | TPRG1L |
| Death effector domain containing 2 | DEDD2 |
| Polyribonucleotide nucleotidyltransferase 1 | PNPT1 |
| Trafficking protein particle complex 2-like | TRAPPC2L |
| Translocase of inner mitochondrial membrane 22 homolog (yeast) | TIMM22 |
| GATA binding protein 2 | GATA2 |
| Immediate early response 3 | IER3 |
| Keratin associated protein 21-2 | KRTAP21-2 |
| NACC family member 2, BEN and BTB (POZ) domain containing | NACC2 |
| Family with sequence similarity 116, member B | FAM116B |
| Variable charge, X-linked 2 | VCX2 |
| Tumor necrosis factor receptor superfamily, member 12A | TNFRSF12A |
| succinate dehydrogenase complex, subunit A, flavoprotein pseudogene 1 (SDHALP1) on chromosome 3. | — |
| Rab9 effector protein with kelch motifs | RABEPK |
| Carboxymethylenebutenolidase homolog (Pseudomonas) | CMBL |
| OAF homolog (Drosophila) | OAF |
| CAMP responsive element binding protein 1 | CREB1 |
| Chromosome 8 open reading frame 33 | C8orf33 |
| Growth differentiation factor 15 | GDF15 |
| Bone morphogenetic protein 4 | BMP4 |
| Interleukin 10 | IL10 |
| Leptin receptor | LEPR |

TABLE 10-continued

| Gene Title | Gene ID |
|---|---|
| E4F transcription factor 1 | E4F1 |
| Zinc fingers and homeoboxes 2 | ZHX2 |
| Tumor suppressing subtransferable candidate 4 | TSSC4 |
| Notch homolog 1, translocation-associated (Drosophila) | NOTCH1 |
| NDRG family member 2 | NDRG2 |
| Transmembrane protein 41B | TMEM41B |
| Chromosome 7 open reading frame 27 | C7orf27 |
| Suppressor of cytokine signaling 2 | SOCS2 |
| Cysteine-rich PDZ-binding protein | CRIPT |
| G protein-coupled receptor 56 | GPR56 |
| Phenylalanyl-tRNA synthetase, beta subunit | FARSB |
| RNA terminal phosphate cyclase-like 1 | RCL1 |
| Histidyl-tRNA synthetase | HARS |
| Cathepsin L2 | CTSL2 |
| Family with sequence similarity 53, member C | FAM53C |
| Cysteine-serine-rich nuclear protein 1 | CSRNP1 |
| Serrate RNA effector molecule homolog (Arabidopsis) | SRRT |
| Leukocyte immunoglobulin-like receptor, subfamily B (with TM and ITIM domains), member 1 | LILRB1 |
| THO complex 5 | THOC5 |
| Transgelin | TAGLN |
| Activin A receptor, type IB | ACVR1B |
| Tripartite motif-containing 8 | TRIM8 |
| Small nuclear RNA activating complex, polypeptide 4, 190 kDa | SNAPC4 |
| zinc finger protein 486 | — |
| Diacylglycerol lipase, beta | DAGLB |
| Transmembrane and ubiquitin-like domain containing 2 | TMUB2 |
| Cyclin D3 | CCND3 |
| Paired-like homeodomain 1 | PITX1 |
| Chromosome 5 open reading frame 28 | C5orf28 |
| Chemokine (C-C motif) receptor 6 | CCR6 |
| tubulin, alpha pseudogene | — |
| Serine hydroxymethyltransferase 1 (soluble) | SHMT1 |
| Williams Beuren syndrome chromosome region 19 pseudogene (LOC389517) on chromosome 7. | — |
| Immediate early response 5 | IER5 |
| Variable charge, X-linked 3B | VCX3B |
| hypothetical protein LOC649598 (FLJ46309), mRNA. | — |
| Ring finger and WD repeat domain 3 | RFWD3 |
| Zinc finger, RAN-binding domain containing 2 | ZRANB2 |
| Variable charge, X-linked | VCX |
| PREDICTED: G-protein signalling modulator 1 (AGS3-like, C. elegans) (GPSM1), mRNA. | — |
| Histone deacetylase 1 | HDAC1 |
| Neuroblastoma breakpoint family, member 10 | NBPF10 |
| Chromosome X open reading frame 40B | CXorf40B |
| CD68 molecule | CD68 |
| REX4, RNA exonuclease 4 homolog (S. cerevisiae) | REXO4 |
| Coiled-coil domain containing 21 | CCDC21 |
| PREDICTED: similar to Keratin, type I cytoskeletal 14 (Cytokeratin-14) (CK-14) (Keratin-14) (K14) (LOC400578), mRNA. | — |
| CD44 molecule (Indian blood group) | CD44 |
| GLI pathogenesis-related 2 | GLIPR2 |
| Interferon regulatory factor 7 | IRF7 |
| Interleukin 18 (interferon-gamma-inducing factor) | IL18 |
| TAR (HIV-1) RNA binding protein 2 | TARBP2 |
| NLR family, pyrin domain containing 8 | NLRP8 |
| Chromodomain helicase DNA binding protein 8 | CHD8 |
| Cyclin-dependent kinase inhibitor 1A (p21, Cip1) | CDKN1A |
| Lectin, galactoside-binding, soluble, 7B | LGALS7B |
| WD repeat domain 75 | WDR75 |
| Protein tyrosine phosphatase, receptor type, A | PTPRA |
| MAP/microtubule affinity-regulating kinase 2 | MARK2 |
| IMP (inosine monophosphate) dehydrogenase 1 | IMPDH1 |
| Chromosome 10 open reading frame 58 | C10orf58 |
| Transcribed locus | — |
| Coagulation factor II (thrombin) receptor | F2R |
| Keratin 17 | KRT17 |
| Block of proliferation 1 | BOP1 |
| Adrenomedullin | ADM |
| Mediator complex subunit 10 | MED10 |
| Four jointed box 1 (Drosophila) | FJX1 |
| 28S ribosomal RNA (LOC100008589). | — |
| Solute carrier family 9 (sodium/hydrogen exchanger), member 3 regulator 1 | SLC9A3R1 |
| Protein inhibitor of activated STAT, 4 | PIAS4 |
| OCIA domain containing 1 | OCIAD1 |
| ankyrin repeat domain 30B | — |
| Sequestosome 1 | SQSTM1 |
| Transcription factor A, mitochondrial | TFAM |
| Pseudouridylate synthase 1 | PUS1 |
| T-box 3 | TBX3 |
| Heat shock 70 kDa protein 1A | HSPA1A |
| Smith-Magenis syndrome chromosome region, candidate 7-like | SMCR7L |
| PREDICTED: similar to Nuclear envelope pore membrane protein POM 121 (Pore membrane protein of 121 kDa) (P145) (LOC730316), mRNA. | — |
| Nasal embryonic LHRH factor | NELF |
| NUAK family, SNF1-like kinase, 2 | NUAK2 |
| Chemokine (C—X—C motif) ligand 14 | CXCL14 |
| Prohibitin | PHB |
| Methylphosphate capping enzyme | MEPCE |
| Upstream transcription factor 1 | USF1 |
| Bromodomain and PHD finger containing, 3 | BRPF3 |
| Forkhead box O4 | FOXO4 |
| Tetratricopeptide repeat domain 4 | TTC4 |
| E74-like factor 4 (ets domain transcription factor) | ELF4 |
| Dual specificity phosphatase 14 | DUSP14 |
| Regulatory solute carrier protein, family 1, member 1 | RSC1A1 |
| Ubiquitin-conjugating enzyme E2, J1 (UBC6 homolog, yeast) | UBE2J1 |
| Exosome component 10 | EXOSC10 |
| Ribosomal protein L29 | RPL29 |
| Neuroblastoma breakpoint family, member 10 | NBPF10 |
| proteasome (prosome, macropain) inhibitor subunit 1 (PI31) | — |
| Peroxisomal proliferator-activated receptor A interacting complex 285 | PRIC285 |
| PREDICTED: similar to Zinc finger protein 418 (LOC400721), mRNA. | — |
| Baculoviral IAP repeat-containing 5 | BIRC5 |
| Methyltransferase like 1 | METTL1 |
| IMP4, U3 small nucleolar ribonucleoprotein, homolog (yeast) | IMP4 |
| Claudin 10 | CLDN10 |
| Bromodomain containing 9 | BRD9 |
| Pleckstrin homology domain containing, family G (with RhoGef domain) member 3 | PLEKHG3 |
| Peter pan homolog (Drosophila) | PPAN |
| CUE domain containing 1 | CUEDC1 |
| Von Willebrand factor C and EGF domains | VWCE |
| Nuclear factor (erythroid-derived 2), 45 kDa | NFE2 |
| Autoimmune regulator | AIRE |
| MAS-related GPR, member F | MRGPRF |
| Mannose-6-phosphate receptor binding protein 1 | M6PRBP1 |
| Hairy and enhancer of split 2 (Drosophila) | HES2 |
| Variable charge, X-linked 3A | VCX3A |
| Growth arrest and DNA-damage-inducible, alpha | GADD45A |
| ATPase, Ca++ transporting, plasma membrane 4 | ATP2B4 |
| Mediator complex subunit 20 | MED20 |
| Thymine-DNA glycosylase | TDG |
| Chromosome 9 open reading frame 80 | C9orf80 |
| CD68 molecule | CD68 |
| Glucosamine-6-phosphate deaminase 1 | GNPDA1 |
| SRY (sex determining region Y)-box 15 | SOX15 |
| Chromosome 16 open reading frame 93 | C16orf93 |
| NMD3 homolog (S. cerevisiae) | NMD3 |
| Spastic paraplegia 7 (pure and complicated autosomal recessive) | SPG7 |
| Collagen, type XVII, alpha 1 | COL17A1 |
| PREDICTED: similar to Keratin, type I cytoskeletal 16 (Cytokeratin-16) (CK-16) (Keratin-16) (K16) (MGC102966), mis TNA. | — |
| Solute carrier family 16, member 12 (monocarboxylic acid transporter 12) | SLC16A12 |

TABLE 10-continued

| Gene Title | Gene ID |
| --- | --- |
| Casein kinase 1, delta | CSNK1D |
| Solute carrier family 2 (facilitated glucose transporter), member 1 | SLC2A1 |
| Congenital dyserythropoietic anemia, type I | CDAN1 |
| Zinc finger protein 430 | ZNF430 |
| Chromosome 11 open reading frame 82 | C11orf82 |
| SPRY domain containing 5 | SPRYD5 |
| H2A histone family, member Y | H2AFY |
| Solute carrier family 2 (facilitated glucose transporter), member 3 | SLC2A3 |
| TRNA splicing endonuclease 34 homolog (*S. cerevisiae*) | TSEN34 |
| NEDD4 binding protein 2 | N4BP2 |
| chromosome 14 open reading frame 80 | — |
| Cingulin | CGN |
| olfactory receptor, family 7, subfamily E, member 156 pseudogene | — |
| Cellular retinoic acid binding protein 2 | CRABP2 |

TABLE 11

| Gene Title | Gene ID |
| --- | --- |
| Zinc finger protein 337 | ZNF337 |
| Basic leucine zipper nuclear factor 1 | BLZF1 |
| NOP58 ribonucleoprotein homolog (yeast) | NOP58 |
| Neurofilament, heavy polypeptide | NEFH |
| Asparagine synthetase domain containing 1 | ASNSD1 |
| Nuclear RNA export factor 1 | NXF1 |
| Family with sequence similarity 175, member B | FAM175B |
| FAST kinase domains 3 | FASTKD3 |
| Four and a half LIM domains 2 | FHL2 |
| Chromosome 9 open reading frame 6 | C9orf6 |
| Leucine zipper protein 1 | LUZP1 |
| Programmed cell death 5 | PDCD5 |
| PREDICTED: hypothetical LOC400879, transcript variant 2 (LOC400879), mRNA. | — |
| PRP40 pre-mRNA processing factor 40 homolog A (*S. cerevisiae*) | PRPF40A |
| NOP56 ribonucleoprotein homolog (yeast) | NOP56 |
| DnaJ (Hsp40) homolog, subfamily C, member 9 | DNAJC9 |
| C-myc-P64 mRNA, initiating from promoter P0, (HLmyc3.1) partial cds | — |
| Anaphase promoting complex subunit 13 | ANAPC13 |
| Dual-specificity tyrosine-(Y)-phosphorylation regulated kinase 2 | DYRK2 |
| Carcinoembryonic antigen-related cell adhesion molecule 1 (biliary glycoprotein) | CEACAM1 |
| RNA binding motif protein 22 | RBM22 |
| Bromodomain and PHD finger containing, 1 | BRPF1 |
| C-myc-P64 mRNA, initiating from promoter P0, (HLmyc3.1) partial cds | — |
| RNA methyltransferase like 1 | RNMTL1 |
| Ankyrin repeat and SOCS box-containing 9 | ASB9 |
| Small nucleolar RNA, C/D box 15B | SNORD15B |
| Interferon gamma receptor 1 | IFNGR1 |
| TSR1, 20S rRNA accumulation, homolog (*S. cerevisiae*) | TSR1 |
| Guanine nucleotide binding protein-like 3 (nucleolar)-like | GNL3L |
| Bromodomain containing 8 | BRD8 |
| Heat shock 105 kDa/110 kDa protein 1 | HSPH1 |
| sideroflexin 4 | — |
| BCL2-associated athanogene 3 | BAG3 |
| Calcium binding tyrosine-(Y)-phosphorylation regulated | CABYR |
| Dynein, light chain, LC8-type 2 | DYNLL2 |
| Family with sequence similarity 123B | FAM123B |
| Annexin A2 | ANXA2 |
| Methyltransferase like 13 | METTL13 |
| Metallothionein 1E | MT1E |
| Ribosomal L1 domain containing 1 | RSL1D1 |
| Dual specificity phosphatase 5 | DUSP5 |
| Muscleblind-like 3 (*Drosophila*) | MBNL3 |
| Zinc finger protein 14 | ZNF14 |
| Sushi domain containing 2 | SUSD2 |
| Glutamate decarboxylase 1 (brain, 67 kDa) | GAD1 |

TABLE 11-continued

| Gene Title | Gene ID |
| --- | --- |
| Methylmalonic aciduria (cobalamin deficiency) cblC type, with homocystinuria | MMACHC |
| Origin recognition complex, subunit 5-like (yeast) | ORC5L |
| HAUS augmin-like complex, subunit 2 | HAUS2 |
| Hypothetical LOC644422 | LOC644422 |
| Zinc finger, DHHC-type containing 6 | ZDHHC6 |
| PRP4 pre-mRNA processing factor 4 homolog (yeast) | PRPF4 |
| Epstein-Barr virus induced 3 | EBI3 |
| Platelet-derived growth factor receptor, beta polypeptide | PDGFRB |
| G-rich RNA sequence binding factor 1 | GRSF1 |
| Cerberus 1, cysteine knot superfamily, homolog (*Xenopus laevis*) | CER1 |
| Polymerase (RNA) I polypeptide C, 30 kDa | POLR1C |
| Ribonuclease P/MRP 40 kDa subunit | RPP40 |
| Nucleoside phosphorylase | NP |
| Heat shock 70 kDa protein 8 | HSPA8 |
| telomerase RNA component | — |
| Damage-regulated autophagy modulator | DRAM |
| MRNA turnover 4 homolog (*S. cerevisiae*) | MRTO4 |
| Solute carrier family 35, member E1 | SLC35E1 |
| double homeobox A pseudogene 3 | — |
| Metastasis associated 1 family, member 2 | MTA2 |
| Guanine nucleotide binding protein-like 2 (nucleolar) | GNL2 |
| Minichromosome maintenance complex component 4 | MCM4 |
| NUAK family, SNF1-like kinase, 2 | NUAK2 |
| Zinc fingers and homeoboxes 2 | ZHX2 |
| SCO cytochrome oxidase deficient homolog 2 (yeast) | SCO2 |
| N-acetyltransferase 5 (GCN5-related, putative) | NAT5 |
| B cell RAG associated protein | GALNAC4S-6ST |
| Guanine nucleotide binding protein-like 3 (nucleolar) | GNL3 |
| Nucleolar protein family 6 (RNA-associated) | NOL6 |
| Follistatin | FST |
| Peroxisome proliferator-activated receptor gamma, coactivator-related 1 | PPRC1 |
| Prostaglandin E synthase | PTGES |
| Hypothetical protein FLJ40504 | FLJ40504 |
| Mitochondrial GTPase 1 homolog (*S. cerevisiae*) | MTG1 |
| RAE1 RNA export 1 homolog (*S. pombe*) | RAE1 |
| Family with sequence similarity 119, member A | FAM119A |
| Fem-1 homolog a (*C. elegans*) | FEM1A |
| Transcribed locus | — |
| Catenin (cadherin-associated protein), beta 1, 88 kDa | CTNNB1 |
| Non-metastatic cells 6, protein expressed in (nucleoside-diphosphate kinase) | NME6 |
| DNA cross-link repair 1C (PSO2 homolog, *S. cerevisiae*) | DCLRE1C |
| Coilin | COIL |
| AOC3 pseudogene (LOC90586) on chromosome 17. | — |
| Mitochondrial ribosomal protein S11 | MRPS11 |
| B-cell CLL/lymphoma 11A (zinc finger protein) | BCL11A |
| Neuron navigator 2 | NAV2 |
| Small nuclear ribonucleoprotein 25 kDa (U11/U12) | SNRNP25 |
| FOS-like antigen 1 | FOSL1 |
| ADAMTS-like 2 | ADAMTSL2 |
| Polymerase (RNA) I polypeptide C, 30 kDa | POLR1C |
| NOP16 nucleolar protein homolog (yeast) | NOP16 |
| Zinc finger and BTB domain containing 33 | ZBTB33 |
| Chromosome 1 open reading frame 163 | C1orf163 |
| Breast cancer metastasis suppressor 1 | BRMS1 |
| GLI pathogenesis-related 1 like 1 | GLIPR1L1 |
| Sideroflexin 4 | SFXN4 |
| PREDICTED: hypothetical LOC644743 (LOC644743), mRNA. | — |
| Chaperonin containing TCP1, subunit 6A (zeta 1) | CCT6A |
| Polymerase (DNA directed), epsilon 3 (p17 subunit) | POLE3 |
| Ankyrin repeat and SOCS box-containing 9 | ASB9 |
| UTP11-like, U3 small nucleolar ribonucleoprotein, (yeast) | UTP11L |
| Eomesodermin homolog (*Xenopus laevis*) | EOMES |

TABLE 11-continued

| Gene Title | Gene ID |
|---|---|
| Polymerase (RNA) III (DNA directed) polypeptide C (62 kD) | POLR3C |
| Zinc finger protein 207 | ZNF207 |
| G patch domain containing 4 | GPATCH4 |
| Chromosome 10 open reading frame 2 | C10orf2 |
| Vasorin | VASN |
| Resistance to inhibitors of cholinesterase 8 homolog A (*C. elegans*) | RIC8A |
| Wilms tumor 1 interacting protein | — |
| Heat shock protein 90 kDa alpha (cytosolic), class A member 1 | HSP90AA1 |
| Mitochondrial ribosomal protein S17 | MRPS17 |
| Ornithine aminotransferase (gyrate atrophy) | OAT |
| Transmembrane 7 superfamily member 3 | TM7SF3 |
| Williams Beuren syndrome chromosome region 22 | WBSCR22 |
| NOP2 nucleolar protein homolog (yeast) | NOP2 |
| Transmembrane protein 99 | TMEM99 |
| Ornithine decarboxylase 1 | ODC1 |
| Zinc finger protein 816A | ZNF816A |
| Calponin 3, acidic | CNN3 |
| Mitochondrial ribosomal protein S11 | MRPS11 |
| PAK1 interacting protein 1 | PAK1IP1 |
| islet cell autoantigen 1, 69 kDa | — |
| Similar to keratin 8 | LOC647954 |
| V-crk sarcoma virus CT10 oncogene homolog (avian) | CRK |
| Growth differentiation factor 11 | GDF11 |
| DEAD (Asp-Glu-Ala-Asp) box polypeptide 24 | DDX24 |
| Serine/threonine kinase 36, fused homolog (*Drosophila*) | STK36 |
| Collagen, type VII, alpha 1 | COL7A1 |
| Methyltransferase like 13 | METTL13 |
| Choline/ethanolamine phosphotransferase 1 | CEPT1 |
| NOP56 ribonucleoprotein homolog (yeast) | NOP56 |
| DEAD (Asp-Glu-Ala-Asp) box polypeptide 51 | DDX51 |
| M-phase phosphoprotein 10 (U3 small nucleolar ribonucleoprotein) | MPHOSPH10 |
| Chromosome 12 open reading frame 41 | C12orf41 |
| Caspase 3, apoptosis-related cysteine peptidase | CASP3 |
| Exosome component 2 | EXOSC2 |
| CLP1, cleavage and polyadenylation factor I subunit, homolog (*S. cerevisiae*) | CLP1 |
| Proteasome (prosome, macropain) subunit, alpha type, 4 | PSMA4 |
| Ring finger protein 34 | RNF34 |
| Regulatory solute carrier protein, family 1, member 1 | RSC1A1 |
| Zinc finger protein 621 | ZNF621 |
| Nucleolar protein 8 | NOL8 |
| Adipose differentiation-related protein | ADFP |
| Solute carrier family 20 (phosphate transporter), member 1 | SLC20A1 |
| JTV1 gene | JTV1 |
| DIM1 dimethyladenosine transferase 1-like (*S. cerevisiae*) | DIMT1L |
| Zinc finger, NFX1-type containing 1 | ZNFX1 |
| Rho GDP dissociation inhibitor (GDI) beta | ARHGDIB |
| Ribosomal protein L9 | RPL9 |
| Neurotensin | NTS |
| DTW domain containing 2 | DTWD2 |
| Peptidyl-tRNA hydrolase 2 | PTRH2 |
| Caveolin 1, caveolae protein, 22 kDa | CAV1 |
| PREDICTED: hypothetical protein LOC642477, transcript variant 2 (LOC642477), mRNA. | — |
| Methionine adenosyltransferase II, alpha | MAT2A |
| Neuroguidin, EIF4E binding protein | NGDN |
| General transcription factor IIIC, polypeptide 6, alpha 35 kDa | GTF3C6 |
| Chromosome 21 open reading frame 59 | C21orf59 |
| PREDICTED: similar to Keratin, type I cytoskeletal 18 (Cytokeratin-18) (CK-18) (Keratin-18) (K18) (LOC646723), mRNA. | — |
| Smu-1 suppressor of mec-8 and unc-52 homolog (*C. elegans*) | SMU1 |
| DnaJ (Hsp40) homolog, subfamily C, member 7 | DNAJC7 |
| Catenin (cadherin-associated protein), beta 1, 88 kDa | CTNNB1 |
| Carbonic anhydrase II | CA2 |
| N-acetyltransferase 5 (GCN5-related, putative) | NAT5 |
| Ribosomal protein L7-like 1 | RPL7L1 |
| Solute carrier family 25 (mitochondrial carrier, brain), member 14 | SLC25A14 |
| Chromosome 20 open reading frame 177 | C20orf177 |
| Inhibitor of DNA binding 3, dominant negative helix-loop-helix protein | ID3 |
| Voltage-dependent anion channel 3 | VDAC3 |
| Zinc finger protein 286A | ZNF286A |
| NOP2 nucleolar protein homolog (yeast) | NOP2 |
| Neurotrophin 3 | NTF3 |
| Proteasome (prosome, macropain) subunit, beta type, 10 | PSMB10 |
| Protein arginine methyltransferase 5 | PRMT5 |
| Zinc finger, matrin type 3 | ZMAT3 |
| Cirrhosis, autosomal recessive 1A (cirhin) | CIRH1A |
| Cathepsin L1 | CTSL1 |
| PREDICTED: hypothetical protein LOC648852 (LOC648852), mRNA. | — |
| Glutamate decarboxylase 1 (brain, 67 kDa) | GAD1 |
| Keratin 8 | KRT8 |
| Protein phosphatase 1, regulatory (inhibitor) subunit 11 | PPP1R11 |
| Zinc finger protein 337 | ZNF337 |
| Basic leucine zipper nuclear factor 1 | BLZF1 |
| NOP58 ribonucleoprotein homolog (yeast) | NOP58 |
| Neurofilament, heavy polypeptide | NEFH |
| Asparagine synthetase domain containing 1 | ASNSD1 |
| Nuclear RNA export factor 1 | NXF1 |
| Family with sequence similarity 175, member B | FAM175B |
| FAST kinase domains 3 | FASTKD3 |
| Four and a half LIM domains 2 | FHL2 |
| Chromosome 9 open reading frame 6 | C9orf6 |
| Leucine zipper protein 1 | LUZP1 |
| Programmed cell death 5 | PDCD5 |
| PREDICTED: hypothetical LOC400879, transcript variant 2 (LOC400879), mRNA. | — |
| PRP40 pre-mRNA processing factor 40 homolog A (*S. cerevisiae*) | PRPF40A |
| NOP56 ribonucleoprotein homolog (yeast) | NOP56 |
| DnaJ (Hsp40) homolog, subfamily C, member 9 | DNAJC9 |
| C-myc-P64 mRNA, initiating from promoter P0, (HLmyc3.1) partial cds | — |
| Anaphase promoting complex subunit 13 | ANAPC13 |
| Dual-specificity tyrosine-(Y)-phosphorylation regulated kinase 2 | DYRK2 |
| Carcinoembryonic antigen-related cell adhesion molecule 1 (biliary glycoprotein) | CEACAM1 |
| RNA binding motif protein 22 | RBM22 |
| Bromodomain and PHD finger containing, 1 | BRPF1 |
| C-myc-P64 mRNA, initiating from promoter P0, (HLmyc3.1) partial cds | — |
| RNA methyltransferase like 1 | RNMTL1 |
| Ankyrin repeat and SOCS box-containing 9 | ASB9 |
| Small nucleolar RNA, C/D box 15B | SNORD15B |
| Interferon gamma receptor 1 | IFNGR1 |
| TSR1, 20S rRNA accumulation, homolog (*S. cerevisiae*) | TSR1 |
| Guanine nucleotide binding protein-like 3 (nucleolar)-like | GNL3L |
| Bromodomain containing 8 | BRD8 |
| Heat shock 105 kDa/110 kDa protein 1 | HSPH1 |
| sideroflexin 4 | — |
| BCL2-associated athanogene 3 | BAG3 |
| Calcium binding tyrosine-(Y)-phosphorylation regulated | CABYR |
| Dynein, light chain, LC8-type 2 | DYNLL2 |
| Family with sequence similarity 123B | FAM123B |
| Annexin A2 | ANXA2 |
| Methyltransferase like 13 | METTL13 |
| Metallothionein 1E | MT1E |
| Ribosomal L1 domain containing 1 | RSL1D1 |
| Dual specificity phosphatase 5 | DUSP5 |
| Muscleblind-like 3 (*Drosophila*) | MBNL3 |
| Zinc finger protein 14 | ZNF14 |
| Sushi domain containing 2 | SUSD2 |
| Glutamate decarboxylase 1 (brain, 67 kDa) | GAD1 |
| Methylmalonic aciduria (cobalamin deficiency) cblC type, with homocystinuria | MMACHC |

TABLE 11-continued

| Gene Title | Gene ID |
|---|---|
| Origin recognition complex, subunit 5-like (yeast) | ORC5L |
| HAUS augmin-like complex, subunit 2 | HAUS2 |
| Hypothetical LOC644422 | LOC644422 |
| Zinc finger, DHHC-type containing 6 | ZDHHC6 |
| PRP4 pre-mRNA processing factor 4 homolog (yeast) | PRPF4 |
| Epstein-Barr virus induced 3 | EBI3 |
| Platelet-derived growth factor receptor, beta polypeptide | PDGFRB |
| G-rich RNA sequence binding factor 1 | GRSF1 |
| Cerberus 1, cysteine knot superfamily, homolog (Xenopus laevis) | CER1 |
| Polymerase (RNA) I polypeptide C, 30 kDa | POLR1C |
| Ribonuclease P/MRP 40 kDa subunit | RPP40 |
| Nucleoside phosphorylase | NP |
| Heat shock 70 kDa protein 8 | HSPA8 |
| telomerase RNA component | — |
| Damage-regulated autophagy modulator | DRAM |
| MRNA turnover 4 homolog (S. cerevisiae) | MRTO4 |
| Solute carrier family 35, member E1 | SLC35E1 |
| double homeobox A pseudogene 3 | — |
| Metastasis associated 1 family, member 2 | MTA2 |
| Guanine nucleotide binding protein-like 2 (nucleolar) | GNL2 |
| Minichromosome maintenance complex component 4 | MCM4 |
| NUAK family, SNF1-like kinase, 2 | NUAK2 |
| Zinc fingers and homeoboxes 2 | ZHX2 |
| SCO cytochrome oxidase deficient homolog 2 (yeast) | SCO2 |
| N-acetyltransferase 5 (GCN5-related, putative) | NAT5 |
| B cell RAG associated protein | GALNAC4S-6ST |
| Guanine nucleotide binding protein-like 3 (nucleolar) | GNL3 |
| Nucleolar protein family 6 (RNA-associated) | NOL6 |
| Follistatin | FST |
| Peroxisome proliferator-activated receptor gamma, coactivator-related 1 | PPRC1 |
| Prostaglandin E synthase | PTGES |
| Hypothetical protein FLJ40504 | FLJ40504 |
| Mitochondrial GTPase 1 homolog (S. cerevisiae) | MTG1 |
| RAE1 RNA export 1 homolog (S. pombe) | RAE1 |
| Family with sequence similarity 119, member A | FAM119A |
| Fem-1 homolog a (C. elegans) | FEM1A |
| Transcribed locus | — |
| Catenin (cadherin-associated protein), beta 1, 88 kDa | CTNNB1 |
| Non-metastatic cells 6, protein expressed in (nucleoside-diphosphate kinase) | NME6 |
| DNA cross-link repair 1C (PSO2 homolog, S. cerevisiae) | DCLRE1C |
| Coilin | COIL |
| AOC3 pseudogene (LOC90586) on chromosome 17. | — |
| Mitochondrial ribosomal protein S11 | MRPS11 |
| B-cell CLL/lymphoma 11A (zinc finger protein) | BCL11A |
| Neuron navigator 2 | NAV2 |
| Small nuclear ribonucleoprotein 25 kDa (U11/U12) | SNRNP25 |
| FOS-like antigen 1 | FOSL1 |
| ADAMTS-like 2 | ADAMTSL2 |
| Polymerase (RNA) I polypeptide C, 30 kDa | POLR1C |
| NOP16 nucleolar protein homolog (yeast) | NOP16 |
| Zinc finger and BTB domain containing 33 | ZBTB33 |
| Chromosome 1 open reading frame 163 | C1orf163 |
| Breast cancer metastasis suppressor 1 | BRMS1 |
| GLI pathogenesis-related 1 like 1 | GLIPR1L1 |
| Sideroflexin 4 | SFXN4 |
| PREDICTED: hypothetical LOC644743 (LOC644743), mRNA. | — |
| Chaperonin containing TCP1, subunit 6A (zeta 1) | CCT6A |
| Polymerase (DNA directed), epsilon 3 (p17 subunit) | POLE3 |
| Ankyrin repeat and SOCS box-containing 9 | ASB9 |
| UTP11-like, U3 small nucleolar ribonucleoprotein, (yeast) | UTP11L |
| Eomesodermin homolog (Xenopus laevis) | EOMES |
| Polymerase (RNA) III (DNA directed) polypeptide C (62 kD) | POLR3C |
| Zinc finger protein 207 | ZNF207 |
| G patch domain containing 4 | GPATCH4 |
| Chromosome 10 open reading frame 2 | C10orf2 |
| Vasorin | VASN |
| Resistance to inhibitors of cholinesterase 8 homolog A (C. elegans) | RIC8A |
| Wilms tumor 1 interacting protein | — |
| Heat shock protein 90 kDa alpha (cytosolic), class A member 1 | HSP90AA1 |
| Mitochondrial ribosomal protein S17 | MRPS17 |
| Ornithine aminotransferase (gyrate atrophy) | OAT |
| Transmembrane 7 superfamily member 3 | TM7SF3 |
| Williams Beuren syndrome chromosome region 22 | WBSCR22 |
| NOP2 nucleolar protein homolog (yeast) | NOP2 |
| Transmembrane protein 99 | TMEM99 |
| Ornithine decarboxylase 1 | ODC1 |
| Zinc finger protein 816A | ZNF816A |
| Calponin 3, acidic | CNN3 |
| Mitochondrial ribosomal protein S11 | MRPS11 |
| PAK1 interacting protein 1 | PAK1IP1 |
| islet cell autoantigen 1, 69 kDa | — |
| Similar to keratin 8 | LOC647954 |
| V-crk sarcoma virus CT10 oncogene homolog (avian) | CRK |
| Growth differentiation factor 11 | GDF11 |
| DEAD (Asp-Glu-Ala-Asp) box polypeptide 24 | DDX24 |
| Serine/threonine kinase 36, fused homolog (Drosophila) | STK36 |
| Collagen, type VII, alpha 1 | COL7A1 |
| Methyltransferase like 13 | METTL13 |
| Choline/ethanolamine phosphotransferase 1 | CEPT1 |
| NOP56 ribonucleoprotein homolog (yeast) | NOP56 |
| DEAD (Asp-Glu-Ala-Asp) box polypeptide 51 | DDX51 |
| M-phase phosphoprotein 10 (U3 small nucleolar ribonucleoprotein) | MPHOSPH10 |
| Chromosome 12 open reading frame 41 | C12orf41 |
| Caspase 3, apoptosis-related cysteine peptidase | CASP3 |
| Exosome component 2 | EXOSC2 |
| CLP1, cleavage and polyadenylation factor I subunit, homolog (S. cerevisiae) | CLP1 |
| Proteasome (prosome, macropain) subunit, alpha type, 4 | PSMA4 |
| Ring finger protein 34 | RNF34 |
| Regulatory solute carrier protein, family 1, member 1 | RSC1A1 |
| Zinc finger protein 621 | ZNF621 |
| Nucleolar protein 8 | NOL8 |
| Adipose differentiation-related protein | ADFP |
| Solute carrier family 20 (phosphate transporter), member 1 | SLC20A1 |
| JTV1 gene | JTV1 |
| DIM1 dimethyladenosine transferase 1-like (S. cerevisiae) | DIMT1L |
| Zinc finger, NFX1-type containing 1 | ZNFX1 |
| Rho GDP dissociation inhibitor (GDI) beta | ARHGDIB |
| Ribosomal protein L9 | RPL9 |
| Neurotensin | NTS |
| DTW domain containing 2 | DTWD2 |
| Peptidyl-tRNA hydrolase 2 | PTRH2 |
| Caveolin 1, caveolae protein, 22 kDa | CAV1 |
| PREDICTED: hypothetical protein LOC642477, transcript variant 2 (LOC642477), mRNA. | — |
| Methionine adenosyltransferase II, alpha | MAT2A |
| Neuroguidin, EIF4E binding protein | NGDN |
| General transcription factor IIIC, polypeptide 6, alpha 35 kDa | GTF3C6 |
| Chromosome 21 open reading frame 59 | C21orf59 |
| PREDICTED: similar to Keratin, type I cytoskeletal 18 (Cytokeratin-18) (CK-18) (Keratin-18) (K18) (LOC646723), mRNA. | — |
| Smu-1 suppressor of mec-8 and unc-52 homolog (C. elegans) | SMU1 |
| DnaJ (Hsp40) homolog, subfamily C, member 7 | DNAJC7 |
| Catenin (cadherin-associated protein), beta 1, 88 kDa | CTNNB1 |
| Carbonic anhydrase II | CA2 |
| N-acetyltransferase 5 (GCN5-related, putative) | NAT5 |
| Ribosomal protein L7-like 1 | RPL7L1 |

TABLE 11-continued

| Gene Title | Gene ID |
| --- | --- |
| Solute carrier family 25 (mitochondrial carrier, brain), member 14 | SLC25A14 |
| Chromosome 20 open reading frame 177 | C20orf177 |
| Inhibitor of DNA binding 3, dominant negative helix-loop-helix protein | ID3 |
| Voltage-dependent anion channel 3 | VDAC3 |
| Zinc finger protein 286A | ZNF286A |
| NOP2 nucleolar protein homolog (yeast) | NOP2 |
| Neurotrophin 3 | NTF3 |
| Proteasome (prosome, macropain) subunit, beta type, 10 | PSMB10 |
| Protein arginine methyltransferase 5 | PRMT5 |
| Zinc finger, matrin type 3 | ZMAT3 |
| Cirrhosis, autosomal recessive 1A (cirhin) | CIRH1A |
| Cathepsin L1 | CTSL1 |
| PREDICTED: hypothetical protein LOC648852 (LOC648852), mRNA. | — |
| Glutamate decarboxylase 1 (brain, 67 kDa) | GAD1 |
| Keratin 8 | KRT8 |
| Protein phosphatase 1, regulatory (inhibitor) subunit 11 | PPP1R11 |

TABLE 12

| Gene Title | Gene ID |
| --- | --- |
| Left-right determination factor 2 | LEFTY2 |
| Tumor protein p53 | TP53 |
| Proliferation-associated 2G4, 38 kDa | PA2G4 |
| Hematopoietic cell-specific Lyn substrate 1 | HCLS1 |
| PREDICTED: phosphoglycerate mutase family member 5 (PGAM5), mRNA. | — |
| Tumor necrosis factor receptor superfamily, member 13B | TNFRSF13B |
| Metallothionein 1G | MT1G |
| UTP14, U3 small nucleolar ribonucleoprotein, homolog A (yeast) | UTP14A |
| FIP1 like 1 (S. cerevisiae) | FIP1L1 |
| Programmed cell death 2 | PDCD2 |
| Eukaryotic translation initiation factor 4 gamma, 2 | EIF4G2 |
| Brix domain containing 2 | BXDC2 |
| Mortality factor 4 like 2 | MORF4L2 |
| SMAD family member 7 | SMAD7 |
| Left-right determination factor 1 | LEFTY1 |
| High-mobility group box 1-like 1 | HMGB1L1 |
| Nuclear receptor coactivator 5 | NCOA5 |
| APEX nuclease (multifunctional DNA repair enzyme) 1 | APEX1 |
| Ribosomal protein L6 | RPL6 |
| UTP14, U3 small nucleolar ribonucleoprotein, homolog A (yeast) | UTP14A |
| NOP56 ribonucleoprotein homolog (yeast) | NOP56 |
| PREDICTED: similar to 60 kDa heat shock protein, mitochondrial precursor (Hsp60) (60 kDa chaperonin) (CPN60) (Heat shock protein 60) (HSP-60) (Mitochondrial matrix protein P1) (P60 lymphocyte protein) (HuCHA60) (LOC643300), mRNA. | — |
| Heat shock 70 kDa protein 8 | HSPA8 |
| Nucleolar and coiled-body phosphoprotein 1 | NOLC1 |
| Polymerase (RNA) mitochondrial (DNA directed) | POLRMT |
| Lectin, galactoside-binding, soluble, 3 binding protein | LGALS3BP |
| Glutamate decarboxylase 1 (brain, 67 kDa) | GAD1 |
| Guanine nucleotide binding protein-like 3 (nucleolar) | GNL3 |
| Mannose-6-phosphate receptor (cation dependent) | M6PR |
| small nucleolar RNA, C/D box 31 | — |
| Glypican 4 | GPC4 |
| MYC-associated zinc finger protein (purine-binding transcription factor) | MAZ |
| Casein kinase 2, alpha 1 polypeptide | CSNK2A1 |
| Chaperonin containing TCP1, subunit 2 (beta) | CCT2 |
| Ly1 antibody reactive homolog (mouse) | LYAR |

TABLE 12-continued

| Gene Title | Gene ID |
| --- | --- |
| Nodal homolog (mouse) | NODAL |
| Chromosome 19 open reading frame 46 | C19orf46 |
| Ribonucleotide reductase M2 polypeptide | RRM2 |
| Hypoxanthine phosphoribosyltransferase 1 | HPRT1 |
| Chromosome 12 open reading frame 11 | C12orf11 |

TABLE 13

| Cluster 5 | Cluster 5 |
| --- | --- |
| EFR3 homolog B (S. cerevisiae) | EFR3B |
| Diacylglycerol kinase, theta 110 kDa | DGKQ |
| Ecotropic viral integration site 5-like | EVI5L |
| Serine/threonine kinase 40 | STK40 |
| FGGY carbohydrate kinase domain containing | FGGY |
| Unc-84 homolog B (C. elegans) | UNC84B |
| DNA (cytosine-5-)-methyltransferase 3 beta | DNMT3B |
| Insulin-like growth factor 2 receptor | IGF2R |
| Galanin prepropeptide | GAL |
| G-protein signaling modulator 2 (AGS3-like, C. elegans) | GPSM2 |
| Leprecan-like 1 | LEPREL1 |
| PREDICTED: hypothetical protein LOC730525 (LOC730525), mRNA. | — |
| Leucine rich repeat containing 26 | LRRC26 |
| Leucine rich repeat containing 20 | LRRC20 |
| Adrenomedullin 2 | ADM2 |
| DNA (cytosine-5-)-methyltransferase 3 beta | DNMT3B |
| X-box binding protein 1 | XBP1 |
| SH3-domain kinase binding protein 1 | SH3KBP1 |
| Guanine nucleotide binding protein (G protein), gamma 7 | GNG7 |
| Solute carrier family 27 (fatty acid transporter), member 1 | SLC27A1 |
| PREDICTED: similar to Ankyrin repeat domain protein 11 (Ankyrin repeat-containing cofactor 1) (LOC653103), mRNA. | — |
| Solute carrier family 3 (activators of dibasic and neutral amino acid transport), member 2 | SLC3A2 |
| Early growth response 1 | EGR1 |
| Ubiquitin-conjugating enzyme E2L 3 | UBE2L3 |
| Carbonic anhydrase IV | CA4 |
| Histone cluster 1, H2bk | HIST1H2BK |
| Methylenetetrahydrofolate dehydrogenase (NADP+ dependent) 2, methenyltetrahydrofolate cyclohydrolase | MTHFD2 |
| Histone cluster 2, H2aa3 | HIST2H2AA3 |
| Leucine proline-enriched proteoglycan (leprecan) 1 | LEPRE1 |
| Unc-5 homolog A (C. elegans) | UNC5A |
| N-acetylglucosaminidase, alpha- | NAGLU |
| Tribbles homolog 3 (Drosophila) | TRIB3 |
| Cytochrome P450, family 2, subfamily F, polypeptide 1 | CYP2F1 |
| Transmembrane protein 145 | TMEM145 |
| Alkaline phosphatase, liver/bone/kidney | ALPL |
| Histone cluster 3, H2a | HIST3H2A |
| Fibulin 2 | FBLN2 |
| Methionine sulfoxide reductase B2 | MSRB2 |
| hypothetical protein FLJ22184 (FLJ22184), mRNA. | — |
| Transcription elongation factor A (SII), 2 | TCEA2 |
| family with sequence similarity 38, member A | — |
| hypothetical LOC441268 | — |
| Oligonucleotide/oligosaccharide-binding fold containing 1 | OBFC1 |
| Endothelial PAS domain protein 1 | EPAS1 |
| Protocadherin 19 | PCDH19 |
| Neuronal pentraxin II | NPTX2 |
| Solute carrier family 25, member 35 | SLC25A35 |
| LEM domain containing 2 | LEMD2 |
| Mediator complex subunit 30 | MED30 |
| Solute carrier family 25 (mitochondrial carrier; phosphate carrier), member 23 | SLC25A23 |
| TRNA splicing endonuclease 15 homolog (S. cerevisiae) | TSEN15 |
| Iroquois homeobox 4 | IRX4 |
| Eukaryotic elongation factor-2 kinase | EEF2K |

TABLE 13-continued

| Cluster 5 | Cluster 5 |
|---|---|
| Nipsnap homolog 1 (*C. elegans*) | NIPSNAP1 |
| Sushi-repeat-containing protein, X-linked | SRPX |
| Neuroligin 4, X-linked | NLGN4X |
| Transmembrane protein 132D | TMEM132D |
| H2A histone family, member J | H2AFJ |
| Galanin receptor 2 | GALR2 |
| Vacuolar protein sorting 8 homolog (*S. cerevisiae*) | VPS8 |
| PREDICTED: similar to NACHT, leucine rich repeat and PYD (pyrin domain) containing 1, transcript variant 1 (LOC730994), mRNA. | — |
| Phosphoenolpyruvate carboxykinase 2 (mitochondrial) | PCK2 |
| Hexokinase 1 | HK1 |
| Phosphoglycerate dehydrogenase | PHGDH |
| DNA-damage-inducible transcript 4 | DDIT4 |
| Histone cluster 2, H2ac | HIST2H2AC |
| Golgi apparatus protein 1 | GLG1 |
| Retinol binding protein 7, cellular | RBP7 |
| Intersectin 1 (SH3 domain protein) | ITSN1 |
| Lysosomal-associated membrane protein 2 | LAMP2 |
| 4-hydroxyphenylpyruvate dioxygenase-like | HPDL |
| Chromosome 16 open reading frame 35 | C16orf35 |
| Brain expressed, X-linked | BEX5 |
| Phospholysine phosphohistidine inorganic pyrophosphate phosphatase | LHPP |
| Asparagine synthetase | ASNS |
| Low density lipoprotein receptor-related protein associated protein 1 | LRPAP1 |
| Ubiquitin-conjugating enzyme E2L 6 | UBE2L6 |
| Cystathionine-beta-synthase | CBS |
| Synuclein, alpha (non A4 component of amyloid precursor) | SNCA |
| Fas (TNFRSF6)-associated via death domain | FADD |
| GDP-mannose pyrophosphorylase A | GMPPA |
| Cysteine conjugate-beta lyase, cytoplasmic | CCBL1 |
| Fas (TNFRSF6) associated factor 1 | FAF1 |
| Chromosome 14 open reading frame 147 | C14orf147 |
| GRAM domain containing 1A | GRAMD1A |
| Lipin 1 | LPIN1 |
| NADH dehydrogenase (ubiquinone) Fe—S protein 7, 20 kDa (NADH-coenzyme Q reductase) | NDUFS7 |
| Interleukin 21 receptor | IL21R |
| Breast carcinoma amplified sequence 4 | BCAS4 |
| Family with sequence similarity 125, member A | FAM125A |
| Spectrin, alpha, non-erythrocytic 1 (alpha-fodrin) | SPTAN1 |
| Mitogen-activated protein kinase kinase 3 | MAP2K3 |
| Sprouty homolog 1, antagonist of FGF signaling (*Drosophila*) | SPRY1 |
| 5-oxoprolinase (ATP-hydrolysing) | OPLAH |
| Glutamic pyruvate transaminase (alanine aminotransferase) 2 | GPT2 |
| Potassium channel, subfamily K, member 12 | KCNK12 |
| Coactivator-associated arginine methyltransferase 1 | CARM1 |
| Adenosine deaminase | ADA |
| Contactin associated protein 1 | CNTNAP1 |
| NADH dehydrogenase (ubiquinone) Fe—S protein 4, 18 kDa (NADH-coenzyme Q reductase) | NDUFS4 |
| DNA (cytosine-5-)-methyltransferase 3 beta | DNMT3B |
| T-cell leukemia/lymphoma 1B | TCL1B |
| Cyclin D2 | CCND2 |
| Roundabout, axon guidance receptor, homolog 3 (*Drosophila*) | ROBO3 |
| Chemokine (C—X—C motif) ligand 16 | CXCL16 |
| Transducin-like enhancer of split 2 (E(sp1) homolog, *Drosophila*) | TLE2 |
| HtrA serine peptidase 1 | HTRA1 |
| NK3 homeobox 2 | NKX3-2 |
| Lysophosphatidylcholine acyltransferase 3 | LPCAT3 |
| CCAAT/enhancer binding protein (C/EBP), beta | CEBPB |
| Hyaluronoglucosaminidase 1 | HYAL1 |
| Histone cluster 1, H1c | HIST1H1C |
| Histone cluster 1, H2bk | HIST1H2BK |
| PREDICTED: similar to ribosomal protein L13a, transcript variant 4 (LOC283340), mRNA. | — |
| RAB3 GTPase activating protein subunit 1 (catalytic) | RAB3GAP1 |
| SH3-domain kinase binding protein 1 | SH3KBP1 |
| V-raf-1 murine leukemia viral oncogene homolog 1 | RAF1 |
| Kelch domain containing 4 | KLHDC4 |
| Protein phosphatase 1B (formerly 2C), magnesium-dependent, beta isoform | PPM1B |
| CDC42 effector protein (Rho GTPase binding) 5 | CDC42EP5 |
| Solute carrier family 8 (sodium/calcium exchanger), member 2 | SLC8A2 |
| Zinc finger, CCHC domain containing 12 | ZCCHC12 |
| Asparagine synthetase | ASNS |
| Developmental pluripotency associated 5 | DPPA5 |
| SH2B adaptor protein 3 | SH2B3 |
| hypothetical protein LOC255783 (LOC255783) on chromosome 19. | — |
| Alanyl-tRNA synthetase | AARS |
| Active BCR-related gene | ABR |
| PREDICTED: similar to protein phosphatase 2A 48 kDa regulatory subunit isoform 1; serine/threonine protein phosphatase 2A, 48 kDa regulatory subunit; PP2A, subunit B, PR48 isoform; PP2A B subunit PR48; NY-REN-8 antigen (LOC390705), misc RNA. | — |
| Delta-like 3 (*Drosophila*) | DLL3 |
| Transient receptor potential cation channel, subfamily C, member 4 associated protein | TRPC4AP |
| CTD (carboxy-terminal domain, RNA polymerase II, polypeptide A) small phosphatase 2 | CTDSP2 |
| Chromosome 16 open reading frame 68 | C16orf68 |
| Deoxyribonuclease II, lysosomal | DNASE2 |
| CD248 molecule, endosialin | CD248 |
| Breast carcinoma amplified sequence 4 | BCAS4 |
| WW domain binding protein 2 | WBP2 |
| Syntaxin 16 | STX16 |
| Integrin, alpha 3 (antigen CD49C, alpha 3 subunit of VLA-3 receptor) | ITGA3 |
| ATP-binding cassette, sub-family B (MDR/TAP), member 9 | ABCB9 |
| PREDICTED: similar to hypothetical LOC389634 (LOC654053), mRNA. | — |
| Calbindin 2 | CALB2 |
| Mannosidase, beta A, lysosomal | MANBA |
| Phosphoenolpyruvate carboxykinase 2 (mitochondrial) | PCK2 |
| Ribosomal protein L39-like | RPL39L |
| GDP-mannose 4,6-dehydratase | GMDS |
| Low density lipoprotein receptor-related protein 5 | LRP5 |

TABLE 14

| Cluster 6 | Cluster 6 |
|---|---|
| Ras interacting protein 1 | RASIP1 |
| Pellino homolog 1 (*Drosophila*) | PELI1 |
| Histone cluster 4, H4 | HIST4H4 |
| Copper metabolism (Murr1) domain containing 1 | COMMD1 |
| KIAA0146 | KIAA0146 |
| Chromosome 4 open reading frame 34 | C4orf34 |
| PREDICTED: hypothetical protein LOC645580 (FLJ37453), mRNA. | — |
| Arrestin, beta 1 | ARRB1 |
| Unc-13 homolog B (*C. elegans*) | UNC13B |
| Kinesin family member 13B | KIF13B |
| Sema domain, immunoglobulin domain (Ig), transmembrane domain (TM) and short cytoplasmic domain, (semaphorin) 4D | SEMA4D |
| UDP glycosyltransferase 3 family, polypeptide A2 | UGT3A2 |
| Chromosome 6 open reading frame 221 | C6orf221 |
| Peroxisomal biogenesis factor 7 | PEX7 |
| Methylenetetrahydrofolate dehydrogenase (NADP+ dependent) 1-like | MTHFD1L |
| Tryptophanyl-tRNA synthetase | WARS |
| Junctophilin 3 | JPH3 |
| Adenylate cyclase 1 (brain) | ADCY1 |

TABLE 14-continued

| Cluster 6 | Cluster 6 |
|---|---|
| Checkpoint with forkhead and ring finger domains | CHFR |
| Nudix (nucleoside diphosphate linked moiety X)-type motif 14 | NUDT14 |
| Acyl-Coenzyme A dehydrogenase family, member 10 | ACAD10 |
| Visinin-like 1 | VSNL1 |
| Myosin IXA | MYO9A |
| Vesicle-associated membrane protein 1 (synaptobrevin 1) | VAMP1 |
| Phosphatidylethanolamine N-methyltransferase | PEMT |
| Hect (homologous to the E6-AP (UBE3A) carboxyl terminus) domain and RCC1 (CHC1)-like domain (RLD) 1 | HERC1 |
| Cystatin SN | CST1 |
| Kinesin family member 1A | KIF1A |
| LIM domain binding 2 | LDB2 |
| Non-SMC element 1 homolog (S. cerevisiae) | NSMCE1 |
| Excision repair cross-complementing rodent repair deficiency, complementation group 1 (includes overlapping antisense sequenc | ERCC1 |
| Zinc finger and BTB domain containing 46 | ZBTB46 |
| Secreted frizzled-related protein 2 | SFRP2 |
| PREDICTED: similar to cis-Golgi matrix protein GM130, transcript variant 2 (LOC653344), mRNA. | — |
| PREDICTED: inositol polyphosphate-5-phosphatase, 40 kDa (INPP5A), mRNA. | — |
| Asparagine-linked glycosylation 9, alpha-1,2-mannosyltransferase homolog (S. cerevisiae) | ALG9 |
| Actinin, alpha 4 | ACTN4 |
| Secretoglobin, family 3A, member 2 | SCGB3A2 |
| Jumonji, AT rich interactive domain 2 | JARID2 |
| Islet cell autoantigen 1, 69 kDa | ICA1 |
| Chromosome 20 open reading frame 54 | C20orf54 |
| RAB3A interacting protein (rabin3)-like 1 | RAB3IL1 |
| Carbohydrate (chondroitin 4) sulfotransferase 13 | CHST13 |
| Transient receptor potential cation channel, subfamily C, member 4 associated protein | TRPC4AP |
| Protein phosphatase 2 (formerly 2A), regulatory subunit B, gamma isoform | PPP2R2C |
| SWI/SNF related, matrix associated, actin dependent regulator of chromatin, subfamily a, member 2 | SMARCA2 |
| Dedicator of cytokinesis 1 | DOCK1 |
| Tripartite motif family-like 2 | TRIML2 |
| Delta-like 3 (Drosophila) | DLL3 |
| Phospholipase A2, group X | PLA2G10 |
| Stanniocalcin 2 | STC2 |
| Protein tyrosine phosphatase-like (proline instead of catalytic arginine), member A | PTPLA |
| Y box binding protein 2 | YBX2 |
| Transmembrane protein 125 | TMEM125 |
| Serine hydroxymethyltransferase 2 (mitochondrial) | SHMT2 |
| WD repeat domain 8 | WDR8 |
| Ubiquitin-conjugating enzyme E2E 2 (UBC4/5 homolog, yeast) | UBE2E2 |
| Collapsin response mediator protein 1 | CRMP1 |
| NODAL modulator 3 | NOMO3 |
| Zinc finger, SWIM-type containing 4 | ZSWIM4 |
| Lipoma HMGIC fusion partner-like 4 | LHFPL4 |
| Acyl-CoA synthetase short-chain family member 2 | ACSS2 |
| Spondin 1, extracellular matrix protein | SPON1 |
| Hydroxyacylglutathione hydrolase | HAGH |
| Cadherin 3, type 1, P-cadherin (placental) | CDH3 |
| Trafficking protein, kinesin binding 1 | TRAK1 |
| ROD1 regulator of differentiation 1 (S. pombe) | ROD1 |
| Protein tyrosine phosphatase, receptor type, A | PTPRA |
| Serine threonine kinase 39 (STE20/SPS1 homolog, yeast) | STK39 |
| Tryptophanyl-tRNA synthetase | WARS |
| Acyl-CoA thioesterase 7 | ACOT7 |
| Interleukin 27 receptor, alpha | IL27RA |
| PDZ domain containing 4 | PDZD4 |
| PREDICTED: chromatin modifying protein 6 (CHMP6), mRNA. | — |
| Phospholipase A2, group XVI | PLA2G16 |
| Protein disulfide isomerase family A, member 5 | PDIA5 |
| DnaJ (Hsp40) homolog, subfamily B, member 6 | DNAJB6 |
| Vesicle-associated membrane protein 1 (synaptobrevin 1) | VAMP1 |
| Deoxyhypusine synthase | DHPS |
| General transcription factor IIIC, polypeptide 1, alpha 220 kDa | GTF3C1 |
| Odz, odd Oz/ten-m homolog 3 (Drosophila) | ODZ3 |
| Propionyl Coenzyme A carboxylase, beta polypeptide | PCCB |
| Chromosome 6 open reading frame 126 | C6orf126 |
| S-adenosylhomocysteine hydrolase-like 2 | AHCYL2 |
| Chromosome 14 open reading frame 37 | C14orf37 |
| Small nuclear ribonucleoprotein polypeptide N | SNRPN |
| Protocadherin beta 5 | PCDHB5 |
| Adaptor-related protein complex 3, beta 1 subunit | AP3B1 |
| Metastasis suppressor 1 | MTSS1 |
| Inositol(myo)-1(or 4)-monophosphatase 2 | IMPA2 |
| Enoyl Coenzyme A hydratase 1, peroxisomal | ECH1 |
| Testis-specific kinase 2 | TESK2 |
| KCNE1-like | KCNE1L |
| Spermidine/spermine N1-acetyltransferase 1 | SAT1 |
| Prolyl 4-hydroxylase, beta polypeptide | P4HB |
| Dihydropyrimidinase-like 3 | DPYSL3 |
| Calcyon neuron-specific vesicular protein | CALY |
| Ets variant 5 | ETV5 |
| Glycoprotein M6B | GPM6B |
| Patatin-like phospholipase domain containing 6 | PNPLA6 |
| COMM domain containing 7 | COMMD7 |
| Chromosome 16 open reading frame 58 | C16orf58 |
| KN motif and ankyrin repeat domains 3 | KANK3 |
| Sprouty homolog 1, antagonist of FGF signaling (Drosophila) | SPRY1 |
| Regulator of G-protein signaling 4 | RGS4 |
| Mitogen-activated protein kinase associated protein 1 | MAPKAP1 |
| Chromosome 1 open reading frame 115 | C1orf115 |
| Makorin ring finger protein 1 | MKRN1 |
| RNA binding protein, autoantigenic (hnRNP-associated with lethal yellow homolog (mouse)) | RALY |
| Transmembrane 7 superfamily member 2 | TM7SF2 |
| Pyruvate carboxylase | PC |
| Sema domain, immunoglobulin domain (Ig), transmembrane domain (TM) and short cytoplasmic domain, (semaphorin) 4B | SEMA4B |
| Protein kinase C, alpha | PRKCA |
| Selenoprotein V | SELV |
| Glutathione S-transferase mu 2 (muscle) | GSTM2 |
| Serine peptidase inhibitor, Kazal type 2 (acrosin-trypsin inhibitor) | SPINK2 |
| 3-hydroxyisobutyrate dehydrogenase | HIBADH |
| Regulating synaptic membrane exocytosis 3 | RIMS3 |
| Trafficking protein particle complex 1 | TRAPPC1 |
| Thymosin beta 15B | TMSB15B |
| RAB37, member RAS oncogene family | RAB37 |
| Yip1 interacting factor homolog B (S. cerevisiae) | YIF1B |
| Growth arrest-specific 7 | GAS7 |
| Phosphoserine aminotransferase 1 | PSAT1 |
| Calcium/calmodulin-dependent serine protein kinase (MAGUK family) | CASK |
| Prostaglandin F2 receptor negative regulator | PTGFRN |
| Acyl-CoA thioesterase 11 | ACOT11 |
| Zinc finger CCCH-type containing 4 | ZC3H4 |
| GTPase activating Rap/RanGAP domain-like 4 | GARNL4 |
| Protein kinase C and casein kinase substrate in neurons 1 | PACSIN1 |
| FYVE, RhoGEF and PH domain containing 1 | FGD1 |
| Nucleobindin 1 | NUCB1 |
| Family with sequence similarity 168, member A | FAM168A |
| Midline 1 (Opitz/BBB syndrome) | MID1 |
| Family with sequence similarity 127, member A | FAM127A |
| Dipeptidase 3 | DPEP3 |
| Glutathione S-transferase mu 1 | GSTM1 |
| G protein-coupled receptor 98 | GPR98 |
| Intelectin 2 | ITLN2 |
| Trafficking protein particle complex 9 | TRAPPC9 |
| Solute carrier family 25, member 42 | SLC25A42 |

TABLE 14-continued

| Cluster 6 | |
|---|---|
| Podoplanin | PDPN |
| Catenin (cadherin-associated protein), alpha 1, 102 kDa | CTNNA1 |
| Transmembrane 9 superfamily protein member 4 | TM9SF4 |
| D-tyrosyl-tRNA deacylase 1 homolog (*S. cerevisiae*) | DTD1 |
| Hairy/enhancer-of-split related with YRPW motif 2 | HEY2 |
| Calcium channel, voltage-dependent, alpha 2/delta subunit 2 | CACNA2D2 |
| PREDICTED: ATPase, Na+/K+ transporting, beta 3 polypeptide, transcript variant 2 (ATP1B3), mRNA. | — |
| Lanosterol synthase (2,3-oxidosqualene-lanosterol cyclase) | LSS |
| SH3-domain GRB2-like endophilin B2 | SH3GLB2 |
| Myosin VC | MYO5C |
| CD19 molecule | CD19 |
| SAM and SH3 domain containing 1 | SASH1 |
| Chromosome 2 open reading frame 34 | C2orf34 |
| PREDICTED: hypothetical protein LOC731835 (LOC731835), mRNA. | — |
| Tetratricopeptide repeat domain 15 | TTC15 |
| Arylsulfatase E (chondrodysplasia punctata 1) | ARSE |
| Phosphatidylinositol-specific phospholipase C, X domain containing 1 | PLCXD1 |
| SET and MYND domain containing 3 | SMYD3 |
| Peptidase D | PEPD |
| Histidine triad nucleotide binding protein 2 | HINT2 |
| Fibroblast growth factor 19 | FGF19 |
| Phenylalanyl-tRNA synthetase 2, mitochondrial | FARS2 |
| Ectonucleotide pyrophosphatase/phosphodiesterase 2 | ENPP2 |
| Transcription factor 7-like 1 (T-cell specific, HMG-box) | TCF7L1 |
| Sortilin-related receptor, L(DLR class) A repeats-containing | SORL1 |
| PREDICTED: hypothetical LOC388755 (LOC388755), mRNA. | — |
| Chromosome 14 open reading frame 159 | C14orf159 |
| Fibroblast growth factor receptor 4 | FGFR4 |
| Nuclear receptor co-repressor 2 | NCOR2 |
| Transmembrane channel-like 6 | TMC6 |
| Coronin, actin binding protein, 1B | CORO1B |
| Small nuclear ribonucleoprotein polypeptide N | SNRPN |
| Nuclear factor (erythroid-derived 2)-like 3 | NFE2L3 |
| CDNA FLJ31750 fis, clone NT2RI2007406 | — |
| Amyloid beta (A4) precursor protein | APP |
| Proline/serine-rich coiled-coil 1 | PSRC1 |
| Tetraspanin 9 | TSPAN9 |
| Dynactin 2 (p50) | DCTN2 |
| Arrestin, beta 1 | ARRB1 |
| F11 receptor | F11R |
| Actin filament associated protein 1 | AFAP1 |
| CUB and Sushi multiple domains 1 | CSMD1 |
| Dehydrogenase/reductase (SDR family) member 7 | DHRS7 |
| Glutamate receptor, metabotropic 4 | GRM4 |
| Homer homolog 2 (*Drosophila*) | HOMER2 |
| Fc fragment of IgG binding protein | FCGBP |
| Acyl-CoA synthetase short-chain family member 2 | ACSS2 |
| Alpha 1,4-galactosyltransferase | A4GALT |
| Phospholipase A2, group III | PLA2G3 |
| Mannosidase, alpha, class 1C, member 1 | MAN1C1 |
| Frizzled homolog 7 (*Drosophila*) | FZD7 |
| DEP domain containing 6 | DEPDC6 |
| Leucine zipper, down-regulated in cancer 1 | LDOC1 |
| Dysferlin, limb girdle muscular dystrophy 2B (autosomal recessive) | DYSF |
| Ankyrin repeat domain 9 | ANKRD9 |
| Cystathionase (cystathionine gamma-lyase) | CTH |
| Sphingomyelin phosphodiesterase, acid-like 3B | SMPDL3B |
| LPS-responsive vesicle trafficking, beach and anchor containing | LRBA |
| Polynucleotide kinase 3'-phosphatase | PNKP |
| Methyltransferase like 7A | METTL7A |
| Glycyl-tRNA synthetase | GARS |
| Phosphatidylinositol transfer protein, cytoplasmic 1 | PITPNC1 |
| Dedicator of cytokinesis 6 | DOCK6 |
| De-etiolated homolog 1 (*Arabidopsis*) | DET1 |
| Chromosome 11 open reading frame 59 | C11orf59 |
| Protein phosphatase 1, regulatory (inhibitor) subunit 1B | PPP1R1B |
| Monocyte to macrophage differentiation-associated | MMD |
| Kinesin family member 1B | KIF1B |
| Chromosome 7 open reading frame 47 | C7orf47 |
| Myeloid/lymphoid or mixed-lineage leukemia (trithorax homolog, *Drosophila*); translocated to, 11 | MLLT11 |
| Cytoplasmic linker associated protein 1 | CLASP1 |
| Sparc/osteonectin, cwcv and kazal-like domains proteoglycan (testican) 1 | SPOCK1 |
| Polymerase (RNA) I polypeptide D, 16 kDa | POLR1D |
| Capping protein (actin filament) muscle Z-line, beta | CAPZB |
| Ribosomal protein S6 kinase, 90 kDa, polypeptide 2 | RPS6KA2 |
| Cat eye syndrome chromosome region, candidate 1 | CECR1 |
| Mitogen-activated protein kinase 3 | MAPK3 |
| Talin 2 | TLN2 |
| Tubulin folding cofactor D | TBCD |
| Lon peptidase 1, mitochondrial | LONP1 |
| EPH receptor A1 | EPHA1 |
| Nerve growth factor receptor (TNFRSF16) associated protein 1 | NGFRAP1 |
| Catenin, beta interacting protein 1 | CTNNBIP1 |
| Cholinergic receptor, nicotinic, beta 1 (muscle) | CHRNB1 |
| Acetyl-Coenzyme A carboxylase alpha | ACACA |
| Procollagen-lysine, 2-oxoglutarate 5-dioxygenase 3 | PLOD3 |
| PQ loop repeat containing 3 | PQLC3 |
| Brain and reproductive organ-expressed (TNFRSF1A modulator) | BRE |
| Exostoses (multiple)-like 3 | EXTL3 |
| Acetyl-Coenzyme A carboxylase alpha | ACACA |
| Nuclear factor (erythroid-derived 2)-like 1 | NFE2L1 |
| Carbohydrate (N-acetylgalactosamine 4-0) sulfotransferase 8 | CHST8 |
| CAP-GLY domain containing linker protein 2 | CLIP2 |
| Surfeit 6 | SURF6 |
| Uromodulin-like 1 | UMODL1 |
| Chromosome 11 open reading frame 71 | C11orf71 |
| Thymosin beta 15a | TMSB15A |
| Solute carrier family 6 (neurotransmitter transporter, glycine), member 9 | SLC6A9 |
| Chromosome 7 open reading frame 26 | C7orf26 |
| Protease, serine, 8 | PRSS8 |
| Tetratricopeptide repeat domain 39B | TTC39B |
| RAS-like, family 11, member B | RASL11B |
| Carbonyl reductase 3 | CBR3 |
| Solute carrier family 39 (metal ion transporter), member 11 | SLC39A11 |
| Mal, T-cell differentiation protein 2 | MAL2 |
| Cytochrome P450, family 2, subfamily S, polypeptide 1 | CYP2S1 |
| Peroxisomal biogenesis factor 11 beta | PEX11B |
| Adaptor-related protein complex 3, delta 1 subunit | AP3D1 |
| Integrin alpha FG-GAP repeat containing 1 | ITFG1 |
| Signal transducer and activator of transcription 5A | STAT5A |
| Fibulin 1 | FBLN1 |
| Rho GTPase activating protein 4 | ARHGAP4 |
| Zinc finger protein, multitype 1 | ZFPM1 |
| Myosin phosphatase Rho interacting protein | MPRIP |
| Chromosome 17 open reading frame 58 | C17orf58 |
| SplA/ryanodine receptor domain and SOCS box containing 2 | SPSB2 |
| Talin 1 | TLN1 |
| Fibroblast growth factor receptor-like 1 | FGFRL1 |
| Fibulin 1 | FBLN1 |
| Transforming, acidic coiled-coil containing protein 2 | TACC2 |
| Protein tyrosine phosphatase, receptor type, K | PTPRK |

TABLE 14-continued

| Cluster 6 | Cluster 6 |
|---|---|
| LanC lantibiotic synthetase component C-like 1 (bacterial) | LANCL1 |
| Carnitine palmitoyltransferase 1A (liver) | CPT1A |
| Fibroblast growth factor receptor 4 | FGFR4 |
| Small nuclear ribonucleoprotein polypeptide N | SNRPN |
| Neuronal PAS domain protein 1 | NPAS1 |
| Pre-B-cell leukemia homeobox 1 | PBX1 |
| Like-glycosyltransferase | LARGE |
| CAP-GLY domain containing linker protein 2 | CLIP2 |
| Notch homolog 3 (*Drosophila*) | NOTCH3 |
| Ankyrin repeat domain 35 | ANKRD35 |
| Low density lipoprotein receptor-related protein 8, apolipoprotein e receptor | LRP8 |
| Mitogen-activated protein kinase kinase kinase 7 interacting protein 1 | MAP3K7IP1 |
| Dymeclin | DYM |
| Acetyl-Coenzyme A acetyltransferase 2 | ACAT2 |
| Pre-B-cell leukemia homeobox 3 | PBX3 |
| Rho guanine nucleotide exchange factor (GEF) 10 | ARHGEF10 |
| Tumor protein, translationally-controlled 1 | TPT1 |
| Receptor accessory protein 6 | REEP6 |
| Cytochrome c oxidase subunit VIIc | COX7C |
| F-box and leucine-rich repeat protein 20 | FBXL20 |
| AarF domain containing kinase 1 | ADCK1 |
| Solute carrier family 23 (nucleobase transporters), member 2 | SLC23A2 |
| Solute carrier family 16, member 10 (aromatic amino acid transporter) | SLC16A10 |
| Tumor suppressing subtransferable candidate 1 | TSSC1 |
| KIAA0319-like | KIAA0319L |
| Chromosome 6 open reading frame 106 | C6orf106 |
| Chromosome 7 open reading frame 50 | C7orf50 |
| Microsomal glutathione S-transferase 3 | MGST3 |
| Solute carrier family 29 (nucleoside transporters), member 2 | SLC29A2 |
| Chromosome 19 open reading frame 62 | C19orf62 |
| PREDICTED: solute carrier family 45, member 4, transcript variant 2 (SLC45A4), mRNA. | — |
| Integrin, alpha 9 | ITGA9 |
| Phosphoglucomutase 1 | PGM1 |
| Transmembrane protein 9 | TMEM9 |
| Acetoacetyl-CoA synthetase | AACS |
| Cysteine-rich secretory protein LCCL domain containing 2 | CRISPLD2 |
| Protein phosphatase 1H (PP2C domain containing) | PPM1H |
| Transmembrane protein 185A | TMEM185A |
| Coiled-coil-helix-coiled-coil-helix domain containing 6 | CHCHD6 |
| Sulfatase modifying factor 2 | SUMF2 |
| Enah/Vasp-like | EVL |
| ArfGAP with GTPase domain, ankyrin repeat and PH domain 1 | AGAP1 |
| Chromosome 17 open reading frame 58 | C17orf58 |
| C-Maf-inducing protein | CMIP |
| Fatty acid desaturase 1 | FADS1 |
| Microtubule-actin crosslinking factor 1 | MACF1 |
| SH3-binding domain kinase 1 | SBK1 |
| ST6 beta-galactosamide alpha-2,6-sialyltranferase 1 | ST6GAL1 |
| COX17 cytochrome c oxidase assembly homolog (*S. cerevisiae*) | COX17 |
| Midline 1 (Opitz/BBB syndrome) | MID1 |
| Fidgetin-like 2 | FIGNL2 |
| Staphylococcal nuclease and tudor domain containing 1 | |
| Solute carrier family 22, member 23 | SLC22A23 |
| Fat mass and obesity associated | FTO |
| Filamin B, beta (actin binding protein 278) | FLNB |
| Stromal cell derived factor 4 | SDF4 |
| Sema domain, transmembrane domain (TM), and cytoplasmic domain, (semaphorin) 6B | SEMA6B |
| Thymosin beta 15B | TMSB15B |
| Thy-1 cell surface antigen | THY1 |
| Sodium channel, nonvoltage-gated 1 alpha | SCNN1A |
| Nucleoporin 210 kDa | NUP210 |
| Ubiquitin specific peptidase 44 | USP44 |
| Glycoprotein M6B | GPM6B |
| Transmembrane emp24 domain trafficking protein 2 | TMED2 |
| Chemokine-like factor | CKLF |
| Leucine rich repeat containing 33 | LRRC33 |
| NOL1/NOP2/Sun domain family, member 7 | NSUN7 |

GSEA results indicated that DNMT3B knockdown interfered with the effects of decitabine treatment to down-regulate pluripotency genes and to up-regulate the expression of p53 target and apoptotic genes in NT2/D1-R1 cells. Gene sets that were depleted in decitabine-treated control cells as compared to decitabine-treated DNMT3B cells (i.e., no longer down-regulated by decitabine in DNMT3B knockout cells) include genes sets for ES genes, OCT4 targets, and genes on chromosome 12p13 which is a hot-spot region for pluripotency in ES and EC cells (Giuliana et al. 2005. *Biochim. Biophys. Acta* 1731:48-56; Korkola et al. 2006. *Cancer Res.* 66:820-827). Gene sets enriched in decitabine-treated control cells as compared to decitabine-treated DNMT3B cells (i.e., no longer up-regulated by decitabine treatment in DNMT3B knockout cells) include gene sets for apoptotic and p53 target genes. Interestingly, a study by Missiaglia et al. (2005. *Oncogene* 24:199-211) assessed global gene expression changes in pancreatic cancer cells 6 days after a 24-hour treatment with high dose decitabine (2 μM). They reported that using GSEA, the genes were no longer regulated to the same extent by low-dose decitabine treatment in DNMT3B knockdown cells. This difference in cell sensitivity indicates that the genes identified by Missiaglia et al. (2005) are distinct and separate genes from the pluripotency and p53 target genes whose expression has been shown to be regulated by low dose decitabine treatment as identified in the present invention.

Genome-wide effects of low-dose decitabine and DNMT3B knockdown on promoter methylation were then assessed (Table 15). In contrast to genome-wide expression analysis where few genes in NT2/D1-R1 cells were altered by DNMT3B knockdown alone, only 11 genes, 1771 gene promoters showed DNA methylation changes upon DNMT3B knockdown alone, with 1618 of these genes exhibiting decreased levels of methylation. These data indicated that knockdown of DNMT3B alone is sufficient for EC cells to undergo wide-spread promoter DNA demethylation, although knockdown of DNMT3B alone is not sufficient for gene re-expression. The results also indicated that promoter DNA demethylation alone does not account fully for the robust effects of decitabine on gene expression in EC cells.

TABLE 15

| Gene | Gene ID | sh-ctrl | | sh-ctrl + 5aza | | sh-3B | | sh-3b + 5aza | |
|---|---|---|---|---|---|---|---|---|---|
| | | Mean | SEM | Mean | SEM | Mean | SEM | Mean | SEM |
| SLC34A2 | cg19616230 | 0.119 | 0.007 | 0.237 | 0.106 | 0.755 | 0.007 | 0.768 | 0.014 |
| ADFP | cg13060646 | 0.131 | 0.004 | 0.200 | 0.070 | 0.670 | 0.029 | 0.673 | 0.014 |

TABLE 15-continued

| Gene | Gene ID | sh-ctrl Mean | sh-ctrl SEM | sh-ctrl + 5aza Mean | sh-ctrl + 5aza SEM | sh-3B Mean | sh-3B SEM | sh-3b + 5aza Mean | sh-3b + 5aza SEM |
|---|---|---|---|---|---|---|---|---|---|
| SYK | cg02608019 | 0.202 | 0.012 | 0.212 | 0.013 | 0.780 | 0.026 | 0.801 | 0.026 |
| SCNN1A | cg18738906 | 0.156 | 0.006 | 0.160 | 0.005 | 0.604 | 0.022 | 0.580 | 0.012 |
| ZDHHC8 | cg25650110 | 0.142 | 0.008 | 0.151 | 0.004 | 0.502 | 0.043 | 0.472 | 0.041 |
| CLDN7 | cg25718402 | 0.117 | 0.006 | 0.110 | 0.005 | 0.536 | 0.020 | 0.507 | 0.057 |
| SH3YL1 | cg21825027 | 0.149 | 0.005 | 0.133 | 0.007 | 0.623 | 0.014 | 0.650 | 0.014 |
| FLJ14001 | cg07312445 | 0.198 | 0.016 | 0.239 | 0.031 | 0.519 | 0.026 | 0.589 | 0.021 |
| SYK | cg14304761 | 0.188 | 0.006 | 0.165 | 0.007 | 0.692 | 0.006 | 0.697 | 0.030 |
| GNMT | cg14338887 | 0.339 | 0.015 | 0.351 | 0.055 | 0.803 | 0.003 | 0.840 | 0.004 |
| CCDC62 | cg05745851 | 0.265 | 0.024 | 0.277 | 0.014 | 0.615 | 0.011 | 0.647 | 0.017 |
| C1orf88 | cg04763192 | 0.174 | 0.008 | 0.193 | 0.040 | 0.375 | 0.016 | 0.414 | 0.020 |
| HIST1H3F | cg06254453 | 0.182 | 0.009 | 0.186 | 0.020 | 0.400 | 0.014 | 0.438 | 0.018 |
| ARC | cg10104451 | 0.305 | 0.018 | 0.327 | 0.014 | 0.697 | 0.010 | 0.689 | 0.036 |
| UBE2C | cg19222480 | 0.165 | 0.008 | 0.149 | 0.004 | 0.510 | 0.041 | 0.582 | 0.022 |
| SYK | cg10025443 | 0.224 | 0.013 | 0.236 | 0.028 | 0.492 | 0.008 | 0.499 | 0.038 |
| ALDH2 | cg10449070 | 0.200 | 0.015 | 0.172 | 0.009 | 0.601 | 0.019 | 0.652 | 0.043 |
| SF3B14 | cg04809136 | 0.202 | 0.006 | 0.215 | 0.031 | 0.413 | 0.015 | 0.391 | 0.008 |
| SYK | cg05801648 | 0.260 | 0.009 | 0.302 | 0.027 | 0.497 | 0.009 | 0.483 | 0.035 |
| SYK | cg07160163 | 0.153 | 0.017 | 0.147 | 0.012 | 0.439 | 0.053 | 0.470 | 0.027 |
| CXCL5 | cg10088985 | 0.182 | 0.011 | 0.190 | 0.020 | 0.335 | 0.023 | 0.359 | 0.034 |
| AGGF1 | cg25836159 | 0.172 | 0.020 | 0.161 | 0.015 | 0.517 | 0.010 | 0.496 | 0.054 |
| HIST1H2BN | cg03833068 | 0.344 | 0.015 | 0.387 | 0.033 | 0.576 | 0.011 | 0.604 | 0.016 |
| TMEM125 | cg04355435 | 0.270 | 0.021 | 0.310 | 0.008 | 0.439 | 0.014 | 0.473 | 0.015 |
| HIST1H3J | cg17965019 | 0.397 | 0.013 | 0.467 | 0.023 | 0.627 | 0.010 | 0.656 | 0.007 |
| HIST1H4K | cg10608333 | 0.491 | 0.017 | 0.627 | 0.042 | 0.718 | 0.014 | 0.775 | 0.011 |
| HIST1H2BH | cg21663122 | 0.382 | 0.007 | 0.431 | 0.020 | 0.595 | 0.007 | 0.625 | 0.024 |
| KCNC3 | cg17838026 | 0.551 | 0.031 | 0.559 | 0.025 | 0.862 | 0.019 | 0.866 | 0.012 |
| HIST1H1A | cg14652095 | 0.537 | 0.022 | 0.607 | 0.031 | 0.838 | 0.022 | 0.775 | 0.019 |
| SYT12 | cg09967877 | 0.415 | 0.014 | 0.453 | 0.025 | 0.668 | 0.035 | 0.592 | 0.032 |
| HIST1H3H | cg18943383 | 0.538 | 0.019 | 0.630 | 0.015 | 0.713 | 0.020 | 0.808 | 0.039 |
| HIST1H2AM | cg17384145 | 0.390 | 0.006 | 0.399 | 0.012 | 0.563 | 0.006 | 0.593 | 0.014 |
| GNMT | cg24101359 | 0.301 | 0.007 | 0.285 | 0.057 | 0.730 | 0.010 | 0.777 | 0.005 |
| HIST1H4J | cg23372001 | 0.569 | 0.006 | 0.638 | 0.012 | 0.775 | 0.038 | 0.834 | 0.030 |
| TACSTD1 | cg16076328 | 0.222 | 0.008 | 0.201 | 0.015 | 0.565 | 0.029 | 0.555 | 0.009 |
| RHBDD1 | cg10523019 | 0.301 | 0.005 | 0.327 | 0.005 | 0.426 | 0.006 | 0.418 | 0.015 |
| CSRP2BP | cg22136753 | 0.629 | 0.016 | 0.695 | 0.018 | 0.895 | 0.016 | 0.844 | 0.006 |
| RLN1 | cg00055233 | 0.215 | 0.012 | 0.210 | 0.006 | 0.509 | 0.020 | 0.534 | 0.003 |
| TERC | cg01389761 | 0.294 | 0.006 | 0.323 | 0.008 | 0.380 | 0.023 | 0.421 | 0.020 |
| RAMP2 | cg14436761 | 0.636 | 0.011 | 0.685 | 0.025 | 0.892 | 0.012 | 0.846 | 0.002 |
| RGS16 | cg18611847 | 0.273 | 0.009 | 0.267 | 0.008 | 0.635 | 0.009 | 0.676 | 0.008 |
| RAMP2 | cg26990660 | 0.649 | 0.022 | 0.736 | 0.013 | 0.862 | 0.006 | 0.852 | 0.003 |
| BMP6 | cg03447931 | 0.132 | 0.002 | 0.157 | 0.009 | 0.185 | 0.006 | 0.155 | 0.007 |
| UNQ9433 | cg26021627 | 0.385 | 0.010 | 0.408 | 0.009 | 0.532 | 0.010 | 0.505 | 0.018 |
| ZDHHC8 | cg16756998 | 0.233 | 0.014 | 0.215 | 0.027 | 0.503 | 0.038 | 0.618 | 0.074 |
| HIST1H2AK | cg25885771 | 0.432 | 0.011 | 0.433 | 0.016 | 0.565 | 0.012 | 0.615 | 0.022 |
| ARFGEF1 | cg04947838 | 0.244 | 0.016 | 0.378 | 0.011 | 0.255 | 0.015 | 0.274 | 0.016 |
| ST13 | cg17660026 | 0.239 | 0.006 | 0.261 | 0.005 | 0.316 | 0.006 | 0.306 | 0.001 |
| TCTEX1D1 | cg24110050 | 0.437 | 0.009 | 0.438 | 0.017 | 0.590 | 0.027 | 0.581 | 0.004 |
| IL20RA | cg04481779 | 0.455 | 0.019 | 0.479 | 0.017 | 0.617 | 0.014 | 0.575 | 0.006 |
| IQCG | cg11787839 | 0.301 | 0.013 | 0.306 | 0.004 | 0.391 | 0.018 | 0.406 | 0.007 |
| HIST1H2AJ | cg03221914 | 0.546 | 0.035 | 0.549 | 0.041 | 0.694 | 0.016 | 0.758 | 0.018 |
| HLA-B | cg17554194 | 0.177 | 0.003 | 0.184 | 0.015 | 0.257 | 0.007 | 0.206 | 0.013 |
| MYH2 | cg06220958 | 0.332 | 0.025 | 0.353 | 0.012 | 0.452 | 0.009 | 0.398 | 0.004 |
| XRCC6 | cg02169098 | 0.141 | 0.007 | 0.209 | 0.012 | 0.146 | 0.009 | 0.154 | 0.006 |
| FLJ39237 | cg19528976 | 0.221 | 0.013 | 0.182 | 0.006 | 0.534 | 0.003 | 0.535 | 0.012 |
| ZNF267 | cg02008169 | 0.455 | 0.014 | 0.559 | 0.005 | 0.556 | 0.013 | 0.528 | 0.009 |
| POU2F2 | cg22054191 | 0.419 | 0.015 | 0.429 | 0.023 | 0.531 | 0.026 | 0.545 | 0.007 |
| FTH1 | cg24898753 | 0.604 | 0.027 | 0.616 | 0.012 | 0.782 | 0.019 | 0.760 | 0.019 |
| GCKR | cg20229788 | 0.353 | 0.012 | 0.450 | 0.008 | 0.411 | 0.014 | 0.399 | 0.010 |
| PRO1853 | cg05257610 | 0.480 | 0.016 | 0.684 | 0.026 | 0.496 | 0.038 | 0.532 | 0.026 |
| SLC2A10 | cg17550582 | 0.504 | 0.020 | 0.533 | 0.024 | 0.614 | 0.009 | 0.647 | 0.009 |
| AGPAT1 | cg15982308 | 0.393 | 0.007 | 0.398 | 0.013 | 0.480 | 0.016 | 0.508 | 0.009 |
| TTC10 | cg18735146 | 0.512 | 0.019 | 0.514 | 0.028 | 0.643 | 0.001 | 0.630 | 0.009 |
| RLN2 | cg03679581 | 0.232 | 0.004 | 0.224 | 0.009 | 0.504 | 0.019 | 0.545 | 0.011 |
| TRPM3 | cg16832407 | 0.473 | 0.004 | 0.489 | 0.011 | 0.604 | 0.003 | 0.540 | 0.010 |
| LOC92345 | cg18023724 | 0.727 | 0.008 | 0.742 | 0.004 | 0.897 | 0.006 | 0.867 | 0.016 |
| ERGIC3 | cg00340102 | 0.348 | 0.009 | 0.383 | 0.008 | 0.421 | 0.008 | 0.381 | 0.009 |
| TWIST1 | cg26312150 | 0.231 | 0.003 | 0.231 | 0.009 | 0.281 | 0.006 | 0.268 | 0.002 |
| MORF4L1 | cg03589001 | 0.301 | 0.008 | 0.309 | 0.004 | 0.375 | 0.014 | 0.331 | 0.003 |
| ABCC11 | cg10631471 | 0.600 | 0.009 | 0.605 | 0.005 | 0.728 | 0.005 | 0.686 | 0.008 |
| RNF121 | cg05492270 | 0.291 | 0.005 | 0.387 | 0.010 | 0.293 | 0.010 | 0.292 | 0.013 |
| STAG1 | cg00841581 | 0.135 | 0.002 | 0.162 | 0.003 | 0.144 | 0.001 | 0.144 | 0.003 |
| ATN1 | cg01437411 | 0.669 | 0.010 | 0.669 | 0.016 | 0.835 | 0.008 | 0.717 | 0.002 |
| SFRS4 | cg14195915 | 0.153 | 0.001 | 0.184 | 0.005 | 0.157 | 0.004 | 0.164 | 0.003 |
| CLPP | cg12562500 | 0.158 | 0.004 | 0.159 | 0.008 | 0.196 | 0.004 | 0.162 | 0.002 |
| NDUFS8 | cg08139833 | 0.153 | 0.011 | 0.116 | 0.011 | 0.369 | 0.041 | 0.315 | 0.036 |

TABLE 15-continued

| Gene | Gene ID | sh-ctrl Mean | sh-ctrl SEM | sh-ctrl + 5aza Mean | sh-ctrl + 5aza SEM | sh-3B Mean | sh-3B SEM | sh-3b + 5aza Mean | sh-3b + 5aza SEM |
|---|---|---|---|---|---|---|---|---|---|
| BRSK2 | cg14021073 | 0.304 | 0.025 | 0.300 | 0.024 | 0.642 | 0.013 | 0.621 | 0.028 |
| MT1E | cg15134649 | 0.229 | 0.005 | 0.227 | 0.012 | 0.436 | 0.026 | 0.490 | 0.038 |
| SYK | cg16896647 | 0.258 | 0.009 | 0.226 | 0.006 | 0.515 | 0.040 | 0.538 | 0.032 |
| NODAL | cg04377282 | 0.240 | 0.006 | 0.220 | 0.001 | 0.486 | 0.010 | 0.464 | 0.014 |
| CYYR1 | cg10238818 | 0.148 | 0.002 | 0.143 | 0.002 | 0.270 | 0.003 | 0.305 | 0.015 |
| GNMT | cg23696834 | 0.327 | 0.016 | 0.286 | 0.010 | 0.606 | 0.015 | 0.665 | 0.007 |
| RBM35A | cg18565355 | 0.221 | 0.003 | 0.211 | 0.015 | 0.428 | 0.014 | 0.404 | 0.009 |
| TERC | cg27020690 | 0.272 | 0.041 | 0.249 | 0.015 | 0.510 | 0.025 | 0.510 | 0.037 |
| ILDR1 | cg08463485 | 0.267 | 0.006 | 0.231 | 0.017 | 0.488 | 0.012 | 0.507 | 0.016 |
| RGS16 | cg16891895 | 0.284 | 0.028 | 0.254 | 0.018 | 0.530 | 0.017 | 0.514 | 0.020 |
| HIST1H1B | cg04676561 | 0.330 | 0.007 | 0.316 | 0.030 | 0.583 | 0.020 | 0.597 | 0.006 |
| LAD1 | cg19713196 | 0.385 | 0.022 | 0.314 | 0.028 | 0.676 | 0.039 | 0.734 | 0.017 |
| LOC349136 | cg24068372 | 0.365 | 0.100 | 0.253 | 0.010 | 0.699 | 0.032 | 0.705 | 0.025 |
| CCDC62 | cg08775774 | 0.373 | 0.005 | 0.360 | 0.008 | 0.619 | 0.026 | 0.659 | 0.020 |
| AMPD3 | cg24921089 | 0.315 | 0.046 | 0.295 | 0.024 | 0.533 | 0.017 | 0.519 | 0.011 |
| KIAA1838 | cg26200580 | 0.272 | 0.007 | 0.223 | 0.009 | 0.495 | 0.035 | 0.489 | 0.044 |
| SLCO2A1 | cg07708788 | 0.291 | 0.012 | 0.275 | 0.029 | 0.481 | 0.010 | 0.468 | 0.038 |
| TINAGL1 | cg22855405 | 0.319 | 0.013 | 0.314 | 0.007 | 0.518 | 0.015 | 0.482 | 0.009 |
| HIST1H3F | cg05414338 | 0.320 | 0.010 | 0.269 | 0.009 | 0.528 | 0.016 | 0.516 | 0.044 |
| SH2D3A | cg15055101 | 0.219 | 0.004 | 0.193 | 0.013 | 0.336 | 0.003 | 0.355 | 0.013 |
| GFRA3 | cg09350274 | 0.373 | 0.019 | 0.334 | 0.021 | 0.559 | 0.026 | 0.611 | 0.044 |
| AVPR1B | cg04633513 | 0.256 | 0.003 | 0.215 | 0.006 | 0.388 | 0.012 | 0.425 | 0.024 |
| GSTM4 | cg15955341 | 0.333 | 0.062 | 0.275 | 0.020 | 0.527 | 0.028 | 0.533 | 0.014 |
| CDH1 | cg20716119 | 0.239 | 0.014 | 0.185 | 0.016 | 0.408 | 0.016 | 0.363 | 0.014 |
| SCNN1A | cg26215727 | 0.229 | 0.002 | 0.217 | 0.007 | 0.353 | 0.005 | 0.330 | 0.010 |
| ABHD9 | cg05488632 | 0.309 | 0.027 | 0.267 | 0.037 | 0.445 | 0.023 | 0.500 | 0.020 |
| SLIT2 | cg03742003 | 0.361 | 0.016 | 0.325 | 0.026 | 0.559 | 0.024 | 0.514 | 0.015 |
| CLCN6 | cg05228408 | 0.345 | 0.006 | 0.344 | 0.020 | 0.502 | 0.006 | 0.466 | 0.009 |
| UGT3A1 | cg23317501 | 0.256 | 0.005 | 0.233 | 0.011 | 0.350 | 0.009 | 0.390 | 0.015 |
| PTEN | cg01228636 | 0.215 | 0.004 | 0.207 | 0.008 | 0.294 | 0.019 | 0.315 | 0.020 |
| MT1E | cg20083730 | 0.187 | 0.012 | 0.160 | 0.008 | 0.261 | 0.013 | 0.293 | 0.018 |
| ST14 | cg10089145 | 0.571 | 0.028 | 0.447 | 0.091 | 0.835 | 0.024 | 0.905 | 0.021 |
| HPGD | cg06366981 | 0.237 | 0.007 | 0.234 | 0.022 | 0.326 | 0.015 | 0.331 | 0.014 |
| SCARF2 | cg14785479 | 0.338 | 0.027 | 0.254 | 0.012 | 0.488 | 0.010 | 0.544 | 0.042 |
| PKP3 | cg08314660 | 0.436 | 0.019 | 0.337 | 0.001 | 0.680 | 0.023 | 0.624 | 0.032 |
| ME3 | cg09645888 | 0.578 | 0.011 | 0.575 | 0.006 | 0.767 | 0.021 | 0.741 | 0.011 |
| ITGA3 | cg14737977 | 0.208 | 0.011 | 0.186 | 0.011 | 0.292 | 0.009 | 0.267 | 0.007 |
| RPS29 | cg02443089 | 0.287 | 0.011 | 0.447 | 0.030 | 0.296 | 0.027 | 0.282 | 0.003 |
| SCARB2 | cg21656748 | 0.256 | 0.009 | 0.218 | 0.018 | 0.383 | 0.008 | 0.319 | 0.017 |
| RANBP2 | cg08733774 | 0.254 | 0.015 | 0.233 | 0.010 | 0.361 | 0.020 | 0.304 | 0.010 |
| HAPLN1 | cg09893305 | 0.424 | 0.007 | 0.422 | 0.002 | 0.549 | 0.013 | 0.519 | 0.013 |
| RGS10 | cg04041960 | 0.328 | 0.003 | 0.264 | 0.036 | 0.487 | 0.010 | 0.413 | 0.017 |
| SIX3 | cg13163729 | 0.837 | 0.016 | 0.801 | 0.017 | 1.103 | 0.032 | 1.030 | 0.004 |
| CEP68 | cg05010058 | 0.190 | 0.016 | 0.261 | 0.006 | 0.217 | 0.011 | 0.185 | 0.001 |
| ZMYND12 | cg20757758 | 0.344 | 0.021 | 0.279 | 0.012 | 0.466 | 0.010 | 0.466 | 0.007 |
| HIST1H1A | cg10146929 | 0.589 | 0.024 | 0.562 | 0.020 | 0.752 | 0.019 | 0.728 | 0.004 |
| FLJ20551 | cg25999267 | 1.027 | 0.004 | 0.993 | 0.017 | 1.278 | 0.007 | 1.269 | 0.020 |
| TCTEX1D1 | cg17819635 | 0.427 | 0.022 | 0.375 | 0.039 | 0.519 | 0.009 | 0.576 | 0.023 |
| GABRE | cg12204574 | 0.618 | 0.015 | 0.588 | 0.005 | 0.752 | 0.009 | 0.780 | 0.011 |
| PIGT | cg07294870 | 0.180 | 0.004 | 0.264 | 0.024 | 0.168 | 0.005 | 0.182 | 0.008 |
| ACOT7 | cg25165880 | 0.557 | 0.018 | 0.523 | 0.003 | 0.735 | 0.013 | 0.636 | 0.019 |
| ACAD8 | cg23927367 | 0.191 | 0.002 | 0.244 | 0.007 | 0.220 | 0.014 | 0.185 | 0.001 |
| LMCD1 | cg20595215 | 0.331 | 0.007 | 0.305 | 0.025 | 0.428 | 0.009 | 0.391 | 0.018 |
| ARHGAP11A | cg18721882 | 0.216 | 0.006 | 0.302 | 0.008 | 0.218 | 0.016 | 0.213 | 0.008 |
| STX5A | cg15494980 | 0.248 | 0.005 | 0.337 | 0.014 | 0.240 | 0.005 | 0.261 | 0.012 |
| FLJ20551 | cg12534466 | 0.906 | 0.013 | 0.860 | 0.015 | 1.106 | 0.028 | 1.098 | 0.022 |
| LANCL3 | cg01975392 | 0.362 | 0.019 | 0.245 | 0.025 | 0.535 | 0.069 | 0.495 | 0.016 |
| CDH13 | cg19369556 | 0.637 | 0.008 | 0.589 | 0.031 | 0.786 | 0.010 | 0.770 | 0.013 |
| EFS | cg07197059 | 0.380 | 0.009 | 0.358 | 0.019 | 0.499 | 0.016 | 0.417 | 0.023 |
| ME1 | cg06836736 | 0.483 | 0.007 | 0.417 | 0.003 | 0.603 | 0.014 | 0.608 | 0.012 |
| ZNF576 | cg16648297 | 0.099 | 0.001 | 0.091 | 0.004 | 0.123 | 0.003 | 0.115 | 0.004 |
| TEK | cg09827833 | 0.606 | 0.016 | 0.591 | 0.020 | 0.750 | 0.009 | 0.668 | 0.024 |
| TTC23 | cg21416022 | 0.420 | 0.032 | 0.570 | 0.025 | 0.382 | 0.025 | 0.442 | 0.004 |
| VAMP8 | cg05656364 | 0.250 | 0.012 | 0.212 | 0.018 | 0.332 | 0.015 | 0.288 | 0.011 |
| KIAA1618 | cg21516384 | 0.515 | 0.006 | 0.494 | 0.002 | 0.621 | 0.011 | 0.589 | 0.021 |
| ADSSL1 | cg02043070 | 0.136 | 0.007 | 0.191 | 0.007 | 0.137 | 0.005 | 0.122 | 0.003 |
| CWF19L1 | cg11187508 | 0.197 | 0.007 | 0.265 | 0.015 | 0.202 | 0.012 | 0.185 | 0.005 |
| IL15 | cg25546588 | 0.277 | 0.014 | 0.249 | 0.010 | 0.365 | 0.004 | 0.301 | 0.005 |
| MGC10992 | cg20687462 | 0.323 | 0.019 | 0.303 | 0.009 | 0.421 | 0.008 | 0.332 | 0.016 |
| DISC1 | cg24499839 | 0.263 | 0.001 | 0.233 | 0.007 | 0.337 | 0.011 | 0.293 | 0.002 |
| LTB4DH | cg23964386 | 0.678 | 0.014 | 0.613 | 0.042 | 0.872 | 0.018 | 0.736 | 0.035 |
| SLC7A3 | cg20622056 | 0.283 | 0.011 | 0.248 | 0.005 | 0.360 | 0.010 | 0.322 | 0.018 |
| MOV10 | cg04564646 | 0.115 | 0.004 | 0.098 | 0.006 | 0.137 | 0.006 | 0.144 | 0.009 |
| TGFBI | cg21034676 | 0.440 | 0.015 | 0.303 | 0.013 | 0.595 | 0.022 | 0.596 | 0.013 |
| CHEK2 | cg22585269 | 0.292 | 0.015 | 0.389 | 0.005 | 0.271 | 0.015 | 0.292 | 0.019 |

TABLE 15-continued

| Gene | Gene ID | sh-ctrl Mean | sh-ctrl SEM | sh-ctrl + 5aza Mean | sh-ctrl + 5aza SEM | sh-3B Mean | sh-3B SEM | sh-3b + 5aza Mean | sh-3b + 5aza SEM |
|---|---|---|---|---|---|---|---|---|---|
| FLJ22624 | cg09480162 | 0.291 | 0.004 | 0.365 | 0.013 | 0.303 | 0.011 | 0.279 | 0.011 |
| ACSS2 | cg03440846 | 0.477 | 0.003 | 0.471 | 0.008 | 0.578 | 0.007 | 0.491 | 0.010 |
| ERCC4 | cg10784067 | 0.156 | 0.002 | 0.209 | 0.007 | 0.162 | 0.013 | 0.136 | 0.006 |
| HMGCS1 | cg11057497 | 0.243 | 0.003 | 0.310 | 0.010 | 0.246 | 0.017 | 0.222 | 0.010 |
| PPWD1 | cg01403114 | 0.412 | 0.003 | 0.508 | 0.012 | 0.395 | 0.013 | 0.417 | 0.021 |
| HAAO | cg01561916 | 0.146 | 0.003 | 0.129 | 0.003 | 0.179 | 0.009 | 0.162 | 0.003 |
| OAF | cg12572278 | 0.416 | 0.002 | 0.361 | 0.023 | 0.524 | 0.005 | 0.444 | 0.012 |
| CBFA2T2 | cg06335889 | 0.366 | 0.003 | 0.328 | 0.010 | 0.440 | 0.002 | 0.394 | 0.004 |
| LAD1 | cg25947945 | 0.531 | 0.017 | 0.431 | 0.036 | 0.627 | 0.018 | 0.640 | 0.015 |
| CDH13 | cg08977371 | 0.721 | 0.003 | 0.649 | 0.026 | 0.871 | 0.023 | 0.756 | 0.018 |
| SPINT2 | cg13301014 | 0.284 | 0.009 | 0.238 | 0.007 | 0.365 | 0.014 | 0.298 | 0.011 |
| NME3 | cg19030554 | 0.292 | 0.007 | 0.248 | 0.006 | 0.357 | 0.005 | 0.318 | 0.011 |
| LOC203427 | cg17439480 | 0.442 | 0.003 | 0.400 | 0.021 | 0.531 | 0.004 | 0.452 | 0.004 |
| CERK | cg05698090 | 0.359 | 0.003 | 0.299 | 0.009 | 0.445 | 0.015 | 0.377 | 0.007 |
| OSR1 | cg02742971 | 0.238 | 0.002 | 0.212 | 0.004 | 0.287 | 0.008 | 0.238 | 0.006 |
| SMAP | cg08466074 | 0.404 | 0.024 | 0.502 | 0.024 | 0.340 | 0.008 | 0.407 | 0.009 |
| PFN4 | cg07265300 | 0.271 | 0.010 | 0.333 | 0.019 | 0.277 | 0.003 | 0.228 | 0.009 |
| HSPB8 | cg22189286 | 0.747 | 0.015 | 0.628 | 0.003 | 0.919 | 0.016 | 0.756 | 0.021 |
| IFIH1 | cg07348311 | 0.307 | 0.016 | 0.243 | 0.004 | 0.361 | 0.021 | 0.333 | 0.014 |
| ZIC1 | cg05073035 | 0.132 | 0.008 | 0.160 | 0.005 | 0.133 | 0.007 | 0.107 | 0.001 |
| TINAGL1 | cg14869028 | 0.499 | 0.002 | 0.402 | 0.011 | 0.540 | 0.011 | 0.550 | 0.005 |
| FBXO2 | cg01420388 | 0.610 | 0.005 | 0.499 | 0.041 | 0.703 | 0.016 | 0.613 | 0.004 |
| ACY1 | cg03891319 | 0.321 | 0.010 | 0.254 | 0.012 | 0.370 | 0.016 | 0.330 | 0.005 |
| NSD1 | cg11316784 | 0.454 | 0.026 | 0.336 | 0.005 | 0.550 | 0.034 | 0.468 | 0.016 |
| C6orf142 | cg13281868 | 1.006 | 0.020 | 0.834 | 0.037 | 1.050 | 0.023 | 1.019 | 0.003 |
| MAP1B | cg07380496 | 0.125 | 0.004 | 0.137 | 0.003 | 0.127 | 0.003 | 0.097 | 0.001 |
| LOC400120 | cg17906786 | 0.515 | 0.007 | 0.516 | 0.015 | 0.541 | 0.006 | 0.404 | 0.010 |
| FAM82C | cg17316750 | 0.297 | 0.014 | 0.300 | 0.011 | 0.304 | 0.007 | 0.230 | 0.005 |
| HNRPA1 | cg14981132 | 0.260 | 0.013 | 0.362 | 0.029 | 0.239 | 0.007 | 0.252 | 0.005 |
| DAXX | cg07689821 | 0.259 | 0.012 | 0.329 | 0.009 | 0.243 | 0.015 | 0.255 | 0.009 |
| KLHL3 | cg13847070 | 0.379 | 0.019 | 0.498 | 0.026 | 0.336 | 0.016 | 0.367 | 0.021 |
| POLA2 | cg17346115 | 0.114 | 0.003 | 0.111 | 0.005 | 0.143 | 0.001 | 0.105 | 0.005 |
| ZNF621 | cg01885635 | 0.285 | 0.005 | 0.254 | 0.009 | 0.360 | 0.007 | 0.285 | 0.009 |
| L3MBTL | cg02611863 | 0.374 | 0.020 | 0.489 | 0.011 | 0.352 | 0.026 | 0.336 | 0.011 |
| ITSN1 | cg06502510 | 0.182 | 0.005 | 0.232 | 0.010 | 0.159 | 0.005 | 0.179 | 0.009 |
| PCBP4 | cg08917718 | 0.399 | 0.027 | 0.363 | 0.006 | 0.486 | 0.005 | 0.390 | 0.005 |
| PAQR8 | cg24323031 | 0.278 | 0.009 | 0.359 | 0.021 | 0.249 | 0.012 | 0.255 | 0.012 |
| LTBP3 | cg16632280 | 0.343 | 0.017 | 0.301 | 0.011 | 0.421 | 0.021 | 0.334 | 0.006 |
| ADAMTS6 | cg14700821 | 0.270 | 0.025 | 0.355 | 0.016 | 0.236 | 0.005 | 0.236 | 0.009 |
| LIN7A | cg05647859 | 0.287 | 0.009 | 0.358 | 0.014 | 0.239 | 0.017 | 0.270 | 0.014 |
| C2orf24 | cg21020082 | 0.238 | 0.013 | 0.293 | 0.004 | 0.209 | 0.008 | 0.216 | 0.014 |
| GNL2 | cg17004373 | 0.229 | 0.008 | 0.292 | 0.008 | 0.212 | 0.004 | 0.190 | 0.005 |
| OTUB1 | cg15564267 | 0.399 | 0.001 | 0.346 | 0.017 | 0.487 | 0.017 | 0.364 | 0.010 |
| DKFZP586H2123 | cg14542839 | 0.438 | 0.011 | 0.356 | 0.017 | 0.531 | 0.018 | 0.435 | 0.032 |
| GBL | cg04490516 | 0.452 | 0.013 | 0.578 | 0.046 | 0.402 | 0.018 | 0.377 | 0.009 |
| MOCS2 | cg21540749 | 0.196 | 0.010 | 0.243 | 0.009 | 0.163 | 0.006 | 0.176 | 0.009 |
| ZC3HAV1 | cg08222662 | 0.302 | 0.011 | 0.415 | 0.014 | 0.256 | 0.013 | 0.238 | 0.021 |
| AACS | cg05303448 | 0.384 | 0.033 | 0.513 | 0.027 | 0.280 | 0.034 | 0.363 | 0.006 |
| CASP8 | cg05130485 | 0.391 | 0.012 | 0.466 | 0.028 | 0.322 | 0.012 | 0.361 | 0.002 |
| KIF22 | cg12688670 | 0.482 | 0.004 | 0.401 | 0.008 | 0.548 | 0.006 | 0.462 | 0.009 |
| RPS6KC1 | cg14576824 | 0.426 | 0.029 | 0.508 | 0.016 | 0.399 | 0.015 | 0.339 | 0.013 |
| LRP2 | cg16691888 | 0.303 | 0.018 | 0.390 | 0.015 | 0.234 | 0.005 | 0.261 | 0.020 |
| UBTD1 | cg17296078 | 0.585 | 0.013 | 0.487 | 0.014 | 0.643 | 0.009 | 0.544 | 0.018 |
| RPS18 | cg20557567 | 0.261 | 0.015 | 0.321 | 0.017 | 0.212 | 0.009 | 0.219 | 0.008 |
| KLHL21 | cg19884658 | 0.623 | 0.009 | 0.542 | 0.023 | 0.741 | 0.011 | 0.503 | 0.021 |
| CABYR | cg21903324 | 0.278 | 0.010 | 0.344 | 0.016 | 0.231 | 0.004 | 0.225 | 0.009 |
| FLJ14346 | cg09204187 | 0.360 | 0.009 | 0.294 | 0.012 | 0.406 | 0.012 | 0.322 | 0.005 |
| ZNF572 | cg12738197 | 0.412 | 0.017 | 0.502 | 0.019 | 0.353 | 0.032 | 0.328 | 0.010 |
| IGF2AS | cg16817891 | 0.552 | 0.006 | 0.571 | 0.012 | 0.534 | 0.014 | 0.452 | 0.004 |
| CAPG | cg04881903 | 0.875 | 0.009 | 0.849 | 0.040 | 0.906 | 0.015 | 0.715 | 0.008 |
| PAK4 | cg24957950 | 0.173 | 0.000 | 0.174 | 0.005 | 0.171 | 0.003 | 0.143 | 0.004 |
| SLC16A8 | cg14014225 | 1.155 | 0.043 | 1.202 | 0.014 | 1.124 | 0.020 | 0.931 | 0.019 |
| BSCL2 | cg07237830 | 0.803 | 0.014 | 0.669 | 0.018 | 0.894 | 0.002 | 0.705 | 0.015 |
| THAP11 | cg13798289 | 0.641 | 0.006 | 0.615 | 0.003 | 0.656 | 0.017 | 0.528 | 0.006 |
| MFSD4 | cg15364537 | 0.893 | 0.029 | 0.992 | 0.018 | 0.841 | 0.031 | 0.697 | 0.011 |
| TMEM55A | cg06688396 | 0.264 | 0.003 | 0.210 | 0.014 | 0.293 | 0.009 | 0.243 | 0.012 |
| KIAA0152 | cg01481441 | 0.199 | 0.003 | 0.214 | 0.008 | 0.181 | 0.007 | 0.164 | 0.006 |
| METRN | cg11027330 | 0.792 | 0.014 | 0.735 | 0.028 | 0.857 | 0.012 | 0.634 | 0.009 |
| KRT8 | cg20324165 | 0.683 | 0.006 | 0.537 | 0.005 | 0.819 | 0.009 | 0.581 | 0.011 |
| ZFYVE9 | cg15683488 | 0.269 | 0.008 | 0.285 | 0.013 | 0.224 | 0.002 | 0.242 | 0.003 |
| CSPG4 | cg21460582 | 0.842 | 0.016 | 0.740 | 0.023 | 0.913 | 0.009 | 0.697 | 0.029 |
| TTC5 | cg20483016 | 0.294 | 0.010 | 0.345 | 0.014 | 0.238 | 0.019 | 0.246 | 0.004 |
| MGC33839 | cg14496375 | 1.049 | 0.013 | 0.873 | 0.013 | 1.062 | 0.031 | 0.978 | 0.009 |
| LOC129285 | cg24076392 | 0.186 | 0.004 | 0.191 | 0.007 | 0.172 | 0.004 | 0.153 | 0.001 |
| NCOA6 | cg19794490 | 0.211 | 0.005 | 0.202 | 0.008 | 0.169 | 0.006 | 0.215 | 0.006 |

TABLE 15-continued

| Gene | Gene ID | sh-ctrl | | sh-ctrl + 5aza | | sh-3B | | sh-3b + 5aza | |
|---|---|---|---|---|---|---|---|---|---|
| | | Mean | SEM | Mean | SEM | Mean | SEM | Mean | SEM |
| EML3 | cg12616487 | 0.910 | 0.008 | 0.836 | 0.023 | 0.938 | 0.015 | 0.751 | 0.013 |
| GALR1 | cg12699371 | 0.219 | 0.003 | 0.234 | 0.009 | 0.199 | 0.001 | 0.178 | 0.006 |
| MYCBP | cg00521598 | 0.273 | 0.010 | 0.297 | 0.006 | 0.226 | 0.010 | 0.234 | 0.009 |
| NDN | cg18552939 | 0.386 | 0.018 | 0.445 | 0.011 | 0.305 | 0.001 | 0.332 | 0.010 |
| HSU79303 | cg12582959 | 0.283 | 0.006 | 0.257 | 0.005 | 0.308 | 0.014 | 0.223 | 0.001 |
| C20orf6 | cg14251536 | 0.259 | 0.002 | 0.309 | 0.021 | 0.223 | 0.009 | 0.198 | 0.007 |
| GNG13 | cg14100184 | 1.007 | 0.011 | 0.934 | 0.027 | 1.021 | 0.014 | 0.826 | 0.006 |
| FES | cg24888049 | 0.948 | 0.013 | 0.865 | 0.010 | 0.976 | 0.005 | 0.776 | 0.014 |
| CKM | cg20444256 | 0.858 | 0.017 | 0.784 | 0.015 | 0.873 | 0.016 | 0.708 | 0.020 |
| ISOC2 | cg09846458 | 0.914 | 0.007 | 0.865 | 0.045 | 0.923 | 0.013 | 0.735 | 0.020 |
| TSPAN9 | cg16405575 | 0.217 | 0.002 | 0.199 | 0.009 | 0.224 | 0.004 | 0.176 | 0.007 |
| LPPR4 | cg26164310 | 0.437 | 0.011 | 0.503 | 0.018 | 0.364 | 0.004 | 0.353 | 0.003 |
| DPY19L3 | cg22892237 | 0.237 | 0.013 | 0.271 | 0.005 | 0.192 | 0.008 | 0.198 | 0.014 |
| RPL35A | cg16927136 | 0.212 | 0.004 | 0.258 | 0.017 | 0.183 | 0.016 | 0.156 | 0.007 |
| TALDO1 | cg26488636 | 0.195 | 0.005 | 0.171 | 0.004 | 0.206 | 0.003 | 0.161 | 0.008 |
| COL6A1 | cg25020459 | 0.776 | 0.010 | 0.782 | 0.006 | 0.724 | 0.038 | 0.628 | 0.002 |
| POLR3E | cg19593572 | 0.483 | 0.007 | 0.520 | 0.010 | 0.428 | 0.010 | 0.386 | 0.020 |
| SLC25A19 | cg08766742 | 0.172 | 0.004 | 0.180 | 0.004 | 0.164 | 0.000 | 0.133 | 0.010 |
| B4GALT2 | cg23001650 | 0.556 | 0.007 | 0.488 | 0.020 | 0.579 | 0.009 | 0.463 | 0.010 |
| AXL | cg10564498 | 0.868 | 0.012 | 0.758 | 0.018 | 0.938 | 0.014 | 0.702 | 0.028 |
| ST6GALNAC4 | cg04416752 | 0.338 | 0.011 | 0.328 | 0.010 | 0.341 | 0.008 | 0.264 | 0.009 |
| ATXN1 | cg10487127 | 0.174 | 0.006 | 0.185 | 0.002 | 0.157 | 0.009 | 0.138 | 0.004 |
| CAMK1 | cg23243617 | 0.794 | 0.009 | 0.808 | 0.009 | 0.705 | 0.009 | 0.659 | 0.018 |
| PDGFRB | cg11042320 | 0.430 | 0.010 | 0.363 | 0.008 | 0.469 | 0.008 | 0.350 | 0.005 |
| ATP2B2 | cg14547335 | 1.056 | 0.009 | 1.069 | 0.029 | 0.940 | 0.017 | 0.874 | 0.003 |
| CRYBB1 | cg04541607 | 0.986 | 0.013 | 0.918 | 0.004 | 0.988 | 0.015 | 0.788 | 0.014 |
| PROK2 | cg15798455 | 0.431 | 0.010 | 0.445 | 0.012 | 0.418 | 0.008 | 0.325 | 0.013 |
| C14orf132 | cg19070873 | 0.446 | 0.007 | 0.476 | 0.006 | 0.405 | 0.004 | 0.346 | 0.016 |
| MGC39715 | cg17199658 | 1.087 | 0.020 | 1.091 | 0.024 | 0.973 | 0.002 | 0.896 | 0.020 |
| LIN28 | cg18634211 | 0.224 | 0.005 | 0.227 | 0.007 | 0.206 | 0.009 | 0.178 | 0.004 |
| MLC1SA | cg23309825 | 0.342 | 0.012 | 0.308 | 0.005 | 0.346 | 0.009 | 0.275 | 0.007 |
| KCNQ4 | cg06885782 | 0.515 | 0.009 | 0.478 | 0.008 | 0.515 | 0.010 | 0.407 | 0.019 |
| TTC22 | cg22130834 | 0.650 | 0.015 | 0.659 | 0.019 | 0.566 | 0.003 | 0.539 | 0.017 |
| TCN2 | cg17693957 | 0.664 | 0.017 | 0.581 | 0.016 | 0.669 | 0.006 | 0.552 | 0.005 |
| RANBP1 | cg11594228 | 0.951 | 0.025 | 0.951 | 0.005 | 0.844 | 0.023 | 0.783 | 0.027 |
| HUS1 | cg14171882 | 0.531 | 0.008 | 0.564 | 0.010 | 0.441 | 0.010 | 0.442 | 0.030 |
| FURIN | cg26377677 | 0.893 | 0.012 | 0.786 | 0.006 | 0.910 | 0.006 | 0.728 | 0.042 |
| NF1 | cg22289810 | 0.221 | 0.009 | 0.248 | 0.007 | 0.185 | 0.008 | 0.175 | 0.009 |
| DDOST | cg08911391 | 0.747 | 0.010 | 0.677 | 0.009 | 0.763 | 0.014 | 0.593 | 0.025 |
| KRTAP26-1 | cg18822544 | 0.722 | 0.021 | 0.777 | 0.023 | 0.585 | 0.009 | 0.610 | 0.019 |
| GLS2 | cg14679587 | 0.232 | 0.007 | 0.265 | 0.002 | 0.189 | 0.002 | 0.185 | 0.017 |
| OR12D3 | cg20856834 | 0.831 | 0.003 | 0.831 | 0.023 | 0.736 | 0.016 | 0.682 | 0.017 |
| LOC205251 | cg24912023 | 0.892 | 0.016 | 0.931 | 0.026 | 0.767 | 0.013 | 0.727 | 0.009 |
| HPD | cg02506908 | 1.140 | 0.009 | 0.950 | 0.019 | 1.165 | 0.013 | 0.972 | 0.012 |
| GGT6 | cg22628873 | 0.569 | 0.014 | 0.508 | 0.010 | 0.571 | 0.010 | 0.460 | 0.022 |
| PDGFRA | cg22736323 | 0.949 | 0.026 | 0.957 | 0.012 | 0.831 | 0.009 | 0.776 | 0.030 |
| MGC52282 | cg10186456 | 1.171 | 0.015 | 1.179 | 0.030 | 1.009 | 0.012 | 0.974 | 0.018 |
| FLJ23878 | cg22005565 | 0.565 | 0.017 | 0.520 | 0.013 | 0.567 | 0.009 | 0.443 | 0.001 |
| CYP27B1 | cg18413900 | 0.985 | 0.025 | 0.875 | 0.013 | 0.993 | 0.021 | 0.794 | 0.010 |
| GDF3 | cg15992730 | 0.325 | 0.023 | 0.404 | 0.030 | 0.258 | 0.013 | 0.241 | 0.009 |
| LPPR4 | cg05596294 | 0.634 | 0.012 | 0.664 | 0.021 | 0.524 | 0.007 | 0.530 | 0.019 |
| PIK3CA | cg22384366 | 0.190 | 0.005 | 0.208 | 0.008 | 0.145 | 0.012 | 0.167 | 0.006 |
| LCE5A | cg05248781 | 0.965 | 0.015 | 0.969 | 0.014 | 0.829 | 0.019 | 0.803 | 0.011 |
| GANC | cg26052367 | 0.277 | 0.011 | 0.304 | 0.009 | 0.224 | 0.006 | 0.226 | 0.006 |
| LANCL1 | cg07063745 | 0.293 | 0.014 | 0.354 | 0.012 | 0.249 | 0.007 | 0.210 | 0.024 |
| ARID3A | cg18084554 | 0.931 | 0.012 | 0.954 | 0.018 | 0.824 | 0.014 | 0.738 | 0.020 |
| TNKS1BP1 | cg12603560 | 0.592 | 0.022 | 0.602 | 0.025 | 0.533 | 0.006 | 0.466 | 0.013 |
| CTSH | cg07448499 | 0.585 | 0.013 | 0.505 | 0.013 | 0.592 | 0.009 | 0.479 | 0.013 |
| SLC31A1 | cg15865742 | 0.480 | 0.008 | 0.551 | 0.037 | 0.385 | 0.020 | 0.375 | 0.023 |
| GBP3 | cg23540651 | 0.833 | 0.017 | 0.848 | 0.036 | 0.697 | 0.025 | 0.693 | 0.014 |
| CBFB | cg06766367 | 0.364 | 0.008 | 0.288 | 0.009 | 0.374 | 0.015 | 0.318 | 0.005 |
| PSPH | cg12555334 | 0.375 | 0.017 | 0.323 | 0.003 | 0.382 | 0.006 | 0.305 | 0.010 |
| ARMC8 | cg05308617 | 0.295 | 0.008 | 0.308 | 0.010 | 0.239 | 0.007 | 0.248 | 0.005 |
| FAM26B | cg18273501 | 0.912 | 0.012 | 0.920 | 0.024 | 0.808 | 0.004 | 0.722 | 0.009 |
| BST2 | cg01254505 | 0.636 | 0.009 | 0.512 | 0.016 | 0.696 | 0.009 | 0.516 | 0.006 |
| KIAA0676 | cg12080675 | 0.898 | 0.016 | 0.943 | 0.021 | 0.831 | 0.026 | 0.662 | 0.008 |
| FUK | cg09881917 | 0.238 | 0.006 | 0.246 | 0.008 | 0.195 | 0.001 | 0.199 | 0.010 |
| MYOD1 | cg07271264 | 1.005 | 0.004 | 1.018 | 0.011 | 0.848 | 0.006 | 0.824 | 0.011 |
| RAB3IL1 | cg15589156 | 0.927 | 0.011 | 0.752 | 0.017 | 0.959 | 0.021 | 0.775 | 0.023 |
| PH-4 | cg21197973 | 0.731 | 0.007 | 0.731 | 0.039 | 0.664 | 0.019 | 0.564 | 0.011 |
| ZDHHC11 | cg18429742 | 1.060 | 0.012 | 1.068 | 0.014 | 0.904 | 0.003 | 0.859 | 0.033 |
| TPI1 | cg07052087 | 0.165 | 0.006 | 0.135 | 0.003 | 0.166 | 0.004 | 0.140 | 0.002 |
| MAGEL2 | cg01678091 | 0.936 | 0.009 | 0.964 | 0.009 | 0.801 | 0.015 | 0.743 | 0.009 |
| MFSD3 | cg03221776 | 0.341 | 0.017 | 0.416 | 0.030 | 0.281 | 0.007 | 0.243 | 0.010 |
| MRPL18 | cg25282410 | 0.319 | 0.008 | 0.346 | 0.005 | 0.239 | 0.021 | 0.276 | 0.008 |

TABLE 15-continued

| Gene | Gene ID | sh-ctrl | | sh-ctrl + 5aza | | sh-3B | | sh-3b + 5aza | |
|---|---|---|---|---|---|---|---|---|---|
| | | Mean | SEM | Mean | SEM | Mean | SEM | Mean | SEM |
| PNPLA4 | cg05508067 | 0.161 | 0.003 | 0.178 | 0.007 | 0.135 | 0.010 | 0.122 | 0.007 |
| CREB3L3 | cg23777956 | 0.845 | 0.009 | 0.853 | 0.008 | 0.729 | 0.013 | 0.671 | 0.006 |
| B4GALT2 | cg15379237 | 0.656 | 0.008 | 0.552 | 0.013 | 0.657 | 0.010 | 0.537 | 0.011 |
| IMPDH2 | cg11819013 | 0.235 | 0.008 | 0.223 | 0.006 | 0.243 | 0.010 | 0.169 | 0.007 |
| TMEPAI | cg26912636 | 0.407 | 0.010 | 0.326 | 0.019 | 0.427 | 0.009 | 0.334 | 0.017 |
| NUT | cg18768283 | 0.845 | 0.029 | 0.668 | 0.032 | 0.896 | 0.028 | 0.699 | 0.007 |
| C20orf38 | cg25125453 | 0.818 | 0.012 | 0.886 | 0.016 | 0.698 | 0.015 | 0.616 | 0.024 |
| SERPINB5 | cg23824713 | 1.078 | 0.027 | 1.097 | 0.033 | 0.889 | 0.013 | 0.880 | 0.030 |
| NCR1 | cg14550066 | 1.095 | 0.032 | 1.130 | 0.002 | 0.977 | 0.009 | 0.823 | 0.021 |
| PCGF6 | cg27217148 | 0.728 | 0.006 | 0.680 | 0.026 | 0.729 | 0.007 | 0.539 | 0.013 |
| HYPK | cg24125648 | 0.787 | 0.013 | 0.819 | 0.022 | 0.661 | 0.017 | 0.619 | 0.008 |
| EIF2B2 | cg20011974 | 0.242 | 0.005 | 0.244 | 0.005 | 0.190 | 0.005 | 0.208 | 0.007 |
| BCL7C | cg07896225 | 0.225 | 0.004 | 0.179 | 0.007 | 0.237 | 0.009 | 0.183 | 0.012 |
| UNC5A | cg12893143 | 0.747 | 0.008 | 0.750 | 0.022 | 0.650 | 0.006 | 0.583 | 0.007 |
| SUHW1 | cg21604856 | 0.601 | 0.016 | 0.630 | 0.020 | 0.480 | 0.018 | 0.491 | 0.013 |
| ANXA11 | cg24334983 | 0.640 | 0.012 | 0.525 | 0.030 | 0.647 | 0.007 | 0.524 | 0.005 |
| GBP2 | cg13629753 | 0.655 | 0.028 | 0.663 | 0.003 | 0.533 | 0.022 | 0.539 | 0.010 |
| TNNI3 | cg03097995 | 1.127 | 0.016 | 1.151 | 0.028 | 0.946 | 0.010 | 0.891 | 0.017 |
| MSC | cg06269753 | 0.472 | 0.005 | 0.477 | 0.022 | 0.388 | 0.011 | 0.383 | 0.013 |
| ANKRD33 | cg19948393 | 1.086 | 0.003 | 1.088 | 0.018 | 0.911 | 0.007 | 0.872 | 0.005 |
| CMTM5 | cg00174500 | 1.054 | 0.005 | 1.061 | 0.033 | 0.898 | 0.024 | 0.830 | 0.015 |
| BHMT | cg05890484 | 1.222 | 0.017 | 1.250 | 0.005 | 1.027 | 0.013 | 0.962 | 0.010 |
| SMS | cg18624866 | 0.493 | 0.018 | 0.383 | 0.014 | 0.541 | 0.012 | 0.394 | 0.022 |
| EML2 | cg08831348 | 0.488 | 0.012 | 0.498 | 0.018 | 0.391 | 0.010 | 0.402 | 0.019 |
| ETS1 | cg11861730 | 0.363 | 0.010 | 0.279 | 0.016 | 0.400 | 0.020 | 0.293 | 0.008 |
| GGTLA1 | cg15448245 | 0.948 | 0.020 | 0.762 | 0.027 | 0.957 | 0.025 | 0.785 | 0.016 |
| BLOC1S2 | cg26610808 | 0.678 | 0.005 | 0.575 | 0.007 | 0.692 | 0.021 | 0.526 | 0.017 |
| ALX4 | cg04549333 | 1.123 | 0.034 | 1.136 | 0.035 | 0.950 | 0.012 | 0.880 | 0.018 |
| DEFB118 | cg03014957 | 0.690 | 0.015 | 0.690 | 0.015 | 0.578 | 0.006 | 0.548 | 0.004 |
| C16orf60 | cg17858663 | 0.239 | 0.002 | 0.245 | 0.006 | 0.214 | 0.011 | 0.177 | 0.009 |
| SNX9 | cg26845300 | 0.970 | 0.011 | 0.985 | 0.015 | 0.861 | 0.018 | 0.722 | 0.010 |
| NOC3L | cg07270175 | 0.613 | 0.007 | 0.614 | 0.011 | 0.538 | 0.008 | 0.464 | 0.013 |
| TNRC4 | cg26093148 | 0.865 | 0.021 | 0.866 | 0.029 | 0.748 | 0.003 | 0.661 | 0.005 |
| CD58 | cg21039631 | 0.364 | 0.010 | 0.251 | 0.022 | 0.400 | 0.007 | 0.325 | 0.016 |
| TADA3L | cg09279263 | 0.438 | 0.018 | 0.445 | 0.006 | 0.355 | 0.012 | 0.350 | 0.006 |
| | cg07512517 | 0.615 | 0.030 | 0.619 | 0.004 | 0.525 | 0.023 | 0.473 | 0.009 |
| ABCC1 | cg20158248 | 0.579 | 0.006 | 0.480 | 0.010 | 0.579 | 0.021 | 0.458 | 0.013 |
| PIGL | cg05310071 | 0.296 | 0.007 | 0.351 | 0.028 | 0.216 | 0.012 | 0.231 | 0.012 |
| GRB10 | cg26163537 | 0.389 | 0.012 | 0.312 | 0.009 | 0.395 | 0.009 | 0.310 | 0.008 |
| ANKRD45 | cg15883716 | 1.012 | 0.048 | 1.017 | 0.024 | 0.834 | 0.034 | 0.793 | 0.020 |
| FXYD7 | cg22392666 | 0.987 | 0.034 | 1.028 | 0.012 | 0.855 | 0.015 | 0.720 | 0.024 |
| CTAGE1 | cg02847216 | 0.908 | 0.036 | 0.955 | 0.025 | 0.704 | 0.013 | 0.727 | 0.012 |
| IGF2AS | cg20792294 | 0.291 | 0.013 | 0.323 | 0.019 | 0.237 | 0.006 | 0.211 | 0.014 |
| DYRK1B | cg18851831 | 1.115 | 0.030 | 1.262 | 0.044 | 0.880 | 0.038 | 0.820 | 0.017 |
| CAMK1G | cg27337148 | 0.927 | 0.030 | 1.021 | 0.026 | 0.714 | 0.034 | 0.715 | 0.027 |
| NDP | cg11614809 | 0.750 | 0.029 | 0.756 | 0.032 | 0.619 | 0.014 | 0.579 | 0.026 |
| ZNF222 | cg09757277 | 0.429 | 0.007 | 0.431 | 0.009 | 0.331 | 0.010 | 0.355 | 0.009 |
| KCNK10 | cg17671157 | 1.050 | 0.009 | 1.059 | 0.044 | 0.856 | 0.008 | 0.820 | 0.012 |
| GABRB2 | cg16509658 | 0.217 | 0.006 | 0.219 | 0.009 | 0.170 | 0.003 | 0.176 | 0.005 |
| POU4F2 | cg24199834 | 0.283 | 0.004 | 0.287 | 0.010 | 0.220 | 0.001 | 0.231 | 0.007 |
| SSTR1 | cg27590397 | 1.179 | 0.015 | 1.209 | 0.006 | 0.966 | 0.001 | 0.900 | 0.011 |
| IL18 | cg11304234 | 0.631 | 0.004 | 0.646 | 0.021 | 0.522 | 0.036 | 0.478 | 0.011 |
| CUL3 | cg09509863 | 0.401 | 0.019 | 0.411 | 0.010 | 0.325 | 0.009 | 0.309 | 0.019 |
| TRAF3 | cg24165760 | 1.049 | 0.021 | 0.878 | 0.034 | 1.049 | 0.031 | 0.797 | 0.019 |
| SFRS16 | cg19317638 | 0.486 | 0.021 | 0.560 | 0.036 | 0.360 | 0.015 | 0.369 | 0.008 |
| S100A12 | cg02813121 | 0.935 | 0.015 | 0.941 | 0.027 | 0.767 | 0.004 | 0.719 | 0.012 |
| NME5 | cg25507001 | 0.874 | 0.005 | 0.889 | 0.002 | 0.710 | 0.024 | 0.671 | 0.029 |
| SMCP | cg09542291 | 0.675 | 0.017 | 0.705 | 0.026 | 0.552 | 0.028 | 0.504 | 0.023 |
| PI3 | cg02442161 | 0.847 | 0.012 | 0.857 | 0.018 | 0.719 | 0.011 | 0.625 | 0.034 |
| PTCH2 | cg15329642 | 0.771 | 0.017 | 0.789 | 0.022 | 0.639 | 0.009 | 0.576 | 0.023 |
| FLT3LG | cg01667384 | 0.237 | 0.009 | 0.249 | 0.011 | 0.189 | 0.001 | 0.179 | 0.007 |
| KLK7 | cg19953406 | 0.937 | 0.020 | 0.983 | 0.008 | 0.782 | 0.004 | 0.680 | 0.006 |
| RPL39L | cg07441272 | 0.625 | 0.002 | 0.691 | 0.010 | 0.449 | 0.015 | 0.505 | 0.027 |
| CYP4F12 | cg25813714 | 0.952 | 0.006 | 0.959 | 0.008 | 0.781 | 0.001 | 0.721 | 0.008 |
| TRPM3 | cg20555507 | 0.398 | 0.013 | 0.413 | 0.008 | 0.331 | 0.010 | 0.291 | 0.018 |
| NME5 | cg13707560 | 1.201 | 0.006 | 1.225 | 0.020 | 0.971 | 0.010 | 0.911 | 0.017 |
| NEFH | cg16042149 | 1.027 | 0.006 | 1.041 | 0.022 | 0.837 | 0.018 | 0.776 | 0.021 |
| SKIP | cg04072323 | 0.415 | 0.019 | 0.432 | 0.011 | 0.335 | 0.007 | 0.310 | 0.017 |
| SEPN1 | cg21187265 | 0.494 | 0.021 | 0.387 | 0.033 | 0.513 | 0.006 | 0.381 | 0.004 |
| SCUBE2 | cg01081263 | 0.681 | 0.003 | 0.693 | 0.019 | 0.564 | 0.034 | 0.505 | 0.026 |
| MC3R | cg19226099 | 1.024 | 0.004 | 1.057 | 0.016 | 0.808 | 0.018 | 0.784 | 0.011 |
| SCUBE2 | cg19237879 | 0.669 | 0.010 | 0.670 | 0.022 | 0.564 | 0.010 | 0.493 | 0.017 |
| KA21 | cg23776012 | 0.559 | 0.023 | 0.641 | 0.024 | 0.421 | 0.041 | 0.410 | 0.021 |
| IL2RG | cg01361446 | 1.096 | 0.015 | 1.103 | 0.036 | 0.882 | 0.016 | 0.834 | 0.034 |
| ALX4 | cg04970352 | 0.869 | 0.037 | 0.964 | 0.036 | 0.663 | 0.022 | 0.645 | 0.007 |

TABLE 15-continued

| Gene | Gene ID | sh-ctrl | | sh-ctrl + 5aza | | sh-3B | | sh-3b + 5aza | |
|---|---|---|---|---|---|---|---|---|---|
| | | Mean | SEM | Mean | SEM | Mean | SEM | Mean | SEM |
| POU3F3 | cg20291049 | 0.363 | 0.008 | 0.387 | 0.023 | 0.286 | 0.004 | 0.268 | 0.013 |
| DNASE2 | cg07955356 | 0.263 | 0.010 | 0.275 | 0.018 | 0.198 | 0.005 | 0.207 | 0.001 |
| CRSP7 | cg24459023 | 0.373 | 0.015 | 0.301 | 0.014 | 0.398 | 0.009 | 0.268 | 0.004 |
| ALX4 | cg19358442 | 1.097 | 0.004 | 1.126 | 0.028 | 0.859 | 0.010 | 0.834 | 0.031 |
| RRM2B | cg07125123 | 0.363 | 0.011 | 0.370 | 0.004 | 0.273 | 0.017 | 0.288 | 0.019 |
| ALDH1A3 | cg19224278 | 0.419 | 0.007 | 0.443 | 0.019 | 0.329 | 0.019 | 0.310 | 0.014 |
| MPHOSPH6 | cg16119274 | 0.393 | 0.010 | 0.444 | 0.041 | 0.304 | 0.012 | 0.280 | 0.013 |
| HRASLS | cg08376864 | 0.515 | 0.035 | 0.853 | 0.099 | 0.330 | 0.014 | 0.309 | 0.052 |
| CDX1 | cg15452204 | 0.592 | 0.007 | 0.595 | 0.008 | 0.500 | 0.011 | 0.424 | 0.017 |
| C14orf173 | cg24404909 | 0.359 | 0.012 | 0.379 | 0.026 | 0.305 | 0.008 | 0.248 | 0.007 |
| INPP5B | cg10784030 | 0.331 | 0.018 | 0.366 | 0.003 | 0.242 | 0.003 | 0.251 | 0.010 |
| GALNT4 | cg16606638 | 0.338 | 0.018 | 0.265 | 0.008 | 0.364 | 0.012 | 0.245 | 0.001 |
| HYPK | cg00480356 | 0.813 | 0.017 | 0.818 | 0.047 | 0.629 | 0.006 | 0.630 | 0.019 |
| DPH1 | cg11516377 | 0.447 | 0.013 | 0.465 | 0.012 | 0.363 | 0.009 | 0.319 | 0.007 |
| COL11A1 | cg12884406 | 0.403 | 0.016 | 0.415 | 0.019 | 0.288 | 0.005 | 0.331 | 0.009 |
| DCTD | cg14892066 | 0.233 | 0.006 | 0.243 | 0.016 | 0.182 | 0.012 | 0.171 | 0.003 |
| HACE1 | cg23047681 | 0.204 | 0.004 | 0.204 | 0.002 | 0.159 | 0.008 | 0.156 | 0.012 |
| EPN3 | cg24006361 | 1.015 | 0.020 | 1.019 | 0.015 | 0.824 | 0.019 | 0.739 | 0.027 |
| LYNX1 | cg24046110 | 0.403 | 0.013 | 0.430 | 0.011 | 0.316 | 0.021 | 0.288 | 0.018 |
| SEMA6C | cg01958916 | 0.346 | 0.021 | 0.267 | 0.010 | 0.362 | 0.008 | 0.255 | 0.014 |
| NOX4 | cg17063929 | 0.689 | 0.009 | 0.483 | 0.018 | 0.693 | 0.008 | 0.575 | 0.008 |
| GAS8 | cg03634997 | 1.075 | 0.015 | 1.082 | 0.018 | 0.823 | 0.017 | 0.814 | 0.013 |
| PCGF5 | cg17001035 | 0.878 | 0.008 | 0.893 | 0.025 | 0.668 | 0.005 | 0.664 | 0.013 |
| MSX1 | cg03199651 | 0.270 | 0.014 | 0.288 | 0.012 | 0.198 | 0.006 | 0.204 | 0.012 |
| FLJ10726 | cg14145762 | 0.417 | 0.016 | 0.436 | 0.016 | 0.336 | 0.015 | 0.292 | 0.011 |
| BTNL8 | cg24024214 | 1.063 | 0.013 | 1.068 | 0.033 | 0.837 | 0.018 | 0.781 | 0.013 |
| EREG | cg19308222 | 0.355 | 0.016 | 0.356 | 0.007 | 0.289 | 0.023 | 0.252 | 0.005 |
| KCNAB3 | cg14918082 | 0.757 | 0.007 | 0.852 | 0.024 | 0.559 | 0.032 | 0.534 | 0.020 |
| PEPD | cg06546607 | 0.328 | 0.008 | 0.266 | 0.009 | 0.334 | 0.016 | 0.229 | 0.008 |
| REM1 | cg26299767 | 0.642 | 0.014 | 0.727 | 0.044 | 0.486 | 0.024 | 0.440 | 0.006 |
| IFNA2 | cg13235447 | 0.660 | 0.017 | 0.697 | 0.012 | 0.496 | 0.014 | 0.480 | 0.013 |
| C10orf107 | cg16063112 | 0.337 | 0.021 | 0.354 | 0.019 | 0.271 | 0.015 | 0.230 | 0.008 |
| CEACAM7 | cg19623751 | 0.879 | 0.021 | 0.886 | 0.034 | 0.703 | 0.010 | 0.616 | 0.018 |
| ADRA2A | cg26926521 | 0.937 | 0.005 | 0.939 | 0.018 | 0.723 | 0.006 | 0.682 | 0.005 |
| FLJ23514 | cg16404106 | 0.600 | 0.004 | 0.628 | 0.025 | 0.447 | 0.014 | 0.436 | 0.013 |
| FLJ11200 | cg09001953 | 0.481 | 0.012 | 0.482 | 0.029 | 0.388 | 0.013 | 0.335 | 0.001 |
| IHH | cg17178336 | 0.685 | 0.012 | 0.709 | 0.029 | 0.507 | 0.022 | 0.504 | 0.031 |
| LIG4 | cg08216792 | 0.354 | 0.010 | 0.356 | 0.022 | 0.261 | 0.005 | 0.266 | 0.012 |
| IGFBP5 | cg19008649 | 0.369 | 0.009 | 0.370 | 0.007 | 0.286 | 0.011 | 0.264 | 0.010 |
| CSPG3 | cg06952310 | 0.473 | 0.013 | 0.480 | 0.007 | 0.350 | 0.018 | 0.350 | 0.005 |
| GUP1 | cg24938727 | 0.636 | 0.009 | 0.640 | 0.011 | 0.507 | 0.005 | 0.441 | 0.014 |
| EIF2B3 | cg16604218 | 0.517 | 0.036 | 0.543 | 0.019 | 0.392 | 0.016 | 0.360 | 0.006 |
| APC | cg16970232 | 0.402 | 0.023 | 0.424 | 0.018 | 0.317 | 0.030 | 0.269 | 0.008 |
| LAMB1 | cg10064162 | 0.419 | 0.016 | 0.426 | 0.019 | 0.319 | 0.004 | 0.295 | 0.020 |
| CHD5 | cg00282347 | 0.992 | 0.020 | 1.005 | 0.004 | 0.769 | 0.004 | 0.682 | 0.027 |
| KCNB2 | cg11754206 | 0.540 | 0.007 | 0.551 | 0.007 | 0.409 | 0.021 | 0.377 | 0.004 |
| SFXN3 | cg04880063 | 0.250 | 0.003 | 0.170 | 0.011 | 0.268 | 0.013 | 0.188 | 0.014 |
| ENOSF1 | cg16112050 | 1.027 | 0.024 | 1.028 | 0.002 | 0.779 | 0.016 | 0.724 | 0.048 |
| ANKRD13C | cg19342782 | 0.533 | 0.005 | 0.544 | 0.028 | 0.402 | 0.007 | 0.372 | 0.006 |
| REM1 | cg12153542 | 0.639 | 0.001 | 0.664 | 0.012 | 0.465 | 0.025 | 0.456 | 0.009 |
| FLRT3 | cg23127998 | 0.382 | 0.019 | 0.397 | 0.005 | 0.308 | 0.007 | 0.249 | 0.015 |
| KCNA3 | cg03483626 | 0.303 | 0.007 | 0.326 | 0.023 | 0.223 | 0.002 | 0.208 | 0.010 |
| FAM111B | cg13864937 | 0.507 | 0.006 | 0.508 | 0.023 | 0.373 | 0.030 | 0.366 | 0.014 |
| ALKBH4 | cg07404418 | 0.439 | 0.008 | 0.458 | 0.004 | 0.316 | 0.020 | 0.312 | 0.025 |
| SH3BGRL2 | cg03080985 | 0.384 | 0.007 | 0.398 | 0.004 | 0.291 | 0.003 | 0.260 | 0.011 |
| SEMA3E | cg08274234 | 0.303 | 0.019 | 0.306 | 0.008 | 0.231 | 0.010 | 0.207 | 0.010 |
| IFI44 | cg07107453 | 0.481 | 0.018 | 0.513 | 0.009 | 0.349 | 0.027 | 0.330 | 0.020 |
| C19orf4 | cg07379574 | 1.073 | 0.020 | 1.078 | 0.034 | 0.823 | 0.029 | 0.733 | 0.017 |
| HGF | cg06745740 | 0.565 | 0.016 | 0.594 | 0.012 | 0.396 | 0.011 | 0.404 | 0.016 |
| TRIM36 | cg10693071 | 0.818 | 0.022 | 0.822 | 0.007 | 0.638 | 0.045 | 0.545 | 0.005 |
| ITGB3BP | cg18464559 | 0.167 | 0.009 | 0.168 | 0.003 | 0.120 | 0.006 | 0.121 | 0.010 |
| IGSF9 | cg19111262 | 0.817 | 0.013 | 0.826 | 0.016 | 0.593 | 0.015 | 0.576 | 0.014 |
| SHH | cg25167838 | 0.170 | 0.001 | 0.175 | 0.005 | 0.115 | 0.003 | 0.127 | 0.017 |
| PEX5L | cg02430692 | 0.493 | 0.009 | 0.511 | 0.017 | 0.376 | 0.041 | 0.322 | 0.012 |
| MYOD1 | cg24322623 | 0.931 | 0.011 | 0.931 | 0.042 | 0.677 | 0.038 | 0.650 | 0.030 |
| ZFHX1B | cg15377518 | 0.677 | 0.011 | 0.680 | 0.021 | 0.491 | 0.019 | 0.472 | 0.023 |
| NRXN1 | cg10917619 | 0.856 | 0.030 | 0.867 | 0.020 | 0.619 | 0.008 | 0.594 | 0.022 |
| SERPING1 | cg12783776 | 0.548 | 0.009 | 0.601 | 0.032 | 0.405 | 0.015 | 0.350 | 0.004 |
| SPRR1B | cg24884084 | 0.477 | 0.011 | 0.488 | 0.030 | 0.332 | 0.005 | 0.334 | 0.012 |
| PCDHB13 | cg24435562 | 0.401 | 0.002 | 0.441 | 0.016 | 0.272 | 0.006 | 0.273 | 0.003 |
| PCDHB13 | cg14592099 | 0.649 | 0.038 | 0.747 | 0.077 | 0.444 | 0.019 | 0.423 | 0.005 |
| WDR13 | cg25053301 | 0.311 | 0.005 | 0.317 | 0.012 | 0.223 | 0.024 | 0.211 | 0.010 |
| CHMP2A | cg14042128 | 0.524 | 0.017 | 0.541 | 0.027 | 0.371 | 0.035 | 0.354 | 0.016 |
| PCDHGA12 | cg11647681 | 0.913 | 0.017 | 0.936 | 0.020 | 0.643 | 0.011 | 0.623 | 0.020 |
| COPS7B | cg05422352 | 0.549 | 0.011 | 0.579 | 0.039 | 0.425 | 0.016 | 0.338 | 0.024 |

TABLE 15-continued

| Gene | Gene ID | sh-ctrl Mean | sh-ctrl SEM | sh-ctrl + 5aza Mean | sh-ctrl + 5aza SEM | sh-3B Mean | sh-3B SEM | sh-3b + 5aza Mean | sh-3b + 5aza SEM |
|---|---|---|---|---|---|---|---|---|---|
| UNC5D | cg00297600 | 0.609 | 0.002 | 0.612 | 0.033 | 0.474 | 0.021 | 0.384 | 0.037 |
| IFI16 | cg07463059 | 0.576 | 0.024 | 0.582 | 0.047 | 0.411 | 0.016 | 0.386 | 0.009 |
| ELSPBP1 | cg19404979 | 0.615 | 0.026 | 0.655 | 0.021 | 0.426 | 0.040 | 0.406 | 0.035 |
| HOXB4 | cg25145670 | 0.482 | 0.008 | 0.488 | 0.039 | 0.354 | 0.023 | 0.311 | 0.007 |
| NCKIPSD | cg04244987 | 0.371 | 0.007 | 0.392 | 0.003 | 0.259 | 0.014 | 0.242 | 0.016 |
| ICAM1 | cg08607082 | 0.235 | 0.017 | 0.244 | 0.018 | 0.171 | 0.006 | 0.149 | 0.008 |
| PTPN5 | cg17233601 | 0.790 | 0.030 | 0.801 | 0.039 | 0.590 | 0.028 | 0.498 | 0.010 |
| TERT | cg02545192 | 0.542 | 0.019 | 0.547 | 0.048 | 0.458 | 0.028 | 0.311 | 0.029 |
| RLN3R1 | cg12238343 | 0.719 | 0.002 | 0.732 | 0.042 | 0.536 | 0.006 | 0.451 | 0.020 |
| ACP1 | cg27226618 | 0.771 | 0.019 | 0.786 | 0.028 | 0.563 | 0.012 | 0.490 | 0.003 |
| TRIM2 | cg12793610 | 0.787 | 0.016 | 0.815 | 0.017 | 0.559 | 0.029 | 0.506 | 0.015 |
| CDKN2B | cg04675937 | 0.253 | 0.007 | 0.256 | 0.009 | 0.177 | 0.014 | 0.167 | 0.012 |
| TAC1 | cg07550362 | 0.783 | 0.014 | 0.798 | 0.019 | 0.549 | 0.008 | 0.507 | 0.012 |
| LDHD | cg24429836 | 0.741 | 0.017 | 0.760 | 0.013 | 0.487 | 0.007 | 0.510 | 0.033 |
| OR10J1 | cg15700197 | 0.670 | 0.011 | 0.679 | 0.016 | 0.460 | 0.010 | 0.444 | 0.023 |
| TNFSF10 | cg16555388 | 0.683 | 0.025 | 0.687 | 0.049 | 0.497 | 0.015 | 0.430 | 0.025 |
| CSTF2T | cg06712026 | 0.419 | 0.025 | 0.431 | 0.011 | 0.282 | 0.026 | 0.277 | 0.022 |
| RBPSUHL | cg21835643 | 1.005 | 0.007 | 1.018 | 0.019 | 0.680 | 0.008 | 0.665 | 0.007 |
| RASGEF1A | cg07871503 | 0.940 | 0.003 | 0.945 | 0.022 | 0.669 | 0.008 | 0.574 | 0.020 |
| DDEF2 | cg22190705 | 0.314 | 0.005 | 0.329 | 0.033 | 0.222 | 0.007 | 0.187 | 0.014 |
| HNRNPG-T | cg22062068 | 0.964 | 0.007 | 0.977 | 0.038 | 0.614 | 0.018 | 0.650 | 0.021 |
| SSH1 | cg11747499 | 0.475 | 0.019 | 0.529 | 0.011 | 0.306 | 0.018 | 0.292 | 0.012 |
| C1orf188 | cg15731815 | 0.538 | 0.019 | 0.541 | 0.031 | 0.386 | 0.007 | 0.321 | 0.038 |
| NEIL2 | cg14329976 | 0.354 | 0.002 | 0.360 | 0.030 | 0.232 | 0.012 | 0.226 | 0.008 |
| G10 | cg02798801 | 0.607 | 0.009 | 0.608 | 0.026 | 0.450 | 0.036 | 0.349 | 0.014 |
| CEACAM4 | cg10237469 | 0.717 | 0.012 | 0.718 | 0.038 | 0.498 | 0.015 | 0.430 | 0.008 |
| TNRC15 | cg07230446 | 0.425 | 0.022 | 0.425 | 0.044 | 0.310 | 0.012 | 0.243 | 0.002 |
| C19orf22 | cg18022193 | 0.286 | 0.011 | 0.288 | 0.032 | 0.184 | 0.005 | 0.180 | 0.004 |
| GBX2 | cg23095584 | 0.452 | 0.003 | 0.468 | 0.048 | 0.304 | 0.010 | 0.268 | 0.027 |
| ADCY4 | cg16761581 | 0.544 | 0.032 | 0.609 | 0.028 | 0.381 | 0.026 | 0.297 | 0.060 |
| NPAS1 | cg09628601 | 0.514 | 0.008 | 0.553 | 0.026 | 0.339 | 0.003 | 0.303 | 0.005 |
| SOX17 | cg21226224 | 0.841 | 0.011 | 0.858 | 0.032 | 0.575 | 0.011 | 0.495 | 0.029 |
| BTBD5 | cg00660989 | 0.347 | 0.007 | 0.347 | 0.020 | 0.227 | 0.012 | 0.214 | 0.011 |
| CDKN2B | cg08390209 | 0.259 | 0.015 | 0.280 | 0.022 | 0.172 | 0.015 | 0.150 | 0.010 |
| MGC26856 | cg07684809 | 0.452 | 0.021 | 0.489 | 0.037 | 0.302 | 0.010 | 0.260 | 0.016 |
| OR1N1 | cg14598387 | 0.575 | 0.023 | 0.606 | 0.033 | 0.374 | 0.016 | 0.339 | 0.005 |
| CGI-38 | cg13067215 | 0.485 | 0.013 | 0.513 | 0.053 | 0.329 | 0.011 | 0.274 | 0.006 |
| RYR1 | cg05471297 | 0.478 | 0.022 | 0.480 | 0.030 | 0.333 | 0.014 | 0.272 | 0.022 |
| GNAS | cg27661264 | 0.559 | 0.011 | 0.565 | 0.016 | 0.355 | 0.006 | 0.334 | 0.020 |
| C1QL1 | cg13818573 | 0.453 | 0.014 | 0.460 | 0.025 | 0.307 | 0.011 | 0.255 | 0.016 |
| SLC30A2 | cg05674944 | 0.624 | 0.011 | 0.658 | 0.017 | 0.428 | 0.024 | 0.337 | 0.027 |
| MLNR | cg02620013 | 0.721 | 0.004 | 0.755 | 0.039 | 0.454 | 0.015 | 0.418 | 0.042 |
| PACS1 | cg01663295 | 0.608 | 0.037 | 0.625 | 0.038 | 0.404 | 0.004 | 0.329 | 0.010 |
| FANCE | cg17803089 | 0.403 | 0.026 | 0.415 | 0.019 | 0.241 | 0.017 | 0.231 | 0.009 |
| GATA4 | cg09626984 | 0.357 | 0.057 | 0.423 | 0.016 | 0.208 | 0.005 | 0.191 | 0.007 |
| KLK10 | cg09254939 | 0.591 | 0.030 | 0.596 | 0.027 | 0.351 | 0.014 | 0.340 | 0.004 |
| IRS1 | cg10098888 | 0.381 | 0.017 | 0.405 | 0.010 | 0.246 | 0.005 | 0.198 | 0.010 |
| ID2 | cg13055278 | 0.777 | 0.026 | 0.781 | 0.015 | 0.452 | 0.017 | 0.454 | 0.004 |
| MGC15523 | cg06850526 | 0.664 | 0.019 | 0.665 | 0.046 | 0.398 | 0.023 | 0.374 | 0.013 |
| SUMO3 | cg21053323 | 0.685 | 0.049 | 0.778 | 0.045 | 0.415 | 0.025 | 0.353 | 0.043 |
| PCDHGA12 | cg07730329 | 0.811 | 0.007 | 0.822 | 0.022 | 0.479 | 0.013 | 0.445 | 0.007 |
| TLR10 | cg19398783 | 0.580 | 0.020 | 0.585 | 0.053 | 0.343 | 0.015 | 0.315 | 0.037 |
| BRUNOL5 | cg26114571 | 0.274 | 0.019 | 0.282 | 0.017 | 0.138 | 0.003 | 0.160 | 0.008 |
| CDH9 | cg12864235 | 0.455 | 0.012 | 0.457 | 0.019 | 0.243 | 0.014 | 0.244 | 0.010 |
| GNAS | cg17414107 | 0.693 | 0.016 | 0.738 | 0.022 | 0.399 | 0.017 | 0.321 | 0.013 |
| ELMO3 | cg19514469 | 0.892 | 0.007 | 0.895 | 0.013 | 0.514 | 0.010 | 0.413 | 0.020 |
| RTBDN | cg08694544 | 0.597 | 0.006 | 0.632 | 0.028 | 0.344 | 0.022 | 0.266 | 0.012 |
| BAIAP3 | cg18282543 | 0.708 | 0.014 | 0.726 | 0.017 | 0.389 | 0.014 | 0.327 | 0.026 |
| PLA2G3 | cg00727590 | 0.599 | 0.012 | 0.660 | 0.047 | 0.345 | 0.016 | 0.250 | 0.014 |
| NTRK2 | cg09539438 | 0.763 | 0.009 | 0.764 | 0.030 | 0.387 | 0.020 | 0.369 | 0.025 |
| TNFRSF1B | cg13836770 | 0.864 | 0.026 | 0.865 | 0.103 | 0.473 | 0.017 | 0.377 | 0.031 |
| DHX40 | cg11000221 | 0.376 | 0.052 | 0.422 | 0.013 | 0.194 | 0.020 | 0.162 | 0.003 |
| SORBS2 | cg20544605 | 0.825 | 0.027 | 0.830 | 0.020 | 0.431 | 0.022 | 0.358 | 0.011 |
| POU4F3 | cg18482268 | 1.152 | 0.022 | 1.150 | 0.007 | 1.121 | 0.022 | 0.955 | 0.023 |
| CACNG6 | cg04080057 | 0.809 | 0.014 | 0.808 | 0.006 | 0.766 | 0.008 | 0.668 | 0.012 |
| POM121 | cg24481163 | 0.532 | 0.008 | 0.525 | 0.011 | 0.505 | 0.003 | 0.439 | 0.009 |
| TP73 | cg04391111 | 0.674 | 0.018 | 0.665 | 0.024 | 0.645 | 0.013 | 0.552 | 0.005 |
| C10orf10 | cg04444771 | 1.028 | 0.029 | 0.986 | 0.039 | 1.025 | 0.011 | 0.830 | 0.015 |
| SEMA3B | cg24816455 | 1.216 | 0.008 | 1.201 | 0.010 | 1.132 | 0.001 | 1.013 | 0.011 |
| SNTB1 | cg08598221 | 0.798 | 0.008 | 0.784 | 0.010 | 0.751 | 0.013 | 0.659 | 0.013 |
| ALX4 | cg00418150 | 0.786 | 0.006 | 0.783 | 0.003 | 0.721 | 0.009 | 0.654 | 0.009 |
| A2BP1 | cg19378133 | 0.993 | 0.006 | 0.986 | 0.003 | 0.919 | 0.017 | 0.821 | 0.012 |
| DNASE1L1 | cg09202373 | 0.774 | 0.008 | 0.760 | 0.006 | 0.716 | 0.008 | 0.645 | 0.009 |
| LHX3 | cg20300246 | 1.138 | 0.013 | 1.127 | 0.023 | 1.058 | 0.016 | 0.930 | 0.025 |
| C17orf53 | cg25425074 | 0.505 | 0.004 | 0.462 | 0.010 | 0.503 | 0.006 | 0.414 | 0.021 |

TABLE 15-continued

| Gene | Gene ID | sh-ctrl Mean | sh-ctrl SEM | sh-ctrl + 5aza Mean | sh-ctrl + 5aza SEM | sh-3B Mean | sh-3B SEM | sh-3b + 5aza Mean | sh-3b + 5aza SEM |
|---|---|---|---|---|---|---|---|---|---|
| RNH1 | cg06417962 | 0.989 | 0.007 | 0.955 | 0.023 | 0.943 | 0.014 | 0.804 | 0.024 |
| PRRX2 | cg04713521 | 0.908 | 0.002 | 0.900 | 0.024 | 0.863 | 0.012 | 0.724 | 0.019 |
| CCL25 | cg21274570 | 1.058 | 0.021 | 1.033 | 0.007 | 0.980 | 0.011 | 0.872 | 0.019 |
| LHPP | cg07596401 | 0.891 | 0.003 | 0.820 | 0.010 | 0.874 | 0.018 | 0.734 | 0.015 |
| MTSS1 | cg18939260 | 1.192 | 0.008 | 1.145 | 0.034 | 1.114 | 0.030 | 0.987 | 0.010 |
| RPS13 | cg05592434 | 0.523 | 0.010 | 0.409 | 0.018 | 0.515 | 0.006 | 0.509 | 0.014 |
| TMEM9 | cg21431091 | 0.945 | 0.014 | 0.880 | 0.022 | 0.922 | 0.033 | 0.772 | 0.003 |
| SULT1A2 | cg12743398 | 0.931 | 0.004 | 0.924 | 0.025 | 0.861 | 0.007 | 0.754 | 0.007 |
| HCN2 | cg01284619 | 0.610 | 0.017 | 0.595 | 0.009 | 0.572 | 0.006 | 0.495 | 0.009 |
| CBLC | cg22780475 | 0.832 | 0.027 | 0.818 | 0.020 | 0.784 | 0.002 | 0.668 | 0.021 |
| HOXB1 | cg07823492 | 1.174 | 0.010 | 1.168 | 0.016 | 1.064 | 0.008 | 0.964 | 0.003 |
| ATP9B | cg10823157 | 0.214 | 0.005 | 0.214 | 0.007 | 0.175 | 0.006 | 0.195 | 0.004 |
| SLC29A4 | cg05168404 | 0.734 | 0.017 | 0.682 | 0.013 | 0.703 | 0.013 | 0.608 | 0.011 |
| SLC25A11 | cg22628926 | 0.855 | 0.006 | 0.814 | 0.021 | 0.848 | 0.022 | 0.672 | 0.012 |
| TMEM130 | cg15279364 | 0.878 | 0.009 | 0.821 | 0.024 | 0.838 | 0.009 | 0.723 | 0.012 |
| GH1 | cg13204181 | 1.025 | 0.006 | 1.004 | 0.011 | 0.976 | 0.005 | 0.813 | 0.013 |
| SEMA3B | cg12069309 | 0.976 | 0.012 | 0.953 | 0.012 | 0.882 | 0.012 | 0.813 | 0.004 |
| THRAP4 | cg14592065 | 0.967 | 0.014 | 0.965 | 0.013 | 0.882 | 0.004 | 0.783 | 0.003 |
| CYP2B6 | cg19756068 | 0.829 | 0.023 | 0.826 | 0.010 | 0.747 | 0.007 | 0.680 | 0.020 |
| PYCARD | cg11970458 | 1.194 | 0.004 | 1.179 | 0.015 | 1.081 | 0.012 | 0.980 | 0.019 |
| STRN3 | cg15301694 | 0.989 | 0.011 | 0.944 | 0.014 | 0.912 | 0.014 | 0.824 | 0.008 |
| SLC39A14 | cg05254747 | 1.012 | 0.017 | 0.984 | 0.021 | 0.927 | 0.014 | 0.831 | 0.012 |
| MIXL1 | cg18354264 | 0.716 | 0.005 | 0.664 | 0.020 | 0.701 | 0.012 | 0.579 | 0.007 |
| LOC133619 | cg04431054 | 0.810 | 0.007 | 0.782 | 0.024 | 0.758 | 0.006 | 0.656 | 0.004 |
| CDC42EP5 | cg03620376 | 0.796 | 0.003 | 0.791 | 0.014 | 0.730 | 0.012 | 0.639 | 0.018 |
| LRRTM3 | cg05626013 | 0.976 | 0.018 | 0.904 | 0.016 | 0.923 | 0.005 | 0.810 | 0.013 |
| CHI3L1 | cg03625911 | 0.844 | 0.013 | 0.746 | 0.008 | 0.843 | 0.006 | 0.696 | 0.004 |
| CCR9 | cg09033997 | 1.159 | 0.015 | 1.060 | 0.023 | 1.103 | 0.018 | 0.965 | 0.022 |
| GRB2 | cg04156850 | 0.948 | 0.008 | 0.938 | 0.009 | 0.845 | 0.013 | 0.780 | 0.007 |
| PUM2 | cg01888166 | 0.964 | 0.008 | 0.871 | 0.012 | 0.928 | 0.020 | 0.802 | 0.004 |
| CCHCR1 | cg04824716 | 0.837 | 0.005 | 0.834 | 0.006 | 0.747 | 0.006 | 0.684 | 0.021 |
| MCEMP1 | cg01556075 | 1.052 | 0.030 | 1.039 | 0.018 | 0.925 | 0.015 | 0.876 | 0.023 |
| ZNF266 | cg21116314 | 0.811 | 0.006 | 0.776 | 0.027 | 0.740 | 0.008 | 0.670 | 0.019 |
| MGC39633 | cg25267732 | 0.308 | 0.008 | 0.305 | 0.004 | 0.278 | 0.007 | 0.249 | 0.003 |
| ZMYND15 | cg19841506 | 1.178 | 0.003 | 1.134 | 0.010 | 1.076 | 0.013 | 0.966 | 0.031 |
| ABR | cg25374854 | 1.025 | 0.009 | 0.979 | 0.011 | 0.929 | 0.006 | 0.852 | 0.002 |
| UCN | cg04527918 | 1.014 | 0.016 | 0.989 | 0.013 | 0.917 | 0.007 | 0.828 | 0.013 |
| EPOR | cg24477567 | 0.853 | 0.013 | 0.810 | 0.004 | 0.783 | 0.008 | 0.705 | 0.008 |
| PIK4CB | cg18598959 | 1.083 | 0.010 | 1.031 | 0.018 | 0.989 | 0.009 | 0.896 | 0.017 |
| EIF2C4 | cg16019273 | 0.767 | 0.007 | 0.748 | 0.021 | 0.692 | 0.007 | 0.627 | 0.013 |
| CNNM4 | cg11158729 | 1.103 | 0.034 | 1.052 | 0.011 | 1.038 | 0.020 | 0.884 | 0.006 |
| CYB5R3 | cg23325242 | 0.783 | 0.005 | 0.736 | 0.020 | 0.729 | 0.018 | 0.642 | 0.008 |
| CALCA | cg09188980 | 1.166 | 0.022 | 1.155 | 0.015 | 1.028 | 0.006 | 0.958 | 0.025 |
| KRTAP15-1 | cg16812893 | 0.910 | 0.017 | 0.853 | 0.006 | 0.830 | 0.005 | 0.758 | 0.014 |
| GDPD5 | cg16393207 | 0.845 | 0.014 | 0.789 | 0.021 | 0.829 | 0.022 | 0.663 | 0.021 |
| LOC284948 | cg10203483 | 1.094 | 0.007 | 0.970 | 0.040 | 1.059 | 0.014 | 0.911 | 0.014 |
| ODF3 | cg10335112 | 0.644 | 0.002 | 0.627 | 0.011 | 0.572 | 0.004 | 0.532 | 0.003 |
| ESR1 | cg20627916 | 0.771 | 0.017 | 0.719 | 0.013 | 0.709 | 0.019 | 0.638 | 0.015 |
| CENTA2 | cg22485810 | 0.740 | 0.010 | 0.675 | 0.011 | 0.694 | 0.014 | 0.614 | 0.014 |
| KIAA0125 | cg02507952 | 0.738 | 0.009 | 0.730 | 0.006 | 0.654 | 0.008 | 0.601 | 0.016 |
| HOXB1 | cg17233506 | 0.941 | 0.016 | 0.935 | 0.025 | 0.867 | 0.027 | 0.738 | 0.017 |
| EVC2 | cg15305511 | 0.671 | 0.009 | 0.653 | 0.018 | 0.638 | 0.015 | 0.521 | 0.012 |
| INSR | cg19371795 | 0.848 | 0.010 | 0.815 | 0.022 | 0.768 | 0.004 | 0.693 | 0.008 |
| CEACAM8 | cg08551633 | 0.897 | 0.027 | 0.884 | 0.018 | 0.783 | 0.004 | 0.742 | 0.017 |
| BBS1 | cg03851112 | 0.631 | 0.001 | 0.582 | 0.012 | 0.592 | 0.010 | 0.517 | 0.005 |
| APC | cg15020645 | 0.774 | 0.023 | 0.737 | 0.017 | 0.716 | 0.017 | 0.626 | 0.009 |
| NXPH3 | cg06405206 | 0.672 | 0.008 | 0.664 | 0.009 | 0.623 | 0.004 | 0.525 | 0.006 |
| C9orf58 | cg25954354 | 0.640 | 0.009 | 0.611 | 0.010 | 0.610 | 0.018 | 0.502 | 0.007 |
| TBC1D10B | cg11919694 | 0.867 | 0.011 | 0.823 | 0.004 | 0.794 | 0.002 | 0.707 | 0.004 |
| CD84 | cg02945019 | 0.846 | 0.027 | 0.811 | 0.013 | 0.761 | 0.007 | 0.695 | 0.013 |
| OR1A2 | cg16678925 | 0.691 | 0.015 | 0.682 | 0.008 | 0.621 | 0.027 | 0.553 | 0.008 |
| POU2F2 | cg21608489 | 1.124 | 0.008 | 1.105 | 0.015 | 0.992 | 0.003 | 0.918 | 0.014 |
| C20orf100 | cg04369341 | 0.529 | 0.010 | 0.458 | 0.005 | 0.528 | 0.008 | 0.435 | 0.013 |
| JM11 | cg14766682 | 0.893 | 0.024 | 0.814 | 0.019 | 0.868 | 0.011 | 0.716 | 0.009 |
| Bles03 | cg13547237 | 1.117 | 0.015 | 1.070 | 0.021 | 1.037 | 0.018 | 0.891 | 0.014 |
| CORO7 | cg19168338 | 1.083 | 0.012 | 0.993 | 0.001 | 1.016 | 0.005 | 0.886 | 0.006 |
| LOC400696 | cg04756629 | 0.796 | 0.008 | 0.770 | 0.007 | 0.715 | 0.012 | 0.646 | 0.013 |
| GP1BB | cg07359545 | 1.063 | 0.028 | 1.057 | 0.020 | 0.907 | 0.005 | 0.885 | 0.009 |
| RTBDN | cg00643392 | 0.834 | 0.020 | 0.827 | 0.014 | 0.753 | 0.004 | 0.660 | 0.012 |
| NUDT3 | cg25055477 | 0.632 | 0.004 | 0.578 | 0.021 | 0.615 | 0.008 | 0.503 | 0.015 |
| C16orf48 | cg06637893 | 0.851 | 0.007 | 0.809 | 0.022 | 0.777 | 0.011 | 0.691 | 0.004 |
| KCNH4 | cg20406482 | 0.701 | 0.006 | 0.697 | 0.010 | 0.623 | 0.012 | 0.560 | 0.007 |
| MGC50559 | cg08647727 | 0.396 | 0.006 | 0.392 | 0.003 | 0.351 | 0.002 | 0.319 | 0.013 |
| FAIM | cg02712878 | 0.614 | 0.006 | 0.535 | 0.010 | 0.609 | 0.003 | 0.500 | 0.011 |
| ST8SIA2 | cg05501584 | 0.984 | 0.025 | 0.952 | 0.018 | 0.860 | 0.015 | 0.817 | 0.012 |

TABLE 15-continued

| Gene | Gene ID | sh-ctrl Mean | sh-ctrl SEM | sh-ctrl + 5aza Mean | sh-ctrl + 5aza SEM | sh-3B Mean | sh-3B SEM | sh-3b + 5aza Mean | sh-3b + 5aza SEM |
|---|---|---|---|---|---|---|---|---|---|
| MID1 | cg20244073 | 0.810 | 0.003 | 0.771 | 0.017 | 0.742 | 0.010 | 0.652 | 0.005 |
| RTN4R | cg03475420 | 0.131 | 0.003 | 0.123 | 0.001 | 0.124 | 0.005 | 0.105 | 0.001 |
| SLC6A6 | cg13763232 | 1.048 | 0.010 | 0.966 | 0.020 | 1.001 | 0.024 | 0.837 | 0.022 |
| CTSB | cg18787975 | 0.535 | 0.021 | 0.446 | 0.009 | 0.535 | 0.012 | 0.453 | 0.009 |
| PPARGC1A | cg05158538 | 0.860 | 0.020 | 0.806 | 0.010 | 0.785 | 0.006 | 0.705 | 0.020 |
| GNG13 | cg24889366 | 1.007 | 0.008 | 0.988 | 0.014 | 0.892 | 0.008 | 0.815 | 0.001 |
| CHL1 | cg00903242 | 0.672 | 0.010 | 0.655 | 0.010 | 0.595 | 0.005 | 0.546 | 0.011 |
| AIRE | cg17356252 | 1.009 | 0.014 | 0.912 | 0.018 | 0.941 | 0.010 | 0.836 | 0.012 |
| SH2D2A | cg12499211 | 1.197 | 0.013 | 1.095 | 0.012 | 1.113 | 0.008 | 0.983 | 0.013 |
| NCBP1 | cg14223444 | 0.476 | 0.012 | 0.436 | 0.001 | 0.435 | 0.003 | 0.396 | 0.011 |
| FLJ22709 | cg25689649 | 0.864 | 0.015 | 0.863 | 0.002 | 0.744 | 0.006 | 0.705 | 0.013 |
| SYT3 | cg12289045 | 0.936 | 0.008 | 0.876 | 0.013 | 0.842 | 0.010 | 0.776 | 0.005 |
| DPYSL5 | cg12045002 | 0.915 | 0.006 | 0.902 | 0.008 | 0.789 | 0.003 | 0.753 | 0.004 |
| FAM65A | cg02225847 | 0.809 | 0.009 | 0.754 | 0.009 | 0.763 | 0.003 | 0.644 | 0.015 |
| KRTAP8-1 | cg24423088 | 1.147 | 0.017 | 1.127 | 0.010 | 1.001 | 0.004 | 0.937 | 0.018 |
| COL8A2 | cg18931815 | 0.957 | 0.008 | 0.912 | 0.016 | 0.853 | 0.012 | 0.784 | 0.016 |
| AANAT | cg09382492 | 1.215 | 0.009 | 1.208 | 0.008 | 1.084 | 0.010 | 0.962 | 0.014 |
| CSTF2T | cg18690395 | 0.359 | 0.044 | 0.470 | 0.056 | 0.156 | 0.010 | 0.150 | 0.010 |
| GPR126 | cg04461802 | 0.718 | 0.004 | 0.687 | 0.006 | 0.645 | 0.000 | 0.582 | 0.011 |
| FRMD5 | cg23074453 | 0.455 | 0.007 | 0.455 | 0.006 | 0.414 | 0.001 | 0.352 | 0.015 |
| DISP1 | cg10942056 | 1.005 | 0.025 | 0.988 | 0.023 | 0.866 | 0.010 | 0.826 | 0.009 |
| PRPH | cg24059075 | 0.956 | 0.006 | 0.954 | 0.034 | 0.844 | 0.003 | 0.760 | 0.015 |
| ARMC4 | cg02512226 | 0.645 | 0.023 | 0.622 | 0.007 | 0.596 | 0.019 | 0.507 | 0.005 |
| OSTalpha | cg05473677 | 0.957 | 0.010 | 0.908 | 0.009 | 0.869 | 0.023 | 0.772 | 0.012 |
| GIPR | cg03879902 | 0.654 | 0.008 | 0.639 | 0.025 | 0.593 | 0.018 | 0.517 | 0.013 |
| TAPBPL | cg22155248 | 0.987 | 0.012 | 0.884 | 0.010 | 0.972 | 0.008 | 0.782 | 0.011 |
| HRAS | cg08141873 | 0.894 | 0.008 | 0.814 | 0.017 | 0.839 | 0.008 | 0.727 | 0.012 |
| CHI3L1 | cg07423149 | 0.838 | 0.016 | 0.746 | 0.018 | 0.814 | 0.016 | 0.673 | 0.016 |
| C11orf9 | cg22627427 | 1.202 | 0.010 | 1.055 | 0.027 | 1.182 | 0.022 | 0.970 | 0.021 |
| LILRA2 | cg19486673 | 0.946 | 0.030 | 0.916 | 0.022 | 0.851 | 0.025 | 0.755 | 0.004 |
| FLG | cg13447818 | 1.009 | 0.009 | 0.963 | 0.030 | 0.885 | 0.007 | 0.834 | 0.009 |
| ESR1 | cg07671949 | 0.784 | 0.002 | 0.729 | 0.011 | 0.700 | 0.021 | 0.652 | 0.004 |
| RAD1 | cg06466479 | 0.872 | 0.015 | 0.800 | 0.003 | 0.801 | 0.019 | 0.715 | 0.007 |
| RGAG1 | cg06617418 | 1.062 | 0.006 | 0.982 | 0.008 | 0.975 | 0.014 | 0.864 | 0.005 |
| CNFN | cg11500727 | 1.014 | 0.017 | 0.989 | 0.039 | 0.920 | 0.012 | 0.797 | 0.010 |
| B3GNT3 | cg23771661 | 1.212 | 0.019 | 1.151 | 0.026 | 1.067 | 0.016 | 1.001 | 0.028 |
| APC2 | cg11722531 | 0.662 | 0.005 | 0.655 | 0.009 | 0.564 | 0.010 | 0.543 | 0.007 |
| WNT7B | cg21104946 | 0.892 | 0.004 | 0.858 | 0.005 | 0.774 | 0.013 | 0.737 | 0.010 |
| ICAM3 | cg06855803 | 0.893 | 0.006 | 0.884 | 0.045 | 0.774 | 0.021 | 0.721 | 0.002 |
| HCRTR2 | cg13948987 | 1.110 | 0.021 | 1.081 | 0.039 | 0.957 | 0.006 | 0.910 | 0.010 |
| RAC2 | cg14072120 | 0.601 | 0.004 | 0.542 | 0.019 | 0.568 | 0.012 | 0.486 | 0.005 |
| PLEKHA6 | cg21581873 | 0.767 | 0.011 | 0.692 | 0.006 | 0.766 | 0.009 | 0.593 | 0.018 |
| MAPK15 | cg22892110 | 1.179 | 0.012 | 1.175 | 0.011 | 1.012 | 0.009 | 0.953 | 0.034 |
| NFAT5 | cg11147886 | 0.828 | 0.023 | 0.707 | 0.004 | 0.818 | 0.006 | 0.678 | 0.017 |
| TENC1 | cg06311778 | 0.751 | 0.007 | 0.723 | 0.010 | 0.688 | 0.020 | 0.589 | 0.026 |
| ESM1 | cg20451680 | 1.058 | 0.009 | 1.017 | 0.022 | 0.918 | 0.006 | 0.871 | 0.006 |
| TBC1D14 | cg12958778 | 0.948 | 0.005 | 0.885 | 0.015 | 0.852 | 0.012 | 0.773 | 0.003 |
| SLC39A4 | cg11800672 | 0.957 | 0.014 | 0.871 | 0.003 | 0.917 | 0.016 | 0.756 | 0.020 |
| MASP1 | cg20725021 | 0.806 | 0.002 | 0.731 | 0.023 | 0.766 | 0.006 | 0.643 | 0.015 |
| FAM107A | cg06638451 | 0.945 | 0.022 | 0.940 | 0.009 | 0.821 | 0.027 | 0.754 | 0.017 |
| SLC7A6OS | cg19356324 | 1.000 | 0.014 | 0.890 | 0.039 | 0.945 | 0.015 | 0.813 | 0.012 |
| LY6K | cg08569678 | 1.020 | 0.002 | 0.967 | 0.011 | 0.898 | 0.008 | 0.837 | 0.015 |
| SAGE1 | cg19856594 | 0.921 | 0.003 | 0.903 | 0.021 | 0.782 | 0.015 | 0.759 | 0.007 |
| DMPK | cg10857774 | 0.862 | 0.009 | 0.714 | 0.018 | 0.834 | 0.008 | 0.737 | 0.015 |
| ZNF287 | cg03565323 | 0.938 | 0.014 | 0.888 | 0.019 | 0.835 | 0.009 | 0.761 | 0.010 |
| SERPINA10 | cg19937039 | 0.997 | 0.017 | 0.935 | 0.027 | 0.888 | 0.019 | 0.815 | 0.025 |
| CXCL5 | cg04559909 | 0.586 | 0.003 | 0.534 | 0.008 | 0.534 | 0.020 | 0.482 | 0.004 |
| FLJ36445 | cg21550442 | 1.099 | 0.014 | 1.024 | 0.022 | 1.037 | 0.021 | 0.860 | 0.007 |
| RELA | cg18746357 | 1.076 | 0.019 | 1.027 | 0.016 | 0.940 | 0.006 | 0.884 | 0.023 |
| CH25H | cg18762485 | 1.048 | 0.004 | 1.022 | 0.034 | 0.899 | 0.031 | 0.860 | 0.018 |
| H6PD | cg22601917 | 0.583 | 0.003 | 0.496 | 0.009 | 0.571 | 0.009 | 0.480 | 0.010 |
| GPR55 | cg20287234 | 0.847 | 0.015 | 0.797 | 0.023 | 0.788 | 0.002 | 0.664 | 0.010 |
| KRTAP13-3 | cg16431978 | 0.983 | 0.012 | 0.952 | 0.030 | 0.835 | 0.010 | 0.817 | 0.007 |
| DPP4 | cg11460364 | 0.845 | 0.012 | 0.788 | 0.007 | 0.751 | 0.015 | 0.693 | 0.008 |
| MAGEB6 | cg10127415 | 0.949 | 0.002 | 0.887 | 0.023 | 0.869 | 0.013 | 0.758 | 0.020 |
| FLJ42486 | cg00107187 | 0.749 | 0.009 | 0.711 | 0.005 | 0.647 | 0.010 | 0.621 | 0.016 |
| LYL1 | cg15013019 | 0.964 | 0.002 | 0.944 | 0.005 | 0.846 | 0.005 | 0.769 | 0.013 |
| FLJ40365 | cg02489552 | 0.872 | 0.030 | 0.849 | 0.007 | 0.761 | 0.010 | 0.702 | 0.028 |
| C16orf25 | cg10163825 | 1.041 | 0.023 | 1.003 | 0.007 | 0.898 | 0.005 | 0.853 | 0.004 |
| SLITL2 | cg12071544 | 0.777 | 0.009 | 0.718 | 0.009 | 0.703 | 0.004 | 0.631 | 0.011 |
| LOC317671 | cg19108718 | 0.478 | 0.014 | 0.464 | 0.014 | 0.448 | 0.015 | 0.363 | 0.008 |
| MMP19 | cg16725130 | 0.966 | 0.024 | 0.773 | 0.016 | 0.953 | 0.007 | 0.836 | 0.012 |
| C21orf121 | cg10569414 | 0.944 | 0.012 | 0.930 | 0.028 | 0.841 | 0.017 | 0.737 | 0.022 |
| SLC38A3 | cg19914607 | 0.556 | 0.004 | 0.535 | 0.007 | 0.490 | 0.016 | 0.446 | 0.007 |
| CTDP1 | cg01589580 | 0.994 | 0.016 | 0.944 | 0.008 | 0.886 | 0.035 | 0.798 | 0.022 |

TABLE 15-continued

| Gene | Gene ID | sh-ctrl Mean | SEM | sh-ctrl + 5aza Mean | SEM | sh-3B Mean | SEM | sh-3b + 5aza Mean | SEM |
|---|---|---|---|---|---|---|---|---|---|
| C1QL1 | cg16772514 | 0.593 | 0.003 | 0.536 | 0.002 | 0.534 | 0.011 | 0.492 | 0.010 |
| SLC5A1 | cg09547224 | 1.090 | 0.014 | 1.039 | 0.007 | 0.931 | 0.024 | 0.908 | 0.024 |
| ADAMTS13 | cg14802951 | 1.124 | 0.033 | 1.017 | 0.017 | 1.064 | 0.008 | 0.893 | 0.023 |
| IL4I1 | cg07603484 | 0.951 | 0.005 | 0.901 | 0.022 | 0.873 | 0.019 | 0.745 | 0.021 |
| SNX19 | cg12179176 | 0.845 | 0.014 | 0.825 | 0.012 | 0.698 | 0.033 | 0.711 | 0.024 |
| CEACAM7 | cg07297178 | 1.056 | 0.025 | 1.036 | 0.014 | 0.915 | 0.015 | 0.847 | 0.010 |
| SLC44A2 | cg21663431 | 1.031 | 0.013 | 0.984 | 0.002 | 0.904 | 0.014 | 0.835 | 0.013 |
| PTPN6 | cg22335340 | 0.526 | 0.014 | 0.486 | 0.010 | 0.501 | 0.014 | 0.407 | 0.003 |
| GSG2 | cg19585196 | 0.273 | 0.006 | 0.271 | 0.006 | 0.218 | 0.013 | 0.234 | 0.002 |
| LCE1E | cg21065959 | 0.925 | 0.023 | 0.877 | 0.019 | 0.802 | 0.010 | 0.760 | 0.007 |
| FXYD3 | cg02633817 | 1.032 | 0.040 | 0.926 | 0.011 | 0.986 | 0.013 | 0.815 | 0.032 |
| CYP4B1 | cg23414387 | 0.952 | 0.022 | 0.899 | 0.017 | 0.871 | 0.015 | 0.747 | 0.026 |
| RAB36 | cg13894021 | 0.368 | 0.013 | 0.358 | 0.004 | 0.294 | 0.010 | 0.321 | 0.008 |
| AKR1C4 | cg09272256 | 0.847 | 0.017 | 0.757 | 0.009 | 0.779 | 0.027 | 0.693 | 0.015 |
| LOC387882 | cg26940261 | 0.442 | 0.008 | 0.410 | 0.007 | 0.401 | 0.007 | 0.353 | 0.008 |
| LTK | cg27494383 | 1.126 | 0.017 | 1.101 | 0.011 | 1.003 | 0.008 | 0.876 | 0.016 |
| CYP2J2 | cg26815229 | 0.844 | 0.019 | 0.842 | 0.034 | 0.718 | 0.018 | 0.674 | 0.015 |
| SERPINF1 | cg22242539 | 1.096 | 0.007 | 0.983 | 0.011 | 0.993 | 0.005 | 0.904 | 0.022 |
| SLURP1 | cg07441143 | 0.821 | 0.021 | 0.774 | 0.010 | 0.734 | 0.004 | 0.656 | 0.023 |
| ALDH3B1 | cg15322932 | 0.792 | 0.011 | 0.722 | 0.027 | 0.749 | 0.017 | 0.619 | 0.012 |
| DHH | cg14445076 | 1.124 | 0.011 | 1.108 | 0.026 | 0.967 | 0.017 | 0.895 | 0.003 |
| NULP1 | cg01161216 | 0.544 | 0.017 | 0.494 | 0.001 | 0.508 | 0.013 | 0.431 | 0.012 |
| LGALS1 | cg19853760 | 0.941 | 0.006 | 0.888 | 0.002 | 0.836 | 0.003 | 0.754 | 0.006 |
| STAT5B | cg04745805 | 0.472 | 0.005 | 0.419 | 0.018 | 0.457 | 0.008 | 0.370 | 0.008 |
| CACNA1G | cg27426707 | 0.613 | 0.012 | 0.596 | 0.008 | 0.534 | 0.013 | 0.487 | 0.011 |
| MSX1 | cg24840099 | 0.692 | 0.004 | 0.685 | 0.016 | 0.599 | 0.014 | 0.544 | 0.020 |
| ACCN4 | cg19210770 | 1.217 | 0.017 | 1.213 | 0.018 | 1.076 | 0.014 | 0.936 | 0.011 |
| XYLT2 | cg05105913 | 1.000 | 0.003 | 0.963 | 0.005 | 0.844 | 0.017 | 0.823 | 0.011 |
| NTF5 | cg01377911 | 0.922 | 0.010 | 0.853 | 0.019 | 0.825 | 0.013 | 0.744 | 0.014 |
| S100A1 | cg20847746 | 0.679 | 0.018 | 0.606 | 0.009 | 0.640 | 0.010 | 0.541 | 0.005 |
| RHOBTB1 | cg13320683 | 1.056 | 0.012 | 1.024 | 0.013 | 0.882 | 0.028 | 0.873 | 0.018 |
| CD97 | cg03954173 | 0.837 | 0.009 | 0.813 | 0.014 | 0.734 | 0.008 | 0.660 | 0.013 |
| PLCD1 | cg15120942 | 0.832 | 0.009 | 0.810 | 0.014 | 0.699 | 0.017 | 0.681 | 0.006 |
| MAN2B1 | cg03143365 | 0.357 | 0.010 | 0.354 | 0.006 | 0.310 | 0.012 | 0.280 | 0.011 |
| ELOVL4 | cg19439399 | 0.307 | 0.002 | 0.286 | 0.008 | 0.272 | 0.007 | 0.247 | 0.006 |
| HOXD10 | cg21591742 | 0.886 | 0.018 | 0.884 | 0.008 | 0.713 | 0.009 | 0.744 | 0.026 |
| KRT17 | cg27236973 | 1.086 | 0.011 | 0.943 | 0.020 | 1.007 | 0.031 | 0.900 | 0.012 |
| CRNN | cg19370451 | 0.943 | 0.008 | 0.922 | 0.018 | 0.795 | 0.009 | 0.767 | 0.017 |
| FLJ36116 | cg03364504 | 0.907 | 0.017 | 0.873 | 0.005 | 0.795 | 0.003 | 0.720 | 0.015 |
| SLC39A5 | cg03343942 | 0.965 | 0.025 | 0.923 | 0.028 | 0.850 | 0.006 | 0.765 | 0.031 |
| PRX | cg24623694 | 1.137 | 0.003 | 1.006 | 0.038 | 1.031 | 0.013 | 0.939 | 0.018 |
| CILP2 | cg10313673 | 1.007 | 0.019 | 0.969 | 0.041 | 0.866 | 0.019 | 0.812 | 0.009 |
| VWA1 | cg14667273 | 1.075 | 0.004 | 0.918 | 0.017 | 1.033 | 0.021 | 0.872 | 0.013 |
| SUSD3 | cg26833602 | 0.980 | 0.010 | 0.929 | 0.022 | 0.859 | 0.010 | 0.785 | 0.017 |
| TSHR | cg09721659 | 1.004 | 0.012 | 0.965 | 0.009 | 0.830 | 0.030 | 0.839 | 0.005 |
| C16orf25 | cg16899442 | 0.931 | 0.005 | 0.910 | 0.016 | 0.773 | 0.005 | 0.763 | 0.018 |
| PTPRD | cg09440243 | 0.917 | 0.016 | 0.863 | 0.024 | 0.792 | 0.010 | 0.748 | 0.012 |
| SOSTDC1 | cg06363129 | 0.866 | 0.018 | 0.823 | 0.020 | 0.760 | 0.008 | 0.688 | 0.021 |
| BCAM | cg08319238 | 0.374 | 0.007 | 0.315 | 0.014 | 0.360 | 0.006 | 0.305 | 0.006 |
| LOC196463 | cg17946995 | 0.850 | 0.013 | 0.778 | 0.020 | 0.787 | 0.018 | 0.666 | 0.027 |
| TETRAN | cg05209463 | 1.017 | 0.011 | 0.974 | 0.013 | 0.886 | 0.007 | 0.809 | 0.020 |
| LOC400120 | cg18401406 | 1.059 | 0.014 | 0.963 | 0.020 | 0.950 | 0.016 | 0.856 | 0.030 |
| C8orf40 | cg14408969 | 0.238 | 0.001 | 0.210 | 0.008 | 0.217 | 0.006 | 0.194 | 0.001 |
| RBM10 | cg21355508 | 0.650 | 0.005 | 0.601 | 0.014 | 0.581 | 0.013 | 0.520 | 0.021 |
| COL7A1 | cg11846236 | 1.172 | 0.016 | 0.971 | 0.016 | 1.091 | 0.010 | 1.001 | 0.017 |
| MAPK8IP1 | cg03491478 | 0.380 | 0.006 | 0.357 | 0.003 | 0.315 | 0.010 | 0.322 | 0.003 |
| FEZ1 | cg19433435 | 0.886 | 0.025 | 0.832 | 0.021 | 0.784 | 0.013 | 0.704 | 0.020 |
| PLOD3 | cg25527547 | 1.023 | 0.013 | 0.939 | 0.001 | 0.910 | 0.013 | 0.825 | 0.024 |
| HMBS | cg21333964 | 0.349 | 0.005 | 0.344 | 0.009 | 0.321 | 0.007 | 0.259 | 0.009 |
| NR1H3 | cg00554250 | 0.669 | 0.007 | 0.660 | 0.012 | 0.604 | 0.012 | 0.502 | 0.011 |
| OFD1 | cg24352688 | 0.974 | 0.021 | 0.934 | 0.005 | 0.823 | 0.012 | 0.793 | 0.022 |
| SLC18A2 | cg00498305 | 1.114 | 0.005 | 1.094 | 0.023 | 0.935 | 0.005 | 0.892 | 0.020 |
| RAI1 | cg15994159 | 0.265 | 0.005 | 0.259 | 0.008 | 0.246 | 0.006 | 0.195 | 0.008 |
| KLK15 | cg04744379 | 1.055 | 0.016 | 0.989 | 0.030 | 0.920 | 0.016 | 0.846 | 0.022 |
| KLK10 | cg11846956 | 0.691 | 0.004 | 0.687 | 0.031 | 0.575 | 0.012 | 0.552 | 0.015 |
| KIAA1199 | cg15973234 | 0.677 | 0.012 | 0.618 | 0.007 | 0.601 | 0.015 | 0.547 | 0.005 |
| KRTHA3B | cg14533138 | 0.989 | 0.003 | 0.928 | 0.003 | 0.824 | 0.042 | 0.829 | 0.019 |
| CD163 | cg07264679 | 0.945 | 0.018 | 0.912 | 0.008 | 0.795 | 0.002 | 0.764 | 0.028 |
| CMA1 | cg08020808 | 0.703 | 0.028 | 0.694 | 0.012 | 0.605 | 0.023 | 0.547 | 0.011 |
| FLJ40365 | cg09601629 | 1.024 | 0.012 | 0.990 | 0.035 | 0.876 | 0.018 | 0.813 | 0.027 |
| MGAM | cg18971054 | 1.031 | 0.040 | 0.961 | 0.016 | 0.896 | 0.015 | 0.832 | 0.004 |
| C20orf42 | cg06668073 | 0.946 | 0.002 | 0.846 | 0.017 | 0.850 | 0.016 | 0.768 | 0.014 |
| ACPL2 | cg00400028 | 0.895 | 0.008 | 0.808 | 0.002 | 0.830 | 0.009 | 0.701 | 0.013 |
| CDK2 | cg09106999 | 0.949 | 0.020 | 0.879 | 0.018 | 0.858 | 0.016 | 0.743 | 0.007 |
| PPM2C | cg14346035 | 0.504 | 0.009 | 0.483 | 0.004 | 0.445 | 0.006 | 0.391 | 0.007 |

TABLE 15-continued

| Gene | Gene ID | sh-ctrl Mean | sh-ctrl SEM | sh-ctrl + 5aza Mean | sh-ctrl + 5aza SEM | sh-3B Mean | sh-3B SEM | sh-3b + 5aza Mean | sh-3b + 5aza SEM |
|---|---|---|---|---|---|---|---|---|---|
| PRMT8 | cg21667836 | 1.039 | 0.018 | 1.008 | 0.017 | 0.891 | 0.018 | 0.820 | 0.012 |
| ANKRD9 | cg16787352 | 0.739 | 0.015 | 0.654 | 0.026 | 0.704 | 0.014 | 0.576 | 0.002 |
| LOXL3 | cg15989091 | 0.841 | 0.021 | 0.757 | 0.026 | 0.774 | 0.007 | 0.663 | 0.008 |
| POPDC3 | cg24273512 | 0.490 | 0.007 | 0.431 | 0.027 | 0.487 | 0.015 | 0.370 | 0.010 |
| SYNGR3 | cg26486663 | 0.880 | 0.018 | 0.867 | 0.037 | 0.759 | 0.006 | 0.682 | 0.001 |
| ZP3 | cg09916572 | 0.884 | 0.005 | 0.840 | 0.029 | 0.770 | 0.019 | 0.697 | 0.011 |
| CYP4F2 | cg05358291 | 0.880 | 0.025 | 0.853 | 0.016 | 0.746 | 0.013 | 0.702 | 0.010 |
| CENTG2 | cg24768561 | 0.916 | 0.009 | 0.848 | 0.013 | 0.836 | 0.003 | 0.708 | 0.002 |
| MARK2 | cg06204948 | 1.054 | 0.020 | 0.967 | 0.009 | 0.974 | 0.019 | 0.812 | 0.009 |
| SLC7A9 | cg05467458 | 0.794 | 0.017 | 0.721 | 0.020 | 0.701 | 0.010 | 0.642 | 0.007 |
| CREB3L3 | cg13509147 | 0.784 | 0.012 | 0.766 | 0.022 | 0.670 | 0.013 | 0.613 | 0.011 |
| ANGPT1 | cg09396217 | 0.890 | 0.033 | 0.756 | 0.023 | 0.850 | 0.020 | 0.714 | 0.011 |
| RARG | cg12820608 | 0.345 | 0.009 | 0.305 | 0.010 | 0.328 | 0.007 | 0.268 | 0.006 |
| TBPL2 | cg16036738 | 0.674 | 0.011 | 0.661 | 0.032 | 0.599 | 0.020 | 0.506 | 0.007 |
| TAAR5 | cg17829936 | 1.048 | 0.017 | 0.984 | 0.024 | 0.876 | 0.016 | 0.864 | 0.023 |
| PIGO | cg14281165 | 0.229 | 0.002 | 0.220 | 0.007 | 0.185 | 0.003 | 0.191 | 0.010 |
| URB | cg02905245 | 0.875 | 0.001 | 0.808 | 0.018 | 0.795 | 0.011 | 0.678 | 0.008 |
| DIO2 | cg00217795 | 0.963 | 0.002 | 0.935 | 0.006 | 0.807 | 0.007 | 0.767 | 0.007 |
| C11orf47 | cg25368651 | 1.169 | 0.006 | 1.090 | 0.039 | 1.032 | 0.016 | 0.920 | 0.032 |
| PRX | cg26200585 | 1.098 | 0.028 | 1.057 | 0.018 | 0.971 | 0.014 | 0.839 | 0.012 |
| OR7C1 | cg11328541 | 0.925 | 0.012 | 0.878 | 0.032 | 0.773 | 0.013 | 0.754 | 0.012 |
| PLP2 | cg12653105 | 1.041 | 0.014 | 0.992 | 0.026 | 0.882 | 0.014 | 0.834 | 0.007 |
| TFEC | cg04663487 | 0.935 | 0.027 | 0.857 | 0.020 | 0.808 | 0.022 | 0.760 | 0.011 |
| SIRPB1 | cg25799433 | 0.935 | 0.004 | 0.857 | 0.014 | 0.792 | 0.016 | 0.775 | 0.019 |
| FLJ23356 | cg25861458 | 0.217 | 0.003 | 0.207 | 0.007 | 0.172 | 0.007 | 0.185 | 0.003 |
| TSSK6 | cg06899329 | 0.964 | 0.025 | 0.880 | 0.034 | 0.891 | 0.011 | 0.739 | 0.010 |
| CXCL6 | cg25432696 | 0.719 | 0.003 | 0.684 | 0.008 | 0.606 | 0.015 | 0.578 | 0.008 |
| ADCY3 | cg17644208 | 0.779 | 0.006 | 0.693 | 0.012 | 0.698 | 0.015 | 0.628 | 0.022 |
| BMP8A | cg17685111 | 0.748 | 0.010 | 0.691 | 0.015 | 0.655 | 0.011 | 0.595 | 0.019 |
| ZAK | cg03608974 | 0.369 | 0.010 | 0.308 | 0.004 | 0.352 | 0.003 | 0.297 | 0.014 |
| WNK2 | cg16158807 | 0.369 | 0.005 | 0.306 | 0.017 | 0.360 | 0.007 | 0.296 | 0.008 |
| PRSS16 | cg03099771 | 0.856 | 0.015 | 0.815 | 0.012 | 0.731 | 0.015 | 0.678 | 0.008 |
| TNNC1 | cg24166628 | 0.934 | 0.005 | 0.806 | 0.030 | 0.865 | 0.026 | 0.750 | 0.010 |
| SLC25A1 | cg12167239 | 0.151 | 0.006 | 0.127 | 0.005 | 0.144 | 0.003 | 0.121 | 0.002 |
| MIF4GD | cg19586645 | 0.161 | 0.004 | 0.158 | 0.006 | 0.138 | 0.004 | 0.124 | 0.003 |
| FHL1 | cg14506668 | 0.569 | 0.007 | 0.505 | 0.013 | 0.522 | 0.011 | 0.448 | 0.018 |
| TJP3 | cg27022827 | 0.933 | 0.034 | 0.796 | 0.025 | 0.881 | 0.006 | 0.745 | 0.011 |
| SULT1C2 | cg10236239 | 0.954 | 0.011 | 0.833 | 0.012 | 0.898 | 0.013 | 0.746 | 0.012 |
| ARMC9 | cg03369671 | 0.170 | 0.003 | 0.141 | 0.003 | 0.139 | 0.002 | 0.160 | 0.000 |
| TSC22D3 | cg00404599 | 0.930 | 0.010 | 0.906 | 0.012 | 0.791 | 0.016 | 0.725 | 0.015 |
| DPPA3 | cg08284151 | 0.846 | 0.010 | 0.827 | 0.022 | 0.714 | 0.012 | 0.661 | 0.022 |
| NPPB | cg14506552 | 1.080 | 0.020 | 1.000 | 0.020 | 0.929 | 0.010 | 0.866 | 0.018 |
| COL5A2 | cg22774472 | 0.676 | 0.013 | 0.643 | 0.025 | 0.603 | 0.003 | 0.514 | 0.004 |
| TMED1 | cg05051316 | 0.141 | 0.004 | 0.114 | 0.000 | 0.127 | 0.003 | 0.123 | 0.004 |
| UPF3A | cg07218880 | 0.639 | 0.014 | 0.549 | 0.005 | 0.634 | 0.012 | 0.485 | 0.038 |
| SPAG6 | cg06908778 | 0.855 | 0.007 | 0.813 | 0.004 | 0.741 | 0.011 | 0.665 | 0.031 |
| SERHL | cg12078929 | 0.913 | 0.020 | 0.880 | 0.026 | 0.745 | 0.032 | 0.745 | 0.018 |
| COL16A1 | cg13299148 | 1.099 | 0.027 | 1.048 | 0.028 | 0.963 | 0.022 | 0.846 | 0.011 |
| PRKG2 | cg16744741 | 1.106 | 0.016 | 1.012 | 0.033 | 0.947 | 0.023 | 0.898 | 0.017 |
| FGF22 | cg22189019 | 1.168 | 0.007 | 1.083 | 0.039 | 1.034 | 0.021 | 0.910 | 0.014 |
| HERPUD1 | cg17808849 | 0.699 | 0.020 | 0.609 | 0.015 | 0.668 | 0.010 | 0.538 | 0.024 |
| BAP1 | cg22753768 | 0.607 | 0.006 | 0.511 | 0.016 | 0.566 | 0.008 | 0.493 | 0.005 |
| SOX10 | cg06614002 | 1.090 | 0.017 | 0.968 | 0.011 | 1.024 | 0.023 | 0.837 | 0.016 |
| DHX40 | cg18062196 | 1.156 | 0.024 | 1.131 | 0.029 | 0.974 | 0.018 | 0.899 | 0.017 |
| ZDHHC3 | cg05161795 | 0.998 | 0.028 | 0.878 | 0.004 | 0.890 | 0.006 | 0.808 | 0.021 |
| BNC1 | cg10398682 | 0.787 | 0.012 | 0.705 | 0.022 | 0.693 | 0.004 | 0.635 | 0.006 |
| SPIN1 | cg11115702 | 0.593 | 0.011 | 0.554 | 0.020 | 0.517 | 0.019 | 0.465 | 0.006 |
| CSDC2 | cg25447894 | 1.159 | 0.006 | 0.966 | 0.026 | 1.104 | 0.006 | 0.930 | 0.010 |
| CLIC5 | cg08748415 | 0.392 | 0.007 | 0.366 | 0.012 | 0.335 | 0.006 | 0.312 | 0.008 |
| PGLYRP3 | cg09448880 | 0.892 | 0.019 | 0.846 | 0.018 | 0.748 | 0.035 | 0.714 | 0.022 |
| MRPL21 | cg26065952 | 0.349 | 0.002 | 0.340 | 0.017 | 0.295 | 0.005 | 0.273 | 0.010 |
| FLJ43339 | cg13474734 | 0.878 | 0.005 | 0.844 | 0.015 | 0.755 | 0.006 | 0.678 | 0.011 |
| GLRX | cg03852144 | 1.035 | 0.007 | 0.929 | 0.028 | 0.926 | 0.002 | 0.818 | 0.014 |
| DBI | cg21085625 | 0.184 | 0.004 | 0.167 | 0.003 | 0.163 | 0.002 | 0.145 | 0.006 |
| DUSP1 | cg16957313 | 0.522 | 0.009 | 0.437 | 0.022 | 0.499 | 0.008 | 0.416 | 0.016 |
| MEIS3 | cg07478208 | 0.847 | 0.014 | 0.824 | 0.017 | 0.725 | 0.018 | 0.651 | 0.015 |
| PDPK1 | cg14444710 | 0.965 | 0.014 | 0.833 | 0.006 | 0.891 | 0.014 | 0.767 | 0.006 |
| CCL8 | cg27000831 | 0.721 | 0.022 | 0.691 | 0.019 | 0.583 | 0.019 | 0.592 | 0.009 |
| LGALS3BP | cg14870271 | 0.821 | 0.016 | 0.743 | 0.009 | 0.764 | 0.011 | 0.623 | 0.004 |
| PROL1 | cg02741177 | 0.796 | 0.014 | 0.745 | 0.025 | 0.664 | 0.015 | 0.645 | 0.026 |
| SRMS | cg22442730 | 1.012 | 0.012 | 0.949 | 0.031 | 0.886 | 0.015 | 0.783 | 0.023 |
| DEFA1 | cg10758292 | 0.995 | 0.008 | 0.940 | 0.006 | 0.830 | 0.030 | 0.799 | 0.007 |
| PAK1 | cg14521746 | 0.580 | 0.004 | 0.554 | 0.008 | 0.523 | 0.005 | 0.430 | 0.009 |
| FLJ25143 | cg10334385 | 0.280 | 0.008 | 0.274 | 0.012 | 0.231 | 0.006 | 0.221 | 0.006 |
| PHKG1 | cg19759064 | 0.909 | 0.032 | 0.828 | 0.012 | 0.807 | 0.017 | 0.710 | 0.022 |

TABLE 15-continued

| Gene | Gene ID | sh-ctrl Mean | sh-ctrl SEM | sh-ctrl + 5aza Mean | sh-ctrl + 5aza SEM | sh-3B Mean | sh-3B SEM | sh-3b + 5aza Mean | sh-3b + 5aza SEM |
|---|---|---|---|---|---|---|---|---|---|
| CDCA5 | cg20537992 | 0.536 | 0.015 | 0.456 | 0.005 | 0.481 | 0.014 | 0.443 | 0.012 |
| FAM26B | cg07895149 | 1.268 | 0.003 | 1.250 | 0.014 | 1.055 | 0.010 | 0.985 | 0.016 |
| EFNB1 | cg04368919 | 0.671 | 0.009 | 0.589 | 0.008 | 0.622 | 0.004 | 0.522 | 0.016 |
| ENO2 | cg17303299 | 0.639 | 0.010 | 0.542 | 0.008 | 0.598 | 0.013 | 0.508 | 0.008 |
| SLC6A8 | cg07446846 | 1.115 | 0.010 | 1.034 | 0.014 | 0.973 | 0.008 | 0.870 | 0.008 |
| TRIM65 | cg15238200 | 0.860 | 0.017 | 0.749 | 0.023 | 0.821 | 0.014 | 0.658 | 0.022 |
| NAT8 | cg08116137 | 1.018 | 0.034 | 0.953 | 0.004 | 0.870 | 0.024 | 0.803 | 0.020 |
| ANXA9 | cg07337598 | 0.776 | 0.014 | 0.705 | 0.012 | 0.709 | 0.007 | 0.592 | 0.004 |
| AIM2 | cg11003133 | 1.071 | 0.008 | 0.976 | 0.031 | 0.929 | 0.029 | 0.852 | 0.011 |
| ADAM11 | cg06374075 | 0.705 | 0.005 | 0.630 | 0.033 | 0.642 | 0.017 | 0.546 | 0.008 |
| SPRR2E | cg00152644 | 1.105 | 0.012 | 1.032 | 0.051 | 0.944 | 0.014 | 0.872 | 0.016 |
| KCNK9 | cg17834752 | 0.233 | 0.002 | 0.208 | 0.008 | 0.201 | 0.006 | 0.190 | 0.005 |
| FLJ39739 | cg09588210 | 0.468 | 0.007 | 0.438 | 0.022 | 0.422 | 0.015 | 0.352 | 0.007 |
| CR1 | cg14726637 | 0.574 | 0.011 | 0.542 | 0.008 | 0.486 | 0.019 | 0.451 | 0.007 |
| MSX1 | cg09748975 | 0.904 | 0.002 | 0.863 | 0.017 | 0.742 | 0.025 | 0.726 | 0.017 |
| FLJ36445 | cg18542098 | 1.145 | 0.013 | 1.041 | 0.027 | 1.030 | 0.013 | 0.882 | 0.008 |
| CD1E | cg12200412 | 0.730 | 0.002 | 0.668 | 0.017 | 0.624 | 0.008 | 0.585 | 0.005 |
| ABTB1 | cg03330058 | 0.670 | 0.007 | 0.598 | 0.004 | 0.589 | 0.012 | 0.534 | 0.024 |
| ANK2 | cg02735486 | 1.196 | 0.018 | 1.122 | 0.057 | 1.019 | 0.016 | 0.939 | 0.022 |
| SOAT2 | cg26556134 | 0.662 | 0.017 | 0.600 | 0.012 | 0.577 | 0.013 | 0.526 | 0.004 |
| GDF3 | cg22956254 | 0.932 | 0.003 | 0.891 | 0.033 | 0.795 | 0.012 | 0.720 | 0.042 |
| MAPK11 | cg00164898 | 0.783 | 0.006 | 0.759 | 0.011 | 0.670 | 0.003 | 0.597 | 0.011 |
| BNC1 | cg15736165 | 0.699 | 0.016 | 0.591 | 0.013 | 0.646 | 0.008 | 0.561 | 0.018 |
| FCGR3B | cg04567009 | 1.016 | 0.004 | 0.958 | 0.022 | 0.850 | 0.026 | 0.807 | 0.004 |
| ANKRD35 | cg07015079 | 0.983 | 0.007 | 0.959 | 0.010 | 0.813 | 0.011 | 0.768 | 0.020 |
| GRAP | cg23276115 | 0.887 | 0.008 | 0.799 | 0.011 | 0.792 | 0.008 | 0.692 | 0.007 |
| SNX15 | cg03101664 | 1.008 | 0.011 | 1.006 | 0.028 | 0.855 | 0.017 | 0.757 | 0.015 |
| LCE1A | cg14696820 | 0.568 | 0.001 | 0.548 | 0.012 | 0.472 | 0.007 | 0.445 | 0.028 |
| LCE1D | cg15531099 | 0.546 | 0.014 | 0.533 | 0.020 | 0.445 | 0.009 | 0.432 | 0.021 |
| EEF1A2 | cg23582408 | 0.848 | 0.006 | 0.809 | 0.023 | 0.729 | 0.023 | 0.651 | 0.018 |
| CCR7 | cg13504059 | 0.860 | 0.008 | 0.762 | 0.007 | 0.782 | 0.008 | 0.669 | 0.018 |
| CSNK1D | cg19761273 | 0.943 | 0.012 | 0.851 | 0.000 | 0.838 | 0.004 | 0.734 | 0.015 |
| LCE2B | cg25098401 | 0.785 | 0.009 | 0.720 | 0.018 | 0.650 | 0.016 | 0.644 | 0.012 |
| P2RY6 | cg06637774 | 1.245 | 0.012 | 1.195 | 0.036 | 1.032 | 0.002 | 0.980 | 0.037 |
| NOSIP | cg05696092 | 1.027 | 0.005 | 0.987 | 0.021 | 0.875 | 0.010 | 0.788 | 0.017 |
| DCUN1D1 | cg06785429 | 0.943 | 0.021 | 0.824 | 0.025 | 0.874 | 0.036 | 0.728 | 0.019 |
| VMO1 | cg24182328 | 0.732 | 0.019 | 0.711 | 0.009 | 0.631 | 0.012 | 0.550 | 0.011 |
| PEPD | cg09411366 | 0.489 | 0.016 | 0.463 | 0.002 | 0.424 | 0.012 | 0.373 | 0.006 |
| ABCA5 | cg06409153 | 0.988 | 0.012 | 0.940 | 0.027 | 0.828 | 0.008 | 0.774 | 0.004 |
| FLG | cg26390526 | 1.016 | 0.008 | 0.948 | 0.028 | 0.885 | 0.027 | 0.782 | 0.015 |
| STAR | cg09793866 | 1.205 | 0.020 | 1.075 | 0.052 | 1.073 | 0.022 | 0.944 | 0.016 |
| SLC17A4 | cg15916061 | 1.009 | 0.023 | 0.978 | 0.025 | 0.823 | 0.006 | 0.799 | 0.013 |
| CETN1 | cg26738010 | 1.036 | 0.013 | 1.016 | 0.028 | 0.806 | 0.015 | 0.853 | 0.007 |
| SULT1A2 | cg00931491 | 0.787 | 0.009 | 0.694 | 0.015 | 0.709 | 0.006 | 0.616 | 0.009 |
| DLG3 | cg20051589 | 0.585 | 0.005 | 0.584 | 0.013 | 0.454 | 0.013 | 0.475 | 0.009 |
| UPK3B | cg19384697 | 1.180 | 0.014 | 1.101 | 0.005 | 1.033 | 0.023 | 0.902 | 0.016 |
| ACMSD | cg18766847 | 0.700 | 0.011 | 0.697 | 0.023 | 0.598 | 0.008 | 0.520 | 0.037 |
| TTLL7 | cg03098721 | 0.867 | 0.006 | 0.827 | 0.036 | 0.716 | 0.016 | 0.686 | 0.014 |
| CRLF1 | cg12970724 | 0.401 | 0.014 | 0.377 | 0.006 | 0.346 | 0.013 | 0.307 | 0.005 |
| SFT2D3 | cg11206634 | 0.570 | 0.005 | 0.520 | 0.012 | 0.531 | 0.017 | 0.421 | 0.015 |
| CYP2A7 | cg25427638 | 0.911 | 0.020 | 0.895 | 0.020 | 0.742 | 0.019 | 0.712 | 0.021 |
| UHRF1 | cg19147390 | 0.786 | 0.011 | 0.713 | 0.005 | 0.721 | 0.013 | 0.589 | 0.004 |
| SYTL1 | cg21604615 | 1.088 | 0.014 | 1.003 | 0.007 | 0.933 | 0.006 | 0.855 | 0.022 |
| TIGD5 | cg23902550 | 0.524 | 0.026 | 0.463 | 0.004 | 0.495 | 0.008 | 0.393 | 0.005 |
| MCF2L | cg03623878 | 1.065 | 0.007 | 1.002 | 0.047 | 0.942 | 0.011 | 0.799 | 0.035 |
| GLB1 | cg27034836 | 0.345 | 0.013 | 0.271 | 0.008 | 0.335 | 0.015 | 0.281 | 0.006 |
| CYP2A13 | cg07905963 | 0.664 | 0.004 | 0.624 | 0.016 | 0.540 | 0.003 | 0.537 | 0.005 |
| LCE2C | cg00406188 | 0.853 | 0.011 | 0.807 | 0.005 | 0.719 | 0.016 | 0.665 | 0.023 |
| P2RXL1 | cg19592945 | 1.021 | 0.008 | 0.936 | 0.010 | 0.940 | 0.034 | 0.755 | 0.014 |
| PPP1R16A | cg12515371 | 1.140 | 0.006 | 1.021 | 0.026 | 1.031 | 0.005 | 0.873 | 0.011 |
| C14orf93 | cg14386691 | 0.708 | 0.016 | 0.625 | 0.012 | 0.672 | 0.028 | 0.526 | 0.013 |
| MTUS1 | cg22807551 | 0.320 | 0.015 | 0.300 | 0.005 | 0.272 | 0.001 | 0.249 | 0.009 |
| FLJ36046 | cg22262140 | 1.004 | 0.004 | 1.002 | 0.035 | 0.824 | 0.011 | 0.766 | 0.023 |
| FAM83F | cg03954858 | 1.052 | 0.017 | 0.866 | 0.048 | 1.016 | 0.009 | 0.820 | 0.023 |
| GSTA3 | cg04340502 | 1.019 | 0.007 | 0.900 | 0.025 | 0.874 | 0.009 | 0.826 | 0.030 |
| APOBEC2 | cg22375610 | 0.784 | 0.010 | 0.695 | 0.006 | 0.710 | 0.020 | 0.604 | 0.029 |
| ADAMTS8 | cg01033938 | 0.867 | 0.019 | 0.826 | 0.013 | 0.714 | 0.012 | 0.682 | 0.015 |
| OTOP3 | cg27243140 | 1.151 | 0.009 | 1.138 | 0.027 | 0.975 | 0.018 | 0.858 | 0.024 |
| HMGCL | cg18888403 | 0.959 | 0.020 | 0.843 | 0.017 | 0.889 | 0.009 | 0.728 | 0.009 |
| UGT2B17 | cg19481811 | 0.647 | 0.023 | 0.591 | 0.005 | 0.515 | 0.010 | 0.548 | 0.020 |
| LEFTY2 | cg22462235 | 1.099 | 0.023 | 0.935 | 0.035 | 1.074 | 0.005 | 0.823 | 0.029 |
| SS18L2 | cg21008709 | 0.277 | 0.007 | 0.263 | 0.005 | 0.236 | 0.014 | 0.212 | 0.004 |
| OR10H2 | cg24926780 | 0.923 | 0.018 | 0.905 | 0.020 | 0.760 | 0.005 | 0.711 | 0.005 |
| DEFB129 | cg00769470 | 0.802 | 0.010 | 0.800 | 0.009 | 0.625 | 0.031 | 0.643 | 0.006 |
| TRIM36 | cg09312149 | 0.811 | 0.001 | 0.767 | 0.018 | 0.679 | 0.006 | 0.631 | 0.007 |

TABLE 15-continued

| Gene | Gene ID | sh-ctrl Mean | SEM | sh-ctrl + 5aza Mean | SEM | sh-3B Mean | SEM | sh-3b + 5aza Mean | SEM |
|---|---|---|---|---|---|---|---|---|---|
| STAC | cg01798589 | 0.915 | 0.017 | 0.783 | 0.008 | 0.849 | 0.029 | 0.709 | 0.010 |
| KRTHA4 | cg25545210 | 1.005 | 0.006 | 0.924 | 0.011 | 0.833 | 0.019 | 0.808 | 0.024 |
| PLOD1 | cg11469137 | 0.765 | 0.015 | 0.671 | 0.008 | 0.714 | 0.015 | 0.576 | 0.015 |
| OSRF | cg02588309 | 0.939 | 0.003 | 0.867 | 0.029 | 0.762 | 0.019 | 0.767 | 0.031 |
| CX36 | cg00792849 | 0.851 | 0.007 | 0.808 | 0.028 | 0.724 | 0.011 | 0.649 | 0.013 |
| BTBD14A | cg22747092 | 1.184 | 0.004 | 1.060 | 0.026 | 1.042 | 0.006 | 0.920 | 0.004 |
| DAB2IP | cg13060154 | 0.883 | 0.006 | 0.847 | 0.013 | 0.746 | 0.010 | 0.673 | 0.011 |
| NTN2L | cg22536398 | 0.986 | 0.024 | 0.899 | 0.022 | 0.862 | 0.015 | 0.760 | 0.031 |
| SLC10A3 | cg23493704 | 0.903 | 0.009 | 0.829 | 0.016 | 0.774 | 0.012 | 0.702 | 0.005 |
| SLC31A2 | cg05706061 | 0.844 | 0.007 | 0.799 | 0.009 | 0.706 | 0.010 | 0.656 | 0.013 |
| LCE2D | cg21312148 | 0.753 | 0.027 | 0.719 | 0.017 | 0.647 | 0.026 | 0.567 | 0.015 |
| C1orf61 | cg18966791 | 0.895 | 0.010 | 0.776 | 0.008 | 0.827 | 0.002 | 0.686 | 0.020 |
| PCDHB12 | cg07899016 | 0.776 | 0.014 | 0.772 | 0.009 | 0.629 | 0.005 | 0.595 | 0.008 |
| GIMAP1 | cg25168545 | 0.771 | 0.018 | 0.687 | 0.004 | 0.662 | 0.007 | 0.615 | 0.009 |
| SFRP4 | cg12515638 | 0.758 | 0.011 | 0.708 | 0.026 | 0.622 | 0.004 | 0.605 | 0.013 |
| C17orf41 | cg18469326 | 0.189 | 0.003 | 0.173 | 0.004 | 0.145 | 0.006 | 0.164 | 0.004 |
| ACCN4 | cg17610929 | 1.248 | 0.007 | 1.163 | 0.058 | 1.089 | 0.027 | 0.943 | 0.019 |
| C20orf195 | cg06661994 | 0.931 | 0.045 | 0.829 | 0.036 | 0.873 | 0.008 | 0.686 | 0.018 |
| C19orf30 | cg21300318 | 0.990 | 0.001 | 0.951 | 0.008 | 0.824 | 0.008 | 0.759 | 0.016 |
| PCDHB11 | cg04270025 | 0.617 | 0.002 | 0.562 | 0.026 | 0.511 | 0.009 | 0.497 | 0.013 |
| BLVRA | cg17571291 | 0.913 | 0.011 | 0.841 | 0.018 | 0.800 | 0.009 | 0.693 | 0.037 |
| CACNA1C | cg20033731 | 0.425 | 0.016 | 0.364 | 0.013 | 0.399 | 0.004 | 0.325 | 0.005 |
| NMU | cg01943185 | 0.299 | 0.009 | 0.275 | 0.010 | 0.249 | 0.005 | 0.238 | 0.002 |
| ALX4 | cg14144305 | 0.931 | 0.023 | 0.897 | 0.024 | 0.757 | 0.023 | 0.729 | 0.015 |
| OR3A3 | cg05674036 | 0.998 | 0.020 | 0.959 | 0.032 | 0.839 | 0.018 | 0.758 | 0.025 |
| ZNF439 | cg11337780 | 0.844 | 0.014 | 0.817 | 0.034 | 0.691 | 0.032 | 0.654 | 0.010 |
| KRTAP21-1 | cg22373097 | 0.813 | 0.023 | 0.775 | 0.001 | 0.689 | 0.010 | 0.617 | 0.019 |
| LGP2 | cg16762195 | 0.906 | 0.009 | 0.802 | 0.031 | 0.825 | 0.020 | 0.687 | 0.035 |
| CCR7 | cg17067993 | 0.914 | 0.021 | 0.788 | 0.036 | 0.852 | 0.016 | 0.694 | 0.024 |
| DMD | cg21836062 | 1.087 | 0.028 | 0.976 | 0.014 | 0.944 | 0.013 | 0.846 | 0.015 |
| EGF | cg24818418 | 1.045 | 0.006 | 0.972 | 0.005 | 0.886 | 0.019 | 0.807 | 0.016 |
| RSPO1 | cg06626655 | 0.401 | 0.007 | 0.390 | 0.016 | 0.356 | 0.006 | 0.287 | 0.007 |
| MAP4K1 | cg15679651 | 1.022 | 0.014 | 0.924 | 0.026 | 0.913 | 0.006 | 0.771 | 0.007 |
| DEPDC2 | cg13652336 | 0.621 | 0.009 | 0.556 | 0.010 | 0.611 | 0.022 | 0.438 | 0.001 |
| DRD2 | cg12758687 | 0.674 | 0.003 | 0.647 | 0.015 | 0.552 | 0.012 | 0.523 | 0.018 |
| B4GALT7 | cg11313997 | 0.175 | 0.006 | 0.162 | 0.004 | 0.146 | 0.001 | 0.138 | 0.005 |
| NAV1 | cg14920846 | 0.134 | 0.007 | 0.131 | 0.001 | 0.098 | 0.002 | 0.116 | 0.004 |
| BTNL9 | cg05886367 | 0.937 | 0.018 | 0.869 | 0.028 | 0.785 | 0.011 | 0.731 | 0.019 |
| C6orf32 | cg12818699 | 0.879 | 0.005 | 0.697 | 0.021 | 0.815 | 0.012 | 0.725 | 0.015 |
| SLC7A5 | cg26907768 | 0.518 | 0.006 | 0.445 | 0.018 | 0.484 | 0.006 | 0.392 | 0.005 |
| SPRR2D | cg14826683 | 0.949 | 0.035 | 0.893 | 0.034 | 0.781 | 0.007 | 0.745 | 0.001 |
| LOC203427 | cg02232922 | 0.459 | 0.001 | 0.395 | 0.012 | 0.444 | 0.008 | 0.339 | 0.006 |
| TMEM48 | cg23780947 | 0.635 | 0.014 | 0.598 | 0.024 | 0.543 | 0.007 | 0.479 | 0.012 |
| CITED4 | cg10705800 | 0.754 | 0.009 | 0.648 | 0.016 | 0.691 | 0.018 | 0.580 | 0.009 |
| ATXN10 | cg20269537 | 0.451 | 0.010 | 0.407 | 0.010 | 0.405 | 0.009 | 0.338 | 0.006 |
| SPRR3 | cg04138756 | 1.017 | 0.006 | 0.974 | 0.002 | 0.847 | 0.010 | 0.773 | 0.010 |
| SYT3 | cg19017177 | 0.877 | 0.009 | 0.864 | 0.016 | 0.713 | 0.003 | 0.667 | 0.001 |
| ICF45 | cg23123362 | 0.750 | 0.024 | 0.742 | 0.013 | 0.579 | 0.022 | 0.598 | 0.015 |
| SAC | cg08205865 | 0.986 | 0.017 | 0.924 | 0.024 | 0.826 | 0.013 | 0.760 | 0.021 |
| LCN6 | cg11873854 | 1.036 | 0.027 | 0.888 | 0.027 | 0.924 | 0.034 | 0.815 | 0.017 |
| C1orf94 | cg08527127 | 1.105 | 0.018 | 1.027 | 0.039 | 0.906 | 0.015 | 0.875 | 0.010 |
| CLK4 | cg22778145 | 0.803 | 0.022 | 0.793 | 0.005 | 0.629 | 0.014 | 0.632 | 0.008 |
| SAGE1 | cg24101388 | 1.123 | 0.013 | 1.066 | 0.020 | 0.914 | 0.007 | 0.877 | 0.013 |
| SYNE1 | cg27316956 | 0.926 | 0.026 | 0.841 | 0.021 | 0.807 | 0.016 | 0.705 | 0.020 |
| SCRN3 | cg22830590 | 0.235 | 0.011 | 0.231 | 0.006 | 0.167 | 0.006 | 0.206 | 0.011 |
| ABHD7 | cg15156367 | 0.828 | 0.017 | 0.723 | 0.040 | 0.752 | 0.013 | 0.630 | 0.009 |
| LOC400986 | cg05399697 | 0.902 | 0.006 | 0.839 | 0.019 | 0.744 | 0.010 | 0.708 | 0.004 |
| SCRG1 | cg01324261 | 0.808 | 0.004 | 0.711 | 0.008 | 0.721 | 0.010 | 0.619 | 0.009 |
| CFHR4 | cg04614339 | 0.773 | 0.005 | 0.765 | 0.040 | 0.623 | 0.018 | 0.590 | 0.017 |
| PHLDA2 | cg01505590 | 0.390 | 0.079 | 0.490 | 0.038 | 0.182 | 0.029 | 0.145 | 0.004 |
| SLC16A4 | cg09494546 | 1.049 | 0.015 | 0.897 | 0.040 | 0.966 | 0.026 | 0.801 | 0.015 |
| MARCH1 | cg07259382 | 0.882 | 0.008 | 0.782 | 0.002 | 0.750 | 0.020 | 0.700 | 0.019 |
| LOC57146 | cg15786879 | 0.575 | 0.010 | 0.511 | 0.007 | 0.512 | 0.020 | 0.437 | 0.008 |
| SPRR2E | cg08555657 | 0.994 | 0.018 | 0.925 | 0.024 | 0.822 | 0.005 | 0.775 | 0.004 |
| SOD2 | cg10002977 | 0.412 | 0.025 | 0.409 | 0.010 | 0.373 | 0.007 | 0.284 | 0.007 |
| SLC35D2 | cg15582789 | 0.381 | 0.007 | 0.357 | 0.010 | 0.318 | 0.008 | 0.293 | 0.007 |
| HSPC111 | cg01684579 | 0.694 | 0.004 | 0.668 | 0.036 | 0.566 | 0.013 | 0.533 | 0.016 |
| SNN | cg09816471 | 0.978 | 0.021 | 0.937 | 0.014 | 0.854 | 0.003 | 0.709 | 0.020 |
| PGLYRP3 | cg06275635 | 0.873 | 0.011 | 0.785 | 0.006 | 0.726 | 0.020 | 0.699 | 0.010 |
| FLJ22555 | cg13038560 | 0.893 | 0.008 | 0.864 | 0.005 | 0.758 | 0.006 | 0.658 | 0.006 |
| MAPK8IP2 | cg00083937 | 0.940 | 0.014 | 0.890 | 0.011 | 0.815 | 0.014 | 0.691 | 0.020 |
| SLC6A3 | cg13202751 | 0.707 | 0.005 | 0.698 | 0.002 | 0.569 | 0.007 | 0.537 | 0.017 |
| PDCD6IP | cg12941369 | 1.090 | 0.016 | 0.994 | 0.025 | 0.906 | 0.011 | 0.860 | 0.009 |
| MYOD1 | cg16519321 | 0.994 | 0.017 | 0.976 | 0.006 | 0.799 | 0.022 | 0.762 | 0.021 |
| C6orf117 | cg26384034 | 0.460 | 0.012 | 0.370 | 0.019 | 0.450 | 0.015 | 0.353 | 0.004 |

TABLE 15-continued

| Gene | Gene ID | sh-ctrl Mean | sh-ctrl SEM | sh-ctrl + 5aza Mean | sh-ctrl + 5aza SEM | sh-3B Mean | sh-3B SEM | sh-3b + 5aza Mean | sh-3b + 5aza SEM |
|---|---|---|---|---|---|---|---|---|---|
| RAB7L1 | cg09635067 | 0.506 | 0.016 | 0.441 | 0.009 | 0.436 | 0.012 | 0.402 | 0.007 |
| BLR1 | cg25087423 | 1.192 | 0.007 | 0.979 | 0.030 | 1.098 | 0.021 | 0.943 | 0.021 |
| ECD | cg21416602 | 0.164 | 0.003 | 0.138 | 0.001 | 0.150 | 0.003 | 0.128 | 0.002 |
| KCTD4 | cg21457147 | 0.935 | 0.005 | 0.886 | 0.014 | 0.781 | 0.018 | 0.709 | 0.007 |
| SNX24 | cg19412675 | 0.309 | 0.010 | 0.285 | 0.012 | 0.265 | 0.004 | 0.234 | 0.001 |
| TTC9B | cg00058938 | 0.677 | 0.006 | 0.586 | 0.018 | 0.566 | 0.011 | 0.554 | 0.004 |
| SLC44A2 | cg17826679 | 1.134 | 0.008 | 1.102 | 0.015 | 0.935 | 0.010 | 0.854 | 0.004 |
| TMEM100 | cg19403377 | 0.597 | 0.006 | 0.544 | 0.007 | 0.527 | 0.007 | 0.445 | 0.008 |
| SNRPB2 | cg24899750 | 0.327 | 0.006 | 0.311 | 0.016 | 0.263 | 0.004 | 0.255 | 0.005 |
| HRC | cg10910525 | 0.886 | 0.026 | 0.885 | 0.005 | 0.720 | 0.011 | 0.661 | 0.014 |
| CTHRC1 | cg19188612 | 0.845 | 0.035 | 0.753 | 0.013 | 0.722 | 0.025 | 0.658 | 0.007 |
| SEZ6L | cg21353232 | 0.709 | 0.010 | 0.635 | 0.005 | 0.634 | 0.008 | 0.530 | 0.012 |
| NDUFAF1 | cg18705301 | 1.056 | 0.040 | 0.924 | 0.009 | 0.890 | 0.020 | 0.848 | 0.021 |
| STUB1 | cg17328659 | 1.087 | 0.011 | 1.004 | 0.019 | 0.977 | 0.016 | 0.788 | 0.018 |
| C20orf141 | cg01143454 | 0.599 | 0.021 | 0.483 | 0.008 | 0.560 | 0.020 | 0.475 | 0.011 |
| NDRG4 | cg00687686 | 0.632 | 0.004 | 0.585 | 0.010 | 0.553 | 0.004 | 0.467 | 0.017 |
| ASTE1 | cg02335441 | 0.641 | 0.003 | 0.627 | 0.028 | 0.505 | 0.024 | 0.500 | 0.013 |
| JUNB | cg20750215 | 0.677 | 0.002 | 0.605 | 0.024 | 0.578 | 0.006 | 0.526 | 0.014 |
| IGF2AS | cg25163476 | 0.520 | 0.005 | 0.503 | 0.010 | 0.424 | 0.004 | 0.395 | 0.017 |
| ESR2 | cg16792632 | 0.646 | 0.006 | 0.595 | 0.009 | 0.530 | 0.001 | 0.507 | 0.003 |
| PROZ | cg25734864 | 1.082 | 0.012 | 0.996 | 0.031 | 0.922 | 0.008 | 0.818 | 0.004 |
| ENTPD5 | cg12774845 | 0.525 | 0.016 | 0.472 | 0.026 | 0.497 | 0.006 | 0.373 | 0.009 |
| FHIT | cg19574488 | 0.443 | 0.009 | 0.436 | 0.011 | 0.348 | 0.015 | 0.343 | 0.007 |
| OR2W1 | cg05779068 | 0.885 | 0.019 | 0.851 | 0.016 | 0.704 | 0.038 | 0.689 | 0.020 |
| GPR88 | cg10298815 | 1.054 | 0.013 | 1.006 | 0.022 | 0.851 | 0.010 | 0.813 | 0.021 |
| AMIGO2 | cg07473175 | 0.630 | 0.013 | 0.542 | 0.015 | 0.579 | 0.009 | 0.472 | 0.011 |
| CACNA1S | cg22815214 | 0.851 | 0.006 | 0.752 | 0.013 | 0.756 | 0.008 | 0.642 | 0.013 |
| FLJ32312 | cg11736869 | 0.432 | 0.003 | 0.405 | 0.005 | 0.344 | 0.015 | 0.343 | 0.004 |
| PAQR7 | cg15662251 | 0.930 | 0.011 | 0.773 | 0.020 | 0.890 | 0.020 | 0.696 | 0.011 |
| NDUFS2 | cg07354440 | 0.938 | 0.033 | 0.803 | 0.031 | 0.850 | 0.016 | 0.714 | 0.019 |
| ZNF663 | cg03334529 | 0.661 | 0.019 | 0.655 | 0.029 | 0.526 | 0.002 | 0.501 | 0.015 |
| ZDHHC5 | cg13473383 | 0.632 | 0.007 | 0.559 | 0.016 | 0.532 | 0.010 | 0.498 | 0.010 |
| GALNT5 | cg24576425 | 0.908 | 0.009 | 0.834 | 0.009 | 0.759 | 0.019 | 0.698 | 0.002 |
| FLJ23554 | cg21795497 | 0.389 | 0.011 | 0.349 | 0.005 | 0.337 | 0.006 | 0.295 | 0.003 |
| INPP1 | cg25753817 | 0.597 | 0.027 | 0.504 | 0.008 | 0.589 | 0.011 | 0.430 | 0.008 |
| ST6GALNAC3 | cg12601757 | 0.256 | 0.007 | 0.223 | 0.005 | 0.215 | 0.007 | 0.205 | 0.003 |
| MSX1 | cg09573795 | 1.144 | 0.011 | 1.050 | 0.017 | 0.912 | 0.029 | 0.921 | 0.043 |
| GRM8 | cg09868882 | 0.882 | 0.010 | 0.774 | 0.026 | 0.757 | 0.021 | 0.688 | 0.007 |
| F8 | cg06306751 | 0.800 | 0.009 | 0.771 | 0.009 | 0.650 | 0.016 | 0.606 | 0.024 |
| CNFN | cg12973651 | 1.090 | 0.001 | 1.022 | 0.006 | 0.920 | 0.011 | 0.815 | 0.016 |
| BCAP31 | cg24964364 | 0.883 | 0.005 | 0.840 | 0.026 | 0.744 | 0.004 | 0.653 | 0.012 |
| IL17RC | cg07705835 | 0.914 | 0.009 | 0.788 | 0.009 | 0.822 | 0.016 | 0.694 | 0.013 |
| ZNF580 | cg15456206 | 0.762 | 0.005 | 0.671 | 0.007 | 0.708 | 0.007 | 0.553 | 0.008 |
| APOBEC3C | cg07186138 | 0.658 | 0.003 | 0.518 | 0.007 | 0.650 | 0.012 | 0.502 | 0.009 |
| CD40 | cg25239996 | 0.655 | 0.028 | 0.595 | 0.002 | 0.528 | 0.004 | 0.522 | 0.005 |
| PITX2 | cg05522383 | 0.207 | 0.005 | 0.186 | 0.005 | 0.174 | 0.008 | 0.160 | 0.003 |
| OSGEP | cg16205058 | 0.890 | 0.024 | 0.815 | 0.031 | 0.791 | 0.017 | 0.647 | 0.029 |
| YTHDC2 | cg07465864 | 0.334 | 0.009 | 0.317 | 0.012 | 0.269 | 0.003 | 0.257 | 0.013 |
| CSEN | cg05443740 | 0.850 | 0.008 | 0.825 | 0.011 | 0.723 | 0.010 | 0.613 | 0.008 |
| GNMT | cg10056627 | 0.907 | 0.021 | 0.797 | 0.022 | 0.747 | 0.003 | 0.729 | 0.022 |
| GIMAP1 | cg12914657 | 0.904 | 0.010 | 0.903 | 0.021 | 0.726 | 0.028 | 0.669 | 0.011 |
| PALMD | cg00729875 | 0.993 | 0.006 | 0.847 | 0.019 | 0.900 | 0.006 | 0.751 | 0.008 |
| RP11-49G10.8 | cg11854007 | 0.657 | 0.013 | 0.615 | 0.018 | 0.529 | 0.023 | 0.510 | 0.025 |
| CSNK1E | cg01346718 | 0.552 | 0.014 | 0.457 | 0.011 | 0.530 | 0.010 | 0.409 | 0.009 |
| AUP1 | cg04755933 | 1.229 | 0.003 | 1.110 | 0.008 | 1.044 | 0.018 | 0.936 | 0.021 |
| CNTNAP3 | cg13059782 | 0.387 | 0.001 | 0.344 | 0.010 | 0.337 | 0.010 | 0.293 | 0.010 |
| CXCL6 | cg22670329 | 0.524 | 0.002 | 0.518 | 0.007 | 0.403 | 0.011 | 0.407 | 0.019 |
| IFIT2 | cg06476606 | 0.888 | 0.033 | 0.830 | 0.033 | 0.724 | 0.011 | 0.683 | 0.005 |
| SUHW2 | cg16184943 | 0.809 | 0.028 | 0.779 | 0.028 | 0.668 | 0.040 | 0.600 | 0.002 |
| TUBA1 | cg01693157 | 0.813 | 0.010 | 0.800 | 0.009 | 0.665 | 0.015 | 0.598 | 0.011 |
| SIRT2 | cg11396509 | 0.743 | 0.004 | 0.654 | 0.014 | 0.643 | 0.013 | 0.568 | 0.012 |
| GAA | cg20269976 | 0.264 | 0.000 | 0.253 | 0.005 | 0.206 | 0.004 | 0.208 | 0.012 |
| TSPAN12 | cg12650011 | 0.236 | 0.010 | 0.225 | 0.003 | 0.199 | 0.011 | 0.173 | 0.003 |
| DYSF | cg15491567 | 0.806 | 0.016 | 0.806 | 0.037 | 0.644 | 0.012 | 0.598 | 0.003 |
| GPR92 | cg15464148 | 1.047 | 0.003 | 0.979 | 0.014 | 0.860 | 0.015 | 0.797 | 0.015 |
| KRT9 | cg10328573 | 1.062 | 0.019 | 0.986 | 0.024 | 0.886 | 0.024 | 0.801 | 0.017 |
| EYA4 | cg07327468 | 0.364 | 0.005 | 0.313 | 0.010 | 0.332 | 0.005 | 0.270 | 0.007 |
| MNDA | cg25119415 | 0.866 | 0.018 | 0.764 | 0.005 | 0.734 | 0.024 | 0.673 | 0.023 |
| SOCS2 | cg24117442 | 0.337 | 0.009 | 0.303 | 0.009 | 0.253 | 0.012 | 0.290 | 0.006 |
| SIGLEC6 | cg16293105 | 0.883 | 0.012 | 0.846 | 0.006 | 0.727 | 0.010 | 0.657 | 0.015 |
| GRP | cg01625242 | 0.938 | 0.019 | 0.873 | 0.009 | 0.756 | 0.018 | 0.727 | 0.017 |
| SNAPC5 | cg16330965 | 0.752 | 0.016 | 0.671 | 0.012 | 0.696 | 0.024 | 0.536 | 0.025 |
| DAPK2 | cg23165541 | 0.929 | 0.003 | 0.880 | 0.006 | 0.785 | 0.009 | 0.680 | 0.010 |
| D4S234E | cg17183546 | 0.445 | 0.005 | 0.416 | 0.008 | 0.379 | 0.017 | 0.327 | 0.007 |

TABLE 15-continued

| Gene | Gene ID | sh-ctrl Mean | sh-ctrl SEM | sh-ctrl + 5aza Mean | sh-ctrl + 5aza SEM | sh-3B Mean | sh-3B SEM | sh-3b + 5aza Mean | sh-3b + 5aza SEM |
|---|---|---|---|---|---|---|---|---|---|
| LRRC20 | cg26869604 | 0.235 | 0.012 | 0.222 | 0.005 | 0.192 | 0.006 | 0.178 | 0.004 |
| FGF23 | cg23219570 | 0.947 | 0.015 | 0.932 | 0.020 | 0.724 | 0.021 | 0.737 | 0.023 |
| C21orf128 | cg19766460 | 0.618 | 0.000 | 0.595 | 0.016 | 0.513 | 0.010 | 0.452 | 0.003 |
| HOXB5 | cg01405107 | 0.346 | 0.012 | 0.325 | 0.013 | 0.294 | 0.007 | 0.254 | 0.005 |
| ELF3 | cg12970084 | 0.898 | 0.023 | 0.819 | 0.024 | 0.771 | 0.014 | 0.667 | 0.009 |
| SPINK7 | cg27488807 | 0.835 | 0.027 | 0.774 | 0.034 | 0.685 | 0.014 | 0.638 | 0.018 |
| CST9L | cg15210427 | 1.039 | 0.010 | 0.916 | 0.015 | 0.879 | 0.016 | 0.803 | 0.018 |
| ST6GALNAC1 | cg13015534 | 0.964 | 0.008 | 0.908 | 0.028 | 0.825 | 0.009 | 0.698 | 0.011 |
| OR2V2 | cg05071677 | 0.848 | 0.022 | 0.831 | 0.029 | 0.666 | 0.022 | 0.643 | 0.021 |
| SH2D2A | cg20839149 | 1.167 | 0.018 | 1.034 | 0.044 | 0.999 | 0.016 | 0.888 | 0.017 |
| KLF1 | cg11220060 | 1.002 | 0.004 | 0.974 | 0.050 | 0.824 | 0.038 | 0.733 | 0.010 |
| L3MBTL2 | cg14679202 | 1.120 | 0.031 | 1.008 | 0.025 | 0.928 | 0.012 | 0.865 | 0.013 |
| KIAA1704 | cg22539738 | 1.119 | 0.025 | 1.011 | 0.033 | 0.956 | 0.021 | 0.837 | 0.022 |
| DAK | cg25406518 | 1.141 | 0.010 | 1.038 | 0.006 | 0.961 | 0.018 | 0.860 | 0.010 |
| TMEM84 | cg24399529 | 0.783 | 0.021 | 0.725 | 0.020 | 0.630 | 0.026 | 0.607 | 0.024 |
| IKBKE | cg22577136 | 0.731 | 0.018 | 0.709 | 0.006 | 0.649 | 0.004 | 0.502 | 0.014 |
| TRPC4AP | cg11277126 | 0.589 | 0.005 | 0.497 | 0.016 | 0.540 | 0.010 | 0.440 | 0.009 |
| TLX2 | cg25361106 | 0.963 | 0.012 | 0.902 | 0.018 | 0.827 | 0.009 | 0.697 | 0.011 |
| LTBP1 | cg27072387 | 0.272 | 0.010 | 0.268 | 0.007 | 0.209 | 0.011 | 0.210 | 0.006 |
| ZFAND2B | cg15278948 | 0.315 | 0.008 | 0.265 | 0.017 | 0.300 | 0.010 | 0.228 | 0.004 |
| ABTB1 | cg18353563 | 0.969 | 0.014 | 0.923 | 0.018 | 0.746 | 0.004 | 0.762 | 0.030 |
| ATG12 | cg26233209 | 0.962 | 0.012 | 0.875 | 0.035 | 0.789 | 0.018 | 0.739 | 0.006 |
| ANK2 | cg03476195 | 0.815 | 0.003 | 0.798 | 0.027 | 0.643 | 0.009 | 0.612 | 0.019 |
| FPR1 | cg05376954 | 0.719 | 0.018 | 0.693 | 0.027 | 0.557 | 0.033 | 0.557 | 0.012 |
| DNALI1 | cg21488617 | 0.682 | 0.007 | 0.646 | 0.012 | 0.565 | 0.004 | 0.502 | 0.020 |
| PPARD | cg00657095 | 0.321 | 0.007 | 0.309 | 0.017 | 0.267 | 0.012 | 0.232 | 0.003 |
| MECP2 | cg00981643 | 0.761 | 0.019 | 0.673 | 0.028 | 0.668 | 0.013 | 0.563 | 0.026 |
| BAK1 | cg07679836 | 0.766 | 0.021 | 0.638 | 0.013 | 0.706 | 0.012 | 0.573 | 0.008 |
| CBR3 | cg14564494 | 0.601 | 0.011 | 0.554 | 0.021 | 0.500 | 0.015 | 0.449 | 0.017 |
| LOC388152 | cg01003992 | 0.214 | 0.004 | 0.203 | 0.012 | 0.181 | 0.006 | 0.155 | 0.003 |
| 9-Sep | cg04452095 | 0.968 | 0.024 | 0.846 | 0.024 | 0.860 | 0.021 | 0.715 | 0.020 |
| NALP11 | cg03789934 | 0.816 | 0.011 | 0.745 | 0.003 | 0.682 | 0.009 | 0.612 | 0.003 |
| FCRL3 | cg25259754 | 0.876 | 0.023 | 0.758 | 0.040 | 0.757 | 0.017 | 0.666 | 0.010 |
| ERAS | cg13192155 | 1.020 | 0.015 | 1.055 | 0.038 | 0.471 | 0.031 | 0.408 | 0.042 |
| C6orf27 | cg00728602 | 1.144 | 0.005 | 0.986 | 0.027 | 0.999 | 0.029 | 0.864 | 0.013 |
| NKX3-1 | cg21481775 | 0.659 | 0.007 | 0.565 | 0.010 | 0.580 | 0.005 | 0.496 | 0.020 |
| CAV2 | cg11825652 | 0.926 | 0.007 | 0.837 | 0.014 | 0.759 | 0.007 | 0.711 | 0.006 |
| BM88 | cg23587532 | 1.083 | 0.020 | 0.980 | 0.012 | 0.954 | 0.002 | 0.778 | 0.019 |
| SERPINF2 | cg04780454 | 0.896 | 0.037 | 0.824 | 0.029 | 0.711 | 0.021 | 0.697 | 0.017 |
| BHLHB3 | cg03046445 | 0.495 | 0.024 | 0.440 | 0.007 | 0.430 | 0.013 | 0.364 | 0.001 |
| IL17E | cg14366598 | 0.808 | 0.032 | 0.792 | 0.008 | 0.656 | 0.008 | 0.585 | 0.007 |
| ST6GALNAC1 | cg15503752 | 1.015 | 0.002 | 0.959 | 0.018 | 0.843 | 0.010 | 0.740 | 0.011 |
| GATA3 | cg06230736 | 0.174 | 0.005 | 0.148 | 0.004 | 0.146 | 0.004 | 0.137 | 0.001 |
| HLCS | cg24523456 | 0.496 | 0.019 | 0.462 | 0.015 | 0.448 | 0.018 | 0.341 | 0.009 |
| C1orf198 | cg02206259 | 0.937 | 0.019 | 0.830 | 0.040 | 0.796 | 0.015 | 0.705 | 0.017 |
| C21orf99 | cg05674444 | 0.893 | 0.009 | 0.790 | 0.009 | 0.733 | 0.017 | 0.695 | 0.019 |
| GTF3C4 | cg09986574 | 0.635 | 0.008 | 0.601 | 0.024 | 0.481 | 0.029 | 0.504 | 0.009 |
| RND1 | cg24928378 | 0.230 | 0.014 | 0.221 | 0.003 | 0.187 | 0.008 | 0.168 | 0.004 |
| EFHD2 | cg22269795 | 0.470 | 0.015 | 0.426 | 0.021 | 0.408 | 0.002 | 0.339 | 0.009 |
| IMP4 | cg09640202 | 0.783 | 0.007 | 0.728 | 0.009 | 0.672 | 0.008 | 0.560 | 0.012 |
| DNAJB13 | cg19692710 | 0.822 | 0.018 | 0.773 | 0.003 | 0.679 | 0.015 | 0.603 | 0.014 |
| GABRA2 | cg21820677 | 1.054 | 0.011 | 0.996 | 0.031 | 0.817 | 0.012 | 0.817 | 0.020 |
| CASR | cg11008866 | 0.814 | 0.018 | 0.734 | 0.021 | 0.625 | 0.025 | 0.663 | 0.003 |
| TBXA2R | cg15861540 | 0.937 | 0.019 | 0.883 | 0.007 | 0.758 | 0.006 | 0.698 | 0.006 |
| MXI1 | cg09770154 | 0.197 | 0.002 | 0.173 | 0.007 | 0.187 | 0.007 | 0.136 | 0.007 |
| DEFB118 | cg20312687 | 0.944 | 0.017 | 0.902 | 0.025 | 0.729 | 0.016 | 0.728 | 0.004 |
| KIFC3 | cg07685869 | 0.904 | 0.006 | 0.779 | 0.028 | 0.795 | 0.028 | 0.673 | 0.027 |
| KCNH1 | cg21092462 | 0.508 | 0.009 | 0.454 | 0.009 | 0.448 | 0.008 | 0.365 | 0.015 |
| ZNF238 | cg02497700 | 0.399 | 0.007 | 0.354 | 0.011 | 0.320 | 0.008 | 0.313 | 0.006 |
| SLC5A8 | cg05722918 | 0.617 | 0.020 | 0.545 | 0.019 | 0.516 | 0.006 | 0.469 | 0.022 |
| IFNA1 | cg11959435 | 0.965 | 0.009 | 0.881 | 0.013 | 0.756 | 0.028 | 0.757 | 0.004 |
| C12orf43 | cg19395441 | 0.412 | 0.009 | 0.388 | 0.008 | 0.352 | 0.002 | 0.292 | 0.005 |
| LCE4A | cg21846488 | 0.820 | 0.032 | 0.736 | 0.015 | 0.677 | 0.026 | 0.621 | 0.014 |
| DTL | cg02451670 | 0.639 | 0.005 | 0.625 | 0.011 | 0.511 | 0.018 | 0.465 | 0.043 |
| FAM19A3 | cg23746359 | 0.792 | 0.009 | 0.740 | 0.004 | 0.641 | 0.025 | 0.592 | 0.011 |
| VSIG4 | cg26561773 | 0.964 | 0.024 | 0.878 | 0.031 | 0.763 | 0.010 | 0.750 | 0.007 |
| SEPP1 | cg04502814 | 0.763 | 0.008 | 0.670 | 0.003 | 0.631 | 0.021 | 0.588 | 0.030 |
| UROS | cg19346193 | 1.026 | 0.023 | 0.900 | 0.005 | 0.849 | 0.006 | 0.790 | 0.006 |
| GALNT5 | cg20469837 | 1.032 | 0.011 | 0.997 | 0.031 | 0.827 | 0.011 | 0.757 | 0.020 |
| AP1G2 | cg02945646 | 0.381 | 0.004 | 0.321 | 0.015 | 0.327 | 0.004 | 0.293 | 0.012 |
| MLC1 | cg05861567 | 1.049 | 0.005 | 0.962 | 0.020 | 0.884 | 0.022 | 0.764 | 0.035 |
| CRHR2 | cg04922810 | 0.279 | 0.003 | 0.240 | 0.010 | 0.225 | 0.005 | 0.224 | 0.007 |
| PTPRJ | cg06780358 | 0.194 | 0.007 | 0.176 | 0.007 | 0.154 | 0.005 | 0.150 | 0.004 |
| FGFBP1 | cg13726191 | 0.701 | 0.011 | 0.588 | 0.022 | 0.640 | 0.024 | 0.514 | 0.010 |
| HRIHFB2122 | cg25404088 | 0.527 | 0.016 | 0.482 | 0.026 | 0.460 | 0.008 | 0.373 | 0.010 |

TABLE 15-continued

| Gene | Gene ID | sh-ctrl Mean | sh-ctrl SEM | sh-ctrl + 5aza Mean | sh-ctrl + 5aza SEM | sh-3B Mean | sh-3B SEM | sh-3b + 5aza Mean | sh-3b + 5aza SEM |
|---|---|---|---|---|---|---|---|---|---|
| CARD4 | cg15815016 | 0.904 | 0.030 | 0.862 | 0.011 | 0.755 | 0.019 | 0.644 | 0.015 |
| MBD3L1 | cg13727946 | 0.800 | 0.021 | 0.730 | 0.023 | 0.666 | 0.020 | 0.590 | 0.009 |
| CHRNB2 | cg21052164 | 0.893 | 0.017 | 0.837 | 0.015 | 0.723 | 0.051 | 0.662 | 0.028 |
| GATA4 | cg20279283 | 0.805 | 0.007 | 0.788 | 0.048 | 0.648 | 0.010 | 0.581 | 0.020 |
| RQCD1 | cg10643489 | 0.402 | 0.005 | 0.338 | 0.015 | 0.343 | 0.013 | 0.310 | 0.001 |
| C1orf85 | cg22377142 | 0.371 | 0.018 | 0.350 | 0.004 | 0.313 | 0.008 | 0.264 | 0.011 |
| RAD54L | cg03262773 | 0.821 | 0.006 | 0.761 | 0.012 | 0.656 | 0.008 | 0.619 | 0.019 |
| C6orf208 | cg10865119 | 0.840 | 0.017 | 0.827 | 0.008 | 0.722 | 0.022 | 0.569 | 0.016 |
| CBFB | cg13500388 | 1.011 | 0.024 | 0.904 | 0.017 | 0.845 | 0.010 | 0.754 | 0.021 |
| DEFB119 | cg18462653 | 0.868 | 0.011 | 0.799 | 0.008 | 0.691 | 0.025 | 0.660 | 0.035 |
| LST1 | cg23509869 | 0.736 | 0.004 | 0.712 | 0.011 | 0.573 | 0.009 | 0.549 | 0.011 |
| UPK1B | cg02019333 | 0.624 | 0.006 | 0.553 | 0.013 | 0.523 | 0.015 | 0.467 | 0.005 |
| SPAG7 | cg12815142 | 0.903 | 0.019 | 0.820 | 0.003 | 0.762 | 0.024 | 0.658 | 0.018 |
| TMCC2 | cg08353146 | 0.294 | 0.011 | 0.224 | 0.001 | 0.247 | 0.004 | 0.253 | 0.002 |
| PHF16 | cg17843048 | 0.386 | 0.007 | 0.370 | 0.013 | 0.299 | 0.010 | 0.291 | 0.006 |
| KRTAP19-5 | cg07374637 | 0.938 | 0.010 | 0.876 | 0.014 | 0.729 | 0.011 | 0.719 | 0.008 |
| CIB2 | cg20761322 | 0.236 | 0.008 | 0.195 | 0.009 | 0.210 | 0.006 | 0.178 | 0.005 |
| SLC5A8 | cg12135976 | 0.624 | 0.014 | 0.608 | 0.000 | 0.484 | 0.006 | 0.463 | 0.021 |
| IGF2AS | cg04112019 | 0.468 | 0.017 | 0.463 | 0.023 | 0.357 | 0.023 | 0.348 | 0.012 |
| ELN | cg27360098 | 1.033 | 0.012 | 0.889 | 0.028 | 0.898 | 0.009 | 0.764 | 0.016 |
| FLJ23657 | cg10409560 | 1.102 | 0.009 | 0.859 | 0.013 | 0.991 | 0.004 | 0.870 | 0.008 |
| TTLL11 | cg11527279 | 1.065 | 0.020 | 0.941 | 0.018 | 0.935 | 0.020 | 0.764 | 0.017 |
| BNC2 | cg24341129 | 0.554 | 0.015 | 0.449 | 0.001 | 0.495 | 0.013 | 0.422 | 0.010 |
| GFI1 | cg20125091 | 0.354 | 0.001 | 0.293 | 0.018 | 0.320 | 0.011 | 0.263 | 0.006 |
| DCHS1 | cg01086895 | 0.985 | 0.063 | 0.942 | 0.013 | 0.776 | 0.013 | 0.731 | 0.022 |
| DOC2A | cg03920233 | 0.343 | 0.015 | 0.299 | 0.004 | 0.296 | 0.003 | 0.252 | 0.006 |
| OMA1 | cg19840532 | 0.441 | 0.008 | 0.399 | 0.021 | 0.370 | 0.007 | 0.321 | 0.005 |
| CDKN1A | cg03714916 | 1.001 | 0.010 | 0.741 | 0.025 | 0.943 | 0.014 | 0.798 | 0.015 |
| NPAS4 | cg22134325 | 0.814 | 0.011 | 0.793 | 0.008 | 0.642 | 0.012 | 0.594 | 0.013 |
| IGF2AS | cg21237591 | 0.680 | 0.013 | 0.647 | 0.002 | 0.544 | 0.004 | 0.498 | 0.027 |
| TBPL2 | cg16249711 | 0.910 | 0.009 | 0.892 | 0.049 | 0.722 | 0.015 | 0.656 | 0.015 |
| SLC15A2 | cg18636558 | 0.713 | 0.003 | 0.709 | 0.034 | 0.568 | 0.035 | 0.507 | 0.029 |
| C8orf34 | cg22199118 | 0.813 | 0.029 | 0.686 | 0.003 | 0.668 | 0.009 | 0.641 | 0.013 |
| ZNF553 | cg16014085 | 0.448 | 0.009 | 0.379 | 0.022 | 0.404 | 0.006 | 0.325 | 0.012 |
| KPNA1 | cg25564800 | 0.565 | 0.013 | 0.487 | 0.012 | 0.515 | 0.019 | 0.400 | 0.017 |
| ZNF575 | cg25999015 | 0.537 | 0.011 | 0.520 | 0.027 | 0.426 | 0.011 | 0.391 | 0.010 |
| ANGPT4 | cg03218374 | 0.957 | 0.012 | 0.869 | 0.027 | 0.806 | 0.029 | 0.693 | 0.007 |
| BAG4 | cg01607495 | 0.544 | 0.023 | 0.515 | 0.011 | 0.458 | 0.017 | 0.381 | 0.017 |
| IL1RAP | cg01120898 | 0.253 | 0.008 | 0.248 | 0.008 | 0.201 | 0.007 | 0.181 | 0.007 |
| GPD1L | cg21255732 | 0.624 | 0.007 | 0.587 | 0.006 | 0.517 | 0.017 | 0.445 | 0.011 |
| PDE9A | cg00516481 | 0.721 | 0.003 | 0.664 | 0.006 | 0.599 | 0.003 | 0.521 | 0.030 |
| FLJ23514 | cg25500444 | 0.879 | 0.042 | 0.851 | 0.019 | 0.687 | 0.021 | 0.645 | 0.013 |
| FSHB | cg27420123 | 0.838 | 0.006 | 0.819 | 0.033 | 0.638 | 0.007 | 0.625 | 0.040 |
| VPS28 | cg05807444 | 0.885 | 0.005 | 0.848 | 0.012 | 0.712 | 0.001 | 0.636 | 0.013 |
| DPYSL5 | cg26195812 | 0.258 | 0.006 | 0.226 | 0.012 | 0.213 | 0.005 | 0.194 | 0.002 |
| TMEM110 | cg22101147 | 0.620 | 0.017 | 0.500 | 0.025 | 0.578 | 0.022 | 0.453 | 0.020 |
| UPK3B | cg22995176 | 0.859 | 0.021 | 0.806 | 0.016 | 0.740 | 0.015 | 0.592 | 0.009 |
| FLJ10786 | cg11644586 | 0.324 | 0.002 | 0.306 | 0.016 | 0.263 | 0.007 | 0.234 | 0.005 |
| TUBGCP6 | cg11808757 | 0.529 | 0.008 | 0.492 | 0.034 | 0.416 | 0.007 | 0.396 | 0.009 |
| RHOJ | cg02210123 | 0.901 | 0.021 | 0.832 | 0.051 | 0.723 | 0.005 | 0.667 | 0.012 |
| GALM | cg05275752 | 0.457 | 0.028 | 0.449 | 0.009 | 0.382 | 0.014 | 0.312 | 0.017 |
| MGC4268 | cg26782833 | 0.741 | 0.018 | 0.666 | 0.015 | 0.585 | 0.027 | 0.569 | 0.011 |
| RGS19 | cg24516061 | 0.770 | 0.016 | 0.688 | 0.008 | 0.629 | 0.010 | 0.576 | 0.008 |
| TM9SF1 | cg13834500 | 0.235 | 0.005 | 0.198 | 0.005 | 0.194 | 0.006 | 0.182 | 0.005 |
| C19orf30 | cg20893022 | 0.989 | 0.018 | 0.951 | 0.017 | 0.784 | 0.011 | 0.717 | 0.005 |
| ISG20 | cg08491125 | 0.589 | 0.001 | 0.433 | 0.037 | 0.572 | 0.005 | 0.454 | 0.013 |
| CD1B | cg15952487 | 0.713 | 0.009 | 0.643 | 0.005 | 0.573 | 0.003 | 0.535 | 0.011 |
| SIGLEC6 | cg16617137 | 0.886 | 0.009 | 0.826 | 0.013 | 0.688 | 0.023 | 0.669 | 0.001 |
| OSBPL7 | cg09911755 | 1.061 | 0.012 | 1.004 | 0.007 | 0.842 | 0.006 | 0.775 | 0.031 |
| PXMP2 | cg18877514 | 0.885 | 0.012 | 0.833 | 0.032 | 0.734 | 0.004 | 0.623 | 0.007 |
| GP2 | cg19238840 | 0.695 | 0.002 | 0.662 | 0.018 | 0.507 | 0.014 | 0.549 | 0.018 |
| HLA-DOA | cg26643856 | 0.359 | 0.013 | 0.327 | 0.007 | 0.287 | 0.011 | 0.269 | 0.006 |
| HOXB8 | cg25928579 | 0.392 | 0.003 | 0.363 | 0.008 | 0.319 | 0.007 | 0.283 | 0.002 |
| C20orf20 | cg25826526 | 0.159 | 0.001 | 0.137 | 0.005 | 0.134 | 0.003 | 0.118 | 0.005 |
| PCSK7 | cg12082129 | 0.538 | 0.008 | 0.502 | 0.008 | 0.411 | 0.003 | 0.411 | 0.015 |
| OR1F1 | cg07879977 | 0.993 | 0.010 | 0.965 | 0.025 | 0.762 | 0.012 | 0.732 | 0.027 |
| ELL3 | cg03835332 | 0.350 | 0.012 | 0.311 | 0.004 | 0.277 | 0.006 | 0.269 | 0.007 |
| MGST2 | cg12229172 | 1.138 | 0.004 | 1.127 | 0.017 | 0.904 | 0.010 | 0.801 | 0.006 |
| TBP | cg24710073 | 0.561 | 0.035 | 0.534 | 0.027 | 0.479 | 0.016 | 0.382 | 0.004 |
| MYR8 | cg14396117 | 0.959 | 0.015 | 0.915 | 0.019 | 0.746 | 0.040 | 0.707 | 0.015 |
| SORCS1 | cg16415058 | 0.669 | 0.016 | 0.607 | 0.012 | 0.546 | 0.008 | 0.490 | 0.006 |
| LYPD3 | cg25340403 | 0.786 | 0.006 | 0.699 | 0.014 | 0.629 | 0.018 | 0.597 | 0.014 |
| DAND5 | cg15177917 | 1.069 | 0.009 | 1.060 | 0.023 | 0.837 | 0.004 | 0.758 | 0.029 |
| C1QTNF5 | cg20483374 | 0.763 | 0.007 | 0.713 | 0.011 | 0.628 | 0.013 | 0.542 | 0.017 |
| CREG2 | cg21388029 | 0.514 | 0.020 | 0.508 | 0.033 | 0.406 | 0.016 | 0.363 | 0.007 |

TABLE 15-continued

| Gene | Gene ID | sh-ctrl Mean | sh-ctrl SEM | sh-ctrl + 5aza Mean | sh-ctrl + 5aza SEM | sh-3B Mean | sh-3B SEM | sh-3b + 5aza Mean | sh-3b + 5aza SEM |
|---|---|---|---|---|---|---|---|---|---|
| FOXQ1 | cg14809191 | 0.261 | 0.004 | 0.229 | 0.004 | 0.216 | 0.007 | 0.193 | 0.008 |
| FLJ31568 | cg00280814 | 0.698 | 0.015 | 0.598 | 0.026 | 0.631 | 0.018 | 0.490 | 0.019 |
| ALX4 | cg08993172 | 0.625 | 0.028 | 0.617 | 0.038 | 0.483 | 0.017 | 0.449 | 0.010 |
| NFATC2 | cg11086066 | 0.536 | 0.014 | 0.449 | 0.005 | 0.444 | 0.018 | 0.414 | 0.006 |
| NADSYN1 | cg20728496 | 0.934 | 0.020 | 0.811 | 0.013 | 0.790 | 0.022 | 0.685 | 0.019 |
| OVCA2 | cg13315690 | 0.804 | 0.013 | 0.720 | 0.008 | 0.680 | 0.011 | 0.575 | 0.008 |
| ENTPD2 | cg25483003 | 0.845 | 0.012 | 0.733 | 0.030 | 0.738 | 0.005 | 0.603 | 0.031 |
| MATK | cg09416313 | 0.969 | 0.012 | 0.919 | 0.024 | 0.749 | 0.020 | 0.717 | 0.013 |
| MGC16372 | cg10883621 | 0.630 | 0.008 | 0.563 | 0.006 | 0.534 | 0.006 | 0.450 | 0.010 |
| CENTD1 | cg15127324 | 0.484 | 0.014 | 0.463 | 0.016 | 0.370 | 0.011 | 0.359 | 0.013 |
| PRCC | cg06106793 | 0.327 | 0.008 | 0.290 | 0.008 | 0.264 | 0.011 | 0.245 | 0.007 |
| LOC153684 | cg04741133 | 1.107 | 0.030 | 1.105 | 0.037 | 0.805 | 0.028 | 0.835 | 0.017 |
| MGC50811 | cg27367952 | 0.740 | 0.012 | 0.706 | 0.030 | 0.587 | 0.022 | 0.531 | 0.018 |
| MGC3020 | cg15119375 | 0.166 | 0.003 | 0.145 | 0.007 | 0.139 | 0.006 | 0.121 | 0.005 |
| PRRG4 | cg19005368 | 0.672 | 0.004 | 0.598 | 0.013 | 0.555 | 0.012 | 0.491 | 0.004 |
| RPL36 | cg17006282 | 0.518 | 0.008 | 0.478 | 0.028 | 0.442 | 0.012 | 0.358 | 0.006 |
| PLEKHF1 | cg05512099 | 0.464 | 0.017 | 0.393 | 0.015 | 0.384 | 0.007 | 0.352 | 0.012 |
| HRASLS3 | cg05897048 | 0.290 | 0.007 | 0.272 | 0.007 | 0.241 | 0.012 | 0.202 | 0.004 |
| C19orf24 | cg13795840 | 0.848 | 0.009 | 0.779 | 0.045 | 0.704 | 0.022 | 0.601 | 0.016 |
| GJB2 | cg11054936 | 0.850 | 0.014 | 0.777 | 0.016 | 0.668 | 0.006 | 0.634 | 0.007 |
| ATP2A3 | cg15443822 | 0.684 | 0.013 | 0.619 | 0.034 | 0.559 | 0.028 | 0.496 | 0.013 |
| CACNG5 | cg06226384 | 0.891 | 0.015 | 0.890 | 0.055 | 0.710 | 0.024 | 0.613 | 0.020 |
| PAX7 | cg11428724 | 0.205 | 0.003 | 0.169 | 0.003 | 0.166 | 0.005 | 0.161 | 0.008 |
| INT1 | cg14480463 | 0.349 | 0.008 | 0.301 | 0.013 | 0.307 | 0.014 | 0.247 | 0.008 |
| GDPD3 | cg03297731 | 0.943 | 0.009 | 0.865 | 0.008 | 0.737 | 0.004 | 0.703 | 0.007 |
| FBXO44 | cg06848073 | 0.722 | 0.008 | 0.545 | 0.021 | 0.686 | 0.007 | 0.542 | 0.008 |
| DEFB125 | cg08088390 | 0.667 | 0.016 | 0.632 | 0.031 | 0.520 | 0.009 | 0.485 | 0.011 |
| VHL | cg16869108 | 0.435 | 0.006 | 0.407 | 0.014 | 0.370 | 0.022 | 0.295 | 0.008 |
| LOC388272 | cg07707498 | 0.289 | 0.005 | 0.264 | 0.010 | 0.219 | 0.013 | 0.221 | 0.005 |
| OR7A17 | cg05112299 | 0.644 | 0.018 | 0.617 | 0.004 | 0.493 | 0.012 | 0.472 | 0.015 |
| GABRA1 | cg24523000 | 0.507 | 0.006 | 0.485 | 0.018 | 0.394 | 0.014 | 0.366 | 0.007 |
| ATP1A2 | cg08390254 | 0.931 | 0.015 | 0.789 | 0.034 | 0.812 | 0.014 | 0.670 | 0.039 |
| IDH1 | cg07915542 | 0.295 | 0.008 | 0.235 | 0.007 | 0.277 | 0.010 | 0.212 | 0.004 |
| UROS | cg04117029 | 0.839 | 0.004 | 0.741 | 0.015 | 0.702 | 0.026 | 0.605 | 0.026 |
| CDX1 | cg24216701 | 0.983 | 0.019 | 0.878 | 0.005 | 0.843 | 0.024 | 0.687 | 0.018 |
| C21orf29 | cg22991148 | 0.959 | 0.008 | 0.882 | 0.012 | 0.794 | 0.016 | 0.673 | 0.029 |
| DPPA3 | cg06872381 | 0.905 | 0.005 | 0.897 | 0.015 | 0.685 | 0.013 | 0.652 | 0.024 |
| BCAN | cg21475402 | 0.258 | 0.009 | 0.223 | 0.014 | 0.226 | 0.005 | 0.182 | 0.007 |
| FLJ12700 | cg08744726 | 0.591 | 0.011 | 0.526 | 0.014 | 0.504 | 0.019 | 0.416 | 0.019 |
| KRTAP17-1 | cg26499286 | 0.638 | 0.021 | 0.584 | 0.019 | 0.501 | 0.007 | 0.473 | 0.032 |
| GJA5 | cg08307963 | 0.846 | 0.008 | 0.785 | 0.021 | 0.711 | 0.005 | 0.584 | 0.022 |
| KIF17 | cg15613048 | 0.509 | 0.019 | 0.496 | 0.016 | 0.401 | 0.021 | 0.359 | 0.012 |
| MYC | cg19972619 | 0.277 | 0.011 | 0.217 | 0.005 | 0.234 | 0.002 | 0.220 | 0.011 |
| ABHD7 | cg13984181 | 0.346 | 0.005 | 0.315 | 0.002 | 0.281 | 0.004 | 0.249 | 0.011 |
| AARSD1 | cg11492403 | 1.098 | 0.019 | 1.001 | 0.020 | 0.889 | 0.013 | 0.791 | 0.016 |
| HS1BP3 | cg04856043 | 0.459 | 0.014 | 0.429 | 0.011 | 0.401 | 0.008 | 0.304 | 0.001 |
| USP20 | cg23300897 | 0.279 | 0.005 | 0.244 | 0.010 | 0.230 | 0.008 | 0.206 | 0.009 |
| GLI4 | cg03773789 | 0.889 | 0.021 | 0.830 | 0.046 | 0.716 | 0.005 | 0.632 | 0.025 |
| HRB | cg19850163 | 0.347 | 0.014 | 0.308 | 0.011 | 0.269 | 0.006 | 0.267 | 0.010 |
| STIM1 | cg06349174 | 0.724 | 0.007 | 0.554 | 0.019 | 0.666 | 0.027 | 0.546 | 0.027 |
| BCAR1 | cg19094438 | 0.349 | 0.002 | 0.336 | 0.032 | 0.321 | 0.005 | 0.219 | 0.009 |
| NAV3 | cg20217872 | 0.714 | 0.017 | 0.657 | 0.031 | 0.557 | 0.020 | 0.528 | 0.011 |
| FNDC3B | cg04848046 | 1.037 | 0.024 | 0.938 | 0.006 | 0.816 | 0.017 | 0.767 | 0.023 |
| APCS | cg13968061 | 0.881 | 0.013 | 0.849 | 0.035 | 0.672 | 0.002 | 0.640 | 0.013 |
| GPM6A | cg19639622 | 0.250 | 0.007 | 0.231 | 0.012 | 0.199 | 0.007 | 0.179 | 0.008 |
| GPR153 | cg14566624 | 1.181 | 0.019 | 1.086 | 0.005 | 0.963 | 0.004 | 0.835 | 0.006 |
| OGDH | cg07408740 | 0.555 | 0.007 | 0.547 | 0.018 | 0.434 | 0.009 | 0.386 | 0.010 |
| NALP14 | cg02347487 | 0.691 | 0.011 | 0.608 | 0.020 | 0.539 | 0.024 | 0.527 | 0.005 |
| EML4 | cg01184449 | 0.488 | 0.008 | 0.432 | 0.012 | 0.384 | 0.005 | 0.367 | 0.009 |
| KRTAP13-1 | cg02764897 | 0.920 | 0.003 | 0.861 | 0.058 | 0.697 | 0.016 | 0.686 | 0.010 |
| GYS2 | cg06141025 | 1.049 | 0.009 | 0.993 | 0.024 | 0.806 | 0.023 | 0.763 | 0.009 |
| ADRA2A | cg16886188 | 0.217 | 0.007 | 0.188 | 0.001 | 0.175 | 0.007 | 0.163 | 0.008 |
| TM4SF11 | cg23713520 | 0.664 | 0.017 | 0.602 | 0.038 | 0.571 | 0.022 | 0.453 | 0.015 |
| SCRT2 | cg22100821 | 0.328 | 0.008 | 0.326 | 0.017 | 0.249 | 0.016 | 0.233 | 0.012 |
| MAFK | cg19778698 | 0.871 | 0.013 | 0.815 | 0.037 | 0.680 | 0.001 | 0.629 | 0.000 |
| CGI-38 | cg18107072 | 0.874 | 0.025 | 0.820 | 0.014 | 0.709 | 0.019 | 0.608 | 0.015 |
| ITGAX | cg26233914 | 1.111 | 0.012 | 0.994 | 0.016 | 0.907 | 0.005 | 0.798 | 0.006 |
| NHLRC1 | cg00772000 | 1.106 | 0.015 | 1.103 | 0.031 | 0.853 | 0.005 | 0.769 | 0.007 |
| NR2F6 | cg16749578 | 0.388 | 0.013 | 0.353 | 0.009 | 0.353 | 0.018 | 0.252 | 0.013 |
| IFNA21 | cg19982860 | 0.960 | 0.012 | 0.885 | 0.006 | 0.733 | 0.004 | 0.715 | 0.009 |
| FLJ45983 | cg04765277 | 0.577 | 0.024 | 0.561 | 0.016 | 0.438 | 0.020 | 0.415 | 0.029 |
| RAB11FIP5 | cg24935900 | 0.428 | 0.022 | 0.369 | 0.009 | 0.374 | 0.011 | 0.298 | 0.009 |
| RHOB | cg01419675 | 0.257 | 0.003 | 0.230 | 0.015 | 0.192 | 0.005 | 0.200 | 0.007 |
| KCNJ5 | cg26624134 | 0.811 | 0.013 | 0.695 | 0.024 | 0.678 | 0.033 | 0.590 | 0.002 |
| CABP1 | cg00113951 | 0.477 | 0.002 | 0.413 | 0.010 | 0.384 | 0.024 | 0.354 | 0.008 |

TABLE 15-continued

| Gene | Gene ID | sh-ctrl Mean | sh-ctrl SEM | sh-ctrl + 5aza Mean | sh-ctrl + 5aza SEM | sh-3B Mean | sh-3B SEM | sh-3b + 5aza Mean | sh-3b + 5aza SEM |
|---|---|---|---|---|---|---|---|---|---|
| ARL6IP | cg11879577 | 0.403 | 0.013 | 0.371 | 0.011 | 0.320 | 0.015 | 0.288 | 0.015 |
| SPRR2D | cg12891678 | 0.665 | 0.005 | 0.634 | 0.010 | 0.524 | 0.012 | 0.467 | 0.021 |
| STMN1 | cg04471507 | 0.867 | 0.011 | 0.832 | 0.052 | 0.694 | 0.007 | 0.598 | 0.007 |
| HCLS1 | cg00141162 | 1.103 | 0.024 | 1.005 | 0.028 | 0.879 | 0.011 | 0.793 | 0.017 |
| MGC33407 | cg20587168 | 0.626 | 0.015 | 0.616 | 0.009 | 0.464 | 0.006 | 0.456 | 0.016 |
| ZNF688 | cg17794261 | 0.401 | 0.016 | 0.367 | 0.006 | 0.327 | 0.011 | 0.281 | 0.007 |
| ACSL1 | cg11414151 | 0.515 | 0.019 | 0.505 | 0.027 | 0.383 | 0.011 | 0.374 | 0.011 |
| TFAP2D | cg15435730 | 0.805 | 0.001 | 0.772 | 0.020 | 0.602 | 0.018 | 0.589 | 0.021 |
| SLC34A2 | cg21200703 | 0.731 | 0.005 | 0.675 | 0.003 | 0.559 | 0.025 | 0.539 | 0.020 |
| PYGO2 | cg01277844 | 0.380 | 0.019 | 0.347 | 0.012 | 0.315 | 0.005 | 0.263 | 0.004 |
| DGKZ | cg18765542 | 0.455 | 0.016 | 0.431 | 0.028 | 0.415 | 0.001 | 0.286 | 0.008 |
| M6PRBP1 | cg18958531 | 0.346 | 0.011 | 0.329 | 0.015 | 0.270 | 0.013 | 0.245 | 0.017 |
| IFNA17 | cg01074640 | 0.986 | 0.004 | 0.921 | 0.008 | 0.739 | 0.014 | 0.734 | 0.015 |
|  | cg13279585 | 0.849 | 0.016 | 0.821 | 0.011 | 0.617 | 0.031 | 0.634 | 0.005 |
| PFDN2 | cg05650171 | 0.987 | 0.020 | 0.920 | 0.026 | 0.787 | 0.001 | 0.694 | 0.004 |
| C20orf195 | cg05004940 | 1.046 | 0.038 | 1.008 | 0.035 | 0.846 | 0.052 | 0.708 | 0.025 |
| BANK1 | cg25023994 | 0.439 | 0.002 | 0.374 | 0.013 | 0.354 | 0.017 | 0.329 | 0.008 |
| GZMH | cg22228134 | 1.067 | 0.022 | 0.945 | 0.027 | 0.856 | 0.009 | 0.775 | 0.020 |
| SLC29A1 | cg01993576 | 0.345 | 0.018 | 0.302 | 0.011 | 0.286 | 0.005 | 0.245 | 0.008 |
| SPPL3 | cg17345480 | 0.328 | 0.005 | 0.303 | 0.008 | 0.260 | 0.012 | 0.232 | 0.020 |
| ACN9 | cg24205633 | 0.160 | 0.009 | 0.142 | 0.002 | 0.136 | 0.001 | 0.110 | 0.007 |
| CDC42SE1 | cg00224508 | 0.251 | 0.007 | 0.209 | 0.011 | 0.199 | 0.005 | 0.193 | 0.004 |
| IL6 | cg15703690 | 0.524 | 0.020 | 0.492 | 0.017 | 0.426 | 0.009 | 0.358 | 0.014 |
| PRKCE | cg11476211 | 0.698 | 0.031 | 0.691 | 0.013 | 0.541 | 0.009 | 0.480 | 0.014 |
| HSD17B6 | cg21922731 | 0.949 | 0.014 | 0.925 | 0.011 | 0.720 | 0.006 | 0.670 | 0.009 |
| CACNG7 | cg13672791 | 0.935 | 0.009 | 0.904 | 0.015 | 0.708 | 0.009 | 0.666 | 0.012 |
| IL16 | cg01001286 | 0.809 | 0.007 | 0.748 | 0.013 | 0.613 | 0.005 | 0.596 | 0.013 |
| ECEL1 | cg25431974 | 0.731 | 0.010 | 0.670 | 0.030 | 0.586 | 0.017 | 0.515 | 0.014 |
| ZNF513 | cg23337289 | 0.703 | 0.009 | 0.700 | 0.006 | 0.516 | 0.022 | 0.505 | 0.040 |
| PLAC8 | cg24402880 | 0.820 | 0.028 | 0.643 | 0.024 | 0.720 | 0.019 | 0.610 | 0.006 |
| DCC1 | cg08197122 | 0.228 | 0.008 | 0.189 | 0.007 | 0.185 | 0.003 | 0.173 | 0.004 |
| JOSD2 | cg13521229 | 0.934 | 0.025 | 0.886 | 0.017 | 0.748 | 0.009 | 0.642 | 0.012 |
| FCGRT | cg15528736 | 0.633 | 0.012 | 0.548 | 0.029 | 0.587 | 0.016 | 0.414 | 0.014 |
| C20orf103 | cg09119967 | 0.837 | 0.008 | 0.711 | 0.025 | 0.712 | 0.009 | 0.594 | 0.002 |
| AK5 | cg26466094 | 0.196 | 0.004 | 0.167 | 0.002 | 0.151 | 0.004 | 0.153 | 0.004 |
| NAGPA | cg02859934 | 0.736 | 0.020 | 0.714 | 0.007 | 0.571 | 0.011 | 0.510 | 0.017 |
| 9-Sep | cg03330678 | 1.102 | 0.002 | 0.962 | 0.025 | 0.923 | 0.031 | 0.774 | 0.017 |
| PYDC1 | cg13974531 | 1.118 | 0.018 | 1.068 | 0.006 | 0.858 | 0.009 | 0.790 | 0.009 |
| XPNPEP1 | cg17093267 | 1.002 | 0.026 | 0.808 | 0.028 | 0.839 | 0.013 | 0.753 | 0.025 |
| SLC15A4 | cg19777783 | 0.457 | 0.019 | 0.424 | 0.021 | 0.363 | 0.021 | 0.321 | 0.006 |
| PTGS2 | cg19155599 | 0.474 | 0.011 | 0.442 | 0.020 | 0.362 | 0.006 | 0.344 | 0.025 |
| KCNIP4 | cg27196467 | 0.724 | 0.022 | 0.652 | 0.028 | 0.570 | 0.024 | 0.523 | 0.018 |
| C10orf91 | cg22045288 | 1.098 | 0.006 | 0.975 | 0.021 | 0.944 | 0.019 | 0.744 | 0.009 |
| HLA-DMB | cg10714284 | 0.462 | 0.014 | 0.419 | 0.019 | 0.342 | 0.012 | 0.352 | 0.016 |
| WEE1 | cg25876934 | 0.286 | 0.006 | 0.249 | 0.011 | 0.211 | 0.011 | 0.225 | 0.003 |
| KRTAP19-1 | cg13139843 | 0.841 | 0.033 | 0.789 | 0.014 | 0.658 | 0.015 | 0.592 | 0.011 |
| RBJ | cg17466768 | 0.274 | 0.007 | 0.224 | 0.000 | 0.238 | 0.011 | 0.196 | 0.002 |
| KRTCAP3 | cg11618577 | 0.795 | 0.017 | 0.765 | 0.003 | 0.611 | 0.023 | 0.556 | 0.020 |
| BCL2L14 | cg24921858 | 0.839 | 0.009 | 0.734 | 0.007 | 0.689 | 0.037 | 0.595 | 0.008 |
| SYT12 | cg12724357 | 0.860 | 0.014 | 0.830 | 0.033 | 0.671 | 0.006 | 0.593 | 0.005 |
| SORCS3 | cg09551147 | 0.896 | 0.027 | 0.869 | 0.028 | 0.690 | 0.021 | 0.621 | 0.019 |
| SERPINE1 | cg02273392 | 0.334 | 0.005 | 0.265 | 0.006 | 0.318 | 0.001 | 0.228 | 0.011 |
| GLYAT | cg15423764 | 0.863 | 0.003 | 0.816 | 0.030 | 0.634 | 0.008 | 0.638 | 0.025 |
| BATF2 | cg17321617 | 0.587 | 0.016 | 0.517 | 0.014 | 0.484 | 0.014 | 0.412 | 0.008 |
| TCEB3C | cg16907024 | 1.041 | 0.025 | 0.967 | 0.019 | 0.801 | 0.022 | 0.745 | 0.019 |
| VPS53 | cg06500079 | 0.381 | 0.013 | 0.357 | 0.010 | 0.288 | 0.020 | 0.276 | 0.006 |
| IL11 | cg26279025 | 0.983 | 0.012 | 0.796 | 0.029 | 0.878 | 0.027 | 0.693 | 0.009 |
| PON1 | cg07404485 | 0.987 | 0.023 | 0.858 | 0.030 | 0.813 | 0.016 | 0.701 | 0.022 |
| SLD5 | cg24599942 | 0.748 | 0.025 | 0.662 | 0.024 | 0.589 | 0.023 | 0.544 | 0.012 |
| FAM57A | cg10981541 | 0.430 | 0.006 | 0.353 | 0.012 | 0.359 | 0.018 | 0.316 | 0.006 |
| B3GAT3 | cg11706746 | 0.194 | 0.008 | 0.160 | 0.004 | 0.162 | 0.001 | 0.141 | 0.003 |
| C9orf112 | cg12757143 | 0.934 | 0.001 | 0.827 | 0.012 | 0.753 | 0.003 | 0.664 | 0.023 |
| STAT5B | cg05780311 | 0.423 | 0.015 | 0.379 | 0.005 | 0.360 | 0.014 | 0.286 | 0.008 |
| TBC1D4 | cg07519011 | 0.287 | 0.013 | 0.221 | 0.001 | 0.231 | 0.004 | 0.232 | 0.005 |
| GATAD1 | cg08871917 | 0.249 | 0.007 | 0.224 | 0.002 | 0.187 | 0.009 | 0.186 | 0.010 |
| MCF2 | cg21557231 | 0.701 | 0.009 | 0.625 | 0.013 | 0.559 | 0.010 | 0.501 | 0.006 |
| MRO | cg19355919 | 0.255 | 0.005 | 0.240 | 0.010 | 0.190 | 0.007 | 0.185 | 0.011 |
| NLGN3 | cg04037732 | 1.216 | 0.012 | 1.163 | 0.012 | 0.941 | 0.021 | 0.846 | 0.024 |
| RAB31 | cg17982102 | 0.494 | 0.012 | 0.422 | 0.007 | 0.414 | 0.008 | 0.350 | 0.014 |
| IFNA8 | cg15669228 | 0.895 | 0.020 | 0.816 | 0.035 | 0.665 | 0.026 | 0.671 | 0.004 |
| BAI3 | cg10244047 | 0.221 | 0.003 | 0.190 | 0.010 | 0.186 | 0.005 | 0.156 | 0.001 |
| SLC26A4 | cg14646244 | 0.782 | 0.031 | 0.685 | 0.030 | 0.659 | 0.019 | 0.539 | 0.023 |
| CNTN6 | cg07664856 | 0.862 | 0.002 | 0.773 | 0.035 | 0.671 | 0.014 | 0.624 | 0.033 |
| KCNK4 | cg01352108 | 0.847 | 0.016 | 0.789 | 0.019 | 0.678 | 0.025 | 0.582 | 0.011 |
| MRPS2 | cg21010262 | 0.872 | 0.015 | 0.795 | 0.027 | 0.706 | 0.022 | 0.602 | 0.007 |

TABLE 15-continued

| Gene | Gene ID | sh-ctrl Mean | sh-ctrl SEM | sh-ctrl + 5aza Mean | sh-ctrl + 5aza SEM | sh-3B Mean | sh-3B SEM | sh-3b + 5aza Mean | sh-3b + 5aza SEM |
|---|---|---|---|---|---|---|---|---|---|
| MYO1B | cg15096140 | 0.836 | 0.016 | 0.704 | 0.033 | 0.705 | 0.039 | 0.594 | 0.022 |
| KNS2 | cg23090046 | 0.783 | 0.009 | 0.657 | 0.013 | 0.698 | 0.016 | 0.534 | 0.004 |
| PAQR7 | cg23799313 | 0.976 | 0.026 | 0.905 | 0.017 | 0.808 | 0.008 | 0.652 | 0.013 |
| EMR1 | cg22889448 | 0.398 | 0.005 | 0.390 | 0.021 | 0.295 | 0.005 | 0.282 | 0.015 |
| C1orf57 | cg10375802 | 0.339 | 0.010 | 0.315 | 0.013 | 0.256 | 0.004 | 0.244 | 0.016 |
| C1orf42 | cg11750883 | 0.819 | 0.013 | 0.723 | 0.047 | 0.655 | 0.014 | 0.585 | 0.008 |
| FLJ36116 | cg13966710 | 0.621 | 0.016 | 0.619 | 0.019 | 0.452 | 0.030 | 0.441 | 0.029 |
| RASSF4 | cg17324128 | 0.375 | 0.005 | 0.296 | 0.003 | 0.328 | 0.005 | 0.273 | 0.019 |
| YIPF1 | cg13262752 | 0.328 | 0.013 | 0.297 | 0.010 | 0.253 | 0.016 | 0.236 | 0.007 |
| INCA1 | cg09307264 | 0.351 | 0.001 | 0.335 | 0.013 | 0.264 | 0.007 | 0.250 | 0.001 |
| CISH | cg07105440 | 0.541 | 0.003 | 0.431 | 0.021 | 0.473 | 0.009 | 0.390 | 0.017 |
| TAL1 | cg00875272 | 0.777 | 0.030 | 0.740 | 0.025 | 0.581 | 0.009 | 0.555 | 0.009 |
| CHGA | cg12422450 | 0.376 | 0.012 | 0.357 | 0.023 | 0.274 | 0.010 | 0.274 | 0.005 |
| CASP14 | cg01999333 | 0.783 | 0.004 | 0.771 | 0.022 | 0.606 | 0.021 | 0.527 | 0.027 |
| GRIK3 | cg06165395 | 0.579 | 0.011 | 0.577 | 0.017 | 0.452 | 0.012 | 0.384 | 0.004 |
| LRRC4 | cg15087147 | 0.273 | 0.017 | 0.192 | 0.011 | 0.264 | 0.013 | 0.203 | 0.002 |
| IFIT2 | cg09398185 | 0.951 | 0.005 | 0.803 | 0.015 | 0.796 | 0.021 | 0.673 | 0.033 |
| NEIL1 | cg12978308 | 0.395 | 0.015 | 0.362 | 0.005 | 0.303 | 0.018 | 0.282 | 0.019 |
| TNRC4 | cg26050734 | 0.468 | 0.006 | 0.415 | 0.009 | 0.382 | 0.015 | 0.325 | 0.004 |
| NR0B1 | cg22705954 | 0.717 | 0.023 | 0.641 | 0.013 | 0.580 | 0.011 | 0.499 | 0.016 |
| EFNA1 | cg03231024 | 0.291 | 0.011 | 0.285 | 0.017 | 0.213 | 0.007 | 0.207 | 0.012 |
| MGC62100 | cg04803153 | 1.013 | 0.021 | 0.839 | 0.005 | 0.822 | 0.007 | 0.747 | 0.028 |
| NFASC | cg22571530 | 0.277 | 0.013 | 0.262 | 0.007 | 0.217 | 0.008 | 0.189 | 0.007 |
| CNTFR | cg12188560 | 1.019 | 0.023 | 0.952 | 0.005 | 0.765 | 0.010 | 0.733 | 0.009 |
| TEAD4 | cg21637033 | 0.221 | 0.007 | 0.177 | 0.003 | 0.172 | 0.006 | 0.175 | 0.005 |
| KCNIP4 | cg15401952 | 0.670 | 0.009 | 0.592 | 0.022 | 0.518 | 0.014 | 0.489 | 0.023 |
| FAM84B | cg15312298 | 0.537 | 0.014 | 0.427 | 0.013 | 0.428 | 0.016 | 0.418 | 0.011 |
| CDKN2A | cg07752420 | 0.211 | 0.003 | 0.206 | 0.012 | 0.168 | 0.005 | 0.138 | 0.006 |
| THRB | cg08319404 | 0.748 | 0.030 | 0.625 | 0.024 | 0.617 | 0.021 | 0.538 | 0.020 |
| TSLP | cg15739437 | 0.652 | 0.018 | 0.632 | 0.050 | 0.469 | 0.007 | 0.473 | 0.009 |
| FGL2 | cg12271671 | 0.848 | 0.024 | 0.808 | 0.031 | 0.662 | 0.021 | 0.577 | 0.006 |
| TAF1C | cg12533335 | 0.313 | 0.006 | 0.282 | 0.009 | 0.255 | 0.008 | 0.215 | 0.005 |
| MAPRE3 | cg17192247 | 0.528 | 0.007 | 0.447 | 0.006 | 0.422 | 0.007 | 0.386 | 0.004 |
| HRH3 | cg10605520 | 1.032 | 0.008 | 1.029 | 0.008 | 0.765 | 0.008 | 0.712 | 0.019 |
| RABL5 | cg11513856 | 0.596 | 0.013 | 0.556 | 0.018 | 0.461 | 0.029 | 0.414 | 0.012 |
| NEUROD1 | cg22359606 | 0.866 | 0.014 | 0.824 | 0.040 | 0.651 | 0.030 | 0.609 | 0.028 |
| PDLIM4 | cg20512303 | 0.783 | 0.009 | 0.766 | 0.012 | 0.609 | 0.013 | 0.524 | 0.012 |
| LOC253012 | cg11608424 | 0.973 | 0.015 | 0.891 | 0.033 | 0.756 | 0.015 | 0.683 | 0.009 |
| TM2D2 | cg16652639 | 0.249 | 0.009 | 0.183 | 0.010 | 0.199 | 0.007 | 0.209 | 0.002 |
| LRRC56 | cg27158867 | 0.859 | 0.010 | 0.832 | 0.022 | 0.647 | 0.010 | 0.595 | 0.016 |
| FZD1 | cg21746887 | 0.307 | 0.010 | 0.269 | 0.011 | 0.240 | 0.012 | 0.223 | 0.005 |
| ABCC9 | cg20025970 | 0.837 | 0.025 | 0.795 | 0.030 | 0.655 | 0.021 | 0.567 | 0.015 |
| IL7 | cg23538854 | 0.733 | 0.016 | 0.676 | 0.007 | 0.547 | 0.006 | 0.530 | 0.007 |
| APOBEC3G | cg26022401 | 0.582 | 0.001 | 0.512 | 0.015 | 0.471 | 0.006 | 0.406 | 0.007 |
| ALDH5A1 | cg25181693 | 0.375 | 0.013 | 0.330 | 0.016 | 0.301 | 0.006 | 0.263 | 0.007 |
| DRD1IP | cg10845200 | 0.936 | 0.017 | 0.902 | 0.006 | 0.689 | 0.014 | 0.664 | 0.002 |
| ARHGEF18 | cg02981853 | 0.952 | 0.012 | 0.884 | 0.011 | 0.743 | 0.007 | 0.656 | 0.004 |
| PTPN6 | cg04956511 | 0.840 | 0.005 | 0.787 | 0.009 | 0.653 | 0.021 | 0.577 | 0.003 |
| HIF3A | cg07022477 | 0.778 | 0.011 | 0.755 | 0.006 | 0.597 | 0.005 | 0.526 | 0.036 |
| CDKN2A | cg11653709 | 0.512 | 0.008 | 0.452 | 0.010 | 0.408 | 0.002 | 0.360 | 0.021 |
| MARK2 | cg17998964 | 1.105 | 0.020 | 0.969 | 0.028 | 0.962 | 0.011 | 0.725 | 0.012 |
| SGCA | cg07826255 | 0.828 | 0.010 | 0.687 | 0.021 | 0.697 | 0.008 | 0.582 | 0.027 |
| NDST4 | cg09511421 | 0.897 | 0.025 | 0.890 | 0.015 | 0.611 | 0.037 | 0.672 | 0.028 |
| SMPX | cg19002579 | 0.681 | 0.021 | 0.634 | 0.016 | 0.535 | 0.011 | 0.466 | 0.016 |
| TMEM100 | cg08762247 | 0.773 | 0.024 | 0.710 | 0.025 | 0.631 | 0.013 | 0.515 | 0.018 |
| ZNF285 | cg09030119 | 0.504 | 0.007 | 0.474 | 0.010 | 0.383 | 0.012 | 0.352 | 0.014 |
| STRA6 | cg00075967 | 0.209 | 0.008 | 0.192 | 0.004 | 0.149 | 0.008 | 0.158 | 0.010 |
| DYNC1LI2 | cg21610192 | 0.262 | 0.006 | 0.243 | 0.011 | 0.203 | 0.005 | 0.182 | 0.006 |
| UGT1A6 | cg23338993 | 0.718 | 0.026 | 0.687 | 0.007 | 0.568 | 0.016 | 0.478 | 0.020 |
| DPP3 | cg27388792 | 0.152 | 0.008 | 0.123 | 0.003 | 0.111 | 0.004 | 0.124 | 0.003 |
| IPO8 | cg19722847 | 0.437 | 0.004 | 0.368 | 0.019 | 0.358 | 0.003 | 0.310 | 0.003 |
| SLC44A3 | cg22424108 | 0.422 | 0.002 | 0.325 | 0.020 | 0.421 | 0.015 | 0.278 | 0.010 |
| PLD2 | cg23808301 | 0.320 | 0.009 | 0.267 | 0.013 | 0.242 | 0.006 | 0.246 | 0.013 |
| SPRR4 | cg08763351 | 0.620 | 0.027 | 0.562 | 0.030 | 0.459 | 0.016 | 0.453 | 0.018 |
| METTL7B | cg15702701 | 0.365 | 0.017 | 0.338 | 0.010 | 0.270 | 0.016 | 0.262 | 0.007 |
| CFHR5 | cg25840094 | 0.849 | 0.036 | 0.783 | 0.009 | 0.630 | 0.006 | 0.611 | 0.016 |
| TMEM17 | cg12385425 | 0.414 | 0.011 | 0.366 | 0.003 | 0.319 | 0.007 | 0.298 | 0.013 |
| LRSAM1 | cg05840553 | 0.191 | 0.009 | 0.173 | 0.006 | 0.162 | 0.005 | 0.124 | 0.011 |
| KA21 | cg01289103 | 0.619 | 0.013 | 0.594 | 0.028 | 0.430 | 0.018 | 0.462 | 0.004 |
| COMMD9 | cg08871189 | 0.250 | 0.002 | 0.195 | 0.008 | 0.218 | 0.010 | 0.180 | 0.001 |
| LYL1 | cg04432009 | 0.870 | 0.008 | 0.836 | 0.012 | 0.659 | 0.013 | 0.595 | 0.006 |
| CPNE3 | cg19078186 | 0.234 | 0.010 | 0.216 | 0.011 | 0.185 | 0.010 | 0.159 | 0.005 |
| PROK2 | cg08555612 | 0.499 | 0.013 | 0.430 | 0.012 | 0.417 | 0.012 | 0.339 | 0.018 |
| TPMT | cg07465480 | 0.280 | 0.013 | 0.231 | 0.009 | 0.214 | 0.003 | 0.214 | 0.007 |
| CDK5RAP2 | cg16956268 | 0.335 | 0.019 | 0.286 | 0.004 | 0.260 | 0.002 | 0.245 | 0.004 |

TABLE 15-continued

| Gene | Gene ID | sh-ctrl | | sh-ctrl + 5aza | | sh-3B | | sh-3b + 5aza | |
|---|---|---|---|---|---|---|---|---|---|
| | | Mean | SEM | Mean | SEM | Mean | SEM | Mean | SEM |
| SLC8A2 | cg22123464 | 0.398 | 0.015 | 0.389 | 0.017 | 0.303 | 0.006 | 0.268 | 0.007 |
| LRRC42 | cg19400876 | 0.326 | 0.009 | 0.267 | 0.001 | 0.272 | 0.004 | 0.232 | 0.008 |
| MYADM | cg19717326 | 0.519 | 0.013 | 0.468 | 0.018 | 0.447 | 0.004 | 0.334 | 0.006 |
| UBE2V1 | cg06926735 | 0.314 | 0.015 | 0.283 | 0.007 | 0.239 | 0.007 | 0.225 | 0.011 |
| FAF1 | cg14343711 | 0.331 | 0.022 | 0.301 | 0.005 | 0.280 | 0.010 | 0.214 | 0.009 |
| C9orf7 | cg19123107 | 0.268 | 0.003 | 0.245 | 0.017 | 0.198 | 0.006 | 0.195 | 0.006 |
| FAM80A | cg13199589 | 0.342 | 0.012 | 0.284 | 0.010 | 0.261 | 0.011 | 0.260 | 0.007 |
| CNIH2 | cg19026260 | 0.434 | 0.007 | 0.373 | 0.010 | 0.374 | 0.022 | 0.289 | 0.017 |
| MLX | cg20724073 | 0.697 | 0.013 | 0.649 | 0.009 | 0.546 | 0.020 | 0.471 | 0.006 |
| KRTAP20-1 | cg25388528 | 0.831 | 0.022 | 0.773 | 0.032 | 0.639 | 0.014 | 0.570 | 0.020 |
| MGC17839 | cg26145103 | 0.375 | 0.017 | 0.359 | 0.017 | 0.266 | 0.009 | 0.272 | 0.016 |
| CD300E | cg04995095 | 0.829 | 0.009 | 0.740 | 0.015 | 0.630 | 0.012 | 0.593 | 0.015 |
| PEX11B | cg06804431 | 0.669 | 0.010 | 0.612 | 0.043 | 0.523 | 0.014 | 0.458 | 0.015 |
| ARMCX5 | cg11810837 | 0.256 | 0.008 | 0.211 | 0.006 | 0.196 | 0.005 | 0.196 | 0.008 |
| CALCOCO2 | cg07460665 | 0.813 | 0.010 | 0.672 | 0.042 | 0.678 | 0.007 | 0.570 | 0.017 |
| C2orf10 | cg13121699 | 0.495 | 0.023 | 0.428 | 0.011 | 0.402 | 0.009 | 0.342 | 0.013 |
| C19orf35 | cg20973210 | 0.896 | 0.002 | 0.858 | 0.011 | 0.698 | 0.018 | 0.594 | 0.009 |
| CACNA1G | cg04216597 | 0.841 | 0.006 | 0.806 | 0.010 | 0.631 | 0.015 | 0.575 | 0.008 |
| GPRC5A | cg08849126 | 0.303 | 0.013 | 0.243 | 0.005 | 0.240 | 0.003 | 0.228 | 0.007 |
| MARCO | cg11009736 | 0.910 | 0.008 | 0.769 | 0.030 | 0.705 | 0.007 | 0.666 | 0.007 |
| GNAZ | cg18593668 | 0.346 | 0.008 | 0.321 | 0.012 | 0.294 | 0.008 | 0.219 | 0.019 |
| BTN1A1 | cg07011110 | 0.443 | 0.004 | 0.391 | 0.011 | 0.373 | 0.003 | 0.292 | 0.009 |
| MPP1 | cg22858728 | 0.537 | 0.015 | 0.504 | 0.007 | 0.424 | 0.012 | 0.355 | 0.014 |
| WDR72 | cg18613421 | 0.525 | 0.010 | 0.468 | 0.023 | 0.406 | 0.002 | 0.366 | 0.007 |
| CGREF1 | cg22740783 | 0.654 | 0.015 | 0.644 | 0.043 | 0.477 | 0.009 | 0.449 | 0.011 |
| PXN | cg16785344 | 0.722 | 0.015 | 0.621 | 0.017 | 0.614 | 0.017 | 0.479 | 0.014 |
| LMNA | cg05898524 | 0.860 | 0.020 | 0.712 | 0.020 | 0.698 | 0.005 | 0.610 | 0.013 |
| HLA-DMB | cg00575744 | 0.832 | 0.014 | 0.813 | 0.030 | 0.610 | 0.012 | 0.570 | 0.019 |
| MUC7 | cg10189763 | 0.792 | 0.033 | 0.758 | 0.054 | 0.564 | 0.007 | 0.566 | 0.023 |
| THBS3 | cg25912717 | 0.604 | 0.012 | 0.561 | 0.017 | 0.479 | 0.018 | 0.400 | 0.021 |
| NINJ1 | cg10072995 | 0.675 | 0.016 | 0.439 | 0.017 | 0.640 | 0.039 | 0.536 | 0.036 |
| C20orf103 | cg01144286 | 0.471 | 0.021 | 0.419 | 0.003 | 0.371 | 0.006 | 0.323 | 0.014 |
| LYK5 | cg06873352 | 0.444 | 0.006 | 0.417 | 0.006 | 0.331 | 0.009 | 0.308 | 0.014 |
| C14orf44 | cg07807817 | 0.412 | 0.010 | 0.405 | 0.004 | 0.291 | 0.032 | 0.289 | 0.021 |
| CD1D | cg13765621 | 0.801 | 0.009 | 0.703 | 0.020 | 0.642 | 0.020 | 0.548 | 0.011 |
| RPL9 | cg07027075 | 0.615 | 0.007 | 0.560 | 0.029 | 0.509 | 0.026 | 0.397 | 0.017 |
| TSPAN33 | cg09916853 | 0.593 | 0.023 | 0.539 | 0.006 | 0.495 | 0.013 | 0.381 | 0.002 |
| SNAPC4 | cg24812167 | 0.680 | 0.025 | 0.578 | 0.024 | 0.587 | 0.014 | 0.447 | 0.020 |
| GPR92 | cg25655096 | 1.082 | 0.025 | 0.967 | 0.023 | 0.825 | 0.057 | 0.758 | 0.019 |
| RPS2 | cg18279742 | 0.780 | 0.002 | 0.713 | 0.014 | 0.609 | 0.012 | 0.526 | 0.007 |
| GPD1L | cg05662500 | 0.444 | 0.010 | 0.358 | 0.016 | 0.402 | 0.005 | 0.293 | 0.004 |
| C10orf47 | cg13904771 | 0.921 | 0.027 | 0.867 | 0.029 | 0.650 | 0.009 | 0.667 | 0.024 |
| RAC2 | cg18265887 | 0.974 | 0.013 | 0.869 | 0.031 | 0.797 | 0.005 | 0.643 | 0.014 |
| KLHL13 | cg00691822 | 0.485 | 0.010 | 0.429 | 0.025 | 0.374 | 0.018 | 0.338 | 0.015 |
| ANKRD43 | cg18840461 | 0.243 | 0.005 | 0.213 | 0.004 | 0.190 | 0.009 | 0.169 | 0.005 |
| DIRAS2 | cg03149130 | 0.280 | 0.006 | 0.243 | 0.015 | 0.219 | 0.007 | 0.196 | 0.008 |
| GRM8 | cg02946850 | 0.732 | 0.017 | 0.671 | 0.029 | 0.516 | 0.011 | 0.541 | 0.027 |
| ARHGAP27 | cg14154330 | 0.712 | 0.018 | 0.600 | 0.020 | 0.580 | 0.009 | 0.490 | 0.011 |
| NDUFS2 | cg17166812 | 0.709 | 0.009 | 0.587 | 0.023 | 0.606 | 0.026 | 0.477 | 0.013 |
| SLC39A7 | cg10940418 | 1.038 | 0.034 | 0.916 | 0.006 | 0.755 | 0.034 | 0.764 | 0.039 |
| FLJ12056 | cg18006568 | 0.655 | 0.004 | 0.639 | 0.012 | 0.472 | 0.023 | 0.451 | 0.041 |
| ESR2 | cg11059483 | 0.681 | 0.025 | 0.669 | 0.032 | 0.483 | 0.005 | 0.473 | 0.030 |
| GIMAP2 | cg25918245 | 0.609 | 0.025 | 0.579 | 0.023 | 0.453 | 0.002 | 0.414 | 0.023 |
| PER3 | cg06487986 | 0.215 | 0.008 | 0.195 | 0.011 | 0.165 | 0.010 | 0.147 | 0.003 |
| SUOX | cg06495347 | 0.734 | 0.009 | 0.696 | 0.036 | 0.536 | 0.005 | 0.508 | 0.010 |
| CHRNA10 | cg07484827 | 0.834 | 0.043 | 0.733 | 0.016 | 0.733 | 0.006 | 0.522 | 0.014 |
| ST3GAL5 | cg18763191 | 0.279 | 0.006 | 0.246 | 0.002 | 0.226 | 0.012 | 0.186 | 0.014 |
| IMP4 | cg26385743 | 0.883 | 0.019 | 0.856 | 0.016 | 0.674 | 0.024 | 0.577 | 0.016 |
| ASS | cg22791453 | 0.605 | 0.012 | 0.496 | 0.006 | 0.563 | 0.011 | 0.383 | 0.018 |
| KCND1 | cg06526829 | 0.663 | 0.035 | 0.648 | 0.055 | 0.509 | 0.010 | 0.428 | 0.014 |
| SLC5A6 | cg01620785 | 0.769 | 0.018 | 0.705 | 0.028 | 0.582 | 0.004 | 0.526 | 0.034 |
| C9orf78 | cg17509612 | 0.933 | 0.022 | 0.800 | 0.018 | 0.715 | 0.015 | 0.664 | 0.018 |
| HAND2 | cg02774439 | 0.255 | 0.013 | 0.216 | 0.012 | 0.200 | 0.005 | 0.179 | 0.004 |
| NOVA2 | cg21451553 | 0.858 | 0.017 | 0.734 | 0.024 | 0.654 | 0.024 | 0.617 | 0.008 |
| KCTD18 | cg22444610 | 1.044 | 0.018 | 1.000 | 0.007 | 0.762 | 0.035 | 0.715 | 0.033 |
| DISP2 | cg06595693 | 0.408 | 0.020 | 0.344 | 0.008 | 0.320 | 0.013 | 0.288 | 0.015 |
| GIMAP5 | cg13043509 | 0.923 | 0.011 | 0.909 | 0.009 | 0.665 | 0.019 | 0.626 | 0.005 |
| GPR153 | cg04055049 | 0.904 | 0.016 | 0.795 | 0.038 | 0.679 | 0.013 | 0.642 | 0.011 |
| KCNK6 | cg24968336 | 0.277 | 0.007 | 0.252 | 0.013 | 0.198 | 0.003 | 0.200 | 0.002 |
| SLC27A3 | cg21279955 | 0.344 | 0.008 | 0.289 | 0.024 | 0.288 | 0.004 | 0.230 | 0.011 |
| BARHL2 | cg06384463 | 0.830 | 0.029 | 0.812 | 0.064 | 0.579 | 0.018 | 0.582 | 0.030 |
| CTSO | cg16181202 | 0.573 | 0.006 | 0.560 | 0.024 | 0.406 | 0.012 | 0.396 | 0.015 |
| SPRR2A | cg26059632 | 0.774 | 0.033 | 0.767 | 0.052 | 0.543 | 0.022 | 0.535 | 0.009 |
| PTP4A2 | cg10184881 | 0.391 | 0.009 | 0.317 | 0.012 | 0.343 | 0.008 | 0.259 | 0.009 |
| APBA2BP | cg15056412 | 0.244 | 0.014 | 0.196 | 0.012 | 0.217 | 0.005 | 0.161 | 0.005 |

TABLE 15-continued

| Gene | Gene ID | sh-ctrl Mean | sh-ctrl SEM | sh-ctrl + 5aza Mean | sh-ctrl + 5aza SEM | sh-3B Mean | sh-3B SEM | sh-3b + 5aza Mean | sh-3b + 5aza SEM |
|---|---|---|---|---|---|---|---|---|---|
| NEIL1 | cg12600197 | 0.505 | 0.015 | 0.460 | 0.027 | 0.398 | 0.025 | 0.332 | 0.006 |
| ARMCX1 | cg23116589 | 0.638 | 0.003 | 0.628 | 0.016 | 0.429 | 0.011 | 0.463 | 0.016 |
| CHGA | cg16290737 | 0.988 | 0.023 | 0.910 | 0.035 | 0.723 | 0.025 | 0.691 | 0.036 |
| SDSL | cg05149586 | 0.993 | 0.017 | 0.810 | 0.021 | 0.858 | 0.022 | 0.663 | 0.010 |
| TSPAN33 | cg11303670 | 0.766 | 0.012 | 0.708 | 0.009 | 0.578 | 0.000 | 0.519 | 0.018 |
| COL14A1 | cg16907566 | 0.702 | 0.012 | 0.666 | 0.006 | 0.514 | 0.015 | 0.479 | 0.021 |
| MCF2 | cg06959635 | 0.679 | 0.009 | 0.620 | 0.008 | 0.516 | 0.009 | 0.460 | 0.008 |
| MAFB | cg02497758 | 0.690 | 0.010 | 0.632 | 0.006 | 0.514 | 0.014 | 0.475 | 0.022 |
| ALOX15 | cg15843823 | 0.739 | 0.001 | 0.685 | 0.015 | 0.549 | 0.011 | 0.505 | 0.005 |
| PSD | cg13548361 | 0.612 | 0.015 | 0.552 | 0.019 | 0.485 | 0.014 | 0.403 | 0.012 |
| C19orf30 | cg19646028 | 0.924 | 0.022 | 0.891 | 0.023 | 0.679 | 0.021 | 0.621 | 0.014 |
| CGB2 | cg11177404 | 1.035 | 0.004 | 0.996 | 0.010 | 0.755 | 0.018 | 0.701 | 0.016 |
| C7orf29 | cg04999691 | 0.929 | 0.026 | 0.815 | 0.040 | 0.774 | 0.012 | 0.600 | 0.009 |
| UXT | cg19206010 | 0.453 | 0.012 | 0.424 | 0.021 | 0.321 | 0.011 | 0.320 | 0.011 |
| TLE2 | cg22271212 | 0.386 | 0.006 | 0.300 | 0.010 | 0.313 | 0.009 | 0.281 | 0.005 |
| ALKBH | cg20385229 | 0.588 | 0.008 | 0.552 | 0.031 | 0.435 | 0.014 | 0.399 | 0.031 |
| TAF10 | cg27560292 | 0.771 | 0.013 | 0.586 | 0.026 | 0.678 | 0.027 | 0.537 | 0.006 |
| OR12D2 | cg21414251 | 0.822 | 0.007 | 0.774 | 0.038 | 0.591 | 0.010 | 0.571 | 0.019 |
| SPIN1 | cg02491012 | 0.257 | 0.010 | 0.208 | 0.013 | 0.211 | 0.002 | 0.178 | 0.005 |
| SUV420H2 | cg14112945 | 0.433 | 0.021 | 0.371 | 0.005 | 0.319 | 0.007 | 0.315 | 0.004 |
| DLX4 | cg03072378 | 0.506 | 0.010 | 0.429 | 0.017 | 0.425 | 0.006 | 0.333 | 0.022 |
| MRPS35 | cg07289581 | 0.232 | 0.010 | 0.190 | 0.001 | 0.175 | 0.002 | 0.171 | 0.009 |
| TTC8 | cg11821536 | 0.141 | 0.007 | 0.109 | 0.003 | 0.114 | 0.002 | 0.104 | 0.002 |
| FOXA3 | cg24278423 | 0.567 | 0.025 | 0.459 | 0.013 | 0.453 | 0.013 | 0.403 | 0.026 |
| CDC42EP5 | cg09227563 | 0.867 | 0.007 | 0.788 | 0.015 | 0.643 | 0.008 | 0.599 | 0.020 |
| CSNK1E | cg01441777 | 0.878 | 0.012 | 0.737 | 0.031 | 0.725 | 0.029 | 0.588 | 0.017 |
| EPIM | cg08169325 | 0.425 | 0.008 | 0.357 | 0.013 | 0.334 | 0.006 | 0.298 | 0.016 |
| TMEM38A | cg16345226 | 0.313 | 0.013 | 0.288 | 0.013 | 0.227 | 0.008 | 0.219 | 0.002 |
| LRRC33 | cg00293409 | 0.388 | 0.019 | 0.323 | 0.015 | 0.305 | 0.010 | 0.273 | 0.008 |
| SERPINB7 | cg17251713 | 0.592 | 0.012 | 0.582 | 0.015 | 0.414 | 0.033 | 0.408 | 0.026 |
| PPM1F | cg09350141 | 0.583 | 0.012 | 0.481 | 0.016 | 0.490 | 0.022 | 0.389 | 0.009 |
| TNFRSF25 | cg02084087 | 0.761 | 0.004 | 0.721 | 0.014 | 0.601 | 0.004 | 0.484 | 0.029 |
| LOC339524 | cg14540297 | 0.498 | 0.007 | 0.465 | 0.039 | 0.374 | 0.009 | 0.332 | 0.006 |
| CLDN19 | cg11075745 | 0.338 | 0.008 | 0.323 | 0.022 | 0.261 | 0.017 | 0.217 | 0.005 |
| PARP4 | cg02943497 | 0.341 | 0.010 | 0.308 | 0.002 | 0.252 | 0.012 | 0.237 | 0.006 |
| SCRN2 | cg11646887 | 0.399 | 0.016 | 0.368 | 0.020 | 0.326 | 0.014 | 0.252 | 0.011 |
| RP11-49G10.8 | cg01775265 | 0.963 | 0.017 | 0.916 | 0.023 | 0.705 | 0.041 | 0.650 | 0.026 |
| FLJ43505 | cg18665384 | 0.660 | 0.007 | 0.623 | 0.017 | 0.511 | 0.005 | 0.427 | 0.017 |
| CHD8 | cg00657582 | 0.700 | 0.024 | 0.574 | 0.015 | 0.624 | 0.017 | 0.450 | 0.019 |
| CLCN4 | cg10246296 | 0.339 | 0.009 | 0.324 | 0.010 | 0.251 | 0.011 | 0.226 | 0.015 |
| TMEM106B | cg21597649 | 0.369 | 0.010 | 0.307 | 0.012 | 0.282 | 0.011 | 0.265 | 0.009 |
| CCDC42 | cg22197033 | 0.966 | 0.032 | 0.929 | 0.010 | 0.713 | 0.018 | 0.641 | 0.046 |
| C20orf35 | cg09882647 | 0.945 | 0.011 | 0.843 | 0.052 | 0.694 | 0.028 | 0.666 | 0.010 |
| TSR1 | cg21870662 | 0.418 | 0.020 | 0.284 | 0.027 | 0.413 | 0.017 | 0.295 | 0.019 |
| SOSTDC1 | cg25533774 | 0.574 | 0.009 | 0.527 | 0.020 | 0.436 | 0.014 | 0.384 | 0.020 |
| SFRP1 | cg02388150 | 0.370 | 0.017 | 0.357 | 0.017 | 0.280 | 0.014 | 0.239 | 0.019 |
| FREQ | cg05251000 | 0.753 | 0.006 | 0.650 | 0.006 | 0.615 | 0.017 | 0.495 | 0.025 |
| USP39 | cg19376794 | 0.266 | 0.006 | 0.230 | 0.015 | 0.203 | 0.009 | 0.184 | 0.004 |
| PTGER2 | cg06738602 | 0.656 | 0.013 | 0.597 | 0.028 | 0.477 | 0.004 | 0.458 | 0.011 |
| GAL3ST4 | cg17518962 | 0.744 | 0.030 | 0.720 | 0.044 | 0.565 | 0.006 | 0.478 | 0.016 |
| LRFN3 | cg15060813 | 0.817 | 0.018 | 0.694 | 0.014 | 0.655 | 0.004 | 0.552 | 0.013 |
| SST | cg02164046 | 0.996 | 0.003 | 0.982 | 0.016 | 0.706 | 0.009 | 0.672 | 0.013 |
| IL17E | cg07258507 | 0.964 | 0.016 | 0.895 | 0.011 | 0.709 | 0.011 | 0.656 | 0.021 |
| PIGQ | cg24014020 | 0.522 | 0.012 | 0.430 | 0.009 | 0.431 | 0.005 | 0.352 | 0.004 |
| PPP1R13L | cg03554552 | 0.180 | 0.007 | 0.154 | 0.009 | 0.139 | 0.005 | 0.125 | 0.006 |
| TTPA | cg14817143 | 0.375 | 0.006 | 0.349 | 0.014 | 0.275 | 0.014 | 0.254 | 0.009 |
| GATA4 | cg21073927 | 0.205 | 0.005 | 0.173 | 0.010 | 0.181 | 0.009 | 0.129 | 0.010 |
| CHST4 | cg05535113 | 0.628 | 0.014 | 0.621 | 0.028 | 0.468 | 0.026 | 0.402 | 0.033 |
| CHRDL2 | cg22994720 | 0.503 | 0.013 | 0.450 | 0.016 | 0.368 | 0.007 | 0.351 | 0.023 |
| BIRC4BP | cg27146152 | 0.869 | 0.018 | 0.752 | 0.006 | 0.695 | 0.020 | 0.575 | 0.004 |
| CHAF1B | cg26024531 | 0.474 | 0.014 | 0.407 | 0.022 | 0.402 | 0.008 | 0.302 | 0.024 |
| VHL | cg22782492 | 0.301 | 0.014 | 0.248 | 0.010 | 0.256 | 0.009 | 0.197 | 0.009 |
| HOM-TES-103 | cg01493517 | 0.808 | 0.008 | 0.702 | 0.010 | 0.653 | 0.006 | 0.530 | 0.008 |
| SMPD3 | cg22116290 | 0.793 | 0.025 | 0.766 | 0.030 | 0.596 | 0.017 | 0.512 | 0.014 |
| ABCG4 | cg03222066 | 0.600 | 0.013 | 0.529 | 0.009 | 0.456 | 0.004 | 0.411 | 0.010 |
| KCNG4 | cg11913615 | 0.745 | 0.026 | 0.687 | 0.034 | 0.571 | 0.023 | 0.488 | 0.021 |
| SYNPO2 | cg00415978 | 0.449 | 0.007 | 0.396 | 0.025 | 0.330 | 0.008 | 0.316 | 0.011 |
| DACH2 | cg01718602 | 0.566 | 0.006 | 0.491 | 0.007 | 0.411 | 0.011 | 0.408 | 0.017 |
| SOD2 | cg14515483 | 0.169 | 0.002 | 0.136 | 0.005 | 0.128 | 0.006 | 0.124 | 0.002 |
| GPR87 | cg09432154 | 0.857 | 0.023 | 0.631 | 0.034 | 0.736 | 0.028 | 0.615 | 0.031 |
| KCNIP2 | cg25123470 | 0.485 | 0.012 | 0.419 | 0.010 | 0.372 | 0.015 | 0.333 | 0.005 |
| ASTN | cg23492043 | 0.743 | 0.028 | 0.633 | 0.015 | 0.543 | 0.003 | 0.540 | 0.009 |
| RAB27A | cg10936230 | 0.607 | 0.018 | 0.530 | 0.013 | 0.481 | 0.008 | 0.402 | 0.010 |
| IL1RAPL1 | cg26810336 | 0.737 | 0.003 | 0.710 | 0.028 | 0.552 | 0.002 | 0.477 | 0.001 |

TABLE 15-continued

| Gene | Gene ID | sh-ctrl Mean | sh-ctrl SEM | sh-ctrl + 5aza Mean | sh-ctrl + 5aza SEM | sh-3B Mean | sh-3B SEM | sh-3b + 5aza Mean | sh-3b + 5aza SEM |
|---|---|---|---|---|---|---|---|---|---|
| ST6GAL1 | cg15928398 | 0.743 | 0.014 | 0.714 | 0.012 | 0.548 | 0.014 | 0.488 | 0.007 |
| ARPC3 | cg20597908 | 0.254 | 0.012 | 0.236 | 0.004 | 0.201 | 0.008 | 0.161 | 0.006 |
| KCNA6 | cg26162582 | 0.264 | 0.005 | 0.231 | 0.013 | 0.194 | 0.002 | 0.186 | 0.005 |
| HSD3B7 | cg10917602 | 0.579 | 0.007 | 0.550 | 0.006 | 0.455 | 0.010 | 0.364 | 0.003 |
| NECAP2 | cg16011258 | 0.265 | 0.011 | 0.250 | 0.015 | 0.192 | 0.009 | 0.179 | 0.010 |
| CTNNBL1 | cg17974185 | 1.070 | 0.004 | 0.988 | 0.003 | 0.800 | 0.013 | 0.713 | 0.011 |
| MMP11 | cg27532722 | 0.796 | 0.003 | 0.711 | 0.011 | 0.596 | 0.009 | 0.542 | 0.007 |
| C1orf71 | cg14460735 | 0.840 | 0.015 | 0.761 | 0.031 | 0.625 | 0.011 | 0.569 | 0.010 |
| TRAM1 | cg25974617 | 0.381 | 0.025 | 0.329 | 0.005 | 0.269 | 0.003 | 0.283 | 0.011 |
| SHMT1 | cg16094520 | 0.304 | 0.014 | 0.267 | 0.016 | 0.223 | 0.003 | 0.214 | 0.002 |
| KCNK6 | cg08980578 | 0.432 | 0.012 | 0.376 | 0.016 | 0.326 | 0.005 | 0.299 | 0.003 |
| CTNNAL1 | cg05485060 | 0.977 | 0.017 | 0.873 | 0.068 | 0.748 | 0.012 | 0.653 | 0.017 |
| DDX23 | cg24791546 | 0.433 | 0.008 | 0.384 | 0.020 | 0.314 | 0.012 | 0.304 | 0.018 |
| MEIS3 | cg21145624 | 0.575 | 0.011 | 0.501 | 0.013 | 0.485 | 0.039 | 0.361 | 0.007 |
| LENG8 | cg18678421 | 0.422 | 0.022 | 0.407 | 0.004 | 0.304 | 0.013 | 0.281 | 0.008 |
| FOXJ1 | cg24164563 | 0.523 | 0.004 | 0.474 | 0.035 | 0.400 | 0.019 | 0.344 | 0.010 |
| EFHD1 | cg09536738 | 0.402 | 0.012 | 0.364 | 0.013 | 0.272 | 0.015 | 0.299 | 0.010 |
| B3GALT3 | cg12716838 | 0.817 | 0.002 | 0.779 | 0.008 | 0.583 | 0.027 | 0.553 | 0.039 |
| CLEC11A | cg13152535 | 0.686 | 0.017 | 0.598 | 0.027 | 0.513 | 0.013 | 0.475 | 0.013 |
|  | cg12687990 | 0.191 | 0.004 | 0.161 | 0.000 | 0.140 | 0.003 | 0.138 | 0.002 |
| TMEM41A | cg11285843 | 0.315 | 0.006 | 0.276 | 0.017 | 0.254 | 0.015 | 0.203 | 0.009 |
| CD44 | cg20143092 | 0.609 | 0.015 | 0.509 | 0.030 | 0.484 | 0.014 | 0.412 | 0.005 |
| SLC25A37 | cg14755852 | 0.797 | 0.036 | 0.620 | 0.022 | 0.682 | 0.026 | 0.540 | 0.003 |
| RIPK3 | cg10318258 | 0.797 | 0.002 | 0.766 | 0.040 | 0.579 | 0.023 | 0.527 | 0.019 |
| MGC42105 | cg23502772 | 0.664 | 0.002 | 0.604 | 0.025 | 0.495 | 0.007 | 0.445 | 0.017 |
| ZNF238 | cg23829949 | 0.941 | 0.010 | 0.854 | 0.001 | 0.726 | 0.036 | 0.615 | 0.019 |
| COMP | cg15784332 | 1.032 | 0.028 | 0.929 | 0.036 | 0.764 | 0.021 | 0.701 | 0.020 |
| CNAP1 | cg16399745 | 0.815 | 0.010 | 0.795 | 0.004 | 0.584 | 0.009 | 0.541 | 0.021 |
| MRPL28 | cg12437481 | 0.778 | 0.009 | 0.635 | 0.005 | 0.684 | 0.009 | 0.497 | 0.004 |
| KCTD18 | cg11388238 | 0.934 | 0.015 | 0.840 | 0.010 | 0.697 | 0.008 | 0.631 | 0.004 |
| ST6GALNAC2 | cg08666623 | 0.957 | 0.004 | 0.916 | 0.024 | 0.701 | 0.007 | 0.629 | 0.009 |
| SYNE1 | cg26620959 | 0.297 | 0.013 | 0.269 | 0.017 | 0.236 | 0.002 | 0.189 | 0.004 |
| MGC10433 | cg15357518 | 0.341 | 0.012 | 0.245 | 0.008 | 0.288 | 0.005 | 0.251 | 0.003 |
| DAB2IP | cg08128768 | 1.055 | 0.004 | 1.003 | 0.012 | 0.838 | 0.025 | 0.649 | 0.012 |
| BCMO1 | cg17465631 | 1.045 | 0.015 | 0.928 | 0.032 | 0.806 | 0.019 | 0.691 | 0.014 |
| REEP5 | cg19239342 | 0.553 | 0.013 | 0.489 | 0.018 | 0.409 | 0.004 | 0.380 | 0.017 |
|  | cg12537796 | 0.260 | 0.020 | 0.239 | 0.008 | 0.177 | 0.006 | 0.188 | 0.003 |
| MAPK11 | cg19184963 | 0.394 | 0.009 | 0.334 | 0.016 | 0.295 | 0.011 | 0.278 | 0.006 |
| GDF15 | cg16929104 | 1.006 | 0.015 | 0.973 | 0.013 | 0.791 | 0.014 | 0.616 | 0.022 |
| TP73 | cg25885108 | 0.290 | 0.010 | 0.277 | 0.021 | 0.227 | 0.002 | 0.179 | 0.011 |
| PUS7L | cg27465569 | 0.788 | 0.008 | 0.715 | 0.030 | 0.576 | 0.024 | 0.537 | 0.010 |
| GGTL3 | cg07148914 | 0.310 | 0.006 | 0.276 | 0.009 | 0.241 | 0.005 | 0.203 | 0.003 |
| NPY5R | cg18438777 | 0.359 | 0.007 | 0.327 | 0.003 | 0.268 | 0.009 | 0.239 | 0.007 |
| SFRP5 | cg25156443 | 0.929 | 0.012 | 0.842 | 0.015 | 0.696 | 0.016 | 0.617 | 0.021 |
| NCOA6 | cg06425556 | 0.714 | 0.014 | 0.653 | 0.027 | 0.550 | 0.002 | 0.461 | 0.013 |
| IVL | cg05440289 | 0.927 | 0.011 | 0.793 | 0.036 | 0.683 | 0.005 | 0.655 | 0.021 |
| MAB21L1 | cg12029639 | 0.500 | 0.003 | 0.446 | 0.025 | 0.344 | 0.017 | 0.364 | 0.013 |
| ALDH4A1 | cg18895413 | 0.230 | 0.004 | 0.180 | 0.005 | 0.182 | 0.004 | 0.164 | 0.004 |
| ALDH1A3 | cg27652350 | 0.337 | 0.007 | 0.321 | 0.019 | 0.245 | 0.016 | 0.222 | 0.003 |
| PGLYRP2 | cg07408456 | 1.022 | 0.021 | 0.960 | 0.027 | 0.742 | 0.009 | 0.680 | 0.007 |
| CACNA1C | cg25519930 | 0.326 | 0.006 | 0.253 | 0.006 | 0.278 | 0.010 | 0.219 | 0.006 |
| GSCL | cg15837252 | 1.035 | 0.009 | 0.911 | 0.012 | 0.789 | 0.010 | 0.690 | 0.029 |
| OSMR | cg03138091 | 0.393 | 0.002 | 0.331 | 0.020 | 0.279 | 0.016 | 0.290 | 0.015 |
| FLJ13614 | cg02782630 | 0.456 | 0.020 | 0.410 | 0.025 | 0.350 | 0.015 | 0.297 | 0.013 |
| UBE2E3 | cg00949554 | 0.405 | 0.022 | 0.353 | 0.014 | 0.292 | 0.005 | 0.285 | 0.008 |
| LOC56901 | cg23240961 | 0.394 | 0.004 | 0.273 | 0.014 | 0.323 | 0.011 | 0.306 | 0.023 |
| HDC | cg16831889 | 0.633 | 0.016 | 0.602 | 0.027 | 0.485 | 0.022 | 0.397 | 0.008 |
| MRPS33 | cg00338893 | 0.181 | 0.005 | 0.157 | 0.011 | 0.134 | 0.006 | 0.126 | 0.007 |
| MAPK6 | cg00410576 | 0.362 | 0.008 | 0.350 | 0.019 | 0.288 | 0.004 | 0.217 | 0.019 |
| HHAT | cg15945769 | 0.245 | 0.009 | 0.214 | 0.003 | 0.188 | 0.009 | 0.163 | 0.007 |
| CREB3 | cg00833393 | 0.532 | 0.017 | 0.465 | 0.013 | 0.413 | 0.017 | 0.350 | 0.003 |
| C7orf33 | cg25043279 | 0.945 | 0.017 | 0.884 | 0.049 | 0.660 | 0.019 | 0.650 | 0.020 |
| ELL2 | cg21091679 | 0.569 | 0.006 | 0.497 | 0.022 | 0.425 | 0.016 | 0.388 | 0.029 |
| UCK1 | cg12894126 | 0.595 | 0.004 | 0.458 | 0.008 | 0.453 | 0.017 | 0.441 | 0.012 |
| C17orf57 | cg17124509 | 0.482 | 0.023 | 0.448 | 0.027 | 0.355 | 0.017 | 0.315 | 0.017 |
| GRB10 | cg15774495 | 0.344 | 0.011 | 0.262 | 0.017 | 0.295 | 0.012 | 0.232 | 0.015 |
| CHFR | cg20066677 | 0.871 | 0.024 | 0.777 | 0.005 | 0.682 | 0.007 | 0.557 | 0.010 |
| HCN1 | cg06498267 | 0.917 | 0.018 | 0.824 | 0.015 | 0.661 | 0.007 | 0.627 | 0.023 |
| GPRASP1 | cg23571457 | 0.396 | 0.002 | 0.356 | 0.009 | 0.306 | 0.014 | 0.254 | 0.013 |
| ZCCHC14 | cg06330621 | 0.572 | 0.011 | 0.505 | 0.015 | 0.451 | 0.032 | 0.366 | 0.019 |
| MDM1 | cg23926526 | 0.340 | 0.011 | 0.269 | 0.004 | 0.289 | 0.015 | 0.224 | 0.009 |
| TSPAN1 | cg04975920 | 0.665 | 0.015 | 0.587 | 0.026 | 0.505 | 0.028 | 0.439 | 0.010 |
| PRR3 | cg21264055 | 0.268 | 0.012 | 0.207 | 0.006 | 0.204 | 0.014 | 0.197 | 0.001 |
| TRPV4 | cg13628514 | 0.636 | 0.015 | 0.605 | 0.011 | 0.471 | 0.012 | 0.406 | 0.008 |
| OSTM1 | cg04650786 | 0.465 | 0.010 | 0.382 | 0.021 | 0.378 | 0.014 | 0.305 | 0.015 |

TABLE 15-continued

| Gene | Gene ID | sh-ctrl Mean | sh-ctrl SEM | sh-ctrl + 5aza Mean | sh-ctrl + 5aza SEM | sh-3B Mean | sh-3B SEM | sh-3b + 5aza Mean | sh-3b + 5aza SEM |
|---|---|---|---|---|---|---|---|---|---|
| INPP5F | cg27613076 | 0.641 | 0.035 | 0.610 | 0.025 | 0.518 | 0.011 | 0.382 | 0.004 |
| MAGEL2 | cg04014889 | 0.921 | 0.007 | 0.908 | 0.024 | 0.653 | 0.012 | 0.598 | 0.023 |
| C10orf26 | cg15227982 | 0.738 | 0.026 | 0.614 | 0.004 | 0.607 | 0.018 | 0.475 | 0.019 |
| RIMS3 | cg00594952 | 0.813 | 0.019 | 0.761 | 0.041 | 0.606 | 0.006 | 0.522 | 0.014 |
| GCAT | cg11368946 | 0.391 | 0.003 | 0.328 | 0.011 | 0.305 | 0.014 | 0.262 | 0.005 |
| CAPS2 | cg15942481 | 0.352 | 0.007 | 0.327 | 0.009 | 0.250 | 0.003 | 0.236 | 0.011 |
| ACTR3B | cg10896886 | 0.318 | 0.015 | 0.262 | 0.006 | 0.240 | 0.011 | 0.223 | 0.015 |
| UBE2F | cg16354207 | 0.759 | 0.017 | 0.691 | 0.027 | 0.580 | 0.028 | 0.486 | 0.050 |
| ZNF619 | cg21942438 | 0.715 | 0.015 | 0.612 | 0.021 | 0.533 | 0.027 | 0.490 | 0.017 |
| TOMM20 | cg05144089 | 0.268 | 0.010 | 0.224 | 0.004 | 0.197 | 0.014 | 0.190 | 0.007 |
| DRD3 | cg25836326 | 0.581 | 0.017 | 0.556 | 0.023 | 0.420 | 0.020 | 0.376 | 0.013 |
| WRN | cg09945801 | 0.307 | 0.006 | 0.270 | 0.013 | 0.226 | 0.011 | 0.208 | 0.011 |
| AGTRL1 | cg25072179 | 0.514 | 0.011 | 0.456 | 0.009 | 0.399 | 0.008 | 0.330 | 0.007 |
| MCOLN3 | cg10515956 | 0.273 | 0.011 | 0.232 | 0.003 | 0.196 | 0.007 | 0.195 | 0.007 |
| ALX4 | cg08914623 | 0.678 | 0.007 | 0.650 | 0.019 | 0.516 | 0.032 | 0.420 | 0.037 |
| RNPEPL1 | cg00497251 | 0.944 | 0.005 | 0.801 | 0.011 | 0.724 | 0.033 | 0.632 | 0.021 |
| FGF5 | cg18638496 | 0.365 | 0.012 | 0.293 | 0.015 | 0.289 | 0.006 | 0.250 | 0.009 |
| TRIM9 | cg17347389 | 0.426 | 0.019 | 0.381 | 0.008 | 0.311 | 0.022 | 0.287 | 0.018 |
| SMPDL3B | cg22421699 | 0.487 | 0.019 | 0.448 | 0.007 | 0.349 | 0.011 | 0.326 | 0.003 |
| UNG2 | cg13352495 | 0.292 | 0.004 | 0.236 | 0.011 | 0.226 | 0.003 | 0.202 | 0.006 |
| PREI3 | cg04056179 | 0.406 | 0.018 | 0.394 | 0.018 | 0.275 | 0.009 | 0.275 | 0.021 |
| STYK1 | cg24401912 | 0.370 | 0.005 | 0.305 | 0.008 | 0.275 | 0.013 | 0.259 | 0.008 |
| PPT1 | cg17130791 | 0.229 | 0.003 | 0.191 | 0.009 | 0.182 | 0.013 | 0.150 | 0.006 |
| ARMCX1 | cg18731813 | 0.700 | 0.008 | 0.634 | 0.014 | 0.478 | 0.014 | 0.496 | 0.003 |
| EPHA3 | cg18055394 | 0.955 | 0.027 | 0.944 | 0.019 | 0.631 | 0.022 | 0.656 | 0.016 |
| SDC4 | cg10876928 | 0.836 | 0.028 | 0.636 | 0.033 | 0.698 | 0.010 | 0.570 | 0.023 |
| HIC1 | cg17210604 | 0.590 | 0.036 | 0.577 | 0.034 | 0.451 | 0.028 | 0.356 | 0.016 |
| PSEN2 | cg25514304 | 0.511 | 0.030 | 0.380 | 0.009 | 0.419 | 0.005 | 0.360 | 0.018 |
| FZD9 | cg20692569 | 0.930 | 0.004 | 0.905 | 0.020 | 0.658 | 0.009 | 0.603 | 0.004 |
| C1QTNF1 | cg24844534 | 0.313 | 0.008 | 0.238 | 0.013 | 0.268 | 0.013 | 0.209 | 0.012 |
| KLHL25 | cg00256166 | 0.346 | 0.006 | 0.303 | 0.012 | 0.261 | 0.006 | 0.229 | 0.012 |
| GRPR | cg13401681 | 0.607 | 0.015 | 0.554 | 0.012 | 0.461 | 0.006 | 0.384 | 0.013 |
| IVL | cg25082710 | 0.762 | 0.017 | 0.701 | 0.025 | 0.555 | 0.005 | 0.498 | 0.001 |
| ZNF256 | cg02959669 | 0.295 | 0.007 | 0.273 | 0.014 | 0.220 | 0.013 | 0.188 | 0.003 |
| PIGC | cg11584111 | 0.360 | 0.021 | 0.315 | 0.009 | 0.253 | 0.011 | 0.253 | 0.007 |
| CNNM2 | cg15439196 | 0.843 | 0.009 | 0.789 | 0.014 | 0.591 | 0.009 | 0.563 | 0.011 |
| RAB25 | cg09243900 | 0.889 | 0.009 | 0.796 | 0.021 | 0.670 | 0.032 | 0.573 | 0.011 |
| ZFR | cg13954292 | 0.750 | 0.001 | 0.621 | 0.032 | 0.607 | 0.019 | 0.484 | 0.038 |
| HOXB6 | cg16848873 | 0.717 | 0.012 | 0.686 | 0.039 | 0.506 | 0.003 | 0.469 | 0.016 |
| TMC6 | cg04947157 | 1.021 | 0.021 | 0.972 | 0.018 | 0.780 | 0.014 | 0.625 | 0.019 |
| EDG1 | cg19038540 | 0.375 | 0.006 | 0.304 | 0.023 | 0.310 | 0.005 | 0.242 | 0.011 |
| SNAPC2 | cg24132694 | 0.611 | 0.008 | 0.541 | 0.011 | 0.467 | 0.008 | 0.392 | 0.011 |
| SOCS2 | cg06630241 | 0.686 | 0.004 | 0.601 | 0.011 | 0.491 | 0.008 | 0.469 | 0.012 |
| SLC17A8 | cg06563300 | 0.495 | 0.021 | 0.466 | 0.025 | 0.342 | 0.016 | 0.332 | 0.021 |
| SPTB | cg13593287 | 0.506 | 0.007 | 0.393 | 0.018 | 0.440 | 0.029 | 0.324 | 0.012 |
| GTF2H4 | cg23142900 | 0.159 | 0.008 | 0.138 | 0.004 | 0.112 | 0.005 | 0.112 | 0.005 |
| DIO3 | cg04623955 | 0.532 | 0.013 | 0.449 | 0.033 | 0.435 | 0.018 | 0.334 | 0.018 |
| ATP6V1B2 | cg01952458 | 0.227 | 0.010 | 0.184 | 0.002 | 0.156 | 0.006 | 0.173 | 0.008 |
| SLC39A2 | cg05245515 | 1.091 | 0.019 | 0.845 | 0.021 | 0.881 | 0.018 | 0.740 | 0.014 |
| S100A7 | cg19836808 | 0.583 | 0.019 | 0.547 | 0.036 | 0.408 | 0.011 | 0.386 | 0.016 |
| STK32B | cg10182321 | 0.257 | 0.006 | 0.190 | 0.005 | 0.196 | 0.011 | 0.192 | 0.008 |
| EGR2 | cg19355190 | 0.782 | 0.019 | 0.724 | 0.037 | 0.546 | 0.012 | 0.522 | 0.011 |
| ALDH9A1 | cg11373746 | 0.541 | 0.014 | 0.530 | 0.016 | 0.377 | 0.017 | 0.348 | 0.014 |
| LCE2C | cg03960217 | 0.604 | 0.010 | 0.538 | 0.011 | 0.442 | 0.009 | 0.397 | 0.016 |
| FZD4 | cg18411891 | 0.209 | 0.007 | 0.197 | 0.010 | 0.151 | 0.008 | 0.133 | 0.002 |
| RSAD2 | cg18201077 | 0.887 | 0.033 | 0.851 | 0.012 | 0.609 | 0.013 | 0.586 | 0.014 |
| SLC14A1 | cg17589341 | 0.779 | 0.018 | 0.709 | 0.029 | 0.581 | 0.015 | 0.495 | 0.035 |
| LHX5 | cg23922454 | 0.298 | 0.001 | 0.255 | 0.015 | 0.226 | 0.005 | 0.195 | 0.009 |
| DTL | cg03938043 | 0.623 | 0.037 | 0.616 | 0.019 | 0.423 | 0.018 | 0.407 | 0.017 |
| LOX | cg01824804 | 0.371 | 0.011 | 0.351 | 0.030 | 0.254 | 0.004 | 0.249 | 0.005 |
| MANEAL | cg18105315 | 0.591 | 0.015 | 0.550 | 0.024 | 0.441 | 0.007 | 0.369 | 0.026 |
| ACSBG2 | cg08256781 | 0.788 | 0.020 | 0.759 | 0.011 | 0.576 | 0.011 | 0.490 | 0.017 |
| MRPL41 | cg15473904 | 0.643 | 0.011 | 0.620 | 0.046 | 0.479 | 0.020 | 0.393 | 0.014 |
| MXRA7 | cg19935424 | 0.358 | 0.006 | 0.313 | 0.014 | 0.274 | 0.007 | 0.230 | 0.010 |
| KCNK3 | cg01643580 | 0.659 | 0.006 | 0.592 | 0.016 | 0.514 | 0.011 | 0.406 | 0.026 |
| MAB21L2 | cg26218269 | 0.748 | 0.022 | 0.716 | 0.033 | 0.504 | 0.011 | 0.503 | 0.030 |
| CDH9 | cg19475870 | 0.717 | 0.022 | 0.667 | 0.026 | 0.489 | 0.018 | 0.486 | 0.017 |
| WNK2 | cg20616414 | 0.295 | 0.006 | 0.222 | 0.008 | 0.220 | 0.003 | 0.219 | 0.014 |
| CHDH | cg12991365 | 0.495 | 0.021 | 0.412 | 0.009 | 0.374 | 0.011 | 0.332 | 0.009 |
| ZNF324 | cg27401095 | 0.875 | 0.010 | 0.751 | 0.030 | 0.665 | 0.038 | 0.569 | 0.024 |
| C11orf16 | cg09674867 | 0.864 | 0.002 | 0.687 | 0.023 | 0.698 | 0.016 | 0.568 | 0.031 |
| PRKCABP | cg23621115 | 0.545 | 0.004 | 0.480 | 0.014 | 0.407 | 0.007 | 0.353 | 0.007 |
| ARSF | cg05699806 | 0.984 | 0.021 | 0.846 | 0.042 | 0.778 | 0.011 | 0.618 | 0.012 |
| NMB | cg27379587 | 0.717 | 0.014 | 0.638 | 0.021 | 0.521 | 0.011 | 0.472 | 0.019 |
| GLTP | cg06236061 | 0.664 | 0.011 | 0.591 | 0.051 | 0.523 | 0.018 | 0.408 | 0.005 |

TABLE 15-continued

| Gene | Gene ID | sh-ctrl Mean | sh-ctrl SEM | sh-ctrl + 5aza Mean | sh-ctrl + 5aza SEM | sh-3B Mean | sh-3B SEM | sh-3b + 5aza Mean | sh-3b + 5aza SEM |
|---|---|---|---|---|---|---|---|---|---|
| CRAMP1L | cg06810647 | 0.881 | 0.003 | 0.799 | 0.010 | 0.646 | 0.018 | 0.566 | 0.014 |
| CSAD | cg03933322 | 0.703 | 0.025 | 0.628 | 0.025 | 0.644 | 0.021 | 0.388 | 0.064 |
| C18orf8 | cg12709412 | 0.295 | 0.008 | 0.266 | 0.013 | 0.216 | 0.000 | 0.191 | 0.008 |
| F2RL2 | cg00415993 | 1.117 | 0.019 | 0.863 | 0.056 | 0.907 | 0.020 | 0.747 | 0.036 |
| DEFB123 | cg26063872 | 1.129 | 0.012 | 1.086 | 0.019 | 0.775 | 0.011 | 0.740 | 0.011 |
| C12orf38 | cg17451138 | 0.212 | 0.011 | 0.198 | 0.012 | 0.146 | 0.006 | 0.141 | 0.005 |
| LOC51136 | cg25905459 | 0.346 | 0.008 | 0.313 | 0.016 | 0.244 | 0.010 | 0.231 | 0.015 |
| FZD10 | cg23054883 | 1.041 | 0.008 | 1.034 | 0.015 | 0.717 | 0.021 | 0.665 | 0.017 |
| TAC1 | cg14221171 | 0.698 | 0.020 | 0.677 | 0.008 | 0.500 | 0.026 | 0.437 | 0.027 |
| PDGFRA | cg13002939 | 0.216 | 0.008 | 0.173 | 0.003 | 0.168 | 0.007 | 0.146 | 0.013 |
| MAN2C1 | cg04008455 | 0.766 | 0.013 | 0.595 | 0.018 | 0.653 | 0.009 | 0.489 | 0.015 |
| PPT1 | cg20900524 | 0.353 | 0.003 | 0.296 | 0.018 | 0.270 | 0.003 | 0.232 | 0.003 |
| MRPS24 | cg21048501 | 0.628 | 0.029 | 0.532 | 0.013 | 0.486 | 0.027 | 0.403 | 0.018 |
| CD244 | cg10106388 | 0.517 | 0.019 | 0.457 | 0.006 | 0.409 | 0.005 | 0.316 | 0.005 |
| GSTM2 | cg03070194 | 0.217 | 0.013 | 0.171 | 0.005 | 0.158 | 0.006 | 0.156 | 0.003 |
| FLJ44881 | cg21306775 | 0.968 | 0.009 | 0.864 | 0.013 | 0.687 | 0.005 | 0.645 | 0.027 |
| FXYD3 | cg00480115 | 0.824 | 0.024 | 0.757 | 0.034 | 0.560 | 0.021 | 0.559 | 0.002 |
| BTK | cg03791917 | 0.990 | 0.008 | 0.844 | 0.025 | 0.749 | 0.003 | 0.643 | 0.010 |
| LIX1 | cg06213287 | 0.606 | 0.014 | 0.528 | 0.020 | 0.427 | 0.044 | 0.411 | 0.019 |
| DEFB125 | cg01958189 | 0.696 | 0.006 | 0.664 | 0.022 | 0.476 | 0.027 | 0.456 | 0.011 |
| MAB21L2 | cg20334738 | 0.744 | 0.005 | 0.711 | 0.028 | 0.551 | 0.007 | 0.453 | 0.010 |
| NTE | cg25025866 | 0.417 | 0.007 | 0.402 | 0.013 | 0.299 | 0.012 | 0.259 | 0.026 |
| THSD3 | cg06469542 | 1.094 | 0.006 | 1.052 | 0.004 | 0.799 | 0.012 | 0.670 | 0.019 |
| DNAJC6 | cg26304237 | 0.378 | 0.019 | 0.351 | 0.010 | 0.290 | 0.010 | 0.228 | 0.005 |
| HPCAL4 | cg22827640 | 0.133 | 0.008 | 0.099 | 0.001 | 0.105 | 0.004 | 0.092 | 0.002 |
| HERC4 | cg03652343 | 0.279 | 0.011 | 0.235 | 0.002 | 0.207 | 0.006 | 0.185 | 0.003 |
| CTAGE1 | cg10421192 | 0.993 | 0.013 | 0.982 | 0.013 | 0.656 | 0.029 | 0.655 | 0.017 |
| SPRR3 | cg25856811 | 0.917 | 0.010 | 0.844 | 0.032 | 0.633 | 0.022 | 0.610 | 0.023 |
| SMARCD1 | cg07210490 | 0.349 | 0.008 | 0.273 | 0.020 | 0.290 | 0.013 | 0.223 | 0.005 |
| STMN4 | cg25762706 | 0.989 | 0.006 | 0.919 | 0.024 | 0.708 | 0.017 | 0.630 | 0.010 |
| HES4 | cg08122545 | 0.973 | 0.016 | 0.906 | 0.015 | 0.684 | 0.020 | 0.628 | 0.014 |
| DPP4 | cg12335708 | 0.329 | 0.007 | 0.319 | 0.020 | 0.213 | 0.013 | 0.224 | 0.009 |
| ITGAX | cg11884546 | 0.942 | 0.017 | 0.828 | 0.013 | 0.734 | 0.014 | 0.580 | 0.011 |
| IZUMO1 | cg08536841 | 0.459 | 0.012 | 0.437 | 0.021 | 0.309 | 0.007 | 0.304 | 0.016 |
| MAPK8IP2 | cg02756845 | 0.444 | 0.008 | 0.441 | 0.015 | 0.321 | 0.018 | 0.268 | 0.005 |
| FAM63A | cg06433658 | 0.748 | 0.008 | 0.666 | 0.017 | 0.550 | 0.023 | 0.478 | 0.011 |
| COPG2 | cg26702875 | 0.307 | 0.013 | 0.237 | 0.013 | 0.231 | 0.013 | 0.215 | 0.003 |
| UNC13D | cg22467534 | 0.896 | 0.021 | 0.766 | 0.027 | 0.675 | 0.017 | 0.575 | 0.022 |
| NMD3 | cg09171381 | 0.287 | 0.014 | 0.249 | 0.015 | 0.216 | 0.012 | 0.183 | 0.008 |
| COPB | cg23984059 | 0.285 | 0.011 | 0.274 | 0.018 | 0.199 | 0.013 | 0.180 | 0.005 |
| PSARL | cg24355091 | 0.417 | 0.021 | 0.326 | 0.022 | 0.361 | 0.007 | 0.259 | 0.000 |
| DNAJC6 | cg09082287 | 0.457 | 0.004 | 0.453 | 0.023 | 0.336 | 0.009 | 0.271 | 0.012 |
| FAM111B | cg21833459 | 0.488 | 0.022 | 0.425 | 0.010 | 0.336 | 0.009 | 0.334 | 0.034 |
| RPRML | cg08631151 | 0.262 | 0.010 | 0.256 | 0.017 | 0.181 | 0.007 | 0.166 | 0.001 |
| ARRDC2 | cg07374145 | 0.137 | 0.006 | 0.102 | 0.005 | 0.107 | 0.004 | 0.095 | 0.007 |
| C1orf89 | cg05588972 | 0.324 | 0.010 | 0.239 | 0.012 | 0.266 | 0.010 | 0.217 | 0.009 |
| C6orf206 | cg01344171 | 0.583 | 0.030 | 0.495 | 0.008 | 0.425 | 0.012 | 0.386 | 0.018 |
| SFN | cg14333454 | 0.815 | 0.010 | 0.650 | 0.014 | 0.656 | 0.028 | 0.520 | 0.016 |
| UBTF | cg10183248 | 0.413 | 0.003 | 0.374 | 0.025 | 0.326 | 0.012 | 0.245 | 0.002 |
| ZNF544 | cg14386312 | 0.636 | 0.011 | 0.616 | 0.022 | 0.455 | 0.019 | 0.391 | 0.012 |
| ACSM2 | cg26825755 | 0.486 | 0.022 | 0.413 | 0.005 | 0.334 | 0.008 | 0.340 | 0.011 |
| REEP2 | cg27264345 | 0.299 | 0.013 | 0.235 | 0.008 | 0.265 | 0.008 | 0.180 | 0.006 |
| ATN1 | cg22475430 | 0.366 | 0.002 | 0.329 | 0.024 | 0.290 | 0.014 | 0.217 | 0.003 |
| GUCY1A3 | cg09750385 | 0.329 | 0.018 | 0.327 | 0.021 | 0.212 | 0.020 | 0.218 | 0.002 |
| SPAG6 | cg25802093 | 1.036 | 0.026 | 1.010 | 0.019 | 0.743 | 0.008 | 0.631 | 0.008 |
| IRAK1 | cg19572242 | 0.555 | 0.006 | 0.482 | 0.022 | 0.416 | 0.011 | 0.352 | 0.014 |
| UBXD3 | cg03167763 | 0.601 | 0.026 | 0.553 | 0.024 | 0.457 | 0.008 | 0.360 | 0.016 |
| SLC15A3 | cg26980692 | 0.875 | 0.011 | 0.769 | 0.014 | 0.671 | 0.026 | 0.538 | 0.015 |
| SECISBP2 | cg20074048 | 0.440 | 0.012 | 0.364 | 0.019 | 0.343 | 0.024 | 0.279 | 0.011 |
| C17orf79 | cg12000587 | 0.831 | 0.027 | 0.670 | 0.005 | 0.658 | 0.033 | 0.531 | 0.014 |
| RAB26 | cg27176536 | 0.771 | 0.011 | 0.753 | 0.016 | 0.541 | 0.017 | 0.477 | 0.003 |
| CCDC47 | cg20131968 | 0.810 | 0.025 | 0.725 | 0.041 | 0.596 | 0.042 | 0.508 | 0.024 |
| FLJ23657 | cg22960952 | 0.753 | 0.009 | 0.584 | 0.041 | 0.601 | 0.020 | 0.493 | 0.016 |
| CTSL | cg11154542 | 0.536 | 0.014 | 0.514 | 0.044 | 0.381 | 0.005 | 0.331 | 0.026 |
| C8orf41 | cg00792687 | 0.239 | 0.005 | 0.202 | 0.004 | 0.176 | 0.007 | 0.156 | 0.007 |
| USP18 | cg27281093 | 0.301 | 0.012 | 0.165 | 0.018 | 0.278 | 0.023 | 0.256 | 0.012 |
| UBE2Q2 | cg09667582 | 0.444 | 0.013 | 0.400 | 0.011 | 0.291 | 0.021 | 0.308 | 0.020 |
| HOXB6 | cg18878432 | 0.613 | 0.011 | 0.588 | 0.012 | 0.422 | 0.011 | 0.389 | 0.027 |
| CYP4F12 | cg05722906 | 0.607 | 0.025 | 0.581 | 0.011 | 0.404 | 0.011 | 0.398 | 0.011 |
| CANT1 | cg01107741 | 0.233 | 0.013 | 0.185 | 0.005 | 0.176 | 0.000 | 0.157 | 0.006 |
| FLJ35530 | cg19399532 | 0.544 | 0.009 | 0.438 | 0.035 | 0.420 | 0.007 | 0.353 | 0.013 |
| MGC15523 | cg00466249 | 0.605 | 0.006 | 0.510 | 0.026 | 0.441 | 0.009 | 0.398 | 0.011 |
| LRDD | cg20225915 | 0.804 | 0.028 | 0.712 | 0.007 | 0.605 | 0.028 | 0.497 | 0.019 |
| DEFB126 | cg00466436 | 0.763 | 0.007 | 0.744 | 0.017 | 0.527 | 0.017 | 0.477 | 0.015 |
| TAT | cg22136365 | 0.697 | 0.006 | 0.641 | 0.028 | 0.476 | 0.020 | 0.457 | 0.012 |

TABLE 15-continued

| Gene | Gene ID | sh-ctrl Mean | sh-ctrl SEM | sh-ctrl + 5aza Mean | sh-ctrl + 5aza SEM | sh-3B Mean | sh-3B SEM | sh-3b + 5aza Mean | sh-3b + 5aza SEM |
|---|---|---|---|---|---|---|---|---|---|
| C1orf52 | cg03848145 | 0.315 | 0.009 | 0.296 | 0.020 | 0.211 | 0.005 | 0.207 | 0.007 |
| CENTG2 | cg04856858 | 0.769 | 0.005 | 0.677 | 0.018 | 0.572 | 0.006 | 0.481 | 0.043 |
| LIPA | cg18701598 | 0.464 | 0.013 | 0.420 | 0.015 | 0.322 | 0.025 | 0.302 | 0.012 |
| CDKN2B | cg01716061 | 0.323 | 0.014 | 0.243 | 0.001 | 0.250 | 0.005 | 0.221 | 0.015 |
| WNT7A | cg00625653 | 0.426 | 0.009 | 0.390 | 0.032 | 0.313 | 0.003 | 0.262 | 0.023 |
| PHLDA2 | cg11961618 | 0.667 | 0.009 | 0.587 | 0.010 | 0.499 | 0.011 | 0.413 | 0.004 |
| PRKCD | cg13908523 | 0.262 | 0.023 | 0.244 | 0.009 | 0.205 | 0.005 | 0.151 | 0.003 |
| PSCD4 | cg21736592 | 0.983 | 0.005 | 0.846 | 0.015 | 0.731 | 0.007 | 0.623 | 0.020 |
| AER61 | cg21785536 | 0.608 | 0.019 | 0.526 | 0.024 | 0.452 | 0.013 | 0.384 | 0.009 |
| DSCR6 | cg13460409 | 0.813 | 0.012 | 0.747 | 0.006 | 0.586 | 0.035 | 0.504 | 0.052 |
| CEACAM4 | cg21529807 | 0.630 | 0.023 | 0.542 | 0.032 | 0.455 | 0.006 | 0.409 | 0.005 |
| C11orf45 | cg19310430 | 0.398 | 0.007 | 0.298 | 0.018 | 0.351 | 0.007 | 0.246 | 0.004 |
| NOX3 | cg21792737 | 0.647 | 0.011 | 0.628 | 0.034 | 0.440 | 0.019 | 0.407 | 0.012 |
| PTPRB | cg17080277 | 0.230 | 0.011 | 0.187 | 0.009 | 0.162 | 0.004 | 0.159 | 0.010 |
| NT5E | cg17966619 | 0.325 | 0.018 | 0.242 | 0.011 | 0.259 | 0.004 | 0.218 | 0.011 |
| CYB561D1 | cg17034109 | 0.390 | 0.019 | 0.344 | 0.014 | 0.265 | 0.009 | 0.262 | 0.009 |
| PHACS | cg20240860 | 0.306 | 0.014 | 0.254 | 0.018 | 0.224 | 0.007 | 0.201 | 0.005 |
| MXI1 | cg13017345 | 1.071 | 0.003 | 0.991 | 0.010 | 0.736 | 0.006 | 0.687 | 0.012 |
| KTI12 | cg19894943 | 0.603 | 0.016 | 0.531 | 0.039 | 0.431 | 0.020 | 0.386 | 0.018 |
| PRG2 | cg15357945 | 0.590 | 0.012 | 0.521 | 0.012 | 0.425 | 0.008 | 0.375 | 0.015 |
| STMN2 | cg23326689 | 0.856 | 0.020 | 0.841 | 0.033 | 0.586 | 0.008 | 0.530 | 0.006 |
| PRELP | cg05955301 | 0.631 | 0.017 | 0.534 | 0.039 | 0.493 | 0.015 | 0.385 | 0.016 |
| RGS19 | cg24513045 | 0.498 | 0.015 | 0.440 | 0.030 | 0.361 | 0.016 | 0.314 | 0.013 |
| ZNHIT2 | cg03591238 | 0.388 | 0.006 | 0.293 | 0.019 | 0.296 | 0.015 | 0.266 | 0.007 |
| BAD | cg07588779 | 0.849 | 0.019 | 0.734 | 0.017 | 0.647 | 0.010 | 0.521 | 0.023 |
| DLX5 | cg06537230 | 0.615 | 0.041 | 0.545 | 0.009 | 0.434 | 0.014 | 0.396 | 0.008 |
| MLLT11 | cg07139440 | 0.618 | 0.009 | 0.569 | 0.038 | 0.422 | 0.024 | 0.399 | 0.017 |
| BTBD11 | cg15796941 | 0.339 | 0.017 | 0.267 | 0.013 | 0.252 | 0.011 | 0.228 | 0.006 |
| UBXD3 | cg06911113 | 0.696 | 0.008 | 0.690 | 0.019 | 0.484 | 0.014 | 0.420 | 0.033 |
| ZNF37A | cg15873633 | 0.469 | 0.017 | 0.406 | 0.025 | 0.326 | 0.014 | 0.311 | 0.009 |
| MGC3121 | cg15928446 | 0.333 | 0.014 | 0.309 | 0.015 | 0.245 | 0.012 | 0.199 | 0.005 |
| REEP1 | cg02870945 | 0.448 | 0.010 | 0.379 | 0.009 | 0.329 | 0.013 | 0.285 | 0.016 |
| CPLX2 | cg22776578 | 0.637 | 0.028 | 0.548 | 0.018 | 0.451 | 0.008 | 0.414 | 0.043 |
| PTPRO | cg09470640 | 0.714 | 0.019 | 0.640 | 0.049 | 0.533 | 0.011 | 0.431 | 0.007 |
| FAM57B | cg16152813 | 0.665 | 0.027 | 0.657 | 0.004 | 0.518 | 0.017 | 0.366 | 0.017 |
| RDH12 | cg04394967 | 0.890 | 0.012 | 0.809 | 0.026 | 0.636 | 0.031 | 0.551 | 0.027 |
| KIF13B | cg18875839 | 0.308 | 0.010 | 0.227 | 0.005 | 0.238 | 0.013 | 0.211 | 0.005 |
| SEMA3B | cg17289734 | 0.325 | 0.009 | 0.273 | 0.018 | 0.229 | 0.014 | 0.215 | 0.003 |
| RFX5 | cg04900486 | 0.566 | 0.005 | 0.549 | 0.036 | 0.381 | 0.010 | 0.354 | 0.015 |
| KCNIP2 | cg04997967 | 0.393 | 0.020 | 0.334 | 0.006 | 0.292 | 0.212 | 0.246 | 0.001 |
| HMG20B | cg09996240 | 0.721 | 0.015 | 0.651 | 0.042 | 0.511 | 0.021 | 0.451 | 0.039 |
| PLAC2 | cg16483916 | 0.265 | 0.005 | 0.194 | 0.007 | 0.214 | 0.002 | 0.176 | 0.018 |
| NAT10 | cg06513075 | 0.302 | 0.014 | 0.287 | 0.018 | 0.208 | 0.001 | 0.187 | 0.004 |
| C1orf115 | cg01471713 | 0.269 | 0.010 | 0.246 | 0.011 | 0.178 | 0.007 | 0.178 | 0.009 |
| HTR6 | cg10741760 | 0.797 | 0.019 | 0.715 | 0.011 | 0.591 | 0.006 | 0.480 | 0.018 |
| CNTNAP2 | cg16254309 | 0.423 | 0.015 | 0.405 | 0.012 | 0.284 | 0.028 | 0.266 | 0.005 |
| SIGLEC5 | cg14740251 | 0.785 | 0.004 | 0.766 | 0.032 | 0.536 | 0.019 | 0.480 | 0.033 |
| XPNPEP2 | cg23026995 | 0.797 | 0.033 | 0.780 | 0.018 | 0.604 | 0.022 | 0.447 | 0.011 |
| SLC4A11 | cg11004890 | 0.888 | 0.002 | 0.760 | 0.011 | 0.684 | 0.012 | 0.536 | 0.010 |
| CBLN4 | cg02501779 | 0.633 | 0.008 | 0.581 | 0.036 | 0.449 | 0.007 | 0.389 | 0.011 |
| C9orf116 | cg12438037 | 0.804 | 0.011 | 0.737 | 0.056 | 0.621 | 0.023 | 0.462 | 0.007 |
| CLN8 | cg23833896 | 0.501 | 0.011 | 0.473 | 0.015 | 0.333 | 0.012 | 0.321 | 0.015 |
| GAS2L1 | cg02293044 | 0.766 | 0.020 | 0.709 | 0.020 | 0.551 | 0.022 | 0.463 | 0.010 |
| EOMES | cg15540820 | 0.568 | 0.019 | 0.500 | 0.032 | 0.417 | 0.019 | 0.349 | 0.008 |
| NTS | cg04916911 | 0.348 | 0.015 | 0.337 | 0.008 | 0.246 | 0.016 | 0.207 | 0.008 |
| ICAM4 | cg03740216 | 1.091 | 0.010 | 1.014 | 0.004 | 0.796 | 0.018 | 0.648 | 0.018 |
| TMEM121 | cg22634689 | 0.716 | 0.012 | 0.657 | 0.039 | 0.510 | 0.018 | 0.438 | 0.026 |
| RAD52B | cg06481786 | 0.480 | 0.027 | 0.433 | 0.007 | 0.331 | 0.014 | 0.306 | 0.006 |
| NFAM1 | cg17568996 | 1.053 | 0.032 | 0.953 | 0.018 | 0.758 | 0.008 | 0.642 | 0.032 |
| PRODH | cg22297305 | 0.229 | 0.009 | 0.178 | 0.006 | 0.176 | 0.011 | 0.148 | 0.004 |
| FES | cg18661868 | 0.823 | 0.012 | 0.676 | 0.035 | 0.663 | 0.004 | 0.491 | 0.014 |
| WFDC10A | cg02605634 | 0.459 | 0.005 | 0.397 | 0.016 | 0.335 | 0.005 | 0.285 | 0.012 |
| SLC35E3 | cg20360244 | 0.433 | 0.019 | 0.414 | 0.032 | 0.293 | 0.005 | 0.269 | 0.008 |
| LAMP3 | cg00119079 | 0.371 | 0.022 | 0.282 | 0.005 | 0.274 | 0.002 | 0.253 | 0.014 |
| CYP4F3 | cg16377880 | 0.814 | 0.025 | 0.726 | 0.025 | 0.571 | 0.005 | 0.512 | 0.031 |
| ROPN1L | cg02227605 | 0.900 | 0.015 | 0.869 | 0.014 | 0.620 | 0.005 | 0.546 | 0.020 |
| HDAC10 | cg01120165 | 0.805 | 0.008 | 0.696 | 0.040 | 0.601 | 0.023 | 0.491 | 0.021 |
| OSBPL2 | cg08364102 | 0.352 | 0.018 | 0.319 | 0.010 | 0.247 | 0.020 | 0.220 | 0.015 |
| PIGS | cg26147132 | 0.462 | 0.019 | 0.415 | 0.035 | 0.337 | 0.003 | 0.280 | 0.008 |
| ARPM2 | cg04716261 | 0.986 | 0.011 | 0.854 | 0.047 | 0.727 | 0.006 | 0.605 | 0.015 |
| PCDHB10 | cg05898102 | 0.487 | 0.025 | 0.444 | 0.027 | 0.352 | 0.025 | 0.292 | 0.007 |
| PET112L | cg13218435 | 0.410 | 0.006 | 0.365 | 0.010 | 0.320 | 0.003 | 0.236 | 0.001 |
| FNDC8 | cg09155905 | 0.721 | 0.037 | 0.673 | 0.025 | 0.498 | 0.015 | 0.443 | 0.027 |
| PRKX | cg09094355 | 0.225 | 0.008 | 0.208 | 0.008 | 0.161 | 0.011 | 0.135 | 0.016 |
| PRKAR1A | cg21256649 | 0.266 | 0.006 | 0.209 | 0.007 | 0.194 | 0.013 | 0.177 | 0.007 |

TABLE 15-continued

| Gene | Gene ID | sh-ctrl Mean | sh-ctrl SEM | sh-ctrl + 5aza Mean | sh-ctrl + 5aza SEM | sh-3B Mean | sh-3B SEM | sh-3b + 5aza Mean | sh-3b + 5aza SEM |
|---|---|---|---|---|---|---|---|---|---|
| MC4R | cg13365022 | 0.651 | 0.026 | 0.557 | 0.013 | 0.453 | 0.023 | 0.422 | 0.024 |
| CKMT1B | cg03679734 | 0.852 | 0.019 | 0.781 | 0.018 | 0.597 | 0.007 | 0.524 | 0.005 |
| SPOCD1 | cg17803965 | 0.526 | 0.003 | 0.449 | 0.011 | 0.393 | 0.008 | 0.321 | 0.016 |
| NFIC | cg26044825 | 0.465 | 0.029 | 0.410 | 0.019 | 0.359 | 0.025 | 0.270 | 0.010 |
| CCRK | cg16386080 | 0.938 | 0.003 | 0.846 | 0.002 | 0.653 | 0.013 | 0.585 | 0.005 |
| SS18L1 | cg15580043 | 0.244 | 0.008 | 0.205 | 0.004 | 0.162 | 0.004 | 0.168 | 0.017 |
| TNFRSF10C | cg27090216 | 0.746 | 0.049 | 0.663 | 0.033 | 0.542 | 0.028 | 0.453 | 0.025 |
| TNFRSF11A | cg07888234 | 0.964 | 0.018 | 0.954 | 0.022 | 0.648 | 0.021 | 0.584 | 0.026 |
| ENG | cg24910675 | 0.853 | 0.005 | 0.733 | 0.030 | 0.659 | 0.010 | 0.505 | 0.016 |
| LCE1B | cg08878744 | 0.622 | 0.017 | 0.600 | 0.029 | 0.436 | 0.012 | 0.370 | 0.015 |
| CACNG3 | cg17234150 | 0.964 | 0.012 | 0.872 | 0.018 | 0.673 | 0.022 | 0.598 | 0.010 |
| GNAZ | cg19764436 | 0.701 | 0.009 | 0.637 | 0.032 | 0.536 | 0.014 | 0.402 | 0.021 |
| TMEM105 | cg15913671 | 0.624 | 0.018 | 0.495 | 0.016 | 0.489 | 0.008 | 0.387 | 0.027 |
| ADCY5 | cg13384396 | 0.532 | 0.002 | 0.479 | 0.033 | 0.383 | 0.008 | 0.322 | 0.004 |
| FOXJ2 | cg08571203 | 0.444 | 0.025 | 0.295 | 0.016 | 0.389 | 0.008 | 0.295 | 0.010 |
| PABPC5 | cg04875162 | 0.218 | 0.005 | 0.187 | 0.006 | 0.149 | 0.007 | 0.142 | 0.002 |
| CEACAM3 | cg23181133 | 0.647 | 0.013 | 0.612 | 0.029 | 0.442 | 0.023 | 0.397 | 0.013 |
| KRTAP13-4 | cg14062083 | 0.772 | 0.014 | 0.679 | 0.017 | 0.541 | 0.002 | 0.485 | 0.012 |
| MFNG | cg18452324 | 1.178 | 0.016 | 1.127 | 0.027 | 0.844 | 0.005 | 0.688 | 0.004 |
| ABCA2 | cg15428653 | 0.974 | 0.012 | 0.921 | 0.025 | 0.660 | 0.021 | 0.599 | 0.018 |
| YBX2 | cg00901493 | 0.358 | 0.005 | 0.302 | 0.013 | 0.246 | 0.009 | 0.236 | 0.009 |
| SCUBE1 | cg25842633 | 0.765 | 0.024 | 0.675 | 0.030 | 0.530 | 0.024 | 0.483 | 0.011 |
| PTPN9 | cg04914105 | 0.354 | 0.012 | 0.289 | 0.003 | 0.252 | 0.006 | 0.232 | 0.010 |
| PTPRO | cg24053587 | 0.318 | 0.011 | 0.273 | 0.009 | 0.217 | 0.017 | 0.209 | 0.016 |
| FLJ37478 | cg08211091 | 0.466 | 0.028 | 0.407 | 0.023 | 0.377 | 0.010 | 0.262 | 0.002 |
| COL19A1 | cg06321883 | 0.255 | 0.010 | 0.213 | 0.011 | 0.177 | 0.007 | 0.168 | 0.005 |
| G1P3 | cg20227766 | 0.282 | 0.001 | 0.260 | 0.011 | 0.202 | 0.005 | 0.168 | 0.003 |
| WDR32 | cg04660234 | 0.446 | 0.015 | 0.324 | 0.028 | 0.345 | 0.002 | 0.298 | 0.020 |
| LYN | cg03973663 | 0.885 | 0.021 | 0.740 | 0.024 | 0.615 | 0.015 | 0.578 | 0.018 |
| SCN1B | cg02017041 | 0.477 | 0.011 | 0.450 | 0.017 | 0.351 | 0.010 | 0.274 | 0.007 |
| CENPB | cg17565490 | 0.632 | 0.009 | 0.574 | 0.025 | 0.460 | 0.005 | 0.373 | 0.010 |
| D4ST1 | cg14837165 | 0.353 | 0.024 | 0.314 | 0.009 | 0.251 | 0.013 | 0.217 | 0.001 |
| MAP4K2 | cg10821722 | 1.033 | 0.032 | 0.953 | 0.046 | 0.783 | 0.011 | 0.586 | 0.031 |
| OLFML2B | cg19130550 | 0.560 | 0.009 | 0.537 | 0.017 | 0.369 | 0.009 | 0.348 | 0.008 |
| KISS1R | cg12998614 | 0.407 | 0.002 | 0.337 | 0.017 | 0.317 | 0.007 | 0.243 | 0.008 |
| RTN4R | cg08557686 | 0.617 | 0.017 | 0.476 | 0.001 | 0.478 | 0.016 | 0.390 | 0.015 |
| STAMBPL1 | cg11917694 | 0.834 | 0.002 | 0.771 | 0.027 | 0.593 | 0.009 | 0.495 | 0.029 |
| IGFBP3 | cg22083798 | 0.523 | 0.010 | 0.492 | 0.031 | 0.335 | 0.007 | 0.338 | 0.016 |
| FLJ43752 | cg04329454 | 0.705 | 0.007 | 0.685 | 0.014 | 0.485 | 0.021 | 0.418 | 0.018 |
| ELAVL3 | cg25434223 | 0.674 | 0.008 | 0.628 | 0.020 | 0.525 | 0.029 | 0.371 | 0.043 |
|  | cg22262964 | 0.528 | 0.011 | 0.484 | 0.023 | 0.356 | 0.007 | 0.330 | 0.018 |
| ALDH1A3 | cg23191950 | 0.893 | 0.019 | 0.774 | 0.025 | 0.630 | 0.010 | 0.559 | 0.009 |
| SOCS1 | cg10784813 | 0.477 | 0.031 | 0.367 | 0.024 | 0.387 | 0.008 | 0.291 | 0.009 |
| ATP13A2 | cg11192270 | 0.391 | 0.002 | 0.328 | 0.010 | 0.278 | 0.007 | 0.247 | 0.011 |
| DYNC1I1 | cg10281478 | 0.664 | 0.016 | 0.570 | 0.029 | 0.466 | 0.007 | 0.419 | 0.014 |
| SEMA5B | cg00212549 | 0.549 | 0.023 | 0.532 | 0.031 | 0.344 | 0.023 | 0.355 | 0.021 |
| HDDC3 | cg27626899 | 0.613 | 0.006 | 0.548 | 0.010 | 0.446 | 0.006 | 0.365 | 0.010 |
| FLJ21736 | cg26538442 | 0.396 | 0.025 | 0.341 | 0.027 | 0.288 | 0.010 | 0.242 | 0.004 |
| SYT10 | cg23950724 | 0.448 | 0.013 | 0.401 | 0.020 | 0.301 | 0.015 | 0.286 | 0.018 |
| OAZ2 | cg07031532 | 0.417 | 0.020 | 0.391 | 0.011 | 0.406 | 0.033 | 0.200 | 0.004 |
| SERPINB1 | cg06148264 | 0.985 | 0.015 | 0.857 | 0.032 | 0.724 | 0.015 | 0.589 | 0.023 |
| SNX15 | cg02554810 | 0.257 | 0.014 | 0.189 | 0.004 | 0.180 | 0.010 | 0.184 | 0.009 |
| CHFR | cg21232015 | 0.806 | 0.006 | 0.696 | 0.034 | 0.606 | 0.021 | 0.477 | 0.020 |
| CHRD | cg25182621 | 0.796 | 0.010 | 0.716 | 0.012 | 0.592 | 0.010 | 0.461 | 0.014 |
| IGF2AS | cg10501065 | 0.527 | 0.011 | 0.472 | 0.016 | 0.375 | 0.016 | 0.317 | 0.014 |
| MTHFS | cg23855392 | 0.611 | 0.021 | 0.450 | 0.023 | 0.475 | 0.028 | 0.398 | 0.022 |
| EML2 | cg27301343 | 0.430 | 0.016 | 0.380 | 0.024 | 0.294 | 0.023 | 0.270 | 0.015 |
| DSCR1 | cg19278165 | 0.397 | 0.012 | 0.378 | 0.012 | 0.268 | 0.012 | 0.239 | 0.011 |
| GPR125 | cg26631477 | 0.339 | 0.009 | 0.281 | 0.015 | 0.245 | 0.020 | 0.212 | 0.012 |
| SNTG1 | cg08896053 | 0.811 | 0.003 | 0.747 | 0.037 | 0.547 | 0.011 | 0.501 | 0.017 |
| ATP13A2 | cg12999103 | 0.348 | 0.007 | 0.283 | 0.007 | 0.237 | 0.006 | 0.234 | 0.011 |
| IPO4 | cg11646704 | 0.335 | 0.017 | 0.286 | 0.014 | 0.216 | 0.006 | 0.228 | 0.016 |
| MYL9 | cg09786221 | 0.741 | 0.012 | 0.677 | 0.023 | 0.534 | 0.009 | 0.434 | 0.022 |
| DCXR | cg01350700 | 0.251 | 0.009 | 0.217 | 0.012 | 0.178 | 0.010 | 0.155 | 0.002 |
| RANBP9 | cg14645085 | 0.563 | 0.021 | 0.486 | 0.028 | 0.353 | 0.015 | 0.391 | 0.027 |
| BLOC1S1 | cg12683929 | 0.536 | 0.007 | 0.513 | 0.030 | 0.354 | 0.003 | 0.329 | 0.023 |
| FBXL16 | cg01934790 | 0.793 | 0.015 | 0.747 | 0.015 | 0.572 | 0.026 | 0.455 | 0.009 |
| FCGR3A | cg04384208 | 0.859 | 0.003 | 0.818 | 0.039 | 0.574 | 0.003 | 0.522 | 0.017 |
| PLAT | cg12091331 | 0.462 | 0.008 | 0.410 | 0.024 | 0.326 | 0.008 | 0.280 | 0.010 |
| GRIA1 | cg17020834 | 0.798 | 0.006 | 0.729 | 0.033 | 0.600 | 0.033 | 0.451 | 0.016 |
| OXTR | cg23391006 | 0.235 | 0.014 | 0.187 | 0.011 | 0.169 | 0.006 | 0.152 | 0.006 |
| PCDHB1 | cg06899976 | 0.383 | 0.014 | 0.286 | 0.017 | 0.277 | 0.008 | 0.259 | 0.005 |
| CHST10 | cg03853987 | 0.409 | 0.011 | 0.334 | 0.021 | 0.287 | 0.025 | 0.264 | 0.014 |
| KIAA1822 | cg06834875 | 0.858 | 0.005 | 0.852 | 0.033 | 0.610 | 0.018 | 0.481 | 0.013 |
| C6orf188 | cg23741330 | 0.818 | 0.013 | 0.732 | 0.009 | 0.556 | 0.005 | 0.509 | 0.044 |

TABLE 15-continued

| Gene | Gene ID | sh-ctrl Mean | sh-ctrl SEM | sh-ctrl + 5aza Mean | sh-ctrl + 5aza SEM | sh-3B Mean | sh-3B SEM | sh-3b + 5aza Mean | sh-3b + 5aza SEM |
|---|---|---|---|---|---|---|---|---|---|
| ASTN2 | cg12024292 | 0.374 | 0.006 | 0.342 | 0.017 | 0.258 | 0.010 | 0.227 | 0.020 |
| AFAP | cg15957394 | 0.360 | 0.024 | 0.332 | 0.028 | 0.245 | 0.009 | 0.219 | 0.010 |
| C3orf39 | cg23057732 | 0.324 | 0.005 | 0.300 | 0.022 | 0.218 | 0.014 | 0.199 | 0.014 |
| C1orf76 | cg05421688 | 0.878 | 0.038 | 0.857 | 0.050 | 0.612 | 0.016 | 0.504 | 0.032 |
| PECAM1 | cg22467071 | 1.035 | 0.010 | 0.983 | 0.008 | 0.718 | 0.005 | 0.608 | 0.009 |
| GREM1 | cg21296230 | 0.402 | 0.003 | 0.341 | 0.016 | 0.280 | 0.031 | 0.253 | 0.004 |
| SOAT1 | cg02275294 | 0.280 | 0.009 | 0.221 | 0.017 | 0.205 | 0.012 | 0.179 | 0.004 |
| PTPRO | cg06357925 | 0.463 | 0.013 | 0.366 | 0.024 | 0.357 | 0.018 | 0.282 | 0.012 |
| KLK2 | cg07947016 | 0.741 | 0.015 | 0.727 | 0.032 | 0.475 | 0.005 | 0.456 | 0.009 |
| SLC16A7 | cg11871280 | 0.830 | 0.002 | 0.755 | 0.006 | 0.536 | 0.019 | 0.531 | 0.038 |
| PLK1 | cg26003813 | 0.429 | 0.005 | 0.381 | 0.009 | 0.304 | 0.012 | 0.256 | 0.010 |
| RGAG1 | cg06338119 | 0.737 | 0.023 | 0.607 | 0.007 | 0.546 | 0.013 | 0.448 | 0.009 |
| C21orf124 | cg21755709 | 0.761 | 0.018 | 0.665 | 0.028 | 0.544 | 0.007 | 0.456 | 0.005 |
| EDAR | cg01124420 | 0.738 | 0.003 | 0.646 | 0.036 | 0.523 | 0.010 | 0.446 | 0.013 |
| PATE | cg19345602 | 0.740 | 0.012 | 0.725 | 0.026 | 0.481 | 0.008 | 0.448 | 0.028 |
| POLD4 | cg09706243 | 0.760 | 0.009 | 0.646 | 0.036 | 0.574 | 0.020 | 0.444 | 0.015 |
| LRFN3 | cg20580177 | 0.521 | 0.017 | 0.406 | 0.013 | 0.392 | 0.009 | 0.325 | 0.034 |
| SLC25A11 | cg04958703 | 0.830 | 0.018 | 0.771 | 0.026 | 0.589 | 0.017 | 0.480 | 0.015 |
| ERBB4 | cg07015629 | 0.306 | 0.017 | 0.282 | 0.025 | 0.191 | 0.003 | 0.200 | 0.010 |
| MGC18079 | cg26062370 | 0.466 | 0.010 | 0.446 | 0.035 | 0.340 | 0.017 | 0.259 | 0.028 |
| AFAP | cg19564367 | 0.416 | 0.008 | 0.358 | 0.011 | 0.316 | 0.021 | 0.239 | 0.016 |
| SYT11 | cg05150177 | 0.420 | 0.009 | 0.387 | 0.030 | 0.273 | 0.009 | 0.263 | 0.015 |
| RND2 | cg22325646 | 0.547 | 0.004 | 0.489 | 0.007 | 0.377 | 0.006 | 0.332 | 0.013 |
| GPR156 | cg19093820 | 0.560 | 0.015 | 0.517 | 0.017 | 0.336 | 0.019 | 0.380 | 0.037 |
| C12orf40 | cg22941086 | 0.724 | 0.020 | 0.722 | 0.031 | 0.443 | 0.033 | 0.456 | 0.012 |
| SPRR1B | cg18780284 | 0.736 | 0.009 | 0.692 | 0.009 | 0.493 | 0.006 | 0.441 | 0.003 |
| RPP25 | cg09619786 | 0.272 | 0.012 | 0.226 | 0.005 | 0.204 | 0.002 | 0.161 | 0.009 |
| DPP8 | cg06993413 | 0.352 | 0.009 | 0.347 | 0.035 | 0.231 | 0.012 | 0.208 | 0.021 |
| ACCN2 | cg23126949 | 0.703 | 0.029 | 0.631 | 0.032 | 0.451 | 0.010 | 0.452 | 0.016 |
| DLG4 | cg02740128 | 0.403 | 0.012 | 0.350 | 0.012 | 0.264 | 0.008 | 0.260 | 0.011 |
| OR10H3 | cg25843439 | 0.487 | 0.026 | 0.449 | 0.016 | 0.338 | 0.011 | 0.286 | 0.030 |
| MED4 | cg24809640 | 0.529 | 0.018 | 0.488 | 0.025 | 0.407 | 0.008 | 0.286 | 0.008 |
| GPX3 | cg17820459 | 0.446 | 0.009 | 0.344 | 0.015 | 0.352 | 0.009 | 0.267 | 0.007 |
| EHD2 | cg26036443 | 0.313 | 0.008 | 0.309 | 0.022 | 0.191 | 0.006 | 0.197 | 0.012 |
| CX3CL1 | cg20427865 | 0.408 | 0.012 | 0.313 | 0.005 | 0.319 | 0.005 | 0.248 | 0.008 |
| PRPSAP1 | cg12612336 | 0.214 | 0.005 | 0.157 | 0.011 | 0.153 | 0.007 | 0.144 | 0.011 |
| SLC38A4 | cg15584813 | 0.359 | 0.017 | 0.247 | 0.014 | 0.261 | 0.017 | 0.256 | 0.009 |
| C16orf52 | cg27247832 | 0.501 | 0.017 | 0.389 | 0.006 | 0.330 | 0.019 | 0.349 | 0.007 |
| MGC39606 | cg09347151 | 0.360 | 0.016 | 0.304 | 0.006 | 0.234 | 0.010 | 0.238 | 0.011 |
| GCC1 | cg08586737 | 0.669 | 0.005 | 0.598 | 0.041 | 0.466 | 0.017 | 0.397 | 0.014 |
| LHX4 | cg25680829 | 0.589 | 0.005 | 0.552 | 0.051 | 0.395 | 0.008 | 0.350 | 0.015 |
| VPS39 | cg27472032 | 0.237 | 0.015 | 0.203 | 0.007 | 0.152 | 0.001 | 0.157 | 0.006 |
| GYPC | cg17105014 | 0.374 | 0.009 | 0.297 | 0.008 | 0.292 | 0.008 | 0.220 | 0.013 |
| C7orf31 | cg26172108 | 0.320 | 0.015 | 0.272 | 0.015 | 0.215 | 0.013 | 0.202 | 0.010 |
| PROCR | cg26806924 | 0.303 | 0.010 | 0.225 | 0.012 | 0.220 | 0.012 | 0.199 | 0.008 |
| SNAPC5 | cg13133148 | 0.258 | 0.010 | 0.233 | 0.023 | 0.184 | 0.007 | 0.147 | 0.004 |
| FLT4 | cg00489401 | 0.197 | 0.009 | 0.168 | 0.006 | 0.141 | 0.010 | 0.117 | 0.004 |
| PLAT | cg22038738 | 0.632 | 0.046 | 0.495 | 0.010 | 0.519 | 0.024 | 0.360 | 0.023 |
| ZNF7 | cg20845050 | 0.540 | 0.013 | 0.482 | 0.024 | 0.347 | 0.002 | 0.342 | 0.022 |
| HHCM | cg24377133 | 0.405 | 0.016 | 0.385 | 0.039 | 0.256 | 0.019 | 0.249 | 0.005 |
| FECH | cg05243804 | 0.460 | 0.011 | 0.380 | 0.012 | 0.321 | 0.008 | 0.285 | 0.020 |
| RGS5 | cg24901474 | 0.614 | 0.026 | 0.572 | 0.005 | 0.371 | 0.015 | 0.401 | 0.020 |
| NT5C1A | cg01656955 | 0.681 | 0.014 | 0.607 | 0.036 | 0.458 | 0.020 | 0.412 | 0.004 |
| TUBA1 | cg09197965 | 0.644 | 0.011 | 0.600 | 0.008 | 0.439 | 0.022 | 0.374 | 0.021 |
| SOAT2 | cg23841186 | 0.743 | 0.022 | 0.589 | 0.011 | 0.521 | 0.018 | 0.470 | 0.006 |
| IGFBP3 | cg08831744 | 0.523 | 0.001 | 0.449 | 0.043 | 0.347 | 0.003 | 0.329 | 0.033 |
| ATAD3A | cg05009249 | 0.279 | 0.004 | 0.219 | 0.020 | 0.196 | 0.004 | 0.178 | 0.009 |
| THBS3 | cg12543649 | 0.352 | 0.006 | 0.294 | 0.006 | 0.254 | 0.005 | 0.209 | 0.011 |
| TBX6 | cg23353982 | 0.487 | 0.014 | 0.423 | 0.004 | 0.350 | 0.010 | 0.282 | 0.015 |
| IL11 | cg16481281 | 0.302 | 0.019 | 0.271 | 0.016 | 0.204 | 0.006 | 0.181 | 0.012 |
| NALP8 | cg22190114 | 0.919 | 0.013 | 0.884 | 0.031 | 0.565 | 0.028 | 0.572 | 0.031 |
| CLCN4 | cg01851385 | 0.597 | 0.003 | 0.551 | 0.029 | 0.402 | 0.021 | 0.351 | 0.012 |
| PDE4B | cg26963271 | 0.394 | 0.006 | 0.303 | 0.014 | 0.285 | 0.013 | 0.249 | 0.015 |
| PRKD1 | cg21794225 | 0.817 | 0.015 | 0.672 | 0.063 | 0.558 | 0.012 | 0.511 | 0.024 |
| PHF20L1 | cg27342122 | 0.296 | 0.006 | 0.245 | 0.010 | 0.206 | 0.003 | 0.182 | 0.007 |
| MYEOV | cg24776407 | 0.796 | 0.006 | 0.790 | 0.016 | 0.528 | 0.025 | 0.453 | 0.011 |
| C20orf161 | cg18285544 | 0.501 | 0.009 | 0.373 | 0.021 | 0.369 | 0.010 | 0.318 | 0.007 |
| ZNF513 | cg11177693 | 0.946 | 0.028 | 0.844 | 0.073 | 0.635 | 0.007 | 0.568 | 0.068 |
| ALG1 | cg00547018 | 0.776 | 0.023 | 0.665 | 0.026 | 0.508 | 0.028 | 0.489 | 0.039 |
| GPSN2 | cg12846938 | 0.367 | 0.028 | 0.268 | 0.000 | 0.245 | 0.003 | 0.260 | 0.009 |
| SP110 | cg02056135 | 0.384 | 0.006 | 0.320 | 0.017 | 0.250 | 0.005 | 0.248 | 0.021 |
| CFLAR | cg17802847 | 0.480 | 0.019 | 0.403 | 0.009 | 0.371 | 0.012 | 0.268 | 0.001 |
| GFI1B | cg01909921 | 0.770 | 0.039 | 0.710 | 0.016 | 0.486 | 0.013 | 0.477 | 0.016 |
| KCNK5 | cg10844844 | 0.395 | 0.007 | 0.315 | 0.014 | 0.297 | 0.007 | 0.233 | 0.004 |
| C9orf75 | cg03041841 | 0.995 | 0.024 | 0.858 | 0.063 | 0.719 | 0.029 | 0.571 | 0.035 |

TABLE 15-continued

| Gene | Gene ID | sh-ctrl Mean | sh-ctrl SEM | sh-ctrl + 5aza Mean | sh-ctrl + 5aza SEM | sh-3B Mean | sh-3B SEM | sh-3b + 5aza Mean | sh-3b + 5aza SEM |
|---|---|---|---|---|---|---|---|---|---|
| TMEM32 | cg21932800 | 0.277 | 0.018 | 0.246 | 0.018 | 0.177 | 0.007 | 0.174 | 0.001 |
| ACADS | cg01535453 | 0.828 | 0.002 | 0.695 | 0.006 | 0.615 | 0.010 | 0.473 | 0.012 |
| VPREB1 | cg14844130 | 0.490 | 0.014 | 0.445 | 0.036 | 0.311 | 0.005 | 0.304 | 0.017 |
| TNNT1 | cg19504245 | 0.265 | 0.015 | 0.200 | 0.005 | 0.188 | 0.010 | 0.170 | 0.011 |
| TMEM39B | cg21682382 | 0.350 | 0.013 | 0.295 | 0.018 | 0.236 | 0.012 | 0.215 | 0.009 |
| GSS | cg08743392 | 0.341 | 0.011 | 0.292 | 0.018 | 0.243 | 0.003 | 0.198 | 0.007 |
| ARHGEF5 | cg23815845 | 0.294 | 0.010 | 0.192 | 0.001 | 0.218 | 0.009 | 0.209 | 0.009 |
| FLJ20097 | cg21262854 | 0.195 | 0.004 | 0.128 | 0.004 | 0.138 | 0.008 | 0.144 | 0.007 |
| RASD1 | cg12601987 | 0.525 | 0.033 | 0.471 | 0.049 | 0.383 | 0.007 | 0.290 | 0.012 |
| CHRNA7 | cg04785227 | 0.341 | 0.008 | 0.323 | 0.013 | 0.222 | 0.011 | 0.200 | 0.009 |
| FGFR1 | cg08722122 | 0.759 | 0.007 | 0.652 | 0.026 | 0.569 | 0.002 | 0.422 | 0.003 |
| CD274 | cg02823866 | 0.464 | 0.008 | 0.350 | 0.016 | 0.341 | 0.025 | 0.287 | 0.009 |
| MRC2 | cg14764661 | 0.487 | 0.038 | 0.382 | 0.020 | 0.374 | 0.005 | 0.283 | 0.014 |
| C3orf37 | cg00135056 | 0.481 | 0.037 | 0.398 | 0.016 | 0.355 | 0.008 | 0.277 | 0.004 |
| NPPB | cg22927043 | 0.466 | 0.021 | 0.458 | 0.021 | 0.303 | 0.003 | 0.265 | 0.012 |
| STRN | cg15556558 | 0.248 | 0.003 | 0.214 | 0.018 | 0.178 | 0.018 | 0.141 | 0.007 |
| LRDD | cg00185839 | 0.286 | 0.016 | 0.216 | 0.015 | 0.200 | 0.007 | 0.184 | 0.005 |
| PCDHB8 | cg02087637 | 0.574 | 0.011 | 0.562 | 0.018 | 0.351 | 0.013 | 0.347 | 0.017 |
| SOCS2 | cg23412850 | 0.164 | 0.012 | 0.120 | 0.005 | 0.110 | 0.004 | 0.113 | 0.006 |
| RASGRP1 | cg06952236 | 0.388 | 0.007 | 0.346 | 0.028 | 0.250 | 0.001 | 0.237 | 0.010 |
| KCNJ10 | cg05768141 | 0.618 | 0.018 | 0.588 | 0.010 | 0.429 | 0.015 | 0.340 | 0.011 |
| SEPN1 | cg15156836 | 0.474 | 0.009 | 0.413 | 0.034 | 0.324 | 0.011 | 0.279 | 0.022 |
| C1orf160 | cg06839953 | 0.169 | 0.008 | 0.146 | 0.009 | 0.108 | 0.005 | 0.106 | 0.007 |
| CASR | cg17453778 | 0.689 | 0.009 | 0.613 | 0.010 | 0.466 | 0.016 | 0.403 | 0.011 |
| CA2 | cg08872550 | 0.329 | 0.023 | 0.275 | 0.010 | 0.246 | 0.014 | 0.185 | 0.004 |
| OR10H2 | cg12513379 | 0.551 | 0.001 | 0.527 | 0.019 | 0.377 | 0.015 | 0.304 | 0.013 |
| BCAM | cg21263196 | 0.534 | 0.028 | 0.511 | 0.058 | 0.364 | 0.012 | 0.296 | 0.010 |
| C9orf23 | cg07557424 | 0.321 | 0.012 | 0.272 | 0.016 | 0.211 | 0.002 | 0.199 | 0.003 |
| CLEC1A | cg13354523 | 0.813 | 0.004 | 0.719 | 0.020 | 0.562 | 0.026 | 0.468 | 0.021 |
| AMT | cg20191453 | 0.240 | 0.019 | 0.199 | 0.004 | 0.153 | 0.010 | 0.156 | 0.010 |
| FABP3 | cg14407437 | 0.441 | 0.005 | 0.379 | 0.015 | 0.307 | 0.010 | 0.256 | 0.012 |
| PPIL2 | cg12228611 | 0.464 | 0.014 | 0.351 | 0.013 | 0.322 | 0.024 | 0.299 | 0.011 |
| IMPDH1 | cg05079794 | 0.626 | 0.028 | 0.521 | 0.019 | 0.426 | 0.002 | 0.379 | 0.014 |
| EDG5 | cg04762346 | 0.248 | 0.012 | 0.203 | 0.017 | 0.178 | 0.009 | 0.146 | 0.006 |
| C20orf28 | cg24889744 | 0.266 | 0.003 | 0.188 | 0.008 | 0.190 | 0.005 | 0.176 | 0.002 |
| IGFBP7 | cg03876618 | 0.662 | 0.016 | 0.554 | 0.040 | 0.452 | 0.032 | 0.397 | 0.023 |
| C1QTNF6 | cg26143719 | 0.473 | 0.010 | 0.392 | 0.012 | 0.349 | 0.023 | 0.267 | 0.012 |
| LNK | cg03799530 | 0.326 | 0.006 | 0.223 | 0.012 | 0.224 | 0.005 | 0.230 | 0.014 |
| VHL | cg20916523 | 0.831 | 0.008 | 0.650 | 0.019 | 0.647 | 0.014 | 0.471 | 0.011 |
| PRKAG1 | cg22153481 | 0.487 | 0.002 | 0.387 | 0.011 | 0.360 | 0.010 | 0.284 | 0.003 |
| DCTN1 | cg01753375 | 0.455 | 0.019 | 0.368 | 0.008 | 0.380 | 0.023 | 0.240 | 0.008 |
| RAB25 | cg19580810 | 0.598 | 0.020 | 0.542 | 0.024 | 0.409 | 0.016 | 0.339 | 0.006 |
| LCE1C | cg24304714 | 0.552 | 0.012 | 0.510 | 0.014 | 0.331 | 0.017 | 0.349 | 0.001 |
| ADAM12 | cg13488201 | 0.380 | 0.007 | 0.278 | 0.018 | 0.256 | 0.021 | 0.257 | 0.021 |
| DIRAS1 | cg17226343 | 0.558 | 0.023 | 0.522 | 0.027 | 0.398 | 0.010 | 0.299 | 0.021 |
| HOXB8 | cg15539420 | 0.537 | 0.007 | 0.483 | 0.032 | 0.359 | 0.011 | 0.311 | 0.011 |
| IGFBP2 | cg25854162 | 0.501 | 0.037 | 0.463 | 0.033 | 0.347 | 0.007 | 0.277 | 0.002 |
| ADAMTSL1 | cg00116234 | 0.429 | 0.011 | 0.377 | 0.027 | 0.270 | 0.029 | 0.267 | 0.019 |
| PITX1 | cg24495017 | 0.429 | 0.013 | 0.341 | 0.022 | 0.307 | 0.009 | 0.255 | 0.013 |
| SLC25A22 | cg10970251 | 0.935 | 0.004 | 0.814 | 0.004 | 0.670 | 0.009 | 0.520 | 0.013 |
| C20orf58 | cg07675169 | 0.592 | 0.013 | 0.493 | 0.021 | 0.425 | 0.002 | 0.338 | 0.010 |
| DHX16 | cg24450157 | 0.719 | 0.048 | 0.708 | 0.029 | 0.454 | 0.010 | 0.412 | 0.022 |
| IL23A | cg00294382 | 0.356 | 0.009 | 0.302 | 0.009 | 0.260 | 0.015 | 0.198 | 0.004 |
| PGM5 | cg09230173 | 0.419 | 0.009 | 0.367 | 0.012 | 0.278 | 0.013 | 0.247 | 0.014 |
| WIG1 | cg18380974 | 0.437 | 0.004 | 0.369 | 0.035 | 0.303 | 0.012 | 0.255 | 0.001 |
| C9orf19 | cg06484397 | 0.274 | 0.005 | 0.236 | 0.002 | 0.178 | 0.003 | 0.166 | 0.011 |
| KHDRBS3 | cg25945374 | 0.331 | 0.013 | 0.240 | 0.017 | 0.256 | 0.015 | 0.196 | 0.004 |
| ANKRD47 | cg20970875 | 0.344 | 0.003 | 0.268 | 0.011 | 0.253 | 0.024 | 0.202 | 0.010 |
| PRKCB1 | cg24250393 | 0.530 | 0.004 | 0.474 | 0.013 | 0.352 | 0.006 | 0.307 | 0.014 |
| ECHDC2 | cg13461509 | 0.506 | 0.004 | 0.443 | 0.031 | 0.322 | 0.003 | 0.309 | 0.002 |
| ATP6V0D1 | cg15301525 | 0.317 | 0.017 | 0.254 | 0.004 | 0.230 | 0.003 | 0.183 | 0.004 |
| CGI-96 | cg11096837 | 0.298 | 0.007 | 0.230 | 0.019 | 0.211 | 0.018 | 0.180 | 0.009 |
| FCRLM2 | cg27495845 | 0.685 | 0.017 | 0.593 | 0.027 | 0.432 | 0.036 | 0.425 | 0.027 |
| LOX | cg01429321 | 0.311 | 0.011 | 0.251 | 0.012 | 0.197 | 0.010 | 0.202 | 0.014 |
| EI24 | cg05739825 | 0.298 | 0.009 | 0.234 | 0.011 | 0.193 | 0.010 | 0.195 | 0.006 |
| GABRG1 | cg03469082 | 0.513 | 0.016 | 0.490 | 0.036 | 0.305 | 0.010 | 0.316 | 0.012 |
| MPST | cg14850181 | 0.302 | 0.007 | 0.246 | 0.019 | 0.190 | 0.010 | 0.197 | 0.012 |
| KSP37 | cg08132711 | 0.723 | 0.019 | 0.602 | 0.005 | 0.507 | 0.001 | 0.418 | 0.036 |
| IMMP2L | cg16218254 | 0.446 | 0.010 | 0.364 | 0.018 | 0.298 | 0.015 | 0.273 | 0.007 |
| NUMBL | cg08450982 | 0.661 | 0.012 | 0.538 | 0.007 | 0.484 | 0.021 | 0.374 | 0.005 |
| CCDC57 | cg02962602 | 1.173 | 0.011 | 1.083 | 0.038 | 0.774 | 0.016 | 0.663 | 0.006 |
| C17orf81 | cg07389922 | 0.458 | 0.009 | 0.364 | 0.011 | 0.334 | 0.007 | 0.263 | 0.014 |
| SYT6 | cg05368341 | 0.453 | 0.034 | 0.419 | 0.026 | 0.263 | 0.024 | 0.289 | 0.004 |
| NXF2 | cg00280894 | 0.576 | 0.005 | 0.510 | 0.017 | 0.371 | 0.014 | 0.341 | 0.027 |
| BAIAP3 | cg26499611 | 1.101 | 0.006 | 1.047 | 0.042 | 0.738 | 0.018 | 0.602 | 0.014 |

TABLE 15-continued

| Gene | Gene ID | sh-ctrl Mean | sh-ctrl SEM | sh-ctrl + 5aza Mean | sh-ctrl + 5aza SEM | sh-3B Mean | sh-3B SEM | sh-3b + 5aza Mean | sh-3b + 5aza SEM |
|---|---|---|---|---|---|---|---|---|---|
| WNT7A | cg04969808 | 0.308 | 0.004 | 0.212 | 0.012 | 0.217 | 0.013 | 0.204 | 0.012 |
| RGS20 | cg00582628 | 0.636 | 0.043 | 0.610 | 0.014 | 0.408 | 0.008 | 0.359 | 0.005 |
| BCL7C | cg22377963 | 0.605 | 0.004 | 0.520 | 0.021 | 0.433 | 0.007 | 0.333 | 0.008 |
| ZNF511 | cg15856055 | 1.043 | 0.003 | 0.888 | 0.021 | 0.719 | 0.001 | 0.595 | 0.004 |
| C16orf50 | cg09212468 | 0.687 | 0.008 | 0.655 | 0.016 | 0.440 | 0.016 | 0.388 | 0.014 |
| ZBTB8 | cg11619390 | 0.816 | 0.011 | 0.734 | 0.011 | 0.538 | 0.004 | 0.466 | 0.002 |
| C12orf34 | cg02351381 | 0.893 | 0.022 | 0.846 | 0.007 | 0.581 | 0.031 | 0.499 | 0.009 |
| LRRC50 | cg19706682 | 0.833 | 0.047 | 0.738 | 0.029 | 0.601 | 0.023 | 0.446 | 0.010 |
| MRPL42 | cg20425293 | 0.525 | 0.018 | 0.416 | 0.022 | 0.390 | 0.010 | 0.295 | 0.006 |
| APH1B | cg17207590 | 0.774 | 0.003 | 0.693 | 0.031 | 0.485 | 0.010 | 0.463 | 0.002 |
| GOLT1A | cg24798047 | 0.427 | 0.011 | 0.377 | 0.011 | 0.291 | 0.014 | 0.239 | 0.010 |
| DLX1 | cg15236866 | 0.637 | 0.009 | 0.552 | 0.018 | 0.412 | 0.005 | 0.377 | 0.015 |
| C1orf176 | cg26776069 | 0.193 | 0.008 | 0.160 | 0.006 | 0.122 | 0.006 | 0.120 | 0.011 |
| RAPGEF3 | cg09114799 | 0.717 | 0.001 | 0.634 | 0.018 | 0.489 | 0.029 | 0.401 | 0.024 |
| WIPI1 | cg25661781 | 0.468 | 0.013 | 0.434 | 0.022 | 0.304 | 0.013 | 0.264 | 0.023 |
| C8orf53 | cg17256555 | 0.634 | 0.006 | 0.529 | 0.015 | 0.444 | 0.003 | 0.360 | 0.014 |
| SLC45A3 | cg11455040 | 0.494 | 0.009 | 0.441 | 0.023 | 0.335 | 0.028 | 0.275 | 0.017 |
| STMN1 | cg23323671 | 0.678 | 0.016 | 0.630 | 0.025 | 0.472 | 0.030 | 0.361 | 0.004 |
| TRADD | cg01025842 | 0.341 | 0.010 | 0.330 | 0.009 | 0.213 | 0.010 | 0.193 | 0.007 |
| MGC23244 | cg14117297 | 0.775 | 0.049 | 0.725 | 0.025 | 0.537 | 0.052 | 0.412 | 0.004 |
| RPL26L1 | cg12936220 | 0.411 | 0.007 | 0.321 | 0.030 | 0.267 | 0.004 | 0.260 | 0.014 |
| BTBD4 | cg21291985 | 0.933 | 0.010 | 0.777 | 0.026 | 0.665 | 0.010 | 0.520 | 0.027 |
| FBLIM1 | cg07846167 | 0.498 | 0.001 | 0.435 | 0.010 | 0.374 | 0.023 | 0.259 | 0.010 |
| WASF3 | cg09185773 | 0.382 | 0.014 | 0.318 | 0.022 | 0.229 | 0.014 | 0.249 | 0.011 |
| TWIST1 | cg09674215 | 0.631 | 0.010 | 0.514 | 0.021 | 0.445 | 0.036 | 0.359 | 0.005 |
| TLR2 | cg19037167 | 0.356 | 0.012 | 0.316 | 0.027 | 0.236 | 0.009 | 0.201 | 0.008 |
| TSNARE1 | cg09628199 | 0.433 | 0.021 | 0.324 | 0.025 | 0.313 | 0.007 | 0.257 | 0.008 |
| TMOD2 | cg00919857 | 0.324 | 0.011 | 0.265 | 0.016 | 0.221 | 0.012 | 0.189 | 0.013 |
| FBXW10 | cg10762615 | 0.851 | 0.014 | 0.742 | 0.010 | 0.574 | 0.007 | 0.478 | 0.008 |
| SNX14 | cg24284910 | 0.494 | 0.008 | 0.461 | 0.008 | 0.312 | 0.020 | 0.281 | 0.011 |
| BCL2 | cg17602451 | 0.433 | 0.023 | 0.379 | 0.034 | 0.292 | 0.004 | 0.242 | 0.017 |
| FLJ37396 | cg16075940 | 0.765 | 0.013 | 0.662 | 0.020 | 0.521 | 0.008 | 0.426 | 0.023 |
| HOXC11 | cg07123069 | 0.322 | 0.003 | 0.258 | 0.013 | 0.204 | 0.011 | 0.203 | 0.004 |
| BDKRB2 | cg08328671 | 0.793 | 0.007 | 0.681 | 0.025 | 0.563 | 0.023 | 0.431 | 0.025 |
| TRPV3 | cg10137010 | 1.058 | 0.006 | 0.901 | 0.004 | 0.796 | 0.022 | 0.553 | 0.016 |
| BCDO2 | cg02119229 | 0.346 | 0.004 | 0.299 | 0.026 | 0.234 | 0.009 | 0.193 | 0.008 |
| KIAA1944 | cg13234863 | 0.379 | 0.015 | 0.325 | 0.012 | 0.248 | 0.007 | 0.219 | 0.006 |
| CHFR | cg02519218 | 0.555 | 0.013 | 0.456 | 0.005 | 0.399 | 0.024 | 0.305 | 0.012 |
| DAB2IP | cg24794433 | 1.026 | 0.013 | 0.946 | 0.022 | 0.697 | 0.025 | 0.547 | 0.009 |
| BAD | cg13620770 | 1.017 | 0.009 | 0.904 | 0.047 | 0.689 | 0.024 | 0.555 | 0.008 |
| JAG2 | cg27177839 | 0.626 | 0.032 | 0.524 | 0.021 | 0.412 | 0.009 | 0.365 | 0.023 |
| CGI-09 | cg27367554 | 0.177 | 0.011 | 0.108 | 0.004 | 0.136 | 0.011 | 0.118 | 0.004 |
| PIN1 | cg02615157 | 0.400 | 0.015 | 0.343 | 0.019 | 0.261 | 0.022 | 0.230 | 0.012 |
| SMCP | cg21948655 | 0.889 | 0.008 | 0.808 | 0.011 | 0.536 | 0.019 | 0.530 | 0.036 |
| CMTM8 | cg01617750 | 0.688 | 0.017 | 0.591 | 0.015 | 0.472 | 0.012 | 0.378 | 0.008 |
| STXBP2 | cg26884154 | 0.368 | 0.002 | 0.275 | 0.023 | 0.259 | 0.016 | 0.218 | 0.003 |
| DENND3 | cg16425577 | 0.805 | 0.026 | 0.720 | 0.035 | 0.516 | 0.015 | 0.455 | 0.015 |
| SDCCAG3 | cg15583058 | 0.966 | 0.013 | 0.821 | 0.025 | 0.667 | 0.020 | 0.530 | 0.009 |
| HRIHFB2122 | cg06521852 | 0.484 | 0.009 | 0.393 | 0.025 | 0.336 | 0.007 | 0.272 | 0.011 |
| DUSP5 | cg20925954 | 0.639 | 0.022 | 0.551 | 0.010 | 0.422 | 0.034 | 0.360 | 0.006 |
| SNTB2 | cg08461397 | 0.493 | 0.019 | 0.473 | 0.025 | 0.310 | 0.010 | 0.271 | 0.010 |
| MOSC1 | cg07185695 | 0.298 | 0.003 | 0.263 | 0.022 | 0.193 | 0.007 | 0.167 | 0.007 |
| XAB1 | cg21144587 | 0.371 | 0.008 | 0.307 | 0.011 | 0.272 | 0.027 | 0.198 | 0.003 |
| SFRP5 | cg09874752 | 0.355 | 0.011 | 0.313 | 0.009 | 0.238 | 0.004 | 0.194 | 0.008 |
| GOLGA1 | cg24412846 | 0.636 | 0.013 | 0.589 | 0.026 | 0.402 | 0.009 | 0.354 | 0.009 |
| OXTR | cg25140571 | 0.641 | 0.029 | 0.585 | 0.021 | 0.372 | 0.024 | 0.390 | 0.019 |
| TBC1D5 | cg01765641 | 0.982 | 0.012 | 0.884 | 0.010 | 0.662 | 0.014 | 0.527 | 0.011 |
| ITGA8 | cg13492340 | 0.395 | 0.020 | 0.360 | 0.013 | 0.258 | 0.004 | 0.215 | 0.001 |
| DEFB126 | cg20305726 | 0.721 | 0.020 | 0.675 | 0.004 | 0.458 | 0.012 | 0.395 | 0.001 |
| OR1G1 | cg27622610 | 0.723 | 0.011 | 0.710 | 0.040 | 0.435 | 0.002 | 0.405 | 0.015 |
| NPTX1 | cg17775235 | 0.500 | 0.025 | 0.467 | 0.031 | 0.333 | 0.013 | 0.264 | 0.019 |
| SLC22A18 | cg24528523 | 0.608 | 0.010 | 0.486 | 0.015 | 0.386 | 0.018 | 0.370 | 0.026 |
| DLX2 | cg02014107 | 0.735 | 0.037 | 0.660 | 0.038 | 0.473 | 0.015 | 0.407 | 0.017 |
| SLC37A3 | cg15002187 | 0.373 | 0.016 | 0.263 | 0.006 | 0.281 | 0.003 | 0.215 | 0.006 |
| P2RY2 | cg04388983 | 0.524 | 0.038 | 0.505 | 0.018 | 0.305 | 0.009 | 0.305 | 0.018 |
| RELB | cg02727285 | 0.651 | 0.014 | 0.623 | 0.066 | 0.395 | 0.004 | 0.366 | 0.009 |
| HGF | cg08005849 | 1.030 | 0.004 | 0.907 | 0.024 | 0.647 | 0.002 | 0.589 | 0.003 |
| PEX6 | cg01125463 | 0.449 | 0.020 | 0.395 | 0.023 | 0.285 | 0.027 | 0.255 | 0.025 |
| AK1 | cg09092161 | 0.802 | 0.029 | 0.739 | 0.028 | 0.583 | 0.023 | 0.398 | 0.025 |
| ISG20L2 | cg00392257 | 0.611 | 0.001 | 0.543 | 0.023 | 0.401 | 0.008 | 0.334 | 0.022 |
| ELOVL1 | cg16858125 | 0.914 | 0.006 | 0.841 | 0.029 | 0.561 | 0.026 | 0.518 | 0.027 |
| SPATA4 | cg23322316 | 0.378 | 0.013 | 0.280 | 0.015 | 0.241 | 0.018 | 0.242 | 0.011 |
| DYRK1B | cg10294836 | 1.145 | 0.041 | 1.037 | 0.031 | 0.732 | 0.012 | 0.630 | 0.008 |
| MGC31967 | cg11326613 | 0.661 | 0.010 | 0.592 | 0.014 | 0.411 | 0.002 | 0.376 | 0.011 |
| EDG8 | cg24807354 | 0.654 | 0.010 | 0.595 | 0.036 | 0.447 | 0.018 | 0.339 | 0.010 |

TABLE 15-continued

| Gene | Gene ID | sh-ctrl Mean | sh-ctrl SEM | sh-ctrl + 5aza Mean | sh-ctrl + 5aza SEM | sh-3B Mean | sh-3B SEM | sh-3b + 5aza Mean | sh-3b + 5aza SEM |
|---|---|---|---|---|---|---|---|---|---|
| MAN2A2 | cg12984356 | 0.453 | 0.001 | 0.357 | 0.009 | 0.303 | 0.011 | 0.263 | 0.015 |
| SCG2 | cg23988310 | 0.841 | 0.001 | 0.754 | 0.037 | 0.559 | 0.015 | 0.449 | 0.025 |
| PER1 | cg16545079 | 0.366 | 0.023 | 0.302 | 0.013 | 0.261 | 0.005 | 0.195 | 0.003 |
| MTHFS | cg02196730 | 0.324 | 0.022 | 0.224 | 0.010 | 0.237 | 0.007 | 0.193 | 0.008 |
| C1orf114 | cg13958426 | 0.621 | 0.007 | 0.608 | 0.028 | 0.371 | 0.017 | 0.345 | 0.006 |
| WNT2 | cg01830294 | 0.631 | 0.019 | 0.588 | 0.050 | 0.414 | 0.004 | 0.332 | 0.013 |
| 10-Sep | cg03552103 | 0.736 | 0.014 | 0.629 | 0.055 | 0.474 | 0.017 | 0.416 | 0.027 |
| HPS6 | cg02840794 | 0.492 | 0.024 | 0.404 | 0.018 | 0.388 | 0.028 | 0.244 | 0.024 |
| EFNB1 | cg12753358 | 0.480 | 0.018 | 0.383 | 0.013 | 0.335 | 0.009 | 0.265 | 0.004 |
| SFRP4 | cg08261094 | 0.583 | 0.018 | 0.523 | 0.017 | 0.371 | 0.040 | 0.321 | 0.028 |
| KCNS1 | cg06288351 | 0.501 | 0.009 | 0.420 | 0.012 | 0.343 | 0.007 | 0.271 | 0.001 |
| SCRIB | cg08996502 | 0.622 | 0.024 | 0.614 | 0.019 | 0.405 | 0.052 | 0.319 | 0.009 |
| SERPINB1 | cg27056119 | 0.393 | 0.027 | 0.377 | 0.022 | 0.258 | 0.017 | 0.203 | 0.014 |
| LCE1F | cg23413307 | 0.717 | 0.027 | 0.637 | 0.016 | 0.474 | 0.008 | 0.384 | 0.035 |
| LRRC8E | cg21215336 | 0.453 | 0.031 | 0.315 | 0.029 | 0.324 | 0.003 | 0.271 | 0.013 |
| PHACTR4 | cg08123074 | 0.792 | 0.013 | 0.696 | 0.026 | 0.484 | 0.011 | 0.457 | 0.025 |
| GMPPB | cg15565533 | 0.327 | 0.003 | 0.262 | 0.010 | 0.210 | 0.013 | 0.193 | 0.008 |
| HOXA11 | cg17950095 | 0.598 | 0.016 | 0.527 | 0.040 | 0.389 | 0.019 | 0.325 | 0.013 |
| FLJ32921 | cg22282672 | 0.732 | 0.006 | 0.651 | 0.020 | 0.452 | 0.003 | 0.414 | 0.034 |
| KCNQ1 | cg19779211 | 0.593 | 0.003 | 0.565 | 0.022 | 0.329 | 0.020 | 0.358 | 0.014 |
| ARRB2 | cg23779331 | 0.611 | 0.009 | 0.532 | 0.012 | 0.405 | 0.007 | 0.329 | 0.007 |
| BAZ2A | cg25683012 | 0.599 | 0.012 | 0.493 | 0.013 | 0.435 | 0.015 | 0.312 | 0.010 |
| FAM5B | cg13843613 | 0.222 | 0.007 | 0.194 | 0.012 | 0.131 | 0.007 | 0.132 | 0.009 |
| LIN7B | cg00430945 | 0.778 | 0.010 | 0.738 | 0.024 | 0.475 | 0.018 | 0.426 | 0.019 |
| TRIM58 | cg20855565 | 0.301 | 0.009 | 0.239 | 0.019 | 0.193 | 0.010 | 0.176 | 0.005 |
| LOX | cg09262269 | 0.531 | 0.026 | 0.437 | 0.043 | 0.345 | 0.007 | 0.302 | 0.016 |
| DAB1 | cg06710648 | 0.755 | 0.019 | 0.650 | 0.007 | 0.482 | 0.019 | 0.421 | 0.008 |
| BRUNOL6 | cg21801378 | 0.171 | 0.003 | 0.148 | 0.011 | 0.096 | 0.002 | 0.108 | 0.004 |
| RASGRF1 | cg15156078 | 0.493 | 0.008 | 0.408 | 0.035 | 0.302 | 0.004 | 0.293 | 0.033 |
| FLJ39370 | cg10525488 | 0.653 | 0.012 | 0.589 | 0.022 | 0.403 | 0.008 | 0.362 | 0.016 |
| ANXA5 | cg03354519 | 0.421 | 0.020 | 0.346 | 0.029 | 0.280 | 0.004 | 0.232 | 0.011 |
| CYP4F3 | cg27067618 | 0.687 | 0.011 | 0.604 | 0.029 | 0.445 | 0.019 | 0.372 | 0.008 |
| C2orf32 | cg10908369 | 0.645 | 0.019 | 0.560 | 0.033 | 0.393 | 0.015 | 0.370 | 0.023 |
| HYDIN | cg20977864 | 0.970 | 0.008 | 0.814 | 0.062 | 0.636 | 0.024 | 0.532 | 0.020 |
| SYN1 | cg13839778 | 0.318 | 0.015 | 0.232 | 0.011 | 0.214 | 0.008 | 0.189 | 0.009 |
| CNP | cg23866755 | 0.816 | 0.008 | 0.703 | 0.047 | 0.517 | 0.001 | 0.454 | 0.023 |
| NFE2L3 | cg14534464 | 0.535 | 0.021 | 0.533 | 0.021 | 0.341 | 0.009 | 0.271 | 0.017 |
| AGC1 | cg06937608 | 0.483 | 0.029 | 0.428 | 0.025 | 0.309 | 0.016 | 0.261 | 0.003 |
| MYCL1 | cg27650434 | 0.439 | 0.018 | 0.371 | 0.018 | 0.277 | 0.013 | 0.247 | 0.011 |
| LOC132321 | cg03916421 | 0.740 | 0.015 | 0.615 | 0.020 | 0.477 | 0.007 | 0.414 | 0.009 |
| BAI2 | cg01653445 | 0.420 | 0.011 | 0.349 | 0.004 | 0.292 | 0.023 | 0.220 | 0.006 |
| SNAPC2 | cg24391122 | 0.500 | 0.012 | 0.413 | 0.029 | 0.355 | 0.015 | 0.259 | 0.008 |
| LGALS3 | cg17403875 | 0.398 | 0.014 | 0.358 | 0.027 | 0.273 | 0.007 | 0.202 | 0.015 |
| LAMA3 | cg14894144 | 0.415 | 0.025 | 0.334 | 0.016 | 0.260 | 0.012 | 0.241 | 0.002 |
| CA5B | cg25376316 | 0.284 | 0.009 | 0.225 | 0.008 | 0.182 | 0.006 | 0.164 | 0.010 |
| MRPS34 | cg01729862 | 0.462 | 0.009 | 0.395 | 0.001 | 0.305 | 0.031 | 0.246 | 0.014 |
| PTX3 | cg15565872 | 0.635 | 0.010 | 0.558 | 0.025 | 0.404 | 0.005 | 0.344 | 0.013 |
| FHIT | cg22215728 | 0.634 | 0.012 | 0.555 | 0.020 | 0.396 | 0.024 | 0.349 | 0.012 |
| B4GALNT3 | cg11065385 | 0.686 | 0.005 | 0.594 | 0.016 | 0.435 | 0.022 | 0.375 | 0.008 |
| SCARA5 | cg07634191 | 0.577 | 0.016 | 0.553 | 0.011 | 0.352 | 0.014 | 0.307 | 0.011 |
| MIB1 | cg12985418 | 0.280 | 0.003 | 0.209 | 0.001 | 0.177 | 0.010 | 0.171 | 0.003 |
| RBM17 | cg00242839 | 0.650 | 0.008 | 0.574 | 0.048 | 0.368 | 0.031 | 0.390 | 0.035 |
| ESR1 | cg11251858 | 0.491 | 0.002 | 0.439 | 0.019 | 0.309 | 0.012 | 0.265 | 0.007 |
| TRIP6 | cg01274660 | 0.305 | 0.019 | 0.236 | 0.011 | 0.208 | 0.012 | 0.169 | 0.007 |
| COL22A1 | cg03396229 | 0.603 | 0.036 | 0.542 | 0.024 | 0.369 | 0.017 | 0.331 | 0.005 |
| C1orf132 | cg11844110 | 0.315 | 0.018 | 0.227 | 0.008 | 0.201 | 0.002 | 0.195 | 0.006 |
| PRSS12 | cg21208104 | 0.346 | 0.014 | 0.291 | 0.019 | 0.197 | 0.016 | 0.213 | 0.012 |
| INPP5E | cg13306784 | 0.510 | 0.012 | 0.421 | 0.016 | 0.318 | 0.009 | 0.291 | 0.002 |
| AUP1 | cg04576203 | 0.818 | 0.012 | 0.687 | 0.012 | 0.563 | 0.019 | 0.425 | 0.008 |
| BCAP31 | cg27453644 | 0.974 | 0.011 | 0.820 | 0.030 | 0.639 | 0.008 | 0.524 | 0.022 |
| MPP6 | cg13931228 | 0.324 | 0.020 | 0.244 | 0.014 | 0.233 | 0.005 | 0.175 | 0.013 |
| EML2 | cg20427879 | 0.507 | 0.030 | 0.483 | 0.036 | 0.295 | 0.016 | 0.281 | 0.003 |
| CMTM4 | cg18693704 | 0.622 | 0.016 | 0.505 | 0.032 | 0.412 | 0.021 | 0.339 | 0.013 |
|  | cg00718513 | 0.732 | 0.013 | 0.651 | 0.026 | 0.442 | 0.007 | 0.407 | 0.024 |
| BAALC | cg10918202 | 0.418 | 0.002 | 0.324 | 0.021 | 0.268 | 0.005 | 0.242 | 0.014 |
| ZNF212 | cg06815817 | 0.364 | 0.012 | 0.327 | 0.005 | 0.208 | 0.003 | 0.213 | 0.013 |
| FLJ43752 | cg08301503 | 0.424 | 0.027 | 0.409 | 0.008 | 0.258 | 0.006 | 0.223 | 0.014 |
| ALX4 | cg27318318 | 0.371 | 0.018 | 0.348 | 0.038 | 0.231 | 0.011 | 0.194 | 0.011 |
| IGF2AS | cg17773950 | 0.303 | 0.021 | 0.218 | 0.006 | 0.202 | 0.010 | 0.179 | 0.005 |
| ZNF546 | cg14213992 | 0.595 | 0.007 | 0.539 | 0.022 | 0.368 | 0.013 | 0.319 | 0.006 |
| SAMD11 | cg14324200 | 0.496 | 0.025 | 0.438 | 0.015 | 0.320 | 0.016 | 0.261 | 0.010 |
| SERPINB8 | cg00615915 | 0.627 | 0.005 | 0.540 | 0.020 | 0.376 | 0.023 | 0.355 | 0.017 |
| IGF2AS | cg12322132 | 0.526 | 0.021 | 0.464 | 0.027 | 0.337 | 0.008 | 0.276 | 0.011 |
| UBE2R2 | cg19367388 | 0.323 | 0.008 | 0.273 | 0.014 | 0.216 | 0.009 | 0.169 | 0.007 |
| CYP4X1 | cg13158571 | 0.492 | 0.016 | 0.429 | 0.020 | 0.304 | 0.016 | 0.268 | 0.004 |

TABLE 15-continued

| Gene | Gene ID | sh-ctrl | | sh-ctrl + 5aza | | sh-3B | | sh-3b + 5aza | |
|---|---|---|---|---|---|---|---|---|---|
| | | Mean | SEM | Mean | SEM | Mean | SEM | Mean | SEM |
| MSX1 | cg20161179 | 0.448 | 0.002 | 0.381 | 0.014 | 0.284 | 0.012 | 0.242 | 0.015 |
| GABRA4 | cg03593419 | 0.376 | 0.011 | 0.306 | 0.029 | 0.268 | 0.008 | 0.191 | 0.020 |
| LHB | cg20173259 | 0.751 | 0.006 | 0.734 | 0.019 | 0.484 | 0.008 | 0.370 | 0.024 |
| PUSL1 | cg00262415 | 0.376 | 0.016 | 0.325 | 0.011 | 0.248 | 0.007 | 0.195 | 0.003 |
| OR1E2 | cg14314889 | 0.421 | 0.018 | 0.325 | 0.018 | 0.268 | 0.016 | 0.242 | 0.007 |
| KLK10 | cg09226684 | 0.692 | 0.013 | 0.674 | 0.018 | 0.407 | 0.015 | 0.367 | 0.019 |
| IFI30 | cg04096365 | 0.670 | 0.014 | 0.514 | 0.018 | 0.459 | 0.020 | 0.363 | 0.009 |
| FGF20 | cg14605021 | 0.361 | 0.004 | 0.279 | 0.013 | 0.242 | 0.010 | 0.198 | 0.010 |
| PWWP2 | cg00259755 | 0.490 | 0.012 | 0.467 | 0.023 | 0.294 | 0.014 | 0.259 | 0.012 |
| RIN1 | cg05998426 | 0.637 | 0.020 | 0.468 | 0.024 | 0.519 | 0.002 | 0.315 | 0.014 |
| OVOL1 | cg03681481 | 0.476 | 0.009 | 0.401 | 0.032 | 0.309 | 0.005 | 0.252 | 0.008 |
| ESR1 | cg15626350 | 0.569 | 0.020 | 0.503 | 0.054 | 0.362 | 0.006 | 0.297 | 0.014 |
| GLT1D1 | cg11877382 | 0.844 | 0.008 | 0.783 | 0.028 | 0.511 | 0.024 | 0.446 | 0.008 |
| JPH2 | cg02551396 | 0.392 | 0.018 | 0.286 | 0.026 | 0.267 | 0.014 | 0.220 | 0.005 |
| PRSS27 | cg20797766 | 0.312 | 0.006 | 0.214 | 0.011 | 0.220 | 0.001 | 0.179 | 0.002 |
| GAL3ST4 | cg25717844 | 0.855 | 0.014 | 0.730 | 0.025 | 0.515 | 0.017 | 0.476 | 0.053 |
| OR1E1 | cg14043602 | 0.433 | 0.005 | 0.337 | 0.021 | 0.272 | 0.009 | 0.248 | 0.006 |
| HOXC4 | cg21487207 | 0.871 | 0.028 | 0.816 | 0.015 | 0.530 | 0.009 | 0.455 | 0.002 |
| IL1F8 | cg10479672 | 0.558 | 0.008 | 0.518 | 0.026 | 0.333 | 0.016 | 0.297 | 0.022 |
| MSX1 | cg01785568 | 0.684 | 0.028 | 0.594 | 0.072 | 0.442 | 0.014 | 0.353 | 0.009 |
| LYPD3 | cg15014458 | 0.389 | 0.005 | 0.300 | 0.018 | 0.242 | 0.008 | 0.225 | 0.003 |
| HOXB3 | cg12910797 | 0.671 | 0.021 | 0.616 | 0.003 | 0.426 | 0.037 | 0.339 | 0.015 |
| EXTL1 | cg04629204 | 0.493 | 0.002 | 0.434 | 0.015 | 0.334 | 0.009 | 0.242 | 0.013 |
| HSPA2 | cg16319578 | 0.570 | 0.040 | 0.554 | 0.048 | 0.350 | 0.032 | 0.286 | 0.006 |
| hCAP-D3 | cg26723847 | 0.879 | 0.010 | 0.734 | 0.008 | 0.613 | 0.011 | 0.437 | 0.014 |
| MC3R | cg13588354 | 0.504 | 0.012 | 0.484 | 0.004 | 0.304 | 0.005 | 0.259 | 0.005 |
| CDKN2A | cg12840719 | 0.647 | 0.031 | 0.571 | 0.034 | 0.389 | 0.029 | 0.349 | 0.009 |
| TMEM115 | cg10061247 | 0.443 | 0.007 | 0.359 | 0.013 | 0.295 | 0.011 | 0.231 | 0.001 |
| C3orf57 | cg18919097 | 0.445 | 0.010 | 0.427 | 0.024 | 0.257 | 0.005 | 0.236 | 0.008 |
| MGC39545 | cg19286604 | 0.412 | 0.036 | 0.359 | 0.031 | 0.239 | 0.022 | 0.230 | 0.005 |
| SLC12A7 | cg23091824 | 0.867 | 0.014 | 0.683 | 0.005 | 0.602 | 0.032 | 0.445 | 0.012 |
| FLJ38377 | cg25784308 | 0.508 | 0.018 | 0.369 | 0.019 | 0.325 | 0.006 | 0.295 | 0.012 |
| HTR7 | cg06291867 | 0.609 | 0.007 | 0.588 | 0.016 | 0.351 | 0.004 | 0.322 | 0.011 |
| SULT1A3 | cg15415545 | 0.360 | 0.011 | 0.291 | 0.022 | 0.252 | 0.011 | 0.180 | 0.007 |
| SYT5 | cg10080004 | 1.009 | 0.031 | 0.972 | 0.011 | 0.606 | 0.013 | 0.516 | 0.008 |
| MGC50721 | cg15703512 | 0.444 | 0.012 | 0.354 | 0.026 | 0.302 | 0.007 | 0.230 | 0.011 |
| SH3GL2 | cg17398595 | 0.503 | 0.008 | 0.467 | 0.012 | 0.289 | 0.005 | 0.273 | 0.005 |
| PAK3 | cg14688956 | 0.257 | 0.009 | 0.201 | 0.002 | 0.157 | 0.004 | 0.147 | 0.011 |
| FLJ13236 | cg07028869 | 0.693 | 0.008 | 0.588 | 0.015 | 0.418 | 0.021 | 0.378 | 0.008 |
| SRCRB4D | cg13594711 | 0.736 | 0.024 | 0.616 | 0.010 | 0.484 | 0.013 | 0.377 | 0.033 |
| BARX2 | cg08893585 | 0.412 | 0.013 | 0.377 | 0.028 | 0.240 | 0.019 | 0.222 | 0.024 |
| SARS | cg13619408 | 0.400 | 0.008 | 0.333 | 0.015 | 0.249 | 0.007 | 0.215 | 0.008 |
| F2RL2 | cg08241785 | 0.877 | 0.020 | 0.675 | 0.018 | 0.626 | 0.025 | 0.444 | 0.021 |
| ITSN2 | cg25477928 | 0.406 | 0.027 | 0.285 | 0.007 | 0.285 | 0.005 | 0.223 | 0.007 |
| RNF39 | cg26014796 | 0.476 | 0.033 | 0.364 | 0.024 | 0.293 | 0.020 | 0.272 | 0.015 |
| B4GALNT4 | cg24194132 | 0.704 | 0.021 | 0.611 | 0.017 | 0.429 | 0.025 | 0.373 | 0.005 |
| GABRA1 | cg02065387 | 0.902 | 0.017 | 0.865 | 0.094 | 0.516 | 0.031 | 0.476 | 0.022 |
| TRIM54 | cg25218351 | 0.664 | 0.019 | 0.477 | 0.012 | 0.457 | 0.027 | 0.362 | 0.005 |
| KCNH7 | cg19965810 | 0.879 | 0.034 | 0.867 | 0.024 | 0.543 | 0.009 | 0.428 | 0.008 |
| HSPA5BP1 | cg07962043 | 0.521 | 0.041 | 0.389 | 0.021 | 0.340 | 0.020 | 0.286 | 0.010 |
| CCDC47 | cg20099806 | 0.717 | 0.008 | 0.673 | 0.014 | 0.402 | 0.018 | 0.389 | 0.016 |
| F5 | cg09891761 | 0.394 | 0.002 | 0.353 | 0.021 | 0.248 | 0.015 | 0.198 | 0.004 |
| ZNFN1A3 | cg13878456 | 0.727 | 0.010 | 0.683 | 0.007 | 0.427 | 0.015 | 0.377 | 0.003 |
| DEF6 | cg07294541 | 0.257 | 0.010 | 0.183 | 0.018 | 0.167 | 0.008 | 0.145 | 0.001 |
| SLC35B3 | cg09548084 | 0.503 | 0.017 | 0.440 | 0.022 | 0.309 | 0.024 | 0.260 | 0.001 |
| CLU | cg19549068 | 0.351 | 0.032 | 0.228 | 0.008 | 0.237 | 0.004 | 0.208 | 0.007 |
| ZNF511 | cg17770886 | 1.100 | 0.032 | 0.877 | 0.029 | 0.707 | 0.009 | 0.580 | 0.020 |
| TMEM15 | cg13812587 | 0.376 | 0.008 | 0.293 | 0.028 | 0.249 | 0.013 | 0.196 | 0.019 |
| SRGAP1 | cg07973246 | 0.327 | 0.007 | 0.230 | 0.004 | 0.192 | 0.008 | 0.206 | 0.002 |
| PDCD6IP | cg12971958 | 0.353 | 0.012 | 0.296 | 0.014 | 0.249 | 0.041 | 0.169 | 0.011 |
| RASD2 | cg14473016 | 0.434 | 0.009 | 0.380 | 0.018 | 0.274 | 0.003 | 0.218 | 0.009 |
| PIB5PA | cg27324619 | 1.032 | 0.012 | 0.848 | 0.029 | 0.667 | 0.022 | 0.529 | 0.003 |
| SMOX | cg15579370 | 0.360 | 0.004 | 0.258 | 0.034 | 0.240 | 0.015 | 0.198 | 0.012 |
| IL7 | cg23512958 | 0.623 | 0.022 | 0.567 | 0.032 | 0.351 | 0.027 | 0.338 | 0.006 |
| PRND | cg16977257 | 0.393 | 0.017 | 0.320 | 0.021 | 0.248 | 0.008 | 0.206 | 0.007 |
| CBLN2 | cg21902544 | 0.581 | 0.008 | 0.503 | 0.022 | 0.354 | 0.022 | 0.302 | 0.025 |
| SPRR1A | cg04505023 | 0.689 | 0.014 | 0.646 | 0.053 | 0.424 | 0.014 | 0.340 | 0.008 |
| MATN2 | cg16202564 | 0.532 | 0.014 | 0.437 | 0.035 | 0.312 | 0.020 | 0.295 | 0.010 |
| PRRT2 | cg05995267 | 0.522 | 0.024 | 0.367 | 0.020 | 0.350 | 0.013 | 0.287 | 0.013 |
| UBL5 | cg17704839 | 0.385 | 0.023 | 0.368 | 0.028 | 0.207 | 0.008 | 0.211 | 0.021 |
| GRIN1 | cg03109047 | 0.578 | 0.001 | 0.542 | 0.010 | 0.364 | 0.009 | 0.278 | 0.006 |
| TINP1 | cg20277250 | 0.589 | 0.021 | 0.584 | 0.027 | 0.347 | 0.008 | 0.290 | 0.006 |
| ALOXE3 | cg10392768 | 0.394 | 0.030 | 0.267 | 0.014 | 0.251 | 0.012 | 0.234 | 0.024 |
| ACSL6 | cg19986872 | 0.685 | 0.007 | 0.637 | 0.009 | 0.422 | 0.020 | 0.336 | 0.009 |
| SPRR1A | cg06101324 | 0.766 | 0.012 | 0.763 | 0.032 | 0.459 | 0.012 | 0.372 | 0.005 |

TABLE 15-continued

| Gene | Gene ID | sh-ctrl Mean | sh-ctrl SEM | sh-ctrl + 5aza Mean | sh-ctrl + 5aza SEM | sh-3B Mean | sh-3B SEM | sh-3b + 5aza Mean | sh-3b + 5aza SEM |
|---|---|---|---|---|---|---|---|---|---|
| ISG20L2 | cg02833725 | 0.860 | 0.005 | 0.736 | 0.019 | 0.564 | 0.031 | 0.419 | 0.014 |
| C9orf9 | cg24293567 | 0.457 | 0.018 | 0.418 | 0.032 | 0.269 | 0.010 | 0.234 | 0.016 |
| CNN1 | cg12854483 | 0.718 | 0.022 | 0.563 | 0.032 | 0.498 | 0.024 | 0.354 | 0.017 |
| TOR3A | cg02709261 | 0.313 | 0.005 | 0.239 | 0.012 | 0.204 | 0.004 | 0.165 | 0.002 |
| UBE2L3 | cg25421647 | 0.597 | 0.018 | 0.535 | 0.034 | 0.353 | 0.019 | 0.308 | 0.004 |
| GEM | cg17943999 | 0.423 | 0.028 | 0.322 | 0.008 | 0.263 | 0.011 | 0.231 | 0.010 |
| PYGM | cg26884581 | 0.835 | 0.016 | 0.708 | 0.044 | 0.528 | 0.033 | 0.420 | 0.005 |
| MGC33367 | cg24642468 | 0.523 | 0.011 | 0.438 | 0.021 | 0.313 | 0.035 | 0.278 | 0.002 |
| HEYL | cg06154570 | 0.467 | 0.006 | 0.377 | 0.020 | 0.288 | 0.029 | 0.247 | 0.009 |
| DOK5 | cg09260441 | 0.450 | 0.010 | 0.366 | 0.021 | 0.276 | 0.003 | 0.238 | 0.008 |
| MSX1 | cg03717979 | 0.309 | 0.015 | 0.257 | 0.007 | 0.187 | 0.011 | 0.163 | 0.007 |
| BATF2 | cg17022914 | 0.445 | 0.010 | 0.310 | 0.011 | 0.276 | 0.017 | 0.258 | 0.010 |
| PARD6A | cg15426734 | 0.870 | 0.004 | 0.835 | 0.006 | 0.522 | 0.016 | 0.422 | 0.010 |
| GRP | cg23357981 | 0.437 | 0.025 | 0.376 | 0.043 | 0.273 | 0.002 | 0.218 | 0.011 |
| ATP6V1C2 | cg22243662 | 0.347 | 0.021 | 0.347 | 0.042 | 0.198 | 0.005 | 0.171 | 0.001 |
| PLAGL1 | cg25350411 | 0.494 | 0.022 | 0.391 | 0.034 | 0.287 | 0.006 | 0.275 | 0.021 |
| C20orf27 | cg14159818 | 0.267 | 0.008 | 0.227 | 0.005 | 0.169 | 0.005 | 0.132 | 0.014 |
| WDRPUH | cg25964007 | 0.256 | 0.017 | 0.240 | 0.011 | 0.143 | 0.013 | 0.133 | 0.010 |
| FLJ13909 | cg05832487 | 0.435 | 0.010 | 0.307 | 0.028 | 0.311 | 0.010 | 0.220 | 0.003 |
| ZNF276 | cg02609749 | 0.592 | 0.026 | 0.490 | 0.031 | 0.356 | 0.008 | 0.309 | 0.015 |
| MGC3020 | cg22609068 | 0.279 | 0.010 | 0.182 | 0.024 | 0.197 | 0.014 | 0.151 | 0.007 |
| LOX | cg02548238 | 0.620 | 0.022 | 0.513 | 0.026 | 0.378 | 0.014 | 0.319 | 0.013 |
| HECA | cg11498188 | 0.573 | 0.013 | 0.510 | 0.013 | 0.347 | 0.008 | 0.284 | 0.015 |
| KCNB1 | cg24507762 | 0.785 | 0.002 | 0.734 | 0.019 | 0.467 | 0.026 | 0.384 | 0.004 |
| ZNF571 | cg17333479 | 0.284 | 0.022 | 0.212 | 0.016 | 0.181 | 0.016 | 0.150 | 0.009 |
| TBX21 | cg20209009 | 0.419 | 0.019 | 0.358 | 0.025 | 0.252 | 0.012 | 0.213 | 0.009 |
| TLR4 | cg05429895 | 0.487 | 0.018 | 0.369 | 0.016 | 0.306 | 0.006 | 0.256 | 0.013 |
| EBI3 | cg19529363 | 0.645 | 0.008 | 0.499 | 0.021 | 0.428 | 0.006 | 0.320 | 0.008 |
| TTPA | cg23602533 | 0.488 | 0.030 | 0.424 | 0.009 | 0.267 | 0.015 | 0.266 | 0.018 |
| EPHX2 | cg24081819 | 0.473 | 0.005 | 0.392 | 0.015 | 0.289 | 0.008 | 0.241 | 0.006 |
| NMBR | cg17256157 | 0.345 | 0.020 | 0.305 | 0.012 | 0.179 | 0.009 | 0.197 | 0.019 |
| SH3GL1 | cg24923526 | 0.269 | 0.006 | 0.182 | 0.012 | 0.166 | 0.010 | 0.157 | 0.015 |
| DHDDS | cg06577005 | 0.468 | 0.019 | 0.404 | 0.028 | 0.272 | 0.011 | 0.241 | 0.008 |
| GCDH | cg19721215 | 0.282 | 0.008 | 0.217 | 0.011 | 0.177 | 0.001 | 0.146 | 0.011 |
| MAPK3 | cg08966293 | 0.486 | 0.001 | 0.381 | 0.009 | 0.308 | 0.005 | 0.246 | 0.005 |
| TM6SF1 | cg17018527 | 0.335 | 0.006 | 0.228 | 0.032 | 0.209 | 0.010 | 0.191 | 0.009 |
| CCDC60 | cg02498063 | 0.831 | 0.013 | 0.779 | 0.014 | 0.462 | 0.023 | 0.424 | 0.008 |
| ZNF507 | cg08084415 | 0.443 | 0.015 | 0.330 | 0.043 | 0.271 | 0.013 | 0.239 | 0.022 |
| APOE | cg08955609 | 0.526 | 0.016 | 0.488 | 0.038 | 0.314 | 0.027 | 0.253 | 0.005 |
| PTGFR | cg24022301 | 0.600 | 0.020 | 0.528 | 0.017 | 0.352 | 0.003 | 0.301 | 0.018 |
| FLJ20489 | cg12391174 | 0.552 | 0.025 | 0.452 | 0.011 | 0.354 | 0.032 | 0.269 | 0.015 |
| PRODH | cg08834018 | 0.496 | 0.020 | 0.377 | 0.036 | 0.321 | 0.022 | 0.250 | 0.017 |
| GPM6B | cg21229055 | 0.675 | 0.018 | 0.607 | 0.020 | 0.406 | 0.010 | 0.327 | 0.005 |
| SQRDL | cg17428950 | 0.678 | 0.003 | 0.652 | 0.036 | 0.405 | 0.019 | 0.318 | 0.011 |
| OSBPL2 | cg24587268 | 0.334 | 0.007 | 0.270 | 0.008 | 0.200 | 0.009 | 0.172 | 0.010 |
| CPNE9 | cg20051033 | 0.441 | 0.027 | 0.332 | 0.002 | 0.282 | 0.008 | 0.226 | 0.012 |
| SLC26A8 | cg15674432 | 0.530 | 0.025 | 0.414 | 0.033 | 0.315 | 0.018 | 0.281 | 0.005 |
| GNAS | cg01817393 | 0.836 | 0.028 | 0.733 | 0.005 | 0.451 | 0.026 | 0.451 | 0.021 |
| ZNF579 | cg15916628 | 0.815 | 0.003 | 0.764 | 0.002 | 0.468 | 0.008 | 0.399 | 0.016 |
| GRIA2 | cg25148589 | 0.771 | 0.019 | 0.716 | 0.020 | 0.461 | 0.013 | 0.366 | 0.014 |
| SSH3 | cg19192120 | 0.482 | 0.030 | 0.399 | 0.029 | 0.282 | 0.005 | 0.248 | 0.005 |
| HBEGF | cg20868410 | 0.295 | 0.020 | 0.212 | 0.012 | 0.167 | 0.013 | 0.174 | 0.008 |
| MGC50721 | cg27015931 | 0.769 | 0.001 | 0.674 | 0.023 | 0.478 | 0.010 | 0.364 | 0.010 |
| TBC1D21 | cg00427635 | 0.566 | 0.018 | 0.487 | 0.015 | 0.306 | 0.013 | 0.304 | 0.017 |
| SLC5A5 | cg01655355 | 0.785 | 0.017 | 0.578 | 0.032 | 0.560 | 0.007 | 0.372 | 0.030 |
| EFNB3 | cg01013324 | 0.261 | 0.018 | 0.191 | 0.017 | 0.165 | 0.008 | 0.136 | 0.009 |
| FLNB | cg08785215 | 0.297 | 0.002 | 0.229 | 0.034 | 0.166 | 0.007 | 0.166 | 0.000 |
| ZNF313 | cg02046340 | 0.423 | 0.009 | 0.368 | 0.004 | 0.247 | 0.015 | 0.209 | 0.010 |
| PRG2 | cg15640375 | 0.727 | 0.009 | 0.639 | 0.024 | 0.424 | 0.012 | 0.360 | 0.016 |
| CX36 | cg21053529 | 0.614 | 0.004 | 0.589 | 0.012 | 0.330 | 0.006 | 0.311 | 0.025 |
| CMKLR1 | cg06933965 | 0.876 | 0.007 | 0.821 | 0.024 | 0.539 | 0.010 | 0.399 | 0.014 |
| PANX2 | cg11896271 | 0.628 | 0.015 | 0.514 | 0.032 | 0.394 | 0.018 | 0.302 | 0.027 |
| LIMK2 | cg14086647 | 0.361 | 0.011 | 0.298 | 0.024 | 0.213 | 0.008 | 0.182 | 0.005 |
| GLRA1 | cg00059225 | 0.471 | 0.028 | 0.347 | 0.027 | 0.293 | 0.006 | 0.245 | 0.008 |
| SNFT | cg06150468 | 0.496 | 0.017 | 0.387 | 0.008 | 0.307 | 0.013 | 0.249 | 0.018 |
| KCNA3 | cg00995520 | 0.412 | 0.021 | 0.350 | 0.023 | 0.242 | 0.006 | 0.205 | 0.011 |
| PLEKHG5 | cg04818845 | 0.676 | 0.013 | 0.560 | 0.020 | 0.419 | 0.013 | 0.326 | 0.010 |
| WDR54 | cg10491648 | 0.597 | 0.006 | 0.559 | 0.020 | 0.351 | 0.008 | 0.281 | 0.021 |
| STARD8 | cg13370916 | 0.436 | 0.013 | 0.291 | 0.018 | 0.273 | 0.021 | 0.242 | 0.006 |
| CCDC60 | cg00230502 | 0.337 | 0.016 | 0.328 | 0.011 | 0.166 | 0.015 | 0.183 | 0.013 |
| CALCOCO2 | cg04154812 | 0.604 | 0.012 | 0.453 | 0.017 | 0.359 | 0.009 | 0.321 | 0.014 |
| ALOX15 | cg09872233 | 0.364 | 0.007 | 0.287 | 0.007 | 0.204 | 0.013 | 0.196 | 0.009 |
| OPRM1 | cg22719623 | 0.681 | 0.014 | 0.585 | 0.023 | 0.394 | 0.019 | 0.338 | 0.010 |
| ESAM | cg18170080 | 0.583 | 0.012 | 0.510 | 0.032 | 0.369 | 0.003 | 0.267 | 0.001 |
| MCHR2 | cg20134215 | 0.478 | 0.011 | 0.336 | 0.022 | 0.312 | 0.011 | 0.245 | 0.019 |

TABLE 15-continued

| Gene | Gene ID | sh-ctrl Mean | SEM | sh-ctrl + 5aza Mean | SEM | sh-3B Mean | SEM | sh-3b + 5aza Mean | SEM |
|---|---|---|---|---|---|---|---|---|---|
| SYT10 | cg00902195 | 0.400 | 0.030 | 0.366 | 0.039 | 0.227 | 0.022 | 0.195 | 0.020 |
| Gcom1 | cg00509616 | 0.379 | 0.009 | 0.294 | 0.003 | 0.247 | 0.016 | 0.182 | 0.008 |
| C3orf54 | cg03833566 | 0.582 | 0.024 | 0.460 | 0.043 | 0.367 | 0.043 | 0.282 | 0.021 |
| GATA4 | cg25216696 | 0.479 | 0.014 | 0.413 | 0.045 | 0.273 | 0.022 | 0.238 | 0.008 |
| F13A1 | cg14047667 | 0.776 | 0.031 | 0.720 | 0.033 | 0.412 | 0.009 | 0.396 | 0.013 |
| GRIK3 | cg06722633 | 0.397 | 0.031 | 0.355 | 0.015 | 0.236 | 0.017 | 0.187 | 0.010 |
| UNC84B | cg20652889 | 0.390 | 0.025 | 0.304 | 0.027 | 0.221 | 0.006 | 0.208 | 0.014 |
| TRAPPC1 | cg01837574 | 0.830 | 0.024 | 0.730 | 0.031 | 0.493 | 0.011 | 0.394 | 0.011 |
| FLJ20097 | cg27402949 | 0.273 | 0.008 | 0.160 | 0.007 | 0.180 | 0.003 | 0.160 | 0.007 |
| LOC284739 | cg12379775 | 0.639 | 0.013 | 0.607 | 0.057 | 0.344 | 0.035 | 0.316 | 0.031 |
| C1orf114 | cg08047907 | 0.622 | 0.043 | 0.556 | 0.013 | 0.348 | 0.003 | 0.307 | 0.006 |
| CELSR2 | cg27014642 | 0.535 | 0.009 | 0.435 | 0.016 | 0.351 | 0.028 | 0.245 | 0.019 |
| SUSD2 | cg03599338 | 0.444 | 0.021 | 0.292 | 0.012 | 0.282 | 0.013 | 0.240 | 0.006 |
| MGC23280 | cg10671802 | 0.792 | 0.005 | 0.663 | 0.016 | 0.463 | 0.011 | 0.389 | 0.009 |
| LGR5 | cg13435381 | 0.565 | 0.015 | 0.450 | 0.010 | 0.327 | 0.025 | 0.289 | 0.011 |
| DSC3 | cg15439862 | 0.473 | 0.022 | 0.454 | 0.041 | 0.283 | 0.038 | 0.212 | 0.012 |
| FAM50A | cg12687215 | 0.358 | 0.005 | 0.326 | 0.022 | 0.216 | 0.012 | 0.163 | 0.010 |
| MSX1 | cg20588069 | 0.686 | 0.004 | 0.621 | 0.004 | 0.387 | 0.011 | 0.330 | 0.009 |
| CNR2 | cg26151675 | 0.566 | 0.018 | 0.523 | 0.016 | 0.314 | 0.029 | 0.273 | 0.005 |
| C17orf79 | cg16910379 | 0.335 | 0.003 | 0.251 | 0.017 | 0.186 | 0.004 | 0.183 | 0.009 |
| SULT1A3 | cg19450025 | 0.463 | 0.020 | 0.321 | 0.023 | 0.290 | 0.008 | 0.242 | 0.037 |
| BMP2 | cg01797527 | 0.327 | 0.022 | 0.316 | 0.046 | 0.167 | 0.005 | 0.166 | 0.005 |
| SNAP29 | cg19669036 | 0.299 | 0.005 | 0.219 | 0.014 | 0.180 | 0.017 | 0.155 | 0.006 |
| NLGN4X | cg24103438 | 0.731 | 0.017 | 0.671 | 0.020 | 0.379 | 0.017 | 0.375 | 0.009 |
| C9orf142 | cg01126560 | 0.998 | 0.026 | 0.857 | 0.025 | 0.603 | 0.014 | 0.464 | 0.025 |
| EIF4EBP3 | cg10731022 | 0.197 | 0.014 | 0.140 | 0.019 | 0.127 | 0.002 | 0.097 | 0.006 |
| EEF1G | cg20518716 | 0.773 | 0.023 | 0.642 | 0.013 | 0.490 | 0.011 | 0.352 | 0.012 |
| MANSC1 | cg13080465 | 0.343 | 0.003 | 0.256 | 0.006 | 0.216 | 0.003 | 0.167 | 0.006 |
| FLJ20032 | cg07360692 | 0.551 | 0.013 | 0.485 | 0.033 | 0.308 | 0.015 | 0.269 | 0.012 |
| RCD-8 | cg13578400 | 0.610 | 0.011 | 0.519 | 0.009 | 0.319 | 0.038 | 0.322 | 0.031 |
| LOC339524 | cg25428451 | 0.701 | 0.006 | 0.530 | 0.012 | 0.441 | 0.002 | 0.338 | 0.007 |
| CLDN2 | cg17051440 | 0.782 | 0.013 | 0.578 | 0.037 | 0.491 | 0.026 | 0.383 | 0.012 |
| PGR | cg23641145 | 0.460 | 0.019 | 0.437 | 0.015 | 0.237 | 0.008 | 0.230 | 0.014 |
| C15orf29 | cg19021732 | 0.468 | 0.008 | 0.413 | 0.030 | 0.253 | 0.007 | 0.232 | 0.020 |
| BNC1 | cg19988449 | 0.641 | 0.024 | 0.490 | 0.036 | 0.377 | 0.004 | 0.323 | 0.029 |
| SMOC1 | cg10979891 | 0.909 | 0.015 | 0.815 | 0.050 | 0.500 | 0.005 | 0.440 | 0.029 |
| KRTHB6 | cg04123507 | 0.749 | 0.008 | 0.628 | 0.008 | 0.425 | 0.009 | 0.366 | 0.013 |
| PCDH15 | cg20588045 | 0.612 | 0.006 | 0.526 | 0.008 | 0.335 | 0.010 | 0.303 | 0.013 |
| POLR2C | cg15047833 | 0.450 | 0.003 | 0.374 | 0.019 | 0.272 | 0.009 | 0.209 | 0.007 |
| ETAA16 | cg09750083 | 0.586 | 0.020 | 0.446 | 0.045 | 0.391 | 0.036 | 0.267 | 0.006 |
| FLJ35784 | cg16732901 | 0.836 | 0.023 | 0.693 | 0.052 | 0.484 | 0.006 | 0.402 | 0.018 |
| HIST2H4 | cg09866173 | 0.276 | 0.018 | 0.175 | 0.009 | 0.180 | 0.015 | 0.144 | 0.015 |
| CRSP3 | cg03277112 | 0.361 | 0.008 | 0.283 | 0.018 | 0.209 | 0.012 | 0.180 | 0.006 |
| TRAK1 | cg24877842 | 0.565 | 0.010 | 0.435 | 0.022 | 0.347 | 0.004 | 0.270 | 0.006 |
| KCNQ1 | cg08303146 | 0.270 | 0.024 | 0.250 | 0.010 | 0.154 | 0.009 | 0.123 | 0.005 |
| SLK | cg22391400 | 0.319 | 0.017 | 0.216 | 0.006 | 0.187 | 0.007 | 0.172 | 0.009 |
| FLJ10815 | cg06320982 | 0.518 | 0.015 | 0.447 | 0.022 | 0.294 | 0.013 | 0.245 | 0.001 |
| PAK7 | cg12645220 | 0.379 | 0.014 | 0.338 | 0.020 | 0.198 | 0.026 | 0.189 | 0.019 |
| MEN1 | cg16668394 | 0.629 | 0.020 | 0.504 | 0.023 | 0.337 | 0.022 | 0.326 | 0.006 |
| CHRNB1 | cg04809787 | 0.408 | 0.013 | 0.281 | 0.016 | 0.258 | 0.013 | 0.204 | 0.005 |
| HOXC8 | cg05022306 | 0.443 | 0.018 | 0.353 | 0.012 | 0.254 | 0.005 | 0.217 | 0.001 |
| C9orf16 | cg13901134 | 0.324 | 0.010 | 0.240 | 0.006 | 0.187 | 0.011 | 0.165 | 0.009 |
| PLAGL1 | cg08263357 | 0.434 | 0.009 | 0.383 | 0.009 | 0.262 | 0.005 | 0.192 | 0.014 |
| ZNF652 | cg13382694 | 0.771 | 0.029 | 0.642 | 0.034 | 0.426 | 0.008 | 0.378 | 0.002 |
| KIAA1919 | cg07352586 | 0.253 | 0.008 | 0.173 | 0.011 | 0.163 | 0.010 | 0.124 | 0.002 |
| B3GNT5 | cg17701886 | 0.539 | 0.021 | 0.450 | 0.021 | 0.334 | 0.011 | 0.239 | 0.010 |
| ZYG11BL | cg05824762 | 0.493 | 0.003 | 0.390 | 0.008 | 0.271 | 0.007 | 0.246 | 0.024 |
| CHAF1B | cg13854874 | 0.514 | 0.025 | 0.396 | 0.013 | 0.274 | 0.016 | 0.270 | 0.005 |
| CREB5 | cg10822172 | 0.726 | 0.013 | 0.592 | 0.038 | 0.420 | 0.007 | 0.340 | 0.025 |
| GPR30 | cg16127845 | 0.903 | 0.006 | 0.586 | 0.039 | 0.649 | 0.012 | 0.419 | 0.025 |
| WFDC10A | cg11953868 | 0.688 | 0.010 | 0.582 | 0.026 | 0.409 | 0.010 | 0.309 | 0.004 |
| DAPK2 | cg21413009 | 0.508 | 0.018 | 0.395 | 0.022 | 0.277 | 0.013 | 0.257 | 0.009 |
| ATG16L1 | cg04712018 | 0.503 | 0.018 | 0.358 | 0.011 | 0.312 | 0.009 | 0.242 | 0.009 |
| GPR173 | cg10530733 | 0.304 | 0.004 | 0.228 | 0.029 | 0.170 | 0.010 | 0.154 | 0.013 |
| SFRP5 | cg09542745 | 0.489 | 0.017 | 0.374 | 0.033 | 0.271 | 0.013 | 0.247 | 0.015 |
| SLC2A4 | cg17663577 | 0.230 | 0.019 | 0.151 | 0.008 | 0.141 | 0.005 | 0.119 | 0.008 |
| GDF15 | cg08162780 | 0.648 | 0.042 | 0.595 | 0.009 | 0.347 | 0.037 | 0.301 | 0.006 |
| TPRKB | cg22338307 | 0.598 | 0.015 | 0.517 | 0.015 | 0.315 | 0.014 | 0.292 | 0.011 |
| TUBB3 | cg13494498 | 0.487 | 0.006 | 0.413 | 0.011 | 0.272 | 0.005 | 0.228 | 0.017 |
| PHLDA2 | cg26799802 | 0.635 | 0.024 | 0.548 | 0.029 | 0.353 | 0.025 | 0.295 | 0.014 |
| ERBB3 | cg19258882 | 0.367 | 0.023 | 0.336 | 0.028 | 0.195 | 0.009 | 0.171 | 0.008 |
| LOC129138 | cg22031736 | 0.314 | 0.021 | 0.247 | 0.018 | 0.177 | 0.007 | 0.152 | 0.008 |
| CT45-2 | cg16144006 | 0.451 | 0.020 | 0.375 | 0.032 | 0.245 | 0.011 | 0.217 | 0.033 |
| CD59 | cg24453664 | 0.664 | 0.015 | 0.562 | 0.037 | 0.363 | 0.014 | 0.312 | 0.011 |
| HTR1E | cg04278702 | 0.313 | 0.024 | 0.257 | 0.028 | 0.185 | 0.017 | 0.139 | 0.003 |

TABLE 15-continued

| Gene | Gene ID | sh-ctrl Mean | sh-ctrl SEM | sh-ctrl + 5aza Mean | sh-ctrl + 5aza SEM | sh-3B Mean | sh-3B SEM | sh-3b + 5aza Mean | sh-3b + 5aza SEM |
|---|---|---|---|---|---|---|---|---|---|
| FBXL8 | cg01457653 | 0.369 | 0.023 | 0.266 | 0.016 | 0.210 | 0.010 | 0.184 | 0.003 |
| ITGA9 | cg13882267 | 0.313 | 0.004 | 0.255 | 0.007 | 0.189 | 0.023 | 0.138 | 0.009 |
| GPR173 | cg11505080 | 0.646 | 0.012 | 0.585 | 0.061 | 0.353 | 0.015 | 0.290 | 0.017 |
| ESPN | cg09549827 | 0.670 | 0.019 | 0.580 | 0.009 | 0.379 | 0.013 | 0.300 | 0.020 |
| AK2 | cg01620569 | 0.381 | 0.017 | 0.250 | 0.007 | 0.229 | 0.021 | 0.193 | 0.014 |
| ROM1 | cg01858173 | 0.370 | 0.019 | 0.253 | 0.007 | 0.210 | 0.006 | 0.191 | 0.016 |
| CAPSL | cg24202119 | 0.487 | 0.004 | 0.485 | 0.008 | 0.241 | 0.017 | 0.227 | 0.016 |
| RPH3A | cg01573562 | 0.374 | 0.005 | 0.304 | 0.020 | 0.218 | 0.007 | 0.168 | 0.004 |
| SYDE1 | cg00666746 | 0.499 | 0.007 | 0.330 | 0.023 | 0.322 | 0.017 | 0.236 | 0.021 |
| VMP | cg01173186 | 0.733 | 0.045 | 0.605 | 0.017 | 0.376 | 0.015 | 0.364 | 0.031 |
| GALE | cg09930410 | 0.297 | 0.017 | 0.229 | 0.028 | 0.161 | 0.008 | 0.146 | 0.010 |
| PPP3CB | cg08805338 | 0.358 | 0.007 | 0.271 | 0.024 | 0.204 | 0.007 | 0.170 | 0.002 |
| DCI | cg20886062 | 0.353 | 0.007 | 0.241 | 0.006 | 0.230 | 0.007 | 0.162 | 0.007 |
| ARNTL2 | cg01986577 | 0.536 | 0.004 | 0.450 | 0.013 | 0.293 | 0.009 | 0.248 | 0.011 |
| WDRPUH | cg04420907 | 0.470 | 0.023 | 0.393 | 0.022 | 0.245 | 0.024 | 0.227 | 0.005 |
| CHST8 | cg13959523 | 0.608 | 0.020 | 0.501 | 0.033 | 0.329 | 0.016 | 0.286 | 0.012 |
| SPAG5 | cg08062469 | 0.792 | 0.013 | 0.706 | 0.018 | 0.443 | 0.010 | 0.347 | 0.015 |
| VPS36 | cg17164340 | 0.389 | 0.009 | 0.271 | 0.017 | 0.223 | 0.011 | 0.192 | 0.004 |
| FGF12 | cg15543551 | 0.584 | 0.020 | 0.442 | 0.020 | 0.332 | 0.011 | 0.275 | 0.034 |
| MGC24381 | cg01979004 | 0.322 | 0.025 | 0.174 | 0.010 | 0.219 | 0.020 | 0.169 | 0.007 |
| PGM5 | cg06190053 | 0.263 | 0.009 | 0.187 | 0.010 | 0.167 | 0.009 | 0.117 | 0.004 |
| DUSP22 | cg11235426 | 0.271 | 0.006 | 0.174 | 0.021 | 0.142 | 0.015 | 0.155 | 0.011 |
| GAB3 | cg12938998 | 0.457 | 0.039 | 0.347 | 0.018 | 0.233 | 0.004 | 0.235 | 0.008 |
| DGKD | cg25506396 | 0.386 | 0.044 | 0.238 | 0.014 | 0.227 | 0.006 | 0.202 | 0.005 |
| STXBP3 | cg11666924 | 0.366 | 0.020 | 0.260 | 0.022 | 0.188 | 0.004 | 0.194 | 0.017 |
| DKK2 | cg01404615 | 0.887 | 0.010 | 0.819 | 0.018 | 0.462 | 0.033 | 0.398 | 0.023 |
| PRDM12 | cg09191327 | 0.512 | 0.019 | 0.457 | 0.049 | 0.257 | 0.004 | 0.240 | 0.037 |
| KRTCAP2 | cg11278262 | 0.532 | 0.034 | 0.432 | 0.017 | 0.274 | 0.015 | 0.257 | 0.018 |
| ELK1 | cg21860846 | 0.408 | 0.002 | 0.343 | 0.017 | 0.225 | 0.003 | 0.181 | 0.007 |
| ANKRD46 | cg23737055 | 0.519 | 0.023 | 0.329 | 0.009 | 0.309 | 0.019 | 0.257 | 0.009 |
| DCTN3 | cg22579849 | 0.686 | 0.008 | 0.613 | 0.011 | 0.335 | 0.004 | 0.325 | 0.007 |
| ARNT2 | cg17788682 | 0.284 | 0.009 | 0.212 | 0.011 | 0.148 | 0.004 | 0.139 | 0.017 |
| PLOD1 | cg23286660 | 0.540 | 0.009 | 0.468 | 0.020 | 0.294 | 0.001 | 0.235 | 0.003 |
| CPSF1 | cg20326853 | 0.537 | 0.005 | 0.408 | 0.047 | 0.306 | 0.025 | 0.241 | 0.016 |
| SEC14L2 | cg14452140 | 0.803 | 0.006 | 0.705 | 0.025 | 0.452 | 0.005 | 0.337 | 0.017 |
| R3HDML | cg17692403 | 0.638 | 0.022 | 0.529 | 0.009 | 0.339 | 0.014 | 0.288 | 0.018 |
| EYA4 | cg01805282 | 0.417 | 0.022 | 0.360 | 0.012 | 0.238 | 0.011 | 0.174 | 0.005 |
| ZGPAT | cg04078896 | 0.414 | 0.032 | 0.308 | 0.020 | 0.229 | 0.010 | 0.191 | 0.009 |
| KCNAB1 | cg23873703 | 0.654 | 0.020 | 0.548 | 0.043 | 0.302 | 0.026 | 0.334 | 0.005 |
| DDX42 | cg05797656 | 0.358 | 0.035 | 0.226 | 0.024 | 0.192 | 0.004 | 0.192 | 0.002 |
| LGALS1 | cg00292662 | 0.552 | 0.007 | 0.493 | 0.019 | 0.305 | 0.013 | 0.230 | 0.005 |
| C10orf10 | cg17186163 | 0.521 | 0.026 | 0.371 | 0.018 | 0.302 | 0.006 | 0.237 | 0.015 |
| CDKN2A | cg10895543 | 0.342 | 0.014 | 0.249 | 0.002 | 0.176 | 0.010 | 0.168 | 0.018 |
| BTBD1 | cg16958189 | 0.544 | 0.009 | 0.392 | 0.036 | 0.293 | 0.005 | 0.259 | 0.021 |
| HCN1 | cg11285003 | 0.431 | 0.011 | 0.369 | 0.055 | 0.210 | 0.011 | 0.202 | 0.016 |
| PTPRO | cg19402885 | 0.732 | 0.003 | 0.671 | 0.026 | 0.396 | 0.018 | 0.303 | 0.010 |
| SLIT1 | cg07143898 | 0.405 | 0.002 | 0.325 | 0.006 | 0.220 | 0.007 | 0.176 | 0.009 |
| RASA4 | cg05749161 | 0.234 | 0.020 | 0.157 | 0.018 | 0.145 | 0.016 | 0.102 | 0.007 |
| OR10J1 | cg25076881 | 0.723 | 0.016 | 0.576 | 0.010 | 0.363 | 0.008 | 0.335 | 0.026 |
| SOX17 | cg02919422 | 0.670 | 0.011 | 0.617 | 0.065 | 0.293 | 0.030 | 0.329 | 0.004 |
| CDC42EP1 | cg13951472 | 0.473 | 0.003 | 0.342 | 0.004 | 0.257 | 0.009 | 0.217 | 0.010 |
| SH3BGRL3 | cg03100146 | 0.814 | 0.008 | 0.661 | 0.031 | 0.453 | 0.012 | 0.341 | 0.018 |
| C17orf40 | cg18042079 | 0.384 | 0.021 | 0.207 | 0.014 | 0.218 | 0.016 | 0.213 | 0.007 |
| HRH3 | cg08186362 | 0.712 | 0.018 | 0.666 | 0.017 | 0.365 | 0.022 | 0.297 | 0.031 |
| SCAMP3 | cg01745448 | 0.455 | 0.006 | 0.308 | 0.009 | 0.258 | 0.007 | 0.209 | 0.005 |
| C20orf29 | cg09158909 | 0.489 | 0.013 | 0.322 | 0.019 | 0.282 | 0.002 | 0.226 | 0.003 |
| C10orf72 | cg02569613 | 0.738 | 0.022 | 0.553 | 0.087 | 0.427 | 0.003 | 0.312 | 0.017 |
| KATNB1 | cg15153383 | 0.616 | 0.008 | 0.474 | 0.012 | 0.339 | 0.003 | 0.265 | 0.010 |
| PABPC4 | cg12585282 | 0.468 | 0.005 | 0.296 | 0.019 | 0.264 | 0.007 | 0.221 | 0.008 |
| PHLDA2 | cg01263716 | 0.582 | 0.017 | 0.504 | 0.039 | 0.296 | 0.006 | 0.248 | 0.009 |
| HES6 | cg24127874 | 0.874 | 0.016 | 0.763 | 0.036 | 0.431 | 0.012 | 0.377 | 0.019 |
| ABLIM3 | cg05026186 | 0.504 | 0.007 | 0.365 | 0.023 | 0.250 | 0.011 | 0.240 | 0.012 |
| FLJ20273 | cg15967525 | 0.835 | 0.025 | 0.759 | 0.032 | 0.396 | 0.016 | 0.362 | 0.022 |
| MT | cg14078309 | 0.309 | 0.008 | 0.213 | 0.003 | 0.150 | 0.001 | 0.154 | 0.004 |
| PTPRO | cg27196745 | 0.672 | 0.011 | 0.570 | 0.034 | 0.367 | 0.021 | 0.267 | 0.004 |
| CCKBR | cg13346411 | 0.462 | 0.005 | 0.411 | 0.040 | 0.225 | 0.011 | 0.197 | 0.004 |
| SLC25A22 | cg02973416 | 0.817 | 0.016 | 0.702 | 0.017 | 0.455 | 0.021 | 0.318 | 0.006 |
| B4GALNT3 | cg05769161 | 0.639 | 0.009 | 0.577 | 0.022 | 0.309 | 0.016 | 0.271 | 0.011 |
| SUSD2 | cg23349242 | 0.845 | 0.031 | 0.631 | 0.022 | 0.516 | 0.006 | 0.329 | 0.035 |
| PHLDA2 | cg04720330 | 0.490 | 0.024 | 0.379 | 0.017 | 0.282 | 0.005 | 0.195 | 0.009 |
| SOX15 | cg01029592 | 0.372 | 0.014 | 0.276 | 0.017 | 0.183 | 0.005 | 0.171 | 0.003 |
| RASL11A | cg06611744 | 0.509 | 0.029 | 0.348 | 0.008 | 0.309 | 0.040 | 0.208 | 0.014 |
| TMEM25 | cg20001829 | 0.553 | 0.029 | 0.424 | 0.056 | 0.288 | 0.022 | 0.238 | 0.015 |
| FAM73B | cg00729541 | 0.498 | 0.013 | 0.365 | 0.029 | 0.269 | 0.009 | 0.213 | 0.004 |
| SORCS3 | cg16787600 | 0.860 | 0.008 | 0.786 | 0.040 | 0.387 | 0.014 | 0.384 | 0.014 |

TABLE 15-continued

| Gene | Gene ID | sh-ctrl Mean | sh-ctrl SEM | sh-ctrl + 5aza Mean | sh-ctrl + 5aza SEM | sh-3B Mean | sh-3B SEM | sh-3b + 5aza Mean | sh-3b + 5aza SEM |
|---|---|---|---|---|---|---|---|---|---|
| SCARA5 | cg10171125 | 0.564 | 0.019 | 0.408 | 0.011 | 0.304 | 0.026 | 0.239 | 0.006 |
| TMEM106C | cg25884854 | 0.572 | 0.027 | 0.482 | 0.017 | 0.297 | 0.003 | 0.229 | 0.009 |
| C12orf34 | cg01335367 | 1.049 | 0.022 | 0.987 | 0.010 | 0.507 | 0.049 | 0.420 | 0.014 |
| MRPL38 | cg11653266 | 0.347 | 0.006 | 0.224 | 0.008 | 0.187 | 0.006 | 0.155 | 0.006 |
| IGFBP3 | cg04796162 | 0.573 | 0.029 | 0.501 | 0.041 | 0.283 | 0.018 | 0.230 | 0.006 |
| C19orf30 | cg07456645 | 0.633 | 0.029 | 0.552 | 0.030 | 0.310 | 0.006 | 0.254 | 0.021 |
| KIAA1822 | cg02867079 | 0.894 | 0.027 | 0.842 | 0.025 | 0.442 | 0.018 | 0.345 | 0.035 |
| RAB37 | cg12448933 | 0.570 | 0.024 | 0.483 | 0.013 | 0.266 | 0.007 | 0.241 | 0.015 |
| GCN5L2 | cg08434547 | 0.613 | 0.005 | 0.555 | 0.033 | 0.287 | 0.008 | 0.249 | 0.006 |
| PDE8B | cg18089852 | 0.305 | 0.017 | 0.203 | 0.013 | 0.161 | 0.009 | 0.130 | 0.010 |
| OSTbeta | cg16029760 | 0.370 | 0.027 | 0.344 | 0.012 | 0.177 | 0.009 | 0.144 | 0.009 |
| MYOD1 | cg18555440 | 0.658 | 0.019 | 0.561 | 0.073 | 0.261 | 0.068 | 0.321 | 0.015 |
| LGR6 | cg23578193 | 0.483 | 0.014 | 0.423 | 0.056 | 0.237 | 0.011 | 0.187 | 0.009 |
| FLJ42486 | cg03734874 | 0.761 | 0.005 | 0.711 | 0.016 | 0.374 | 0.030 | 0.287 | 0.037 |
| C22orf9 | cg11221513 | 0.565 | 0.013 | 0.402 | 0.037 | 0.298 | 0.029 | 0.229 | 0.007 |
| CACNA1G | cg18454685 | 0.695 | 0.015 | 0.587 | 0.043 | 0.324 | 0.026 | 0.286 | 0.050 |
| PPCDC | cg11632617 | 0.685 | 0.012 | 0.523 | 0.026 | 0.354 | 0.011 | 0.269 | 0.005 |
| CHST8 | cg24739326 | 0.803 | 0.005 | 0.660 | 0.017 | 0.391 | 0.023 | 0.319 | 0.011 |
| DUSP8 | cg02271621 | 0.386 | 0.011 | 0.296 | 0.029 | 0.236 | 0.035 | 0.135 | 0.012 |
| LOX | cg06508445 | 0.244 | 0.005 | 0.190 | 0.007 | 0.116 | 0.005 | 0.101 | 0.011 |
| SHH | cg00577464 | 0.552 | 0.026 | 0.433 | 0.024 | 0.283 | 0.017 | 0.212 | 0.009 |
| KCNC2 | cg18573383 | 0.365 | 0.022 | 0.277 | 0.011 | 0.164 | 0.007 | 0.159 | 0.010 |
| ZGPAT | cg18611245 | 0.997 | 0.009 | 0.736 | 0.021 | 0.532 | 0.032 | 0.379 | 0.032 |
| THAP3 | cg11688219 | 0.868 | 0.040 | 0.581 | 0.010 | 0.470 | 0.017 | 0.344 | 0.020 |
| ABCA3 | cg02331561 | 0.314 | 0.018 | 0.189 | 0.017 | 0.153 | 0.010 | 0.145 | 0.019 |
| ACTL6B | cg08572611 | 0.311 | 0.004 | 0.210 | 0.011 | 0.142 | 0.014 | 0.138 | 0.008 |
| OGG1 | cg25415932 | 0.673 | 0.013 | 0.526 | 0.007 | 0.361 | 0.011 | 0.240 | 0.006 |
| EHD2 | cg12603043 | 0.440 | 0.013 | 0.398 | 0.020 | 0.187 | 0.015 | 0.176 | 0.008 |
| VPREB1 | cg18441959 | 0.623 | 0.037 | 0.524 | 0.013 | 0.301 | 0.013 | 0.230 | 0.006 |
| FCHSD2 | cg17114257 | 0.505 | 0.018 | 0.423 | 0.013 | 0.258 | 0.007 | 0.179 | 0.004 |
| C1RL | cg22593785 | 0.502 | 0.019 | 0.347 | 0.024 | 0.267 | 0.010 | 0.188 | 0.005 |
| MAP6D1 | cg03705396 | 0.594 | 0.013 | 0.522 | 0.004 | 0.311 | 0.017 | 0.201 | 0.026 |
| ZNF585B | cg03751813 | 0.447 | 0.015 | 0.392 | 0.028 | 0.184 | 0.011 | 0.182 | 0.020 |
| SLC6A5 | cg20632573 | 0.457 | 0.011 | 0.291 | 0.012 | 0.219 | 0.007 | 0.192 | 0.004 |
| DGKI | cg06277657 | 0.510 | 0.068 | 0.365 | 0.029 | 0.257 | 0.012 | 0.190 | 0.012 |
| SLC35C2 | cg02413850 | 0.390 | 0.013 | 0.254 | 0.011 | 0.190 | 0.006 | 0.155 | 0.010 |
| UNQ2446 | cg10574499 | 0.658 | 0.005 | 0.619 | 0.020 | 0.323 | 0.017 | 0.218 | 0.005 |
| TBXA2R | cg09998229 | 0.724 | 0.023 | 0.659 | 0.024 | 0.328 | 0.012 | 0.256 | 0.029 |
| PRMT8 | cg23739862 | 0.240 | 0.030 | 0.125 | 0.009 | 0.112 | 0.011 | 0.116 | 0.012 |
| UBA52 | cg24356797 | 0.349 | 0.027 | 0.192 | 0.041 | 0.181 | 0.016 | 0.145 | 0.006 |
| SOX15 | cg13098960 | 0.665 | 0.004 | 0.472 | 0.019 | 0.302 | 0.004 | 0.261 | 0.007 |
| FLJ20273 | cg01704534 | 0.544 | 0.021 | 0.410 | 0.033 | 0.222 | 0.009 | 0.222 | 0.012 |
| EMP3 | cg01795122 | 0.310 | 0.012 | 0.187 | 0.006 | 0.143 | 0.008 | 0.127 | 0.008 |
| FAM70B | cg15350194 | 0.591 | 0.092 | 0.396 | 0.012 | 0.270 | 0.009 | 0.222 | 0.008 |
| HBQ1 | cg07703401 | 0.650 | 0.004 | 0.587 | 0.021 | 0.279 | 0.005 | 0.220 | 0.009 |
| MGC9850 | cg21097640 | 0.547 | 0.034 | 0.292 | 0.043 | 0.273 | 0.031 | 0.218 | 0.005 |
| ZNF702 | cg07559730 | 0.608 | 0.020 | 0.457 | 0.031 | 0.249 | 0.007 | 0.221 | 0.009 |
| CAMKK2 | cg01369981 | 0.521 | 0.040 | 0.344 | 0.025 | 0.229 | 0.006 | 0.191 | 0.011 |
| KIAA1840 | cg06121469 | 0.557 | 0.034 | 0.365 | 0.024 | 0.258 | 0.011 | 0.191 | 0.007 |
| ICAM1 | cg22874046 | 0.427 | 0.010 | 0.349 | 0.061 | 0.174 | 0.027 | 0.144 | 0.019 |
| PIB5PA | cg18053607 | 0.722 | 0.013 | 0.403 | 0.008 | 0.360 | 0.019 | 0.247 | 0.003 |
| CSMD1 | cg22619018 | 0.551 | 0.024 | 0.365 | 0.045 | 0.221 | 0.014 | 0.201 | 0.006 |
| TRAPPC1 | cg01667702 | 0.662 | 0.022 | 0.471 | 0.012 | 0.262 | 0.022 | 0.231 | 0.008 |
| HEYL | cg25462291 | 0.700 | 0.025 | 0.576 | 0.035 | 0.270 | 0.033 | 0.218 | 0.012 |
| ID2 | cg23525180 | 0.617 | 0.021 | 0.576 | 0.030 | 0.207 | 0.015 | 0.201 | 0.014 |
| CART | cg23300372 | 0.547 | 0.013 | 0.445 | 0.010 | 0.215 | 0.010 | 0.160 | 0.006 |
| GALR1 | cg04534765 | 0.559 | 0.020 | 0.440 | 0.033 | 0.201 | 0.014 | 0.176 | 0.013 |
| GNAS | cg00943909 | 0.589 | 0.021 | 0.621 | 0.041 | 0.147 | 0.014 | 0.097 | 0.003 |

Three days of treatment with low-dose decitabine in control NT2/D1-R1 cells altered the promoter methylation of a smaller set of genes (388 genes) compared to DNMT3B knockdown (1771 genes), however, again, the majority of genes had decreased levels of methylation (305 of 388 genes). Approximately 60% of the genes with decreased promoter methylation in response to decitabine treatment also demonstrated decreased methylation in DNMT3B knockdown cells. Hierarchical clustering was performed for the 4 treatment arm values for the 388 genes with significant methylation changes in response to decitabine treatment in control cells. As expected, there was little overlap in the genes associated with increased promoter methylation in response to decitabine treatment in control cells as compared to cells with DNMT3B knockdown. Approximately 10% of genes with decreased methylation in response to decitabine treatment also showed increased gene expression levels after decitabine treatment. In contrast, approximately 4% of the genes with increased methylation showed an unexpected increase in gene expression levels after treatment with decitabine. Global DNA promoter methylation analysis was also performed in NT2/D1 cells after 3 day treatment with low dose decitabine. However, methylation changes were less robust in the experiments in NT2/D1 cells. Only 12 genes were identified as having significant decreases in promoter methylation. However, 6 of the 12 genes with decreased methylation in NT2/D1 cells also had decreased methylation in NT2/D1-R1 cells when treated with low dose decitabine. These six genes included RIN1, SOX15, TLR4, GPER, TRIM54, and CD164L2. Importantly, bisulfite pyrosequencing and real-time PCR of independent samples confirmed that three of the genes, RIN1, SOX15 and TLR4 exhibited decreased promoter methylation and increased expression in NT2/D1 cells when treated for 3 days with low-dose decitabine (FIGS. 13 and 14).

The exact anticancer mechanism of decitabine is not known. Most studies have used somatic cells at doses substantially higher than the low doses employed in the present invention. Doses of decitabine as low as 10 nM now have been shown to be sufficient to induce DNA damage and apoptosis in EC cells, and that these effects are associated with the induction of a classic p53 target gene signature coupled with transcriptional repression of core pluripotency genes. It is also important to note that the transcriptional effects associated with decitabine exposure were observed even after only 1 day of low dose dectiabine treatment, indicating these effects precede any direct effects of decitabine on EC cells. These data also indicate that either one cell cycle is sufficient to meet threshold decitabine incorporation for demethylation/DNA damage responses or that decitabine has additional effects on EC cells independent of DNA incorporation.

It has also been suggested that p53 can directly repress pluripotency genes including NANOG, OCT4 and GDF3 after treatment with DNA damaging agents (Lin et al. 2005. *Nat. Cell Biol.* 7:165-171; Li et al. 2012. *Mol. Cell* 46:30-42). Although the experiments described herein did not demonstrate an effect of cisplatin to down-regulate expression of pluripotency genes, the dramatic and genome-wide down-regulation of pluripotency gene expression in response to low dose decitabine treatment indicates that genes both up-regulated and down-regulated by decitabine in EC cells may be related to a stem cell-like function of p53. Interestingly, only low dose decitabine treatment was associated with up-regulation of a subset of the p53 target genes that have been shown to be up-regulated by cisplatin treatment. This provides further evidence that decitabine and cisplatin activate p53 in distinct manners, which for decitabine likely includes mechanisms other than a DNA damage response.

The results of the present experiments have shown that doses of 5-aza as low as 10 nM lead to global demethylation of LINE-1 repetitive elements and a decrease in promoter methylation in EC cells. The promoter demethylation was in both CpG islands and non, CpG island promoters. The genes up-regulated in response to decitabine treatment alone (Cluster 1) may be induced by a demethylation mechanism and are likely important in mediating the acute hypersensitivity of decitabine in EC cells. There was also a substantial degree of overlap between genes with decreased promoter DNA methylation and induced expression with low-dose 5-aza, indicating that effective re-expression through DNA demethylation has occurred. Additionally, the results of the present invention demonstrate that the genes RIN1, TLR4 and SOX15 are novel candidate biomarkers and tumors suppressor genes in TGCTs. In addition, GSEA analysis indicates that a subset of genes whose expression levels are altered with high-dose decitabine treatment in other tumor types are also altered in response to low-dose decitabine treatment in EC cells, providing further support for demethylation as a mechanism responsible for the hypersensitivity of EC cells to decitabine.

TGCT-derived pluripotent EC cells, even those resistant to cisplatin, are hypersensitive to low-dose decitabine as compared to solid somatic tumors cells. Additionally, it has been shown that the acute, low-dose sensitivity to decitabine is likely mediated through a multifactorial mechanism related to the pluripotent, stem cell-like properties of EC cells.

The results described herein demonstrate that the present invention is a novel biomarker for cancer cells that are responsive to low dose decitabine treatment. The biomarker is a group of genes, namely RIN1, TLR4 and SOX15 that have been shown to be up-regulated by low dose decitabine treatment and also associated with decreases in promoter methylation. Thus, these genes are novel candidate biomarkers and tumors suppressor genes in TGCTs. The present invention is not limited, however, as a biomarker for TGCT cells. It is likely that the genes of the present invention will prove to be a biomarker of cancer stem cells of other cancers as well. Thus, it is contemplated that one of skill would understand that the present invention includes biomarkers for cancer stem cells which would include but not be limited to TGCTs, breast cancer stem cells, pancreatic cancer stem cells, and brain cancer stem cells.

The present invention can also be considered to relate to the use of gene expression panel (or profiles or "signatures") which are clinically relevant to cancer, in particular testicular germ cell cancer. In particular, the identities of genes that are correlated with sensitivity to treatment with decitabine, which can lead to increased patient survival are provided. Although the present invention has focused on the identification of a set of biomarkers for a gene expression panel or profile in decitabine-sensitive testicular germ cell cancer, the genes identified herein as biomarkers could be expanded to include other genes that are listed in Tables 1-4.

Also contemplated by the present invention is a method and kit for determining sensitivity to decitabine treatment. The method and kit employ a detection mechanism for determining the expression of one or more genes of the panel of biomarker genes of the instant invention. A detection mechanism can be any standard technique or platform for determining gene expression. Examples of detection mechanisms of use in the kit and method include, e.g., a microarray, which contains some or all of the biomarkers of the instant invention arrayed on chip; an assay such as a reverse transcription polymerase chain reaction (RT-PCR), wherein the method and kit include primers for amplifying some or all of the biomarkers of the instant invention; or northern blot or dot blot analysis, wherein the kit and method include probes. Microarry chips, primers and probes for this type of analysis are routinely generated by the skilled artisan and can be designed using the nucleotide sequences disclosed herein.

When using the method and kit, the expression of the gene expression panel, i.e., RIN1, TLR4 and SOX15, in a patient sample (e.g., a cancer patient administered a dose of decitabine) is analyzed and compared to a control panel (e.g., the expression of said genes in the same individual prior to treatment), wherein an increase in expression of RIN1, TLR4 and SOX15 is indicative of sensitivity to decitabine treatment.

The following non-limiting examples are provided to further illustrate the present invention.

EXAMPLE 1

Cell Culture and Drug Treatments

NT2/D1, NT2D1-R1, 833K, 833K-CP, Tera-1, U20S, and HCT116 cells were cultured in DMEM with 10% FBS supplemented with glutamine and antibiotics except for MCF7 cells that were cultured in F12-DMEM. The derivation of the NT2/D1-resistant NT2/D1-R1 cell line has been previously described (Curtin et al. 2001. *Oncogene* 20:2559-2569; Kerley-Hamilton et al. 2007. *Biochim. Biophys. Acta* 1769:209-219). Cells were treated with the indicated dosages of 5-azadeoxycytidine (5-aza-CdR) for 3 days. This drug was replenished each day. Cisplatin (Bristol Laboratories) treatments were performed at the concentrations and time points indicated. To assess cell proliferation and survival, CELL-TITRE GLO (Promega) assays were performed.

EXAMPLE 2

Real-Time PCR and Western Blot Analysis

Reverse transcription (RT) was performed on 1 µg RNA using the TAQMAN RT kit (Applied Biosystems). Twenty ng of the resulting cDNA was used with SYBR green (Applied Biosystems) for quantitative real-time PCR assays utilizing the ddCT method normalized to GAPDH and the ABI Prism Sequence Detection System 7700. For Western analysis, cells were lysed in a radioimmune precipitation buffer, separated by SDS-PAGE. Antibodies to DNMT3B (H-230; sc-20704, Santa Cruz, and Ab2851, Abcam) and actin (C-1; sc01615, Santa Cruz) were employed.

EXAMPLE 3

Lentiviral Production

Silencing shRNAs to human DNMT3B were purchased (Open Biosystems). Lentiviral particles were generated as previously described and cells were selected in 1.0 µg/ml puromycin (Sigma Chemical Company, St. Louis, Mo.) (Kerley-Hamilton et al. 2007. *Biochim. Biophys. Acta* 1769: 209-219).

EXAMPLE 4

Cell Proliferation and Cell Cycle Analysis

Cells were cultured in DMEM media (Gibco) with 10% FBS. Decitabine was added fresh each day. Lentiviral control cells and the stable shRNA DNMT3B knockdown cell line (NT2/D1-R1-sh84) were described previously (Beyrouthy et al. 2009. *Cancer Res.* 69:9360-9366). DNMT3B knockdown was greater than 90% as confirmed by western blot analysis. Cell proliferation and survival were assessed with the CELL-TITRE GLO assay (Promega). Cell cycle analysis with propidium iodine has been previously described (Kerley-Hamilton et al. 2005. *Oncogene* 24:6090-6100).

EXAMPLE 5

Western Blot Analysis and Real-Time PCR

SYBR green-based real-time PCR (Applied Biosystems) was employed using the ddCT method normalized to GAPDH. For western blot analysis cells were lysed in radioimmune precipitation buffer and separated by SDS-PAGE. Antibodies to actin (sc01615, Santa Cruz), 139-H2AX (Cell Signaling), PARP (c-2-10, Biomol International) and p53 (D0-1, Santa Cruz) were used.

EXAMPLE 6

Gene Expression Microarray Analysis

Expression analysis was performed on the ILLUMINA HumanHT-12 v3 or ILLUMINA HumanHT-12 v4 bead chip arrays (ILLUMINA) and scanned on the BeadArray Reader (ILLUMINA) according to manufacturer's instructions. Raw data was normalized (quantile) and analyzed in Genome Studio software (ILLUMINA). Data was imported in GeneSifter (vizX Labs) for pairwise and ANOVA statistical analyses. Hierarchal clustering was performed using a correlation metric for similarity and average linkage clustering. Partitioning around mediods (PAM) analysis was performed in GeneSifter using a correlation metric for similarity. The number of clusters was chosen empirically to obtain the best mean silhouette value. GSEA software was obtained from the Broad Institute. The number of permutations was 1,000 and the permutation type was gene_set.

EXAMPLE 7

Genome-Wide Methylation Analysis

DNA methylation analysis was performed in samples in triplicate using the ILLUMINA INFINIUM assay with the HumanMethylation27 BeadChip (ILLUMINA) and the BeadChip was scanned on the BeadArray Reader (ILLUMINA), according to the manufacturer's instructions. Raw data was normalized and analyzed with Genome Studio software (ILLUMINA). The HumanMethylation27 BeadChip assays 27,578 CpGs covering more than 14,000 genes, mostly from promoter regions. Data was imported in GeneSifter (vizX labs) for pairwise and ANOVA statistical analyses. Hierarchical clustering was performed as stated above. HumanMethylation27 BeadChip data and gene expression microarray data were submitted to NCBI GEO.

EXAMPLE 8

LINE and Promoter Specific Pyrosequencing

Genomic DNA was isolated with the QIAMP DNA mini kit (Qiagen) and bisulfite converted with the EZ DNA methylation kit (Zymo Research). DNA was amplified with HOTSTARTAQ plus DNA polymerase (Qiagen). The LINE-1 pyrosequencing assay averages across four CpG sites and has been described previously (Kashiwagi et al. 2011. *Nucleic Acids Res.* 39:874-888). Pyrosequencing assays for RIN1, SOX15, and TLR4 were designed with PyroMark assay design software (Qiagen) to sequence across corresponding probes cg0599842, cg02515422 and cg13098960 on the HumanMethylation27 BeadChip.

What is claimed is:

1. A method for determining sensitivity to decitabine and treating drug-resistant cancer comprising
    (a) obtaining cancer cells from a patient with a drug-resistant cancer, (b) contacting the cancer cells of (a) with decitabine,
(c) determining the expression of Toll-Like Receptor 4 (TLR4), Ras and Rab interactor 1 (RIN1), and Sex Determining Region Y-box 15 (SOX15) in the cancer cells of (b),
(d) comparing said expression with the expression of TLR4, RIN1, and SOX15 in untreated control cells,
(e) determining that the cancer cells from the patient are sensitive to decitabine based on the detection of an increase in expression of TLR4, RIN1, and SOX15 in the cancer cells as compared to the untreated cells; and
(f) treating the patient determined in (e) to have cancer cells that are sensitive to decitabine with decitabine and a cytotoxic agent, thereby treating the drug-resistant cancer.

2. The method of claim 1, wherein the cytotoxic agent is cisplatin.

3. The method of claim 1, wherein said cancer cells are testicular cancer germ cells, breast cancer stem cells, pancreatic cancer stem cells, or glioblastoma stem cells.

* * * * *